(12) United States Patent
Tymianski et al.

(10) Patent No.: US 7,858,322 B2
(45) Date of Patent: Dec. 28, 2010

(54) METHOD OF DETERMINING INHIBITION OF BINDING TO TRPM7 PROTEIN

(75) Inventors: Michael Tymianski, Toronto (CA); Jonathan David Garman, San Jose, CA (US); Michael P. Belmares, San Jose, CA (US)

(73) Assignees: NoNo, Inc., Ontario (CA); Arbor Vita Corporation, Fremont, CA (US)

( * ) Notice: Subject to any disclaimer, the term of this patent is extended or adjusted under 35 U.S.C. 154(b) by 0 days.

(21) Appl. No.: 11/021,928

(22) Filed: Dec. 22, 2004

(65) Prior Publication Data

US 2005/0164933 A1    Jul. 28, 2005

Related U.S. Application Data

(60) Provisional application No. 60/532,169, filed on Dec. 23, 2003.

(51) Int. Cl.
*G01N 33/53* (2006.01)
*G01N 33/567* (2006.01)
*G01N 33/566* (2006.01)

(52) U.S. Cl. ................... 435/7.1; 435/7.21; 436/501

(58) Field of Classification Search ............ None
See application file for complete search history.

(56) References Cited

FOREIGN PATENT DOCUMENTS

| CA | 2450236 | 1/2003 |
|----|---------|--------|
| CA | 2457424 | 2/2003 |
| WO | 2004/45535 A2 | 6/2004 |

OTHER PUBLICATIONS

Aarts et al., "Treatment of ischemic brain damage by perturbing NMDA receptor- PSD-95 protein interactions", *Science*, 298:5594: 846-850, (Oct. 25, 2002).
Aarts et al., "Uncoupling of NMDAR signaling from neurotoxicity by Tat-fusion peptides" *Science For Neuroscience* Abstract Viewer And Itinerary Planner, Abstract No. 245.2; & 32nd Annual Meeting Of The Society For Neuroscience; Orlando, Florida, USA; (Nov. 2-7, 2002).
Aarts et al., "On the mechanism of anoxic neuronal death: TRPM7 as a final common pathway." *Society For Neuroscience* Abstract Viewer And Itinerary Planner, Abstract No. 302.19, & 33rd Annual Meeting Of The Society For Neuroscience; New Orleans, LA, USA; (Nov. 8-12, 2003).
Supplementary Partial European Search Report dated Apr. 28, 2008 for EP 04802368.3.
Aarts et al., "A Key Role for TRPM7 Channels in Anoxic Neuronal Death," *Cell*, 115:863-877 (2003).
Boels et al., "The neuropeptide head activator induces activation and translocation of the growth-factor-regulated $Ca^{2+}$ permeable channel GRC," *J. Cell Science*, 114(20):3599-3606 (2001).
Clapham, D. E., "TRP Channels as Cellular Sensors," *Nature*, 426:517-524 (2003).
Fanning et al., "PDZ Domains: Fundamental Building Blocks in the Organization of Protein Complexes at the Plasma Membrane," *J. Clinical Investigation*, 103(6):767-772 (1999).
Jiang et al., "Regulation of a TRPM7-like Current in Rat Brain Microgila," *J. Biol. Chem.*, 278(44):42867-4286 (2003).
Montell et al., "A United Nomenclature for the Superfamily of TRP Cation Channels," *Molecular Cell*, 9:229-231 (2002).
Nicotera et al., "The Enemy at the Gates:$Ca^{2+}$ Entry through TRPM7 Cahnnels and Anoxic Neuronal Death," *Cell*, 115:768-770 (2003).
Takezawa et al., "Receptor-mediated Regulation of the TRPM7 Channel Through its Endogenous Protein Kinase Domain," *PNAS*, 101(16):6009-6014 (2004).
PCT International Search Report mailed Apr. 20, 2005, PCT Application No. PCT/CA2004/002193, filed Dec. 22, 2004.

*Primary Examiner*—Olga N Chernyshev
(74) *Attorney, Agent, or Firm*—Alston & Bird LLP

(57) ABSTRACT

This invention relates to methods of reducing the damaging effect of an injury to mammalian cells by treatment with compounds which reduce cell death or dysfunction, including cellular damage following episodes of tissue ischemia, trauma, epilepsy, and acute or chronic degeneration. The invention discloses methods of treating these disorders by administering inhibitors that disrupt protein-protein interactions involved in these disorders, screening methods to identify such inhibitors and specific compositions useful for treating these disorders.

6 Claims, 14 Drawing Sheets

Figure 3
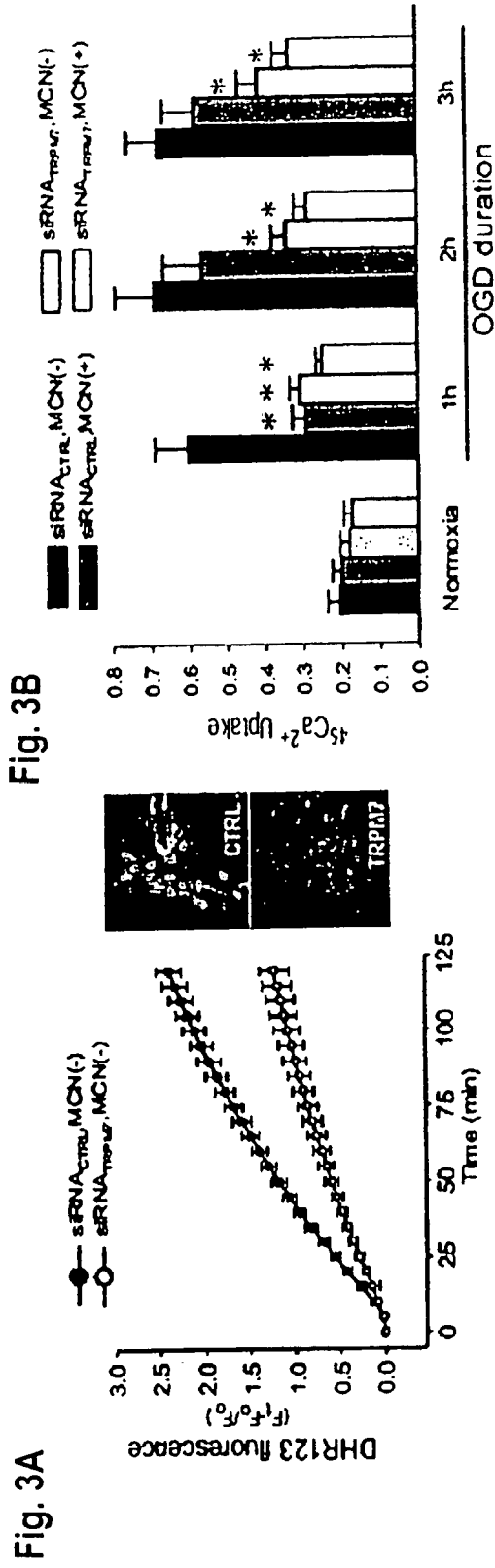
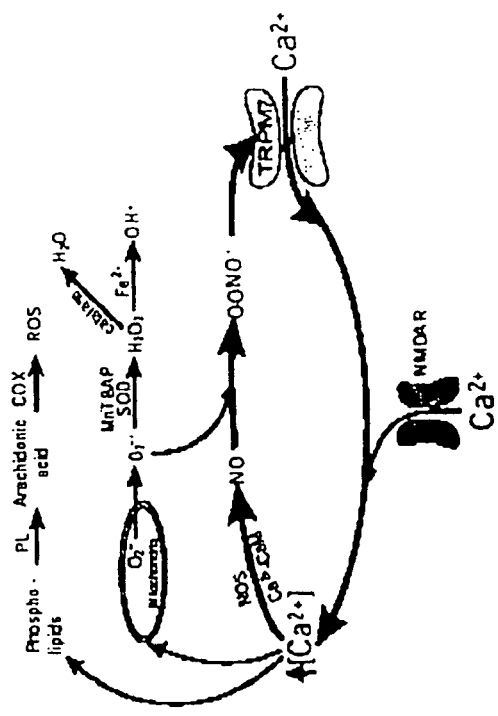
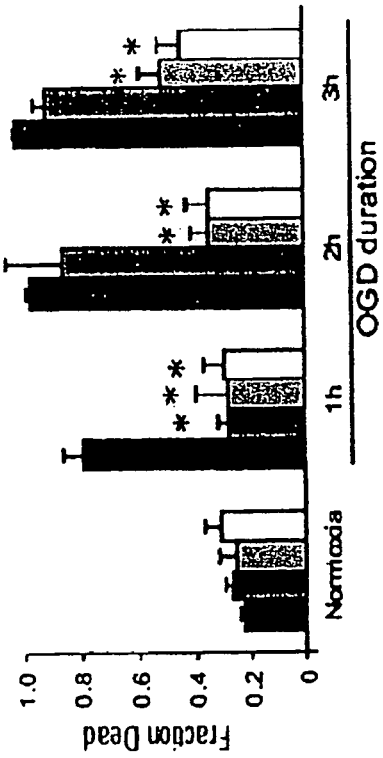

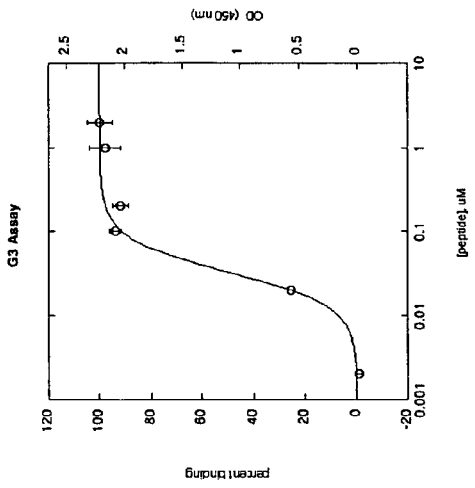
Fig. 9C Titration: TRPM7 peptide/ ZO-1 d2
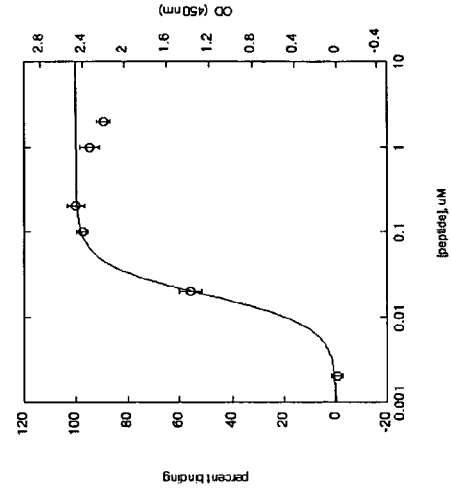
Fig. 9D Titration: TRPM7 peptide/ Par3 d3
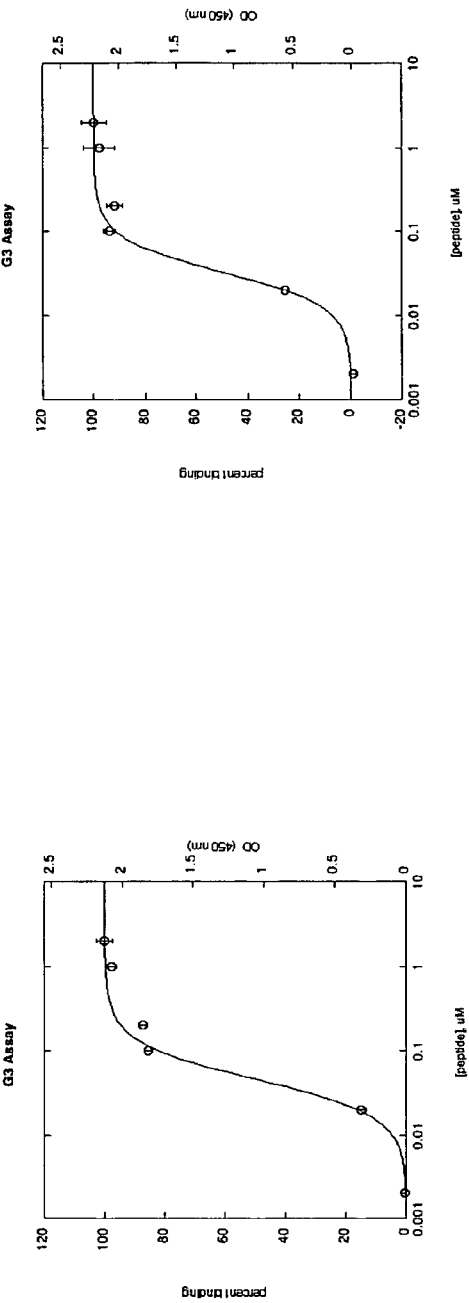
Fig. 9A Titration: TRPM7 peptide/ RIM2 d1
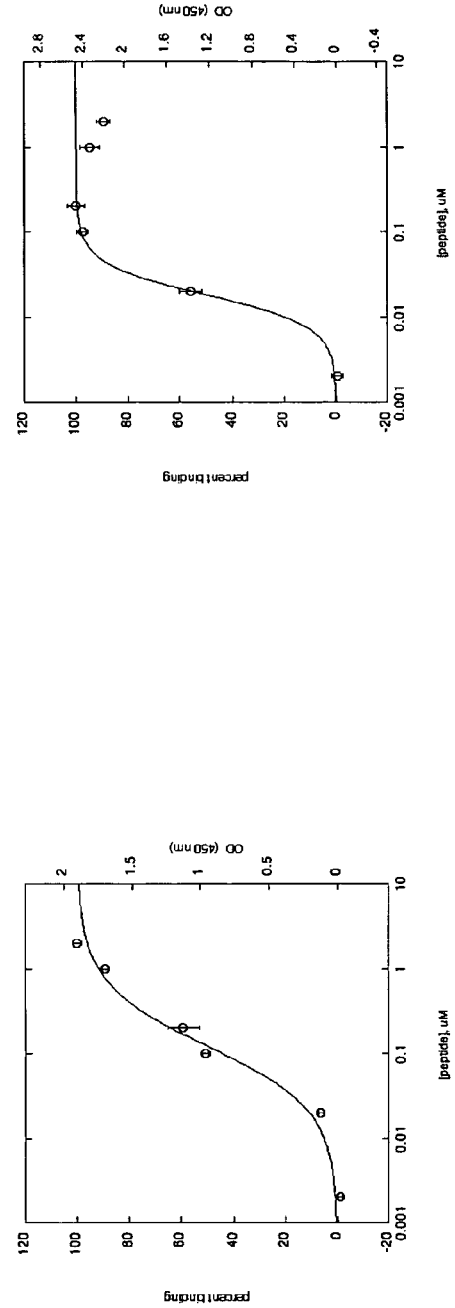
Fig. 9B Titration: TRPM7 peptide/ INADL d3

Titration: Peptide 1839/ INADL d3

Titration: Peptide 1829/ ZO-1 d2

Layout of construct

Enzyme site (EcoRI) – H1 promoter – enzyme site (BamHI) – sense siRNA – loop – antisense siRNA – termination sequence – enzyme site (HindIII)

Sequence of Construct

GAATTCATATTTGCATGTCGCTATGTGTTCTGGGAAATCACCATAAACGTGAAATGT
CTTTGGATTTGGGAATCTTATAAGTTCTGTATGAGACCACTCGGATCCGAGTGCATG
ACTGGTGAATTTCAAGAGAATTCACCAGTCATGCACTCTTTTTGGAAAAGCTT siRNA Hairpin sequence

GAGUGCAUGACUGGUGAAUUCAAGAGAAUUCACCAGUCAUGCACUCUU

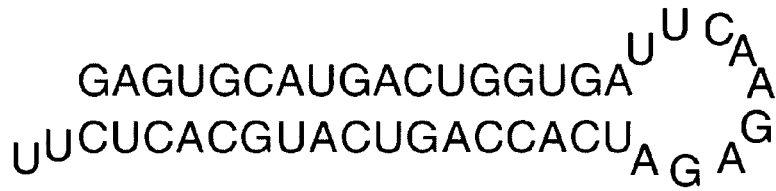

TRPM7 siRNA hairpin in pAdTrack vector

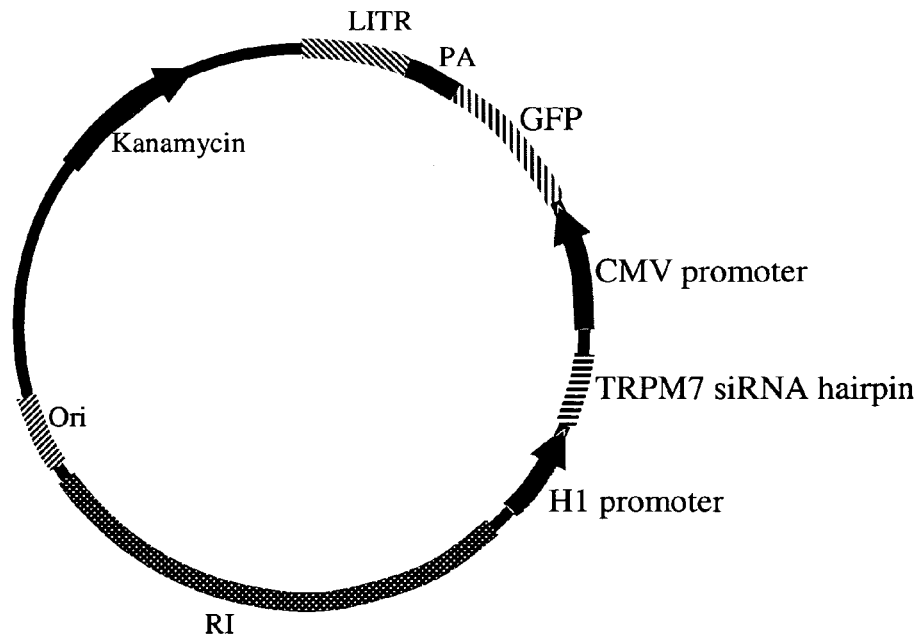

FIGURE 11

A
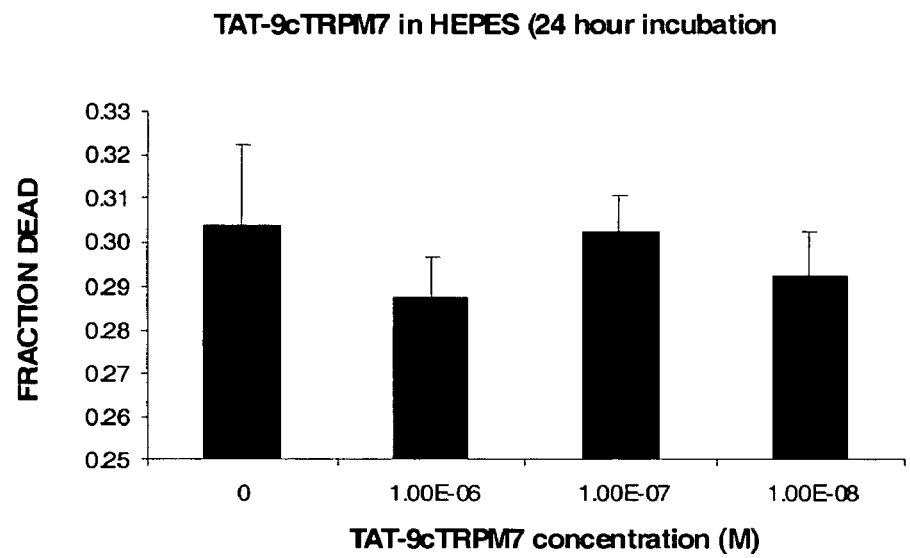
B
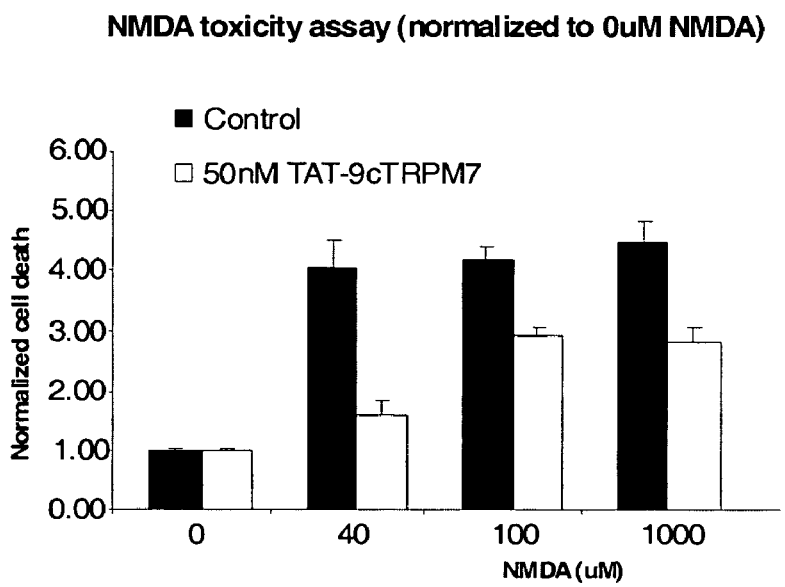
FIGURE 14

SEQUENCE LISTING

```
<160> NUMBER OF SEQ ID NOS: 384

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)
<223> OTHER INFORMATION: 'Xaa' is any amino acid

<400> SEQUENCE: 1

Xaa Leu Met Leu
1

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Glu Trp Lys Phe Ala Arg
1               5

<210> SEQ ID NO 3
<211> LENGTH: 93
<212> TYPE: PRT
<213> ORGANISM: Artificial Sequence
<220> FEATURE:
<223> OTHER INFORMATION: Synthetic peptide

<400> SEQUENCE: 3

Leu Arg Lys Glu Pro Glu Ile Ile Thr Val Thr Leu Lys Lys Gln Asn
1               5                   10                  15

Gly Met Gly Leu Ser Ile Val Ala Ala Lys Gly Ala Gly Gln Asp Lys
            20                  25                  30

Leu Gly Ile Tyr Val Lys Ser Val Val Lys Gly Gly Ala Ala Asp Val
        35                  40                  45
```

```
Asp Gly Arg Leu Ala Ala Gly Asp Gln Leu Leu Ser Val Asp Gly Arg
    50                  55                  60

Ser Leu Val Gly Leu Ser Gln Glu Arg Ala Ala Glu Leu Met Thr Arg
65                  70                  75                  80

Thr Ser Ser Val Val Thr Leu Glu Val Ala Lys Gln Gly
                85                  90

<210> SEQ ID NO 4
<211> LENGTH: 105
<212> TYPE: PRT
<213> ORGANISM: Artificial Sequence
<220> FEATURE:
<223> OTHER INFORMATION: Synthetic peptide

<400> SEQUENCE: 4

Leu Ile Arg Pro Ser Val Ile Ser Ile Ile Gly Leu Tyr Lys Glu Lys
1               5                   10                  15

Gly Lys Gly Leu Gly Phe Ser Ile Ala Gly Gly Arg Asp Cys Ile Arg
                20                  25                  30

Gly Gln Met Gly Ile Phe Val Lys Thr Ile Phe Pro Asn Gly Ser Ala
            35                  40                  45

Ala Glu Asp Gly Arg Leu Lys Glu Gly Asp Glu Ile Leu Asp Val Asn
    50                  55                  60

Gly Ile Pro Ile Lys Gly Leu Thr Phe Gln Glu Ala Ile His Thr Phe
65                  70                  75                  80

Lys Gln Ile Arg Ser Gly Leu Phe Val Leu Thr Val Arg Thr Lys Leu
                85                  90                  95

Val Ser Pro Ser Leu Thr Asn Ser Ser
            100                 105

<210> SEQ ID NO 5
<211> LENGTH: 105
<212> TYPE: PRT
<213> ORGANISM: Artificial Sequence
<220> FEATURE:
<223> OTHER INFORMATION: Synthetic peptide

<400> SEQUENCE: 5

Gln Ser Glu Asn Glu Glu Asp Val Cys Phe Ile Val Leu Asn Arg Lys
1               5                   10                  15

Glu Gly Ser Gly Leu Gly Phe Ser Val Ala Gly Gly Thr Asp Val Glu
                20                  25                  30

Pro Lys Ser Ile Thr Val His Arg Val Phe Ser Gln Gly Ala Ala Ser
            35                  40                  45

Gln Glu Gly Thr Met Asn Arg Gly Asp Phe Leu Leu Ser Val Asn Gly
    50                  55                  60

Ala Ser Leu Ala Gly Leu Ala His Gly Asn Val Leu Lys Val Leu His
65                  70                  75                  80

Gln Ala Gln Leu His Lys Asp Ala Leu Val Val Ile Lys Lys Gly Met
                85                  90                  95

Asp Gln Pro Arg Pro Ser Asn Ser Ser
            100                 105

<210> SEQ ID NO 6
<211> LENGTH: 132
<212> TYPE: PRT
<213> ORGANISM: Artificial Sequence
<220> FEATURE:
<223> OTHER INFORMATION: Synthetic peptide
```

```
<400> SEQUENCE: 6

Gly Ile Ser Ser Leu Gly Arg Lys Thr Pro Gly Pro Lys Asp Arg Ile
1               5                   10                  15

Val Met Glu Val Thr Leu Asn Lys Glu Pro Arg Val Gly Leu Gly Ile
            20                  25                  30

Gly Ala Cys Cys Leu Ala Leu Glu Asn Ser Pro Pro Gly Ile Tyr Ile
        35                  40                  45

His Ser Leu Ala Pro Gly Ser Val Ala Lys Met Glu Ser Asn Leu Ser
    50                  55                  60

Arg Gly Asp Gln Ile Leu Glu Val Asn Ser Val Asn Val Arg His Ala
65                  70                  75                  80

Ala Leu Ser Lys Val His Ala Ile Leu Ser Lys Cys Pro Pro Gly Pro
                85                  90                  95

Val Arg Leu Val Ile Gly Arg His Pro Asn Pro Lys Val Ser Glu Gln
            100                 105                 110

Glu Met Asp Glu Val Ile Ala Arg Ser Thr Tyr Gln Glu Ser Lys Glu
            115                 120                 125

Ala Asn Ser Ser
        130

<210> SEQ ID NO 7
<211> LENGTH: 101
<212> TYPE: PRT
<213> ORGANISM: Artificial Sequence
<220> FEATURE:
<223> OTHER INFORMATION: Synthetic peptide

<400> SEQUENCE: 7

Leu Gly Arg Ser Val Ala Val His Asp Ala Leu Cys Val Glu Val Leu
1               5                   10                  15

Lys Thr Ser Ala Gly Leu Gly Leu Ser Leu Asp Gly Gly Lys Ser Ser
            20                  25                  30

Val Thr Gly Asp Gly Pro Leu Val Ile Lys Arg Val Tyr Lys Gly Gly
        35                  40                  45

Ala Ala Glu Gln Ala Gly Ile Ile Glu Ala Gly Asp Glu Ile Leu Ala
    50                  55                  60

Ile Asn Gly Lys Pro Leu Val Gly Leu Met His Phe Asp Ala Trp Asn
65                  70                  75                  80

Ile Met Lys Ser Val Pro Glu Gly Pro Val Gln Leu Leu Ile Arg Lys
                85                  90                  95

His Arg Asn Ser Ser
            100

<210> SEQ ID NO 8
<211> LENGTH: 98
<212> TYPE: PRT
<213> ORGANISM: Artificial Sequence
<220> FEATURE:
<223> OTHER INFORMATION: Synthetic peptide

<400> SEQUENCE: 8

Arg Glu Glu Gly Gly Met Pro Gln Thr Val Ile Leu Pro Gly Pro Ala
1               5                   10                  15

Pro Trp Gly Phe Arg Leu Ser Gly Gly Ile Asp Phe Asn Gln Pro Leu
            20                  25                  30

Val Ile Thr Arg Ile Thr Pro Gly Ser Lys Ala Ala Ala Ala Asn Leu
        35                  40                  45
```

```
Cys Pro Gly Asp Val Ile Leu Ala Ile Asp Gly Phe Gly Thr Glu Ser
 50                  55                  60

Met Thr His Ala Asp Ala Gln Asp Arg Ile Lys Ala Ala His Gln
 65                  70                  75                  80

Leu Cys Leu Lys Ile Asp Arg Gly Glu Thr His Leu Trp Ser Pro Asn
                 85                  90                  95

Ser Ser

<210> SEQ ID NO 9
<211> LENGTH: 85
<212> TYPE: PRT
<213> ORGANISM: Artificial Sequence
<220> FEATURE:
<223> OTHER INFORMATION: Synthetic peptide

<400> SEQUENCE: 9

Ile Leu Val Glu Val Gln Leu Ser Gly Gly Ala Pro Trp Gly Phe Thr
 1               5                  10                  15

Leu Lys Gly Gly Arg Glu His Gly Glu Pro Leu Val Ile Thr Lys Ile
                 20                  25                  30

Glu Glu Gly Ser Lys Ala Ala Val Asp Lys Leu Leu Ala Gly Asp
                 35                  40                  45

Glu Ile Val Gly Ile Asn Asp Ile Gly Leu Ser Gly Phe Arg Gln Glu
 50                  55                  60

Ala Ile Cys Leu Val Lys Gly Ser His Lys Thr Leu Lys Leu Val Val
 65                  70                  75                  80

Lys Arg Asn Ser Ser
                 85

<210> SEQ ID NO 10
<211> LENGTH: 106
<212> TYPE: PRT
<213> ORGANISM: Artificial Sequence
<220> FEATURE:
<223> OTHER INFORMATION: Synthetic peptide

<400> SEQUENCE: 10

Ser Val Gly His Val Arg Gly Pro Gly Pro Ser Val Gln His Thr Thr
 1               5                  10                  15

Leu Asn Gly Asp Ser Leu Thr Ser Gln Leu Thr Leu Leu Gly Gly Asn
                 20                  25                  30

Ala Arg Gly Ser Phe Val His Ser Val Lys Pro Gly Ser Leu Ala Glu
                 35                  40                  45

Lys Ala Gly Leu Arg Glu Gly His Gln Leu Leu Leu Leu Glu Gly Cys
 50                  55                  60

Ile Arg Gly Glu Arg Gln Ser Val Pro Leu Asp Thr Cys Thr Lys Glu
 65                  70                  75                  80

Glu Ala His Trp Thr Ile Gln Arg Cys Ser Gly Pro Val Thr Leu His
                 85                  90                  95

Tyr Lys Val Asn His Glu Gly Tyr Arg Lys
                100                 105

<210> SEQ ID NO 11
<211> LENGTH: 105
<212> TYPE: PRT
<213> ORGANISM: Artificial Sequence
<220> FEATURE:
<223> OTHER INFORMATION: Synthetic peptide

<400> SEQUENCE: 11
```

Arg Arg Pro Ala Arg Arg Ile Leu Ser Gln Val Thr Met Leu Ala Phe
1               5                   10                  15

Gln Gly Asp Ala Leu Leu Glu Gln Ile Ser Val Ile Gly Gly Asn Leu
            20                  25                  30

Thr Gly Ile Phe Ile His Arg Val Thr Pro Gly Ser Ala Ala Asp Gln
        35                  40                  45

Met Ala Leu Arg Pro Gly Thr Gln Ile Val Met Val Asp Tyr Glu Ala
50                  55                  60

Ser Glu Pro Leu Phe Lys Ala Val Leu Glu Asp Thr Thr Leu Glu Glu
65                  70                  75                  80

Ala Val Gly Leu Leu Arg Arg Val Asp Gly Phe Cys Cys Leu Ser Val
                85                  90                  95

Lys Val Asn Thr Asp Gly Tyr Lys Arg
                100                 105

<210> SEQ ID NO 12
<211> LENGTH: 100
<212> TYPE: PRT
<213> ORGANISM: Artificial Sequence
<220> FEATURE:
<223> OTHER INFORMATION: Synthetic peptide

<400> SEQUENCE: 12

Ile Leu Ser Gln Val Thr Met Leu Ala Phe Gln Gly Asp Ala Leu Leu
1               5                   10                  15

Glu Gln Ile Ser Val Ile Gly Gly Asn Leu Thr Gly Ile Phe Ile His
            20                  25                  30

Arg Val Thr Pro Gly Ser Ala Ala Asp Gln Met Ala Leu Arg Pro Gly
        35                  40                  45

Thr Gln Ile Val Met Val Asp Tyr Glu Ala Ser Glu Pro Leu Phe Lys
50                  55                  60

Ala Val Leu Glu Asp Thr Thr Leu Glu Glu Ala Val Gly Leu Leu Arg
65                  70                  75                  80

Arg Val Asp Gly Phe Cys Cys Leu Ser Val Lys Val Asn Thr Asp Gly
                85                  90                  95

Tyr Lys Arg Leu
            100

<210> SEQ ID NO 13
<211> LENGTH: 90
<212> TYPE: PRT
<213> ORGANISM: Artificial Sequence
<220> FEATURE:
<223> OTHER INFORMATION: Synthetic peptide

<400> SEQUENCE: 13

Thr Arg Val Arg Leu Val Gln Phe Gln Lys Asn Thr Asp Glu Pro Met
1               5                   10                  15

Gly Ile Thr Leu Lys Met Asn Glu Leu Asn His Cys Ile Val Ala Arg
            20                  25                  30

Ile Met His Gly Gly Met Ile His Arg Gln Gly Thr Leu His Val Gly
        35                  40                  45

Asp Glu Ile Arg Glu Ile Asn Gly Ile Ser Val Ala Asn Gln Thr Val
50                  55                  60

Glu Gln Leu Gln Lys Met Leu Arg Glu Met Arg Gly Ser Ile Thr Phe
65                  70                  75                  80

Lys Ile Val Pro Ser Tyr Arg Thr Gln Ser

```
<210> SEQ ID NO 14
<211> LENGTH: 88
<212> TYPE: PRT
<213> ORGANISM: Artificial Sequence
<220> FEATURE:
<223> OTHER INFORMATION: Synthetic peptide

<400> SEQUENCE: 14

Leu Glu Gln Lys Ala Val Leu Glu Gln Val Gln Leu Asp Ser Pro Leu
1               5                   10                  15

Gly Leu Glu Ile His Thr Thr Ser Asn Cys Gln His Phe Val Ser Gln
            20                  25                  30

Val Asp Thr Gln Val Pro Thr Asp Ser Arg Leu Gln Ile Gln Pro Gly
        35                  40                  45

Asp Glu Val Val Gln Ile Asn Glu Gln Val Val Gly Trp Pro Arg
    50                  55                  60

Lys Asn Met Val Arg Glu Leu Leu Arg Glu Pro Ala Gly Leu Ser Leu
65                  70                  75                  80

Val Leu Lys Lys Ile Pro Ile Pro
                85

<210> SEQ ID NO 15
<211> LENGTH: 92
<212> TYPE: PRT
<213> ORGANISM: Artificial Sequence
<220> FEATURE:
<223> OTHER INFORMATION: Synthetic peptide

<400> SEQUENCE: 15

Gln Arg Lys Leu Val Thr Val Glu Lys Gln Asp Asn Glu Thr Phe Gly
1               5                   10                  15

Phe Glu Ile Gln Ser Tyr Arg Pro Gln Asn Gln Asn Ala Cys Ser Ser
            20                  25                  30

Glu Met Phe Thr Leu Ile Cys Lys Ile Gln Glu Asp Ser Pro Ala His
        35                  40                  45

Cys Ala Gly Leu Gln Ala Gly Asp Val Leu Ala Asn Ile Asn Gly Val
    50                  55                  60

Ser Thr Glu Gly Phe Thr Tyr Lys Gln Val Val Asp Leu Ile Arg Ser
65                  70                  75                  80

Ser Gly Asn Leu Leu Thr Ile Glu Thr Leu Asn Gly
                85                  90

<210> SEQ ID NO 16
<211> LENGTH: 109
<212> TYPE: PRT
<213> ORGANISM: Artificial Sequence
<220> FEATURE:
<223> OTHER INFORMATION: Synthetic peptide

<400> SEQUENCE: 16

Arg Cys Leu Ile Gln Thr Lys Gly Gln Arg Ser Met Asp Gly Tyr Pro
1               5                   10                  15

Glu Gln Phe Cys Val Arg Ile Glu Lys Asn Pro Gly Leu Gly Phe Ser
            20                  25                  30

Ile Ser Gly Gly Ile Ser Gly Gln Gly Asn Pro Phe Lys Pro Ser Asp
        35                  40                  45

Lys Gly Ile Phe Val Thr Arg Val Gln Pro Asp Gly Pro Ala Ser Asn
    50                  55                  60
```

```
Leu Leu Gln Pro Gly Asp Lys Ile Leu Gln Ala Asn Gly His Ser Phe
 65                  70                  75                  80

Val His Met Glu His Glu Lys Ala Val Leu Leu Lys Ser Phe Gln
                 85                  90                  95

Asn Thr Val Asp Leu Val Ile Gln Arg Glu Leu Thr Val
            100                 105

<210> SEQ ID NO 17
<211> LENGTH: 97
<212> TYPE: PRT
<213> ORGANISM: Artificial Sequence
<220> FEATURE:
<223> OTHER INFORMATION: Synthetic peptide

<400> SEQUENCE: 17

Pro Thr Ser Pro Glu Ile Gln Glu Leu Arg Gln Met Leu Gln Ala Pro
  1               5                  10                  15

His Phe Lys Gly Ala Thr Ile Lys Arg His Glu Met Thr Gly Asp Ile
                 20                  25                  30

Leu Val Ala Arg Ile Ile His Gly Gly Leu Ala Glu Arg Ser Gly Leu
             35                  40                  45

Leu Tyr Ala Gly Asp Lys Leu Val Glu Val Asn Gly Val Ser Val Glu
         50                  55                  60

Gly Leu Asp Pro Glu Gln Val Ile His Ile Leu Ala Met Ser Arg Gly
 65                  70                  75                  80

Thr Ile Met Phe Lys Val Val Pro Val Ser Asp Pro Pro Val Asn Ser
                 85                  90                  95

Ser

<210> SEQ ID NO 18
<211> LENGTH: 141
<212> TYPE: PRT
<213> ORGANISM: Artificial Sequence
<220> FEATURE:
<223> OTHER INFORMATION: Synthetic peptide

<400> SEQUENCE: 18

Pro Thr Ser Pro Glu Ile Gln Glu Leu Arg Gln Met Leu Gln Ala Pro
  1               5                  10                  15

His Phe Lys Ala Leu Leu Ser Ala His Asp Thr Ile Ala Gln Lys Asp
                 20                  25                  30

Phe Glu Pro Leu Leu Pro Pro Leu Pro Asp Asn Ile Pro Glu Ser Glu
             35                  40                  45

Glu Ala Met Arg Ile Val Cys Leu Val Lys Asn Gln Gln Pro Leu Gly
         50                  55                  60

Ala Thr Ile Lys Arg His Glu Met Thr Gly Asp Ile Leu Val Ala Arg
 65                  70                  75                  80

Ile Ile His Gly Gly Leu Ala Glu Arg Ser Gly Leu Leu Tyr Ala Gly
                 85                  90                  95

Asp Lys Leu Val Glu Val Asn Gly Val Ser Val Glu Gly Leu Asp Pro
            100                 105                 110

Glu Gln Val Ile His Ile Leu Ala Met Ser Arg Gly Thr Ile Met Phe
        115                 120                 125

Lys Val Val Pro Val Ser Asp Pro Pro Val Asn Ser Ser
            130                 135                 140

<210> SEQ ID NO 19
```

```
<211> LENGTH: 101
<212> TYPE: PRT
<213> ORGANISM: Artificial Sequence
<220> FEATURE:
<223> OTHER INFORMATION: Synthetic peptide

<400> SEQUENCE: 19

Ile Gln Val Asn Gly Thr Asp Ala Asp Tyr Glu Tyr Glu Glu Ile Thr
1               5                   10                  15

Leu Glu Arg Gly Asn Ser Gly Leu Gly Phe Ser Ile Ala Gly Gly Thr
                20                  25                  30

Asp Asn Pro His Ile Gly Asp Asp Ser Ser Ile Phe Ile Thr Lys Ile
            35                  40                  45

Ile Thr Gly Gly Ala Ala Ala Gln Asp Gly Arg Leu Arg Val Asn Asp
        50                  55                  60

Cys Ile Leu Gln Val Asn Glu Val Asp Val Arg Asp Val Thr His Ser
65                  70                  75                  80

Lys Ala Val Glu Ala Leu Lys Glu Ala Gly Ser Ile Val Arg Leu Tyr
                85                  90                  95

Val Lys Arg Arg Asn
            100

<210> SEQ ID NO 20
<211> LENGTH: 95
<212> TYPE: PRT
<213> ORGANISM: Artificial Sequence
<220> FEATURE:
<223> OTHER INFORMATION: Synthetic peptide

<400> SEQUENCE: 20

Ile Gln Leu Ile Lys Gly Pro Lys Gly Leu Gly Phe Ser Ile Ala Gly
1               5                   10                  15

Gly Val Gly Asn Gln His Ile Pro Gly Asp Asn Ser Ile Tyr Val Thr
                20                  25                  30

Lys Ile Ile Glu Gly Gly Ala Ala His Lys Asp Gly Lys Leu Gln Ile
            35                  40                  45

Gly Asp Lys Leu Leu Ala Val Asn Asn Val Cys Leu Glu Glu Val Thr
        50                  55                  60

His Glu Glu Ala Val Thr Ala Leu Lys Asn Thr Ser Asp Phe Val Tyr
65                  70                  75                  80

Leu Lys Val Ala Lys Pro Thr Ser Met Tyr Met Asn Asp Gly Asn
                85                  90                  95

<210> SEQ ID NO 21
<211> LENGTH: 203
<212> TYPE: PRT
<213> ORGANISM: Artificial Sequence
<220> FEATURE:
<223> OTHER INFORMATION: Synthetic peptide

<400> SEQUENCE: 21

Val Asn Gly Thr Asp Ala Asp Tyr Glu Tyr Glu Glu Ile Thr Leu Glu
1               5                   10                  15

Arg Gly Asn Ser Gly Leu Gly Phe Ser Ile Ala Gly Gly Thr Asp Asn
                20                  25                  30

Pro His Ile Gly Asp Asp Ser Ser Ile Phe Ile Thr Lys Ile Ile Thr
            35                  40                  45

Gly Gly Ala Ala Ala Gln Asp Gly Arg Leu Arg Val Asn Asp Cys Ile
        50                  55                  60
```

```
Leu Gln Val Asn Glu Val Asp Val Arg Asp Val Thr His Ser Lys Ala
 65                  70                  75                  80

Val Glu Ala Leu Lys Glu Ala Gly Ser Ile Val Arg Leu Tyr Val Lys
                 85                  90                  95

Arg Arg Lys Pro Val Ser Glu Lys Ile Met Glu Ile Lys Leu Ile Lys
            100                 105                 110

Gly Pro Lys Gly Leu Gly Phe Ser Ile Ala Gly Gly Val Gly Asn Gln
            115                 120                 125

His Ile Pro Gly Asp Asn Ser Ile Tyr Val Thr Lys Ile Ile Glu Gly
            130                 135                 140

Gly Ala Ala His Lys Asp Gly Lys Leu Gln Ile Gly Asp Lys Leu Leu
145                 150                 155                 160

Ala Val Asn Asn Val Cys Leu Glu Glu Val Thr His Glu Glu Ala Val
                165                 170                 175

Thr Ala Leu Lys Asn Thr Ser Asp Phe Val Tyr Leu Lys Val Ala Lys
            180                 185                 190

Pro Thr Ser Met Tyr Met Asn Asp Gly Tyr Ala
            195                 200

<210> SEQ ID NO 22
<211> LENGTH: 85
<212> TYPE: PRT
<213> ORGANISM: Artificial Sequence
<220> FEATURE:
<223> OTHER INFORMATION: Synthetic peptide

<400> SEQUENCE: 22

Ile Leu His Arg Gly Ser Thr Gly Leu Gly Phe Asn Ile Val Gly Gly
 1               5                  10                  15

Glu Asp Gly Glu Gly Ile Phe Ile Ser Phe Ile Leu Ala Gly Gly Pro
             20                  25                  30

Ala Asp Leu Ser Gly Glu Leu Arg Lys Gly Asp Arg Ile Ile Ser Val
             35                  40                  45

Asn Ser Val Asp Leu Arg Ala Ala Ser His Glu Gln Ala Ala Ala Ala
 50                  55                  60

Leu Lys Asn Ala Gly Gln Ala Val Thr Ile Val Ala Gln Tyr Arg Pro
 65                  70                  75                  80

Glu Glu Tyr Ser Arg
             85

<210> SEQ ID NO 23
<211> LENGTH: 110
<212> TYPE: PRT
<213> ORGANISM: Artificial Sequence
<220> FEATURE:
<223> OTHER INFORMATION: Synthetic peptide

<400> SEQUENCE: 23

Ile Glu Gly Arg Gly Ile Leu Glu Gly Glu Pro Arg Lys Val Val Leu
 1               5                  10                  15

His Lys Gly Ser Thr Gly Leu Gly Phe Asn Ile Val Gly Gly Glu Asp
             20                  25                  30

Gly Glu Gly Ile Phe Val Ser Phe Ile Leu Ala Gly Gly Pro Ala Asp
             35                  40                  45

Leu Ser Gly Glu Leu Gln Arg Gly Asp Gln Ile Leu Ser Val Asn Gly
 50                  55                  60

Ile Asp Leu Arg Gly Ala Ser His Glu Gln Ala Ala Ala Ala Leu Lys
 65                  70                  75                  80
```

```
Gly Ala Gly Gln Thr Val Thr Ile Ile Ala Gln His Gln Pro Glu Asp
            85                  90                  95

Tyr Ala Arg Phe Glu Ala Lys Ile His Asp Leu Asn Ser Ser
            100                 105                 110

<210> SEQ ID NO 24
<211> LENGTH: 101
<212> TYPE: PRT
<213> ORGANISM: Artificial Sequence
<220> FEATURE:
<223> OTHER INFORMATION: Synthetic peptide

<400> SEQUENCE: 24

Ile Ser Tyr Val Asn Gly Thr Glu Ile Glu Tyr Glu Phe Glu Ile
1               5                   10                  15

Thr Leu Glu Arg Gly Asn Ser Gly Leu Gly Phe Ser Ile Ala Gly Gly
            20                  25                  30

Thr Asp Asn Pro His Ile Gly Asp Asp Pro Gly Ile Phe Ile Thr Lys
            35                  40                  45

Ile Ile Pro Gly Gly Ala Ala Ala Glu Asp Gly Arg Leu Arg Val Asn
50                  55                  60

Asp Cys Ile Leu Arg Val Asn Glu Val Asp Val Ser Glu Val Ser His
65                  70                  75                  80

Ser Lys Ala Val Glu Ala Leu Lys Glu Ala Gly Ser Ile Val Arg Leu
            85                  90                  95

Tyr Val Arg Arg Arg
            100

<210> SEQ ID NO 25
<211> LENGTH: 113
<212> TYPE: PRT
<213> ORGANISM: Artificial Sequence
<220> FEATURE:
<223> OTHER INFORMATION: Synthetic peptide

<400> SEQUENCE: 25

Ile Pro Ile Leu Glu Thr Val Val Glu Ile Lys Leu Phe Lys Gly Pro
1               5                   10                  15

Lys Gly Leu Gly Phe Ser Ile Ala Gly Gly Val Gly Asn Gln His Ile
            20                  25                  30

Pro Gly Asp Asn Ser Ile Tyr Val Thr Lys Ile Ile Asp Gly Gly Ala
            35                  40                  45

Ala Gln Lys Asp Gly Arg Leu Gln Val Gly Asp Arg Leu Leu Met Val
            50                  55                  60

Asn Asn Tyr Ser Leu Glu Glu Val Thr His Glu Glu Ala Val Ala Ile
65                  70                  75                  80

Leu Lys Asn Thr Ser Glu Val Val Tyr Leu Lys Val Gly Lys Pro Thr
            85                  90                  95

Thr Ile Tyr Met Thr Asp Pro Tyr Gly Pro Pro Asn Ser Ser Leu Thr
            100                 105                 110

Asp

<210> SEQ ID NO 26
<211> LENGTH: 101
<212> TYPE: PRT
<213> ORGANISM: Artificial Sequence
<220> FEATURE:
<223> OTHER INFORMATION: Synthetic peptide
```

```
-continued

<400> SEQUENCE: 26

Gly Ile Pro Tyr Val Glu Glu Pro Arg His Val Lys Val Gln Lys Gly
1               5                   10                  15

Ser Glu Pro Leu Gly Ile Ser Ile Val Ser Gly Glu Lys Gly Gly Ile
            20                  25                  30

Tyr Val Ser Lys Val Thr Val Gly Ser Ile Ala His Gln Ala Gly Leu
        35                  40                  45

Glu Tyr Gly Asp Gln Leu Leu Glu Phe Asn Gly Ile Asn Leu Arg Ser
    50                  55                  60

Ala Thr Glu Gln Gln Ala Arg Leu Ile Ile Gly Gln Gln Cys Asp Thr
65                  70                  75                  80

Ile Thr Ile Leu Ala Gln Tyr Asn Pro His Val His Gln Leu Arg Asn
                85                  90                  95

Ser Ser Leu Thr Asp
            100

<210> SEQ ID NO 27
<211> LENGTH: 103
<212> TYPE: PRT
<213> ORGANISM: Artificial Sequence
<220> FEATURE:
<223> OTHER INFORMATION: Synthetic peptide

<400> SEQUENCE: 27

Gly Ile Leu Ala Gly Asp Ala Asn Lys Lys Thr Leu Glu Pro Arg Val
1               5                   10                  15

Val Phe Ile Lys Lys Ser Gln Leu Glu Leu Gly Val His Leu Cys Gly
            20                  25                  30

Gly Asn Leu His Gly Val Phe Val Ala Glu Val Glu Asp Asp Ser Pro
        35                  40                  45

Ala Lys Gly Pro Asp Gly Leu Val Pro Gly Asp Leu Ile Leu Glu Tyr
    50                  55                  60

Gly Ser Leu Asp Val Arg Asn Lys Thr Val Glu Val Tyr Val Glu
65                  70                  75                  80

Met Leu Lys Pro Arg Asp Gly Val Arg Leu Lys Val Gln Tyr Arg Pro
                85                  90                  95

Glu Glu Phe Ile Val Thr Asp
            100

<210> SEQ ID NO 28
<211> LENGTH: 93
<212> TYPE: PRT
<213> ORGANISM: Artificial Sequence
<220> FEATURE:
<223> OTHER INFORMATION: Synthetic peptide

<400> SEQUENCE: 28

Leu Asn Ile Val Thr Val Thr Leu Asn Met Glu Arg His His Phe Leu
1               5                   10                  15

Gly Ile Ser Ile Val Gly Gln Ser Asn Asp Arg Gly Asp Gly Gly Ile
            20                  25                  30

Tyr Ile Gly Ser Ile Met Lys Gly Gly Ala Val Ala Ala Asp Gly Arg
        35                  40                  45

Ile Glu Pro Gly Asp Met Leu Leu Gln Val Asn Asp Val Asn Phe Glu
    50                  55                  60

Asn Met Ser Asn Asp Asp Ala Val Arg Val Leu Arg Glu Ile Val Ser
65                  70                  75                  80
```

```
Gln Thr Gly Pro Ile Ser Leu Thr Val Ala Lys Cys Trp
                85                  90
```

<210> SEQ ID NO 29
<211> LENGTH: 100
<212> TYPE: PRT
<213> ORGANISM: Artificial Sequence
<220> FEATURE:
<223> OTHER INFORMATION: Synthetic peptide

<400> SEQUENCE: 29

```
Leu Asn Ile Ile Thr Val Thr Leu Asn Met Glu Lys Tyr Asn Phe Leu
1               5                   10                  15

Gly Ile Ser Ile Val Gly Gln Ser Asn Glu Arg Gly Asp Gly Gly Ile
            20                  25                  30

Tyr Ile Gly Ser Ile Met Lys Gly Gly Ala Val Ala Ala Asp Gly Arg
        35                  40                  45

Ile Glu Pro Gly Asp Met Leu Leu Gln Val Asn Asp Met Asn Phe Glu
    50                  55                  60

Asn Met Ser Asn Asp Asp Ala Val Arg Val Leu Arg Asp Ile Val His
65                  70                  75                  80

Lys Pro Gly Pro Ile Val Leu Thr Val Ala Lys Cys Trp Asp Pro Ser
                85                  90                  95

Pro Gln Asn Ser
            100
```

<210> SEQ ID NO 30
<211> LENGTH: 95
<212> TYPE: PRT
<213> ORGANISM: Artificial Sequence
<220> FEATURE:
<223> OTHER INFORMATION: Synthetic peptide

<400> SEQUENCE: 30

```
Ile Ile Thr Val Thr Leu Asn Met Glu Lys Tyr Asn Phe Leu Gly Ile
1               5                   10                  15

Ser Ile Val Gly Gln Ser Asn Glu Arg Gly Asp Gly Gly Ile Tyr Ile
            20                  25                  30

Gly Ser Ile Met Lys Gly Gly Ala Val Ala Ala Asp Gly Arg Ile Glu
        35                  40                  45

Pro Gly Asp Met Leu Leu Gln Val Asn Glu Ile Asn Phe Glu Asn Met
    50                  55                  60

Ser Asn Asp Asp Ala Val Arg Val Leu Arg Glu Ile Val His Lys Pro
65                  70                  75                  80

Gly Pro Ile Thr Leu Thr Val Ala Lys Cys Trp Asp Pro Ser Pro
                85                  90                  95
```

<210> SEQ ID NO 31
<211> LENGTH: 98
<212> TYPE: PRT
<213> ORGANISM: Artificial Sequence
<220> FEATURE:
<223> OTHER INFORMATION: Synthetic peptide

<400> SEQUENCE: 31

```
Gln Gln Arg Glu Leu Arg Pro Arg Leu Cys Thr Met Lys Lys Gly Pro
1               5                   10                  15

Ser Gly Tyr Gly Phe Asn Leu His Ser Asp Lys Ser Lys Pro Gly Gln
            20                  25                  30

Phe Ile Arg Ser Val Asp Pro Asp Ser Pro Ala Glu Ala Ser Gly Leu
```

```
                35                  40                  45
Arg Ala Gln Asp Arg Ile Val Glu Val Asn Gly Val Cys Met Glu Gly
             50                  55                  60
Lys Gln His Gly Asp Val Val Ser Ala Ile Arg Ala Gly Gly Asp Glu
 65                  70                  75                  80
Thr Lys Leu Leu Val Val Asp Arg Glu Thr Asp Glu Phe Phe Lys Asn
                 85                  90                  95
Ser Ser

<210> SEQ ID NO 32
<211> LENGTH: 155
<212> TYPE: PRT
<213> ORGANISM: Artificial Sequence
<220> FEATURE:
<223> OTHER INFORMATION: Synthetic peptide

<400> SEQUENCE: 32

Gly Ile Gln Met Ser Ala Asp Ala Ala Ala Gly Ala Pro Leu Pro Arg
 1               5                  10                  15
Leu Cys Cys Leu Glu Lys Gly Pro Asn Gly Tyr Gly Phe His Leu His
                20                  25                  30
Gly Glu Lys Gly Lys Leu Gly Gln Tyr Ile Arg Leu Val Glu Pro Gly
             35                  40                  45
Ser Pro Ala Glu Lys Ala Gly Leu Leu Ala Gly Asp Arg Leu Val Glu
         50                  55                  60
Val Asn Gly Glu Asn Val Glu Lys Glu Thr His Gln Gln Val Val Ser
 65                  70                  75                  80
Arg Ile Arg Ala Ala Leu Asn Ala Val Arg Leu Leu Val Val Asp Pro
                 85                  90                  95
Glu Thr Asp Glu Gln Leu Gln Lys Leu Gly Val Gln Val Arg Glu Glu
                100                 105                 110
Leu Leu Arg Ala Gln Glu Ala Pro Gly Gln Ala Glu Pro Pro Ala Ala
             115                 120                 125
Ala Glu Val Gln Gly Ala Gly Asn Glu Asn Glu Pro Arg Glu Ala Asp
         130                 135                 140
Lys Ser His Pro Glu Gln Arg Glu Leu Arg Asn
145                 150                 155

<210> SEQ ID NO 33
<211> LENGTH: 243
<212> TYPE: PRT
<213> ORGANISM: Artificial Sequence
<220> FEATURE:
<223> OTHER INFORMATION: Synthetic peptide

<400> SEQUENCE: 33

Gly Ile Gln Met Ser Ala Asp Ala Ala Ala Gly Ala Pro Leu Pro Arg
 1               5                  10                  15
Leu Cys Cys Leu Glu Lys Gly Pro Asn Gly Tyr Gly Phe His Leu His
                20                  25                  30
Gly Glu Lys Gly Lys Leu Gly Gln Tyr Ile Arg Leu Val Glu Pro Gly
             35                  40                  45
Ser Pro Ala Glu Lys Ala Gly Leu Leu Ala Gly Asp Arg Leu Val Glu
         50                  55                  60
Val Asn Gly Glu Asn Val Glu Lys Glu Thr His Gln Gln Val Val Ser
 65                  70                  75                  80
Arg Ile Arg Ala Ala Leu Asn Ala Val Arg Leu Leu Val Val Asp Pro
```

```
                    85                  90                  95
Glu Thr Asp Glu Gln Leu Gln Lys Leu Gly Val Gln Val Arg Glu Glu
                100                 105                 110
Leu Leu Arg Ala Gln Glu Ala Pro Gly Gln Ala Glu Pro Pro Ala Ala
            115                 120                 125
Ala Glu Val Gln Gly Ala Gly Asn Glu Asn Glu Pro Arg Glu Ala Asp
        130                 135                 140
Lys Ser His Pro Glu Gln Arg Glu Leu Arg Pro Arg Leu Cys Thr Met
145                 150                 155                 160
Lys Lys Gly Pro Ser Gly Tyr Gly Phe Asn Leu His Ser Asp Lys Ser
                165                 170                 175
Lys Pro Gly Gln Phe Ile Arg Ser Val Asp Pro Asp Ser Pro Ala Glu
            180                 185                 190
Ala Ser Gly Leu Arg Ala Gln Asp Arg Ile Val Glu Val Asn Gly Val
        195                 200                 205
Cys Met Glu Gly Lys Gln His Gly Asp Val Val Ser Ala Ile Arg Ala
    210                 215                 220
Gly Gly Asp Glu Thr Lys Leu Leu Val Val Asp Arg Glu Thr Asp Glu
225                 230                 235                 240
Phe Phe Lys

<210> SEQ ID NO 34
<211> LENGTH: 155
<212> TYPE: PRT
<213> ORGANISM: Artificial Sequence
<220> FEATURE:
<223> OTHER INFORMATION: Synthetic peptide

<400> SEQUENCE: 34

Gln Met Ser Ala Asp Ala Ala Ala Gly Ala Pro Leu Pro Arg Leu Cys
1               5                   10                  15
Cys Leu Glu Lys Gly Pro Asn Gly Tyr Gly Phe His Leu His Gly Glu
                20                  25                  30
Lys Gly Lys Leu Gly Gln Tyr Ile Arg Leu Val Glu Pro Gly Ser Pro
            35                  40                  45
Ala Glu Lys Ala Gly Leu Leu Ala Gly Asp Arg Leu Val Glu Val Asn
        50                  55                  60
Gly Glu Asn Val Glu Lys Glu Thr His Gln Gln Val Val Ser Arg Ile
65                  70                  75                  80
Arg Ala Ala Leu Asn Ala Val Arg Leu Leu Val Val Asp Pro Glu Thr
                85                  90                  95
Asp Glu Gln Leu Gln Lys Leu Gly Val Gln Val Arg Glu Glu Leu Leu
                100                 105                 110
Arg Ala Gln Glu Ala Pro Gly Gln Ala Glu Pro Pro Ala Ala Ala Glu
            115                 120                 125
Val Gln Gly Ala Gly Asn Glu Asn Glu Pro Arg Glu Ala Asp Lys Ser
        130                 135                 140
His Pro Glu Gln Arg Glu Leu Arg Asn Ser Ser
145                 150                 155

<210> SEQ ID NO 35
<211> LENGTH: 98
<212> TYPE: PRT
<213> ORGANISM: Artificial Sequence
<220> FEATURE:
<223> OTHER INFORMATION: Synthetic peptide
```

<400> SEQUENCE: 35

```
Leu Thr Thr Gln Gln Ile Asp Leu Gln Gly Pro Gly Pro Trp Gly Phe
1               5                   10                  15

Arg Leu Val Gly Gly Lys Asp Phe Glu Gln Pro Leu Ala Ile Ser Arg
            20                  25                  30

Val Thr Pro Gly Ser Lys Ala Ala Leu Ala Asn Leu Cys Ile Gly Asp
        35                  40                  45

Val Ile Thr Ala Ile Asp Gly Glu Asn Thr Ser Asn Met Thr His Leu
    50                  55                  60

Glu Ala Gln Asn Arg Ile Lys Gly Cys Thr Asp Asn Leu Thr Leu Thr
65                  70                  75                  80

Val Ala Arg Ser Glu His Lys Val Trp Ser Pro Leu Val Thr Asn Ser
                85                  90                  95

Ser Trp
```

<210> SEQ ID NO 36
<211> LENGTH: 89
<212> TYPE: PRT
<213> ORGANISM: Artificial Sequence
<220> FEATURE:
<223> OTHER INFORMATION: Synthetic peptide

<400> SEQUENCE: 36

```
Ile Phe Met Asp Ser Phe Lys Val Val Leu Glu Gly Pro Ala Pro Trp
1               5                   10                  15

Gly Phe Arg Leu Gln Gly Gly Lys Asp Phe Asn Val Pro Leu Ser Ile
            20                  25                  30

Ser Arg Leu Thr Pro Gly Gly Lys Ala Ala Gln Ala Gly Val Ala Val
        35                  40                  45

Gly Asp Trp Val Leu Ser Ile Asp Gly Glu Asn Ala Gly Ser Leu Thr
    50                  55                  60

His Ile Glu Ala Gln Asn Lys Ile Arg Ala Cys Gly Glu Arg Leu Ser
65                  70                  75                  80

Leu Gly Leu Ser Arg Ala Gln Pro Val
                85
```

<210> SEQ ID NO 37
<211> LENGTH: 100
<212> TYPE: PRT
<213> ORGANISM: Artificial Sequence
<220> FEATURE:
<223> OTHER INFORMATION: Synthetic peptide

<400> SEQUENCE: 37

```
Gln Gly His Glu Leu Ala Lys Gln Glu Ile Arg Val Arg Val Glu Lys
1               5                   10                  15

Asp Pro Glu Leu Gly Phe Ser Ile Ser Gly Gly Val Gly Gly Arg Gly
            20                  25                  30

Asn Pro Phe Arg Pro Asp Asp Asp Gly Ile Phe Val Thr Arg Val Gln
        35                  40                  45

Pro Glu Gly Pro Ala Ser Lys Leu Leu Gln Pro Gly Asp Lys Ile Ile
    50                  55                  60

Gln Ala Asn Gly Tyr Ser Phe Ile Asn Ile Glu His Gly Gln Ala Val
65                  70                  75                  80

Ser Leu Leu Lys Thr Phe Gln Asn Thr Val Glu Leu Ile Ile Val Arg
                85                  90                  95

Glu Val Ser Ser
```

```
<210> SEQ ID NO 38
<211> LENGTH: 107
<212> TYPE: PRT
<213> ORGANISM: Artificial Sequence
<220> FEATURE:
<223> OTHER INFORMATION: Synthetic peptide

<400> SEQUENCE: 38
```

Lys Asn Pro Ser Gly Glu Leu Lys Thr Val Thr Leu Ser Lys Met Lys
1               5                   10                  15

Gln Ser Leu Gly Ile Ser Ile Ser Gly Gly Ile Glu Ser Lys Val Gln
            20                  25                  30

Pro Met Val Lys Ile Glu Lys Ile Phe Pro Gly Gly Ala Ala Phe Leu
        35                  40                  45

Ser Gly Ala Leu Gln Ala Gly Phe Glu Leu Val Ala Val Asp Gly Glu
    50                  55                  60

Asn Leu Glu Gln Val Thr His Gln Arg Ala Val Asp Thr Ile Arg Arg
65                  70                  75                  80

Ala Tyr Arg Asn Lys Ala Arg Glu Pro Met Glu Leu Val Val Arg Val
                85                  90                  95

Pro Gly Pro Ser Pro Arg Pro Ser Pro Ser Asp
            100                 105

```
<210> SEQ ID NO 39
<211> LENGTH: 97
<212> TYPE: PRT
<213> ORGANISM: Artificial Sequence
<220> FEATURE:
<223> OTHER INFORMATION: Synthetic peptide

<400> SEQUENCE: 39
```

Glu Gly His Ser His Pro Arg Val Val Glu Leu Pro Lys Thr Glu Glu
1               5                   10                  15

Gly Leu Gly Phe Asn Ile Met Gly Gly Lys Glu Gln Asn Ser Pro Ile
            20                  25                  30

Tyr Ile Ser Arg Ile Ile Pro Gly Gly Ile Ala Asp Arg His Gly Gly
        35                  40                  45

Leu Lys Arg Gly Asp Gln Leu Leu Ser Val Asn Gly Val Ser Val Glu
    50                  55                  60

Gly Glu His His Glu Lys Ala Val Glu Leu Leu Lys Ala Ala Gln Gly
65                  70                  75                  80

Lys Val Lys Leu Val Val Arg Tyr Thr Pro Lys Val Leu Glu Glu Met
                85                  90                  95

Glu

```
<210> SEQ ID NO 40
<211> LENGTH: 88
<212> TYPE: PRT
<213> ORGANISM: Artificial Sequence
<220> FEATURE:
<223> OTHER INFORMATION: Synthetic peptide

<400> SEQUENCE: 40
```

Pro Gly Ala Pro Tyr Ala Arg Lys Thr Phe Thr Ile Val Gly Asp Ala
1               5                   10                  15

Val Gly Trp Gly Phe Val Val Arg Gly Ser Lys Pro Cys His Ile Gln
            20                  25                  30

```
Ala Val Asp Pro Ser Gly Pro Ala Ala Ala Gly Met Lys Val Cys
        35                  40                  45

Gln Phe Val Val Ser Val Asn Gly Leu Asn Val Leu His Val Asp Tyr
 50                  55                  60

Arg Thr Val Ser Asn Leu Ile Leu Thr Gly Pro Arg Thr Ile Val Met
 65                  70                  75                  80

Glu Val Met Glu Glu Leu Glu Cys
                 85

<210> SEQ ID NO 41
<211> LENGTH: 97
<212> TYPE: PRT
<213> ORGANISM: Artificial Sequence
<220> FEATURE:
<223> OTHER INFORMATION: Synthetic peptide

<400> SEQUENCE: 41

Gly Gln Tyr Gly Gly Glu Thr Val Lys Ile Val Arg Ile Glu Lys Ala
 1               5                  10                  15

Arg Asp Ile Pro Leu Gly Ala Thr Val Arg Asn Glu Met Asp Ser Val
                20                  25                  30

Ile Ile Ser Arg Ile Val Lys Gly Gly Ala Ala Glu Lys Ser Gly Leu
            35                  40                  45

Leu His Glu Gly Asp Glu Val Leu Glu Ile Asn Gly Ile Glu Ile Arg
     50                  55                  60

Gly Lys Asp Val Asn Glu Val Phe Asp Leu Leu Ser Asp Met His Gly
 65                  70                  75                  80

Thr Leu Thr Phe Val Leu Ile Pro Ser Gln Gln Ile Lys Pro Pro Pro
                 85                  90                  95

Ala

<210> SEQ ID NO 42
<211> LENGTH: 104
<212> TYPE: PRT
<213> ORGANISM: Artificial Sequence
<220> FEATURE:
<223> OTHER INFORMATION: Synthetic peptide

<400> SEQUENCE: 42

Lys Pro Ser Gln Ala Ser Gly His Phe Ser Val Glu Leu Val Arg Gly
 1               5                  10                  15

Tyr Ala Gly Phe Gly Leu Thr Leu Gly Gly Gly Arg Asp Val Ala Gly
                20                  25                  30

Asp Thr Pro Leu Ala Val Arg Gly Leu Leu Lys Asp Gly Pro Ala Gln
            35                  40                  45

Arg Cys Gly Arg Leu Glu Val Gly Asp Leu Val Leu His Ile Asn Gly
     50                  55                  60

Glu Ser Thr Gln Gly Leu Thr His Ala Gln Ala Val Glu Arg Ile Arg
 65                  70                  75                  80

Ala Gly Gly Pro Gln Leu His Leu Val Ile Arg Arg Pro Leu Glu Thr
                 85                  90                  95

His Pro Gly Lys Pro Arg Gly Val
                100

<210> SEQ ID NO 43
<211> LENGTH: 101
<212> TYPE: PRT
<213> ORGANISM: Artificial Sequence
<220> FEATURE:
```

-continued

<223> OTHER INFORMATION: Synthetic peptide

<400> SEQUENCE: 43

```
Pro Val Met Ser Gln Cys Ala Cys Leu Glu Glu Val His Leu Pro Asn
1               5                   10                  15

Ile Lys Pro Gly Glu Gly Leu Gly Met Tyr Ile Lys Ser Thr Tyr Asp
            20                  25                  30

Gly Leu His Val Ile Thr Gly Thr Thr Glu Asn Ser Pro Ala Asp Arg
        35                  40                  45

Ser Gln Lys Ile His Ala Gly Asp Glu Val Thr Gln Val Asn Gln Gln
    50                  55                  60

Thr Val Val Gly Trp Gln Leu Lys Asn Leu Val Lys Lys Leu Arg Glu
65                  70                  75                  80

Asn Pro Thr Gly Val Val Leu Leu Leu Lys Lys Arg Pro Thr Gly Ser
                85                  90                  95

Phe Asn Phe Thr Pro
            100
```

<210> SEQ ID NO 44
<211> LENGTH: 97
<212> TYPE: PRT
<213> ORGANISM: Artificial Sequence
<220> FEATURE:
<223> OTHER INFORMATION: Synthetic peptide

<400> SEQUENCE: 44

```
Ile Asp Asp Glu Glu Asp Ser Val Lys Ile Ile Arg Leu Val Lys Asn
1               5                   10                  15

Arg Glu Pro Leu Gly Ala Thr Ile Lys Lys Asp Glu Gln Thr Gly Ala
            20                  25                  30

Ile Ile Val Ala Arg Ile Met Arg Gly Gly Ala Ala Asp Arg Ser Gly
        35                  40                  45

Leu Ile His Val Gly Asp Glu Leu Arg Glu Val Asn Gly Ile Pro Val
    50                  55                  60

Glu Asp Lys Arg Pro Glu Glu Ile Ile Gln Ile Leu Ala Gln Ser Gln
65                  70                  75                  80

Gly Ala Ile Thr Phe Lys Ile Ile Pro Gly Ser Lys Glu Glu Thr Pro
                85                  90                  95

Ser
```

<210> SEQ ID NO 45
<211> LENGTH: 452
<212> TYPE: PRT
<213> ORGANISM: Artificial Sequence
<220> FEATURE:
<223> OTHER INFORMATION: Synthetic peptide

<400> SEQUENCE: 45

```
Met Gly Ser Ser Gln Ser Val Glu Ile Pro Gly Gly Thr Glu Gly
1               5                   10                  15

Tyr His Val Leu Arg Val Gln Glu Asn Ser Pro Gly His Arg Ala Gly
            20                  25                  30

Leu Glu Pro Phe Phe Asp Phe Ile Val Ser Ile Asn Gly Ser Arg Leu
        35                  40                  45

Asn Lys Asp Asn Asp Thr Leu Lys Asp Leu Leu Lys Ala Asn Val Glu
    50                  55                  60

Lys Pro Val Lys Met Leu Ile Tyr Ser Ser Lys Thr Leu Glu Leu Arg
65                  70                  75                  80
```

```
Glu Thr Ser Val Thr Pro Ser Asn Leu Trp Gly Gly Gln Gly Leu Leu
                85                  90                  95

Gly Val Ser Ile Arg Phe Cys Ser Phe Asp Gly Ala Asn Glu Asn Val
            100                 105                 110

Trp His Val Leu Glu Val Glu Ser Asn Ser Pro Ala Ala Leu Ala Gly
        115                 120                 125

Leu Arg Pro His Ser Asp Tyr Ile Ile Gly Ala Asp Thr Val Met Asn
    130                 135                 140

Glu Ser Glu Asp Leu Phe Ser Leu Ile Glu Thr His Glu Ala Lys Pro
145                 150                 155                 160

Leu Lys Leu Tyr Val Tyr Asn Thr Asp Thr Asp Asn Cys Arg Glu Val
                165                 170                 175

Ile Ile Thr Pro Asn Ser Ala Trp Gly Glu Gly Ser Leu Gly Cys
            180                 185                 190

Gly Ile Gly Tyr Gly Tyr Leu His Arg Ile Pro Thr Arg Pro Phe Glu
            195                 200                 205

Glu Gly Lys Lys Ile Ser Leu Pro Gly Gln Met Ala Gly Thr Pro Ile
        210                 215                 220

Thr Pro Leu Lys Asp Gly Phe Thr Glu Val Gln Leu Ser Ser Val Asn
225                 230                 235                 240

Pro Pro Ser Leu Ser Pro Gly Thr Thr Gly Ile Glu Gln Ser Leu
                245                 250                 255

Thr Gly Leu Ser Ile Ser Ser Thr Pro Pro Ala Val Ser Ser Val Leu
            260                 265                 270

Ser Thr Gly Val Pro Thr Val Pro Leu Leu Pro Pro Gln Val Asn Gln
        275                 280                 285

Ser Leu Thr Ser Val Pro Pro Met Asn Pro Ala Thr Thr Leu Pro Gly
290                 295                 300

Leu Met Pro Leu Pro Ala Gly Leu Pro Asn Leu Pro Asn Leu Asn Leu
305                 310                 315                 320

Asn Leu Pro Ala Pro His Ile Met Pro Gly Val Gly Leu Pro Glu Leu
                325                 330                 335

Val Asn Pro Gly Leu Pro Leu Pro Ser Met Pro Pro Arg Asn Leu
            340                 345                 350

Pro Gly Ile Ala Pro Leu Pro Leu Pro Ser Glu Phe Leu Pro Ser Phe
            355                 360                 365

Pro Leu Val Pro Glu Ser Ser Ser Ala Ala Ser Ser Gly Glu Leu Leu
        370                 375                 380

Ser Ser Leu Pro Pro Thr Ser Asn Ala Pro Ser Asp Pro Ala Thr Thr
385                 390                 395                 400

Thr Ala Lys Ala Asp Ala Ala Ser Ser Leu Thr Val Asp Val Thr Pro
                405                 410                 415

Pro Thr Ala Lys Ala Pro Thr Thr Val Glu Asp Arg Val Gly Asp Ser
            420                 425                 430

Thr Pro Val Ser Glu Lys Pro Val Ser Ala Ala Val Asp Ala Asn Ala
        435                 440                 445

Ser Glu Ser Pro
    450

<210> SEQ ID NO 46
<211> LENGTH: 97
<212> TYPE: PRT
<213> ORGANISM: Artificial Sequence
<220> FEATURE:
```

-continued

<223> OTHER INFORMATION: Synthetic peptide

<400> SEQUENCE: 46

Asn Glu Asn Val Trp His Val Leu Glu Val Glu Ser Asn Ser Pro Ala
1               5                   10                  15

Ala Leu Ala Gly Leu Arg Pro His Ser Asp Tyr Ile Ile Gly Ala Asp
            20                  25                  30

Thr Val Met Asn Glu Ser Glu Asp Leu Phe Ser Leu Ile Glu Thr His
        35                  40                  45

Glu Ala Lys Pro Leu Lys Leu Tyr Val Tyr Asn Thr Asp Thr Asp Asn
    50                  55                  60

Cys Arg Glu Val Ile Ile Thr Pro Asn Ser Ala Trp Gly Gly Glu Gly
65                  70                  75                  80

Ser Leu Gly Cys Gly Ile Gly Tyr Gly Tyr Leu His Arg Ile Pro Thr
                85                  90                  95

Arg

<210> SEQ ID NO 47
<211> LENGTH: 110
<212> TYPE: PRT
<213> ORGANISM: Artificial Sequence
<220> FEATURE:
<223> OTHER INFORMATION: Synthetic peptide

<400> SEQUENCE: 47

Met Gly Ser Ser Gln Ser Val Glu Ile Pro Gly Gly Thr Glu Gly
1               5                   10                  15

Tyr His Val Leu Arg Val Gln Glu Asn Ser Pro Gly His Arg Ala Gly
            20                  25                  30

Leu Glu Pro Phe Phe Asp Phe Ile Val Ser Ile Asn Gly Ser Arg Leu
        35                  40                  45

Asn Lys Asp Asn Asp Thr Leu Lys Asp Leu Leu Lys Ala Asn Val Glu
    50                  55                  60

Lys Pro Val Lys Met Leu Ile Tyr Ser Ser Lys Thr Leu Glu Leu Arg
65                  70                  75                  80

Glu Thr Ser Val Thr Pro Ser Asn Leu Trp Gly Gln Gly Leu Leu
                85                  90                  95

Gly Val Ser Ile Arg Phe Cys Ser Phe Asp Gly Ala Asn Glu
            100                 105                 110

<210> SEQ ID NO 48
<211> LENGTH: 99
<212> TYPE: PRT
<213> ORGANISM: Artificial Sequence
<220> FEATURE:
<223> OTHER INFORMATION: Synthetic peptide

<400> SEQUENCE: 48

Arg Ala Ser Glu Gln Val Trp His Val Leu Asp Val Glu Pro Ser Ser
1               5                   10                  15

Pro Ala Ala Leu Ala Gly Leu Arg Pro Tyr Thr Asp Tyr Val Val Gly
            20                  25                  30

Ser Asp Gln Ile Leu Gln Glu Ser Glu Asp Phe Phe Thr Leu Ile Glu
        35                  40                  45

Ser His Glu Gly Lys Pro Leu Lys Leu Met Val Tyr Asn Ser Lys Ser
    50                  55                  60

Asp Ser Cys Arg Glu Val Thr Val Thr Pro Asn Ala Ala Trp Gly Gly
65                  70                  75                  80

```
Glu Gly Ser Leu Gly Cys Gly Ile Gly Tyr Gly Tyr Leu His Arg Ile
                85                  90                  95

Pro Thr Gln
```

<210> SEQ ID NO 49
<211> LENGTH: 110
<212> TYPE: PRT
<213> ORGANISM: Artificial Sequence
<220> FEATURE:
<223> OTHER INFORMATION: Synthetic peptide

<400> SEQUENCE: 49

```
Met Gly Leu Gly Val Ser Ala Glu Gln Pro Ala Gly Gly Ala Glu Gly
1               5                   10                  15

Phe His Leu His Gly Val Gln Glu Asn Ser Pro Ala Gln Gln Ala Gly
                20                  25                  30

Leu Glu Pro Tyr Phe Asp Phe Ile Ile Thr Ile Gly His Ser Arg Leu
            35                  40                  45

Asn Lys Glu Asn Asp Thr Leu Lys Ala Leu Leu Lys Ala Asn Val Glu
    50                  55                  60

Lys Pro Val Lys Leu Glu Val Phe Asn Met Lys Thr Met Arg Val Arg
65                  70                  75                  80

Glu Val Glu Val Val Pro Ser Asn Met Trp Gly Gly Gln Gly Leu Leu
                85                  90                  95

Gly Ala Ser Val Arg Phe Cys Ser Phe Arg Arg Ala Ser Glu
            100                 105                 110
```

<210> SEQ ID NO 50
<211> LENGTH: 440
<212> TYPE: PRT
<213> ORGANISM: Artificial Sequence
<220> FEATURE:
<223> OTHER INFORMATION: Synthetic peptide

<400> SEQUENCE: 50

```
Met Gly Leu Gly Val Ser Ala Glu Gln Pro Ala Gly Gly Ala Glu Gly
1               5                   10                  15

Phe His Leu His Gly Val Gln Glu Asn Ser Pro Ala Gln Gln Ala Gly
                20                  25                  30

Leu Glu Pro Tyr Phe Asp Phe Ile Ile Thr Ile Gly His Ser Arg Leu
            35                  40                  45

Asn Lys Glu Asn Asp Thr Leu Lys Ala Leu Leu Lys Ala Asn Val Glu
    50                  55                  60

Lys Pro Val Lys Leu Glu Val Phe Asn Met Lys Thr Met Arg Val Arg
65                  70                  75                  80

Glu Val Glu Val Val Pro Ser Asn Met Trp Gly Gly Gln Gly Leu Leu
                85                  90                  95

Gly Ala Ser Val Arg Phe Cys Ser Phe Arg Arg Ala Ser Glu Gln Val
            100                 105                 110

Trp His Val Leu Asp Val Glu Pro Ser Ser Pro Ala Ala Leu Ala Gly
            115                 120                 125

Leu Arg Pro Tyr Thr Asp Tyr Val Val Gly Ser Asp Gln Ile Leu Gln
        130                 135                 140

Glu Ser Glu Asp Phe Phe Thr Leu Ile Glu Ser His Glu Gly Lys Pro
145                 150                 155                 160

Leu Lys Leu Met Val Tyr Asn Ser Lys Ser Asp Ser Cys Arg Glu Val
                165                 170                 175
```

```
Thr Val Thr Pro Asn Ala Ala Trp Gly Gly Glu Gly Ser Leu Gly Cys
            180                 185                 190

Gly Ile Gly Tyr Gly Tyr Leu His Arg Ile Pro Thr Gln Pro Pro Ser
        195                 200                 205

Tyr His Lys Lys Pro Pro Gly Thr Pro Pro Ser Ala Leu Pro Leu
        210                 215                 220

Gly Ala Pro Pro Asp Ala Leu Pro Gly Pro Thr Pro Glu Asp
225                 230                 235                 240

Ser Pro Ser Leu Glu Thr Gly Ser Arg Gln Ser Asp Tyr Met Glu Ala
            245                 250                 255

Leu Leu Gln Ala Pro Gly Ser Ser Met Glu Asp Pro Leu Pro Gly Pro
            260                 265                 270

Gly Ser Pro Ser His Ser Ala Pro Asp Pro Asp Gly Leu Pro His Phe
            275                 280                 285

Met Glu Thr Pro Leu Gln Pro Pro Pro Val Gln Arg Val Met Asp
        290                 295                 300

Pro Gly Phe Leu Asp Val Ser Gly Ile Ser Leu Leu Asp Asn Ser Asn
305                 310                 315                 320

Ala Ser Val Trp Pro Ser Leu Pro Ser Ser Thr Glu Leu Thr Thr Thr
                325                 330                 335

Ala Val Ser Thr Ser Gly Pro Glu Asp Ile Cys Ser Ser Ser Ser Ser
            340                 345                 350

His Glu Arg Gly Gly Glu Ala Thr Trp Ser Gly Ser Glu Phe Glu Val
            355                 360                 365

Ser Phe Leu Asp Ser Pro Gly Ala Gln Ala Gln Ala Asp His Leu Pro
    370                 375                 380

Gln Leu Thr Leu Pro Asp Ser Leu Thr Ser Ala Ala Ser Pro Glu Asp
385                 390                 395                 400

Gly Leu Ser Ala Glu Leu Leu Glu Ala Gln Ala Glu Glu Pro Ala
                405                 410                 415

Ser Thr Glu Gly Leu Asp Thr Gly Thr Glu Ala Glu Gly Leu Asp Ser
            420                 425                 430

Gln Ala Gln Ile Ser Thr Thr Glu
        435                 440

<210> SEQ ID NO 51
<211> LENGTH: 90
<212> TYPE: PRT
<213> ORGANISM: Artificial Sequence
<220> FEATURE:
<223> OTHER INFORMATION: Synthetic peptide

<400> SEQUENCE: 51

Ile Tyr Thr Val Glu Leu Lys Arg Tyr Gly Gly Pro Leu Gly Ile Thr
1               5                   10                  15

Ile Ser Gly Thr Glu Glu Pro Phe Asp Pro Ile Ile Ile Ser Ser Leu
            20                  25                  30

Thr Lys Gly Gly Leu Ala Glu Arg Thr Gly Ala Ile His Ile Gly Asp
        35                  40                  45

Arg Ile Leu Ala Ile Asn Ser Ser Ser Leu Lys Gly Lys Pro Leu Ser
    50                  55                  60

Glu Ala Ile His Leu Leu Gln Met Ala Gly Glu Thr Val Thr Leu Lys
65                  70                  75                  80

Ile Lys Lys Gln Thr Asp Ala Gln Ser Ala
            85                  90
```

<210> SEQ ID NO 52
<211> LENGTH: 83
<212> TYPE: PRT
<213> ORGANISM: Artificial Sequence
<220> FEATURE:
<223> OTHER INFORMATION: Synthetic peptide

<400> SEQUENCE: 52

Val Val Glu Leu Met Lys Lys Glu Gly Thr Thr Leu Gly Leu Thr Val
1               5                   10                  15

Ser Gly Gly Ile Asp Lys Asp Gly Lys Pro Arg Val Ser Asn Leu Arg
            20                  25                  30

Gln Gly Gly Ile Ala Ala Arg Ser Asp Gln Leu Asp Val Gly Asp Tyr
        35                  40                  45

Ile Lys Ala Val Asn Gly Ile Asn Leu Ala Lys Phe Arg His Asp Glu
50                  55                  60

Ile Ile Ser Leu Leu Lys Asn Val Gly Glu Arg Val Val Leu Glu Val
65                  70                  75                  80

Glu Tyr Glu

<210> SEQ ID NO 53
<211> LENGTH: 106
<212> TYPE: PRT
<213> ORGANISM: Artificial Sequence
<220> FEATURE:
<223> OTHER INFORMATION: Synthetic peptide

<400> SEQUENCE: 53

His Val Ala Thr Ala Ser Gly Pro Leu Leu Val Glu Val Ala Lys Thr
1               5                   10                  15

Pro Gly Ala Ser Leu Gly Val Ala Leu Thr Thr Ser Met Cys Cys Asn
            20                  25                  30

Lys Gln Val Ile Val Ile Asp Lys Ile Lys Ser Ala Ser Ile Ala Asp
        35                  40                  45

Arg Cys Gly Ala Leu His Val Gly Asp His Ile Leu Ser Ile Asp Gly
50                  55                  60

Thr Ser Met Glu Tyr Cys Thr Leu Ala Glu Ala Thr Gln Phe Leu Ala
65                  70                  75                  80

Asn Thr Thr Asp Gln Val Lys Leu Glu Ile Leu Pro His His Gln Thr
                85                  90                  95

Arg Leu Ala Leu Lys Gly Pro Asn Ser Ser
            100                 105

<210> SEQ ID NO 54
<211> LENGTH: 95
<212> TYPE: PRT
<213> ORGANISM: Artificial Sequence
<220> FEATURE:
<223> OTHER INFORMATION: Synthetic peptide

<400> SEQUENCE: 54

Ile Met Ser Pro Thr Pro Val Glu Leu His Lys Val Thr Leu Tyr Lys
1               5                   10                  15

Asp Ser Asp Met Glu Asp Phe Gly Phe Ser Val Ala Asp Gly Leu Leu
            20                  25                  30

Glu Lys Gly Val Tyr Val Lys Asn Ile Arg Pro Ala Gly Pro Gly Asp
        35                  40                  45

Leu Gly Gly Leu Lys Pro Tyr Asp Arg Leu Leu Gln Val Asn His Val

```
                50                  55                  60
Arg Thr Arg Asp Phe Asp Cys Cys Leu Val Val Pro Leu Ile Ala Glu
 65                  70                  75                  80

Ser Gly Asn Lys Leu Asp Leu Val Ile Ser Arg Asn Pro Leu Ala
                 85                  90                  95

<210> SEQ ID NO 55
<211> LENGTH: 90
<212> TYPE: PRT
<213> ORGANISM: Artificial Sequence
<220> FEATURE:
<223> OTHER INFORMATION: Synthetic peptide

<400> SEQUENCE: 55

Ile Tyr Thr Val Glu Leu Lys Arg Tyr Gly Gly Pro Leu Gly Ile Thr
 1               5                  10                  15

Ile Ser Gly Thr Glu Glu Pro Phe Asp Pro Ile Ile Ile Ser Ser Leu
                20                  25                  30

Thr Lys Gly Gly Leu Ala Glu Arg Thr Gly Ala Ile His Ile Gly Asp
             35                  40                  45

Arg Ile Leu Ala Ile Asn Ser Ser Ser Leu Lys Gly Lys Pro Leu Ser
         50                  55                  60

Glu Ala Ile His Leu Leu Gln Met Ala Gly Glu Thr Val Thr Leu Lys
 65                  70                  75                  80

Ile Lys Lys Gln Thr Asp Ala Gln Ser Ala
                 85                  90

<210> SEQ ID NO 56
<211> LENGTH: 95
<212> TYPE: PRT
<213> ORGANISM: Artificial Sequence
<220> FEATURE:
<223> OTHER INFORMATION: Synthetic peptide

<400> SEQUENCE: 56

Ile Met Ser Pro Thr Pro Val Glu Leu His Lys Val Thr Leu Tyr Lys
 1               5                  10                  15

Asp Ser Asp Met Glu Asp Phe Gly Phe Ser Val Ala Asp Gly Leu Leu
                20                  25                  30

Glu Lys Gly Val Tyr Val Lys Asn Ile Arg Pro Ala Gly Pro Gly Asp
             35                  40                  45

Leu Gly Gly Leu Lys Pro Tyr Asp Arg Leu Leu Gln Val Asn His Val
         50                  55                  60

Arg Thr Arg Asp Phe Asp Cys Cys Leu Val Val Pro Leu Ile Ala Glu
 65                  70                  75                  80

Ser Gly Asn Lys Leu Asp Leu Val Ile Ser Arg Asn Pro Leu Ala
                 85                  90                  95

<210> SEQ ID NO 57
<211> LENGTH: 88
<212> TYPE: PRT
<213> ORGANISM: Artificial Sequence
<220> FEATURE:
<223> OTHER INFORMATION: Synthetic peptide

<400> SEQUENCE: 57

Ser Arg Gly Cys Glu Thr Arg Glu Leu Ala Leu Pro Arg Asp Gly Gln
 1               5                  10                  15

Gly Arg Leu Gly Phe Glu Val Asp Ala Glu Gly Phe Val Thr His Val
                20                  25                  30
```

```
Glu Arg Phe Thr Phe Ala Glu Thr Ala Gly Leu Arg Pro Gly Ala Arg
            35                  40                  45

Leu Leu Arg Val Cys Gly Gln Thr Leu Pro Ser Leu Arg Pro Glu Ala
        50                  55                  60

Ala Ala Gln Leu Leu Arg Ser Ala Pro Lys Val Cys Val Thr Val Leu
65                  70                  75                  80

Pro Pro Asp Glu Ser Gly Arg Pro
                85
```

<210> SEQ ID NO 58
<211> LENGTH: 108
<212> TYPE: PRT
<213> ORGANISM: Artificial Sequence
<220> FEATURE:
<223> OTHER INFORMATION: Synthetic peptide

<400> SEQUENCE: 58

```
Cys Ser Val Met Ile Phe Glu Val Val Glu Gln Ala Gly Ala Ile Ile
1               5                   10                  15

Leu Glu Asp Gly Gln Glu Leu Asp Ser Trp Tyr Val Ile Leu Asn Gly
            20                  25                  30

Thr Val Glu Ile Ser His Pro Asp Gly Lys Val Glu Asn Leu Phe Met
        35                  40                  45

Gly Asn Ser Phe Gly Ile Thr Pro Thr Leu Asp Lys Gln Tyr Met His
    50                  55                  60

Gly Ile Val Arg Thr Lys Val Asp Asp Cys Gln Phe Val Cys Ile Ala
65                  70                  75                  80

Gln Gln Asp Tyr Trp Arg Ile Leu Asn His Val Glu Lys Asn Thr His
                85                  90                  95

Lys Val Glu Glu Glu Gly Glu Ile Val Met Val His
            100                 105
```

<210> SEQ ID NO 59
<211> LENGTH: 82
<212> TYPE: PRT
<213> ORGANISM: Artificial Sequence
<220> FEATURE:
<223> OTHER INFORMATION: Synthetic peptide

<400> SEQUENCE: 59

```
Pro Arg Glu Thr Val Lys Ile Pro Asp Ser Ala Asp Gly Leu Gly Phe
1               5                   10                  15

Gln Ile Arg Gly Phe Gly Pro Ser Val Val His Ala Val Gly Arg Gly
            20                  25                  30

Thr Val Ala Ala Ala Gly Leu His Pro Gly Gln Cys Ile Ile Lys
        35                  40                  45

Val Asn Gly Ile Asn Val Ser Lys Glu Thr His Ala Ser Val Ile Ala
    50                  55                  60

His Val Thr Ala Cys Arg Lys Tyr Arg Arg Pro Thr Lys Gln Asp Ser
65                  70                  75                  80

Ile Gln
```

<210> SEQ ID NO 60
<211> LENGTH: 89
<212> TYPE: PRT
<213> ORGANISM: Artificial Sequence
<220> FEATURE:
<223> OTHER INFORMATION: Synthetic peptide -continued

```
<400> SEQUENCE: 60

Leu Glu Asn Val Ile Ala Lys Ser Leu Leu Ile Lys Ser Asn Glu Gly
1               5                   10                  15

Ser Tyr Gly Phe Gly Leu Glu Asp Lys Asn Lys Val Pro Ile Ile Lys
            20                  25                  30

Leu Val Glu Lys Gly Ser Asn Ala Glu Met Ala Gly Met Glu Val Gly
        35                  40                  45

Lys Lys Ile Phe Ala Ile Asn Gly Asp Leu Val Phe Met Arg Pro Phe
    50                  55                  60

Asn Glu Val Asp Cys Phe Leu Lys Ser Cys Leu Asn Ser Arg Lys Pro
65                  70                  75                  80

Leu Arg Val Leu Val Ser Thr Lys Pro
                85

<210> SEQ ID NO 61
<211> LENGTH: 100
<212> TYPE: PRT
<213> ORGANISM: Artificial Sequence
<220> FEATURE:
<223> OTHER INFORMATION: Synthetic peptide

<400> SEQUENCE: 61

Glu Asp Phe Cys Tyr Val Phe Thr Val Glu Leu Glu Arg Gly Pro Ser
1               5                   10                  15

Gly Leu Gly Met Gly Leu Ile Asp Gly Met His Thr His Leu Gly Ala
            20                  25                  30

Pro Gly Leu Tyr Ile Gln Thr Leu Leu Pro Gly Ser Pro Ala Ala Ala
        35                  40                  45

Asp Gly Arg Leu Ser Leu Gly Asp Arg Ile Leu Glu Val Asn Gly Ser
    50                  55                  60

Ser Leu Leu Gly Leu Gly Tyr Leu Arg Ala Val Asp Leu Ile Arg His
65                  70                  75                  80

Gly Gly Lys Lys Met Arg Phe Leu Val Ala Lys Ser Asp Val Glu Thr
                85                  90                  95

Ala Lys Lys Ile
            100

<210> SEQ ID NO 62
<211> LENGTH: 91
<212> TYPE: PRT
<213> ORGANISM: Artificial Sequence
<220> FEATURE:
<223> OTHER INFORMATION: Synthetic peptide

<400> SEQUENCE: 62

Ile Tyr Leu Glu Ala Phe Leu Glu Gly Gly Ala Pro Trp Gly Phe Thr
1               5                   10                  15

Leu Lys Gly Gly Leu Glu His Gly Glu Pro Leu Ile Ile Ser Lys Val
            20                  25                  30

Glu Glu Gly Gly Lys Ala Asp Thr Leu Ser Ser Lys Leu Gln Ala Gly
        35                  40                  45

Asp Glu Val Val His Ile Asn Glu Val Thr Leu Ser Ser Ser Arg Lys
    50                  55                  60

Glu Ala Val Ser Leu Val Lys Gly Ser Tyr Lys Thr Leu Arg Leu Val
65                  70                  75                  80

Val Arg Arg Asp Val Cys Thr Asp Pro Gly His
                85                  90
```

```
<210> SEQ ID NO 63
<211> LENGTH: 100
<212> TYPE: PRT
<213> ORGANISM: Artificial Sequence
<220> FEATURE:
<223> OTHER INFORMATION: Synthetic peptide

<400> SEQUENCE: 63

Asn Asn Glu Leu Thr Gln Phe Leu Pro Arg Thr Ile Thr Leu Lys Lys
1               5                   10                  15

Pro Pro Gly Ala Gln Leu Gly Phe Asn Ile Arg Gly Gly Lys Ala Ser
            20                  25                  30

Gln Leu Gly Ile Phe Ile Ser Lys Val Ile Pro Asp Ser Asp Ala His
        35                  40                  45

Arg Ala Gly Leu Gln Glu Gly Asp Gln Val Leu Ala Val Asn Asp Val
    50                  55                  60

Asp Phe Gln Asp Ile Glu His Ser Lys Ala Val Glu Ile Leu Lys Thr
65                  70                  75                  80

Ala Arg Glu Ile Ser Met Arg Val Arg Phe Phe Pro Tyr Asn Tyr His
                85                  90                  95

Arg Gln Lys Glu
            100

<210> SEQ ID NO 64
<211> LENGTH: 107
<212> TYPE: PRT
<213> ORGANISM: Artificial Sequence
<220> FEATURE:
<223> OTHER INFORMATION: Synthetic peptide

<400> SEQUENCE: 64

Phe Leu Thr Glu Phe Gln Asp Lys Gln Ile Lys Asp Trp Lys Lys Arg
1               5                   10                  15

Phe Ile Gly Ile Arg Met Arg Thr Ile Thr Pro Ser Leu Val Asp Glu
            20                  25                  30

Leu Lys Ala Ser Asn Pro Asp Phe Pro Glu Val Ser Ser Gly Ile Tyr
        35                  40                  45

Val Gln Glu Val Ala Pro Asn Ser Pro Ser Gln Arg Gly Gly Ile Gln
    50                  55                  60

Asp Gly Asp Ile Ile Val Lys Val Asn Gly Arg Pro Leu Val Asp Ser
65                  70                  75                  80

Ser Glu Leu Gln Glu Ala Val Leu Thr Glu Ser Pro Leu Leu Leu Glu
                85                  90                  95

Val Arg Arg Gly Asn Asp Asp Leu Leu Phe Ser
            100                 105

<210> SEQ ID NO 65
<211> LENGTH: 94
<212> TYPE: PRT
<213> ORGANISM: Artificial Sequence
<220> FEATURE:
<223> OTHER INFORMATION: Synthetic peptide

<400> SEQUENCE: 65

Asn Lys Lys Tyr Leu Gly Leu Gln Met Leu Ser Leu Thr Val Pro Leu
1               5                   10                  15

Ser Glu Glu Leu Lys Met His Tyr Pro Asp Phe Pro Asp Val Ser Ser
            20                  25                  30

Gly Val Tyr Val Cys Lys Val Val Glu Gly Thr Ala Ala Gln Ser Ser
```

```
                35                  40                  45
Gly Leu Arg Asp His Asp Val Ile Val Asn Ile Asn Gly Lys Pro Ile
 50                  55                  60

Thr Thr Thr Thr Asp Val Val Lys Ala Leu Asp Ser Asp Ser Leu Ser
 65                  70                  75                  80

Met Ala Val Leu Arg Gly Lys Asp Asn Leu Leu Leu Thr Val
                 85                  90

<210> SEQ ID NO 66
<211> LENGTH: 111
<212> TYPE: PRT
<213> ORGANISM: Artificial Sequence
<220> FEATURE:
<223> OTHER INFORMATION: Synthetic peptide

<400> SEQUENCE: 66

Pro Gly Ser Asp Ser Ser Leu Phe Glu Thr Tyr Asn Val Glu Leu Val
 1               5                  10                  15

Arg Lys Asp Gly Gln Ser Leu Gly Ile Arg Ile Val Gly Tyr Val Gly
                 20                  25                  30

Thr Ser His Thr Gly Glu Ala Ser Gly Ile Tyr Val Lys Ser Ile Ile
                 35                  40                  45

Pro Gly Ser Ala Ala Tyr His Asn Gly His Ile Gln Val Asn Asp Lys
 50                  55                  60

Ile Val Ala Val Asp Gly Val Asn Ile Gln Gly Phe Ala Asn His Asp
 65                  70                  75                  80

Val Val Glu Val Leu Arg Asn Ala Gly Gln Val Val His Leu Thr Leu
                 85                  90                  95

Val Arg Arg Lys Thr Ser Ser Thr Ser Arg Ile His Arg Asp
                100                 105                 110

<210> SEQ ID NO 67
<211> LENGTH: 93
<212> TYPE: PRT
<213> ORGANISM: Artificial Sequence
<220> FEATURE:
<223> OTHER INFORMATION: Synthetic peptide

<400> SEQUENCE: 67

Pro Ala Thr Cys Pro Ile Val Pro Gly Gln Glu Met Ile Ile Glu Ile
 1               5                  10                  15

Ser Lys Gly Arg Ser Gly Leu Gly Leu Ser Ile Val Gly Gly Lys Asp
                 20                  25                  30

Thr Pro Leu Asn Ala Ile Val Ile His Glu Val Tyr Glu Glu Gly Ala
                 35                  40                  45

Ala Ala Arg Asp Gly Arg Leu Trp Ala Gly Asp Gln Ile Leu Glu Val
 50                  55                  60

Asn Gly Val Asp Leu Arg Asn Ser Ser His Glu Glu Ala Ile Thr Ala
 65                  70                  75                  80

Leu Arg Gln Thr Pro Gln Lys Val Arg Leu Val Val Tyr
                 85                  90

<210> SEQ ID NO 68
<211> LENGTH: 100
<212> TYPE: PRT
<213> ORGANISM: Artificial Sequence
<220> FEATURE:
<223> OTHER INFORMATION: Synthetic peptide

<400> SEQUENCE: 68
```

-continued

Leu Pro Glu Thr Val Cys Trp Gly His Val Glu Glu Val Leu Ile
1               5                   10                  15

Asn Asp Gly Ser Gly Leu Gly Phe Gly Ile Val Gly Gly Lys Thr Ser
                20                  25                  30

Gly Val Val Arg Thr Ile Val Pro Gly Gly Leu Ala Asp Arg Asp
        35                  40                  45

Gly Arg Leu Gln Thr Gly Asp His Ile Leu Lys Ile Gly Gly Thr Asn
    50                  55                  60

Val Gln Gly Met Thr Ser Glu Gln Val Ala Gln Val Leu Arg Asn Cys
65                  70                  75                  80

Gly Asn Ser Val Arg Met Leu Val Ala Arg Asp Pro Ala Gly Asp Ile
                85                  90                  95

Gln Ser Pro Ile
            100

<210> SEQ ID NO 69
<211> LENGTH: 119
<212> TYPE: PRT
<213> ORGANISM: Artificial Sequence
<220> FEATURE:
<223> OTHER INFORMATION: Synthetic peptide

<400> SEQUENCE: 69

Pro Asn Phe Ser His Trp Gly Pro Pro Arg Ile Val Glu Ile Phe Arg
1               5                   10                  15

Glu Pro Asn Val Ser Leu Gly Ile Ser Ile Val Val Gly Gln Thr Val
                20                  25                  30

Ile Lys Arg Leu Lys Asn Gly Glu Glu Leu Lys Gly Ile Phe Ile Lys
            35                  40                  45

Gln Val Leu Glu Asp Ser Pro Ala Gly Lys Thr Asn Ala Leu Lys Thr
    50                  55                  60

Gly Asp Lys Ile Leu Glu Val Ser Gly Val Asp Leu Gln Asn Ala Ser
65                  70                  75                  80

His Ser Glu Ala Val Glu Ala Ile Lys Asn Ala Gly Asn Pro Val Val
                85                  90                  95

Phe Ile Val Gln Ser Leu Ser Ser Thr Pro Arg Val Ile Pro Asn Val
            100                 105                 110

His Asn Lys Ala Asn Ser Ser
        115

<210> SEQ ID NO 70
<211> LENGTH: 99
<212> TYPE: PRT
<213> ORGANISM: Artificial Sequence
<220> FEATURE:
<223> OTHER INFORMATION: Synthetic peptide

<400> SEQUENCE: 70

Pro Gly Glu Leu His Ile Ile Glu Leu Glu Lys Asp Lys Asn Gly Leu
1               5                   10                  15

Gly Leu Ser Leu Ala Gly Asn Lys Asp Arg Ser Arg Met Ser Ile Phe
                20                  25                  30

Val Val Gly Ile Asn Pro Glu Gly Pro Ala Ala Ala Asp Gly Arg Met
            35                  40                  45

Arg Ile Gly Asp Glu Leu Leu Glu Ile Asn Asn Gln Ile Leu Tyr Gly
    50                  55                  60

Arg Ser His Gln Asn Ala Ser Ala Ile Ile Lys Thr Ala Pro Ser Lys

-continued

```
                65                  70                  75                  80
Val Lys Leu Val Phe Ile Arg Asn Glu Asp Ala Val Asn Gln Met Ala
                    85                  90                  95

Asn Ser Ser

<210> SEQ ID NO 71
<211> LENGTH: 102
<212> TYPE: PRT
<213> ORGANISM: Artificial Sequence
<220> FEATURE:
<223> OTHER INFORMATION: Synthetic peptide

<400> SEQUENCE: 71

Leu Ser Ser Pro Glu Val Lys Ile Val Glu Leu Val Lys Asp Cys Lys
1               5                   10                  15

Gly Leu Gly Phe Ser Ile Leu Asp Tyr Gln Asp Pro Leu Asp Pro Thr
                20                  25                  30

Arg Ser Val Ile Val Ile Arg Ser Leu Val Ala Asp Gly Val Ala Glu
            35                  40                  45

Arg Ser Gly Gly Leu Leu Pro Gly Asp Arg Leu Val Ser Val Asn Glu
        50                  55                  60

Tyr Cys Leu Asp Asn Thr Ser Leu Ala Glu Ala Val Glu Ile Leu Lys
65                  70                  75                  80

Ala Val Pro Pro Gly Leu Val His Leu Gly Ile Cys Lys Pro Leu Val
                85                  90                  95

Glu Phe Ile Val Thr Asp
            100

<210> SEQ ID NO 72
<211> LENGTH: 104
<212> TYPE: PRT
<213> ORGANISM: Artificial Sequence
<220> FEATURE:
<223> OTHER INFORMATION: Synthetic peptide

<400> SEQUENCE: 72

Ile Trp Gln Ile Glu Tyr Ile Asp Ile Glu Arg Pro Ser Thr Gly Gly
1               5                   10                  15

Leu Gly Phe Ser Val Val Ala Leu Arg Ser Gln Asn Leu Gly Lys Val
                20                  25                  30

Asp Ile Phe Val Lys Asp Val Gln Pro Gly Ser Val Ala Asp Arg Asp
            35                  40                  45

Gln Arg Leu Lys Glu Asn Asp Gln Ile Leu Ala Ile Asn His Thr Pro
        50                  55                  60

Leu Asp Gln Asn Ile Ser His Gln Gln Ala Ile Ala Leu Leu Gln Gln
65                  70                  75                  80

Thr Thr Gly Ser Leu Arg Leu Ile Val Ala Arg Glu Pro Val His Thr
                85                  90                  95

Lys Ser Ser Thr Ser Ser Ser Glu
            100

<210> SEQ ID NO 73
<211> LENGTH: 96
<212> TYPE: PRT
<213> ORGANISM: Artificial Sequence
<220> FEATURE:
<223> OTHER INFORMATION: Synthetic peptide

<400> SEQUENCE: 73
```

-continued

```
Asn Ser Asp Asp Ala Glu Leu Gln Lys Tyr Ser Lys Leu Leu Pro Ile
1               5                   10                  15

His Thr Leu Arg Leu Gly Val Glu Val Asp Ser Phe Asp Gly His His
                20                  25                  30

Tyr Ile Ser Ser Ile Val Ser Gly Gly Pro Val Asp Thr Leu Gly Leu
                35                  40                  45

Leu Gln Pro Glu Asp Glu Leu Leu Glu Val Asn Gly Met Gln Leu Tyr
            50                  55                  60

Gly Lys Ser Arg Arg Glu Ala Val Ser Phe Leu Lys Glu Val Pro Pro
65                  70                  75                  80

Pro Phe Thr Leu Val Cys Cys Arg Arg Leu Phe Asp Asp Glu Ala Ser
                85                  90                  95
```

<210> SEQ ID NO 74
<211> LENGTH: 118
<212> TYPE: PRT
<213> ORGANISM: Artificial Sequence
<220> FEATURE:
<223> OTHER INFORMATION: Synthetic peptide

<400> SEQUENCE: 74

```
His Leu Arg Leu Leu Asn Ile Ala Cys Ala Ala Lys Ala Lys Arg Arg
1               5                   10                  15

Leu Met Thr Leu Thr Lys Pro Ser Arg Glu Ala Pro Leu Pro Phe Ile
                20                  25                  30

Leu Leu Gly Gly Ser Glu Lys Gly Phe Gly Ile Phe Val Asp Ser Val
                35                  40                  45

Asp Ser Gly Ser Lys Ala Thr Glu Ala Gly Leu Lys Arg Gly Asp Gln
            50                  55                  60

Ile Leu Glu Val Asn Gly Gln Asn Phe Glu Asn Ile Gln Leu Ser Lys
65                  70                  75                  80

Ala Met Glu Ile Leu Arg Asn Asn Thr His Leu Ser Ile Thr Val Lys
                85                  90                  95

Thr Asn Leu Phe Val Phe Lys Glu Leu Leu Thr Arg Leu Ser Glu Glu
                100                 105                 110

Lys Arg Asn Gly Ala Pro
            115
```

<210> SEQ ID NO 75
<211> LENGTH: 88
<212> TYPE: PRT
<213> ORGANISM: Artificial Sequence
<220> FEATURE:
<223> OTHER INFORMATION: Synthetic peptide

<400> SEQUENCE: 75

```
Ile Pro Pro Ala Pro Arg Lys Val Glu Met Arg Arg Asp Pro Val Leu
1               5                   10                  15

Gly Phe Gly Phe Val Ala Gly Ser Glu Lys Pro Val Val Val Arg Ser
                20                  25                  30

Val Thr Pro Gly Gly Pro Ser Glu Gly Lys Leu Ile Pro Gly Asp Gln
            35                  40                  45

Ile Val Met Ile Asn Asp Glu Pro Val Ser Ala Ala Pro Arg Glu Arg
            50                  55                  60

Val Ile Asp Leu Val Arg Ser Cys Lys Glu Ser Ile Leu Leu Thr Val
65                  70                  75                  80

Ile Gln Pro Tyr Pro Ser Pro Lys
                85
```

```
<210> SEQ ID NO 76
<211> LENGTH: 101
<212> TYPE: PRT
<213> ORGANISM: Artificial Sequence
<220> FEATURE:
<223> OTHER INFORMATION: Synthetic peptide

<400> SEQUENCE: 76

Leu Asn Lys Arg Thr Thr Met Pro Lys Asp Ser Gly Ala Leu Leu Gly
1               5                   10                  15

Leu Lys Val Val Gly Gly Lys Met Thr Asp Leu Gly Arg Leu Gly Ala
            20                  25                  30

Phe Ile Thr Lys Val Lys Lys Gly Ser Leu Ala Asp Val Val Gly His
        35                  40                  45

Leu Arg Ala Gly Asp Glu Val Leu Glu Trp Asn Gly Lys Pro Leu Pro
    50                  55                  60

Gly Ala Thr Asn Glu Glu Val Tyr Asn Ile Ile Leu Glu Ser Lys Ser
65                  70                  75                  80

Glu Pro Gln Val Glu Ile Ile Val Ser Arg Pro Ile Gly Asp Ile Pro
                85                  90                  95

Arg Ile His Arg Asp
            100

<210> SEQ ID NO 77
<211> LENGTH: 77
<212> TYPE: PRT
<213> ORGANISM: Artificial Sequence
<220> FEATURE:
<223> OTHER INFORMATION: Synthetic peptide

<400> SEQUENCE: 77

Arg Cys Val Ile Ile Gln Lys Asp Gln His Gly Phe Gly Phe Thr Val
1               5                   10                  15

Ser Gly Asp Arg Ile Val Leu Val Gln Ser Val Arg Pro Gly Gly Ala
            20                  25                  30

Ala Met Lys Ala Gly Val Lys Glu Gly Asp Arg Ile Ile Lys Val Asn
        35                  40                  45

Gly Thr Met Val Thr Asn Ser Ser His Leu Glu Val Val Lys Leu Ile
    50                  55                  60

Lys Ser Gly Ala Tyr Val Ala Leu Thr Leu Leu Gly Ser
65                  70                  75

<210> SEQ ID NO 78
<211> LENGTH: 87
<212> TYPE: PRT
<213> ORGANISM: Artificial Sequence
<220> FEATURE:
<223> OTHER INFORMATION: Synthetic peptide

<400> SEQUENCE: 78

Ile Leu Val Gln Arg Cys Val Ile Ile Gln Lys Asp Asp Asn Gly Phe
1               5                   10                  15

Gly Leu Thr Val Ser Gly Asp Asn Pro Val Phe Val Gln Ser Val Lys
            20                  25                  30

Glu Asp Gly Ala Ala Met Arg Ala Gly Val Gln Thr Gly Asp Arg Ile
        35                  40                  45

Ile Lys Val Asn Gly Thr Leu Val Thr His Ser Asn His Leu Glu Val
    50                  55                  60
```

-continued

```
Val Lys Leu Ile Lys Ser Gly Ser Tyr Val Ala Leu Thr Val Gln Gly
 65                  70                  75                  80

Arg Pro Pro Gly Asn Ser Ser
                 85

<210> SEQ ID NO 79
<211> LENGTH: 78
<212> TYPE: PRT
<213> ORGANISM: Artificial Sequence
<220> FEATURE:
<223> OTHER INFORMATION: Synthetic peptide

<400> SEQUENCE: 79

Ser Val Glu Met Thr Leu Arg Arg Asn Gly Leu Gly Gln Leu Gly Phe
 1               5                  10                  15

His Val Asn Tyr Glu Gly Ile Val Ala Asp Val Glu Pro Tyr Gly Tyr
             20                  25                  30

Ala Trp Gln Ala Gly Leu Arg Gln Gly Ser Arg Leu Val Glu Ile Cys
         35                  40                  45

Lys Val Ala Val Ala Thr Leu Ser His Glu Gln Met Ile Asp Leu Leu
     50                  55                  60

Arg Thr Ser Val Thr Val Lys Val Val Ile Pro Pro His
 65                  70                  75

<210> SEQ ID NO 80
<211> LENGTH: 96
<212> TYPE: PRT
<213> ORGANISM: Artificial Sequence
<220> FEATURE:
<223> OTHER INFORMATION: Synthetic peptide

<400> SEQUENCE: 80

Leu Lys Val Met Thr Ser Gly Trp Glu Thr Val Asp Met Thr Leu Arg
 1               5                  10                  15

Arg Asn Gly Leu Gly Gln Leu Gly Phe His Val Lys Tyr Asp Gly Thr
             20                  25                  30

Val Ala Glu Val Glu Asp Tyr Gly Phe Ala Trp Gln Ala Gly Leu Arg
         35                  40                  45

Gln Gly Ser Arg Leu Val Glu Ile Cys Lys Val Ala Val Val Thr Leu
     50                  55                  60

Thr His Asp Gln Met Ile Asp Leu Leu Arg Thr Ser Val Thr Val Lys
 65                  70                  75                  80

Val Val Ile Ile Pro Pro Phe Glu Asp Gly Thr Pro Arg Arg Gly Trp
                 85                  90                  95

<210> SEQ ID NO 81
<211> LENGTH: 105
<212> TYPE: PRT
<213> ORGANISM: Artificial Sequence
<220> FEATURE:
<223> OTHER INFORMATION: Synthetic peptide

<400> SEQUENCE: 81

His Tyr Ile Phe Pro His Ala Arg Ile Lys Ile Thr Arg Asp Ser Lys
 1               5                  10                  15

Asp His Thr Val Ser Gly Asn Gly Leu Gly Ile Arg Ile Val Gly Gly
             20                  25                  30

Lys Glu Ile Pro Gly His Ser Gly Glu Ile Gly Ala Tyr Ile Ala Lys
         35                  40                  45

Ile Leu Pro Gly Gly Ser Ala Glu Gln Thr Gly Lys Leu Met Glu Gly
```

```
                50                  55                  60
Met Gln Val Leu Glu Trp Asn Gly Ile Pro Leu Thr Ser Lys Thr Tyr
 65                  70                  75                  80

Glu Glu Val Gln Ser Ile Ile Ser Gln Ser Gly Glu Ala Glu Ile
                 85                  90                  95

Cys Val Arg Leu Asp Leu Asn Met Leu
                100                 105

<210> SEQ ID NO 82
<211> LENGTH: 86
<212> TYPE: PRT
<213> ORGANISM: Artificial Sequence
<220> FEATURE:
<223> OTHER INFORMATION: Synthetic peptide

<400> SEQUENCE: 82

Ser Tyr Ser Val Thr Leu Thr Gly Pro Gly Pro Trp Gly Phe Arg Leu
 1               5                  10                  15

Gln Gly Gly Lys Asp Phe Asn Met Pro Leu Thr Ile Ser Arg Ile Thr
                20                  25                  30

Pro Gly Ser Lys Ala Ala Gln Ser Gln Leu Ser Gln Gly Asp Leu Val
            35                  40                  45

Val Ala Ile Asp Gly Val Asn Thr Asp Thr Met Thr His Leu Glu Ala
        50                  55                  60

Gln Asn Lys Ile Lys Ser Ala Ser Tyr Asn Leu Ser Leu Thr Leu Gln
 65                  70                  75                  80

Lys Ser Lys Asn Ser Ser
                85

<210> SEQ ID NO 83
<211> LENGTH: 94
<212> TYPE: PRT
<213> ORGANISM: Artificial Sequence
<220> FEATURE:
<223> OTHER INFORMATION: Synthetic peptide

<400> SEQUENCE: 83

Phe Ser Asp Met Arg Ile Ser Ile Asn Gln Thr Pro Gly Lys Ser Leu
 1               5                  10                  15

Asp Phe Gly Phe Thr Ile Lys Trp Asp Ile Pro Gly Ile Phe Val Ala
                20                  25                  30

Ser Val Glu Ala Gly Ser Pro Ala Glu Phe Ser Gln Leu Gln Val Asp
            35                  40                  45

Asp Glu Ile Ile Ala Ile Asn Asn Thr Lys Phe Ser Tyr Asn Asp Ser
        50                  55                  60

Lys Glu Trp Glu Glu Ala Met Ala Lys Ala Gln Glu Thr Gly His Leu
 65                  70                  75                  80

Val Met Asp Val Arg Arg Tyr Gly Lys Ala Gly Ser Pro Glu
                85                  90

<210> SEQ ID NO 84
<211> LENGTH: 98
<212> TYPE: PRT
<213> ORGANISM: Artificial Sequence
<220> FEATURE:
<223> OTHER INFORMATION: Synthetic peptide

<400> SEQUENCE: 84

Gln Ser Ala His Leu Glu Val Ile Gln Leu Ala Asn Ile Lys Pro Ser
 1               5                  10                  15
```

```
Glu Gly Leu Gly Met Tyr Ile Lys Ser Thr Tyr Asp Gly Leu His Val
            20                  25                  30

Ile Thr Gly Thr Thr Glu Asn Ser Pro Ala Asp Arg Cys Lys Lys Ile
        35                  40                  45

His Ala Gly Asp Glu Val Ile Gln Val Asn His Gln Thr Val Val Gly
    50                  55                  60

Trp Gln Leu Lys Asn Leu Val Asn Ala Leu Arg Glu Asp Pro Ser Gly
65                  70                  75                  80

Val Ile Leu Thr Leu Lys Lys Arg Pro Gln Ser Met Leu Thr Ser Ala
                85                  90                  95

Pro Ala

<210> SEQ ID NO 85
<211> LENGTH: 100
<212> TYPE: PRT
<213> ORGANISM: Artificial Sequence
<220> FEATURE:
<223> OTHER INFORMATION: Synthetic peptide

<400> SEQUENCE: 85

Ile Leu Thr Gln Thr Leu Ile Pro Val Arg His Thr Val Lys Ile Asp
1               5                   10                  15

Lys Asp Thr Leu Leu Gln Asp Tyr Gly Phe His Ile Ser Glu Ser Leu
            20                  25                  30

Pro Leu Thr Val Val Ala Val Thr Ala Gly Gly Ser Ala His Gly Lys
        35                  40                  45

Leu Phe Pro Gly Asp Gln Ile Leu Gln Met Asn Asn Glu Pro Ala Glu
    50                  55                  60

Asp Leu Ser Trp Glu Arg Ala Val Asp Ile Leu Arg Glu Ala Glu Asp
65                  70                  75                  80

Ser Leu Ser Ile Thr Val Val Arg Cys Thr Ser Gly Val Pro Lys Ser
                85                  90                  95

Ser Asn Ser Ser
            100

<210> SEQ ID NO 86
<211> LENGTH: 91
<212> TYPE: PRT
<213> ORGANISM: Artificial Sequence
<220> FEATURE:
<223> OTHER INFORMATION: Synthetic peptide

<400> SEQUENCE: 86

Arg Ser Phe Gln Tyr Val Pro Val Gln Leu Gln Gly Gly Ala Pro Trp
1               5                   10                  15

Gly Phe Thr Leu Lys Gly Gly Leu Glu His Cys Glu Pro Leu Thr Val
            20                  25                  30

Ser Lys Ile Glu Asp Gly Gly Lys Ala Ala Leu Ser Gln Lys Met Arg
        35                  40                  45

Thr Gly Asp Glu Leu Val Asn Ile Asn Gly Thr Pro Leu Tyr Gly Ser
    50                  55                  60

Arg Gln Glu Ala Leu Ile Leu Ile Lys Gly Ser Phe Arg Ile Leu Lys
65                  70                  75                  80

Leu Ile Val Arg Arg Arg Asn Ala Pro Val Ser
                85                  90

<210> SEQ ID NO 87
```

-continued

```
<211> LENGTH: 103
<212> TYPE: PRT
<213> ORGANISM: Artificial Sequence
<220> FEATURE:
<223> OTHER INFORMATION: Synthetic peptide

<400> SEQUENCE: 87

Ile Leu Glu Lys Leu Glu Leu Phe Pro Val Glu Leu Glu Lys Asp Glu
1               5                   10                  15

Asp Gly Leu Gly Ile Ser Ile Ile Gly Met Gly Val Gly Ala Asp Ala
            20                  25                  30

Gly Leu Glu Lys Leu Gly Ile Phe Val Lys Thr Val Thr Glu Gly Gly
        35                  40                  45

Ala Ala Gln Arg Asp Gly Arg Ile Gln Val Asn Asp Gln Ile Val Glu
    50                  55                  60

Val Asp Gly Ile Ser Leu Val Gly Val Thr Gln Asn Phe Ala Ala Thr
65                  70                  75                  80

Val Leu Arg Asn Thr Lys Gly Asn Val Arg Phe Val Ile Gly Arg Glu
                85                  90                  95

Lys Pro Gly Gln Val Ser Glu
            100

<210> SEQ ID NO 88
<211> LENGTH: 113
<212> TYPE: PRT
<213> ORGANISM: Artificial Sequence
<220> FEATURE:
<223> OTHER INFORMATION: Synthetic peptide

<400> SEQUENCE: 88

Lys Asp Val Asn Val Tyr Val Asn Pro Lys Lys Leu Thr Val Ile Lys
1               5                   10                  15

Ala Lys Glu Gln Leu Lys Leu Leu Glu Val Leu Val Gly Ile Ile His
            20                  25                  30

Gln Thr Lys Trp Ser Trp Arg Arg Thr Gly Lys Gln Gly Asp Gly Glu
        35                  40                  45

Arg Leu Val Val His Gly Leu Leu Pro Gly Gly Ser Ala Met Lys Ser
    50                  55                  60

Gly Gln Val Leu Ile Gly Asp Val Leu Val Ala Val Asn Asp Val Asp
65                  70                  75                  80

Val Thr Thr Glu Asn Ile Glu Arg Val Leu Ser Cys Ile Pro Gly Pro
                85                  90                  95

Met Gln Val Lys Leu Thr Phe Glu Asn Ala Tyr Asp Val Lys Arg Glu
            100                 105                 110

Thr

<210> SEQ ID NO 89
<211> LENGTH: 90
<212> TYPE: PRT
<213> ORGANISM: Artificial Sequence
<220> FEATURE:
<223> OTHER INFORMATION: Synthetic peptide

<400> SEQUENCE: 89

Thr Arg Gly Cys Glu Thr Val Glu Met Thr Leu Arg Arg Asn Gly Leu
1               5                   10                  15

Gly Gln Leu Gly Phe His Val Asn Phe Glu Gly Ile Val Ala Asp Val
            20                  25                  30

Glu Pro Phe Gly Phe Ala Trp Lys Ala Gly Leu Arg Gln Gly Ser Arg
```

-continued

```
                35                  40                  45
Leu Val Glu Ile Cys Lys Val Ala Val Ala Thr Leu Thr His Glu Gln
 50                  55                  60

Met Ile Asp Leu Leu Arg Thr Ser Val Thr Val Lys Val Val Ile Ile
 65                  70                  75                  80

Gln Pro His Asp Asp Gly Ser Pro Arg Arg
                 85                  90

<210> SEQ ID NO 90
<211> LENGTH: 96
<212> TYPE: PRT
<213> ORGANISM: Artificial Sequence
<220> FEATURE:
<223> OTHER INFORMATION: Synthetic peptide

<400> SEQUENCE: 90

Val Glu Asn Ile Leu Ala Lys Arg Leu Leu Ile Leu Pro Gln Glu Glu
 1               5                  10                  15

Asp Tyr Gly Phe Asp Ile Glu Glu Lys Asn Lys Ala Val Val Val Lys
                20                  25                  30

Ser Val Gln Arg Gly Ser Leu Ala Glu Val Ala Gly Leu Gln Val Gly
             35                  40                  45

Arg Lys Ile Tyr Ser Ile Asn Glu Asp Leu Val Phe Leu Arg Pro Phe
 50                  55                  60

Ser Glu Val Glu Ser Ile Leu Asn Gln Ser Phe Cys Ser Arg Arg Pro
 65                  70                  75                  80

Leu Arg Leu Leu Val Ala Thr Lys Ala Lys Glu Ile Ile Lys Ile Pro
                 85                  90                  95

<210> SEQ ID NO 91
<211> LENGTH: 103
<212> TYPE: PRT
<213> ORGANISM: Artificial Sequence
<220> FEATURE:
<223> OTHER INFORMATION: Synthetic peptide

<400> SEQUENCE: 91

Pro Asp Ser Ala Gly Pro Gly Glu Val Arg Leu Val Ser Leu Arg Arg
 1               5                  10                  15

Ala Lys Ala His Glu Gly Leu Gly Phe Ser Ile Arg Gly Gly Ser Glu
                20                  25                  30

His Gly Val Gly Ile Tyr Val Ser Leu Val Glu Pro Gly Ser Leu Ala
             35                  40                  45

Glu Lys Glu Gly Leu Arg Val Gly Asp Gln Ile Leu Arg Val Asn Asp
 50                  55                  60

Lys Ser Leu Ala Arg Val Thr His Ala Glu Ala Val Lys Ala Leu Lys
 65                  70                  75                  80

Gly Ser Lys Lys Leu Val Leu Ser Val Tyr Ser Ala Gly Arg Ile Pro
                 85                  90                  95

Gly Gly Tyr Val Thr Asn His
            100

<210> SEQ ID NO 92
<211> LENGTH: 100
<212> TYPE: PRT
<213> ORGANISM: Artificial Sequence
<220> FEATURE:
<223> OTHER INFORMATION: Synthetic peptide

<400> SEQUENCE: 92
```

```
Leu Gln Gly Gly Asp Glu Lys Lys Val Asn Leu Val Leu Gly Asp Gly
1               5                   10                  15

Arg Ser Leu Gly Leu Thr Ile Arg Gly Gly Ala Glu Tyr Gly Leu Gly
            20                  25                  30

Ile Tyr Ile Thr Gly Val Asp Pro Gly Ser Glu Ala Glu Gly Ser Gly
        35                  40                  45

Leu Lys Val Gly Asp Gln Ile Leu Glu Val Asn Gly Arg Ser Phe Leu
    50                  55                  60

Asn Ile Leu His Asp Glu Ala Val Arg Leu Leu Lys Ser Ser Arg His
65                  70                  75                  80

Leu Ile Leu Thr Val Lys Asp Val Gly Arg Leu Pro His Ala Arg Thr
                85                  90                  95

Thr Val Asp Glu
            100
```

<210> SEQ ID NO 93
<211> LENGTH: 98
<212> TYPE: PRT
<213> ORGANISM: Artificial Sequence
<220> FEATURE:
<223> OTHER INFORMATION: Synthetic peptide

<400> SEQUENCE: 93

```
Leu Arg Arg Ala Glu Leu Val Glu Ile Ile Val Glu Thr Glu Ala Gln
1               5                   10                  15

Thr Gly Val Ser Gly Ile Asn Val Ala Gly Gly Gly Lys Glu Gly Ile
            20                  25                  30

Phe Val Arg Glu Leu Arg Glu Asp Ser Pro Ala Ala Arg Ser Leu Ser
        35                  40                  45

Leu Gln Glu Gly Asp Gln Leu Leu Ser Ala Arg Val Phe Phe Glu Asn
    50                  55                  60

Phe Lys Tyr Glu Asp Ala Leu Arg Leu Leu Gln Cys Ala Glu Pro Tyr
65                  70                  75                  80

Lys Val Ser Phe Cys Leu Lys Arg Thr Val Pro Thr Gly Asp Leu Ala
                85                  90                  95

Leu Arg
```

<210> SEQ ID NO 94
<211> LENGTH: 94
<212> TYPE: PRT
<213> ORGANISM: Artificial Sequence
<220> FEATURE:
<223> OTHER INFORMATION: Synthetic peptide

<400> SEQUENCE: 94

```
Ile Gln Thr Thr Gly Ala Val Ser Tyr Thr Val Glu Leu Lys Arg Tyr
1               5                   10                  15

Gly Gly Pro Leu Gly Ile Thr Ile Ser Gly Thr Glu Glu Pro Phe Asp
            20                  25                  30

Pro Ile Val Ile Ser Gly Leu Thr Lys Arg Gly Leu Ala Glu Arg Thr
        35                  40                  45

Gly Ala Ile His Val Gly Asp Arg Ile Leu Ala Ile Asn Asn Val Ser
    50                  55                  60

Leu Lys Gly Arg Pro Leu Ser Glu Ala Ile His Leu Leu Gln Val Ala
65                  70                  75                  80

Gly Glu Thr Val Thr Leu Lys Ile Lys Lys Gln Leu Asp Arg
                85                  90
```

<210> SEQ ID NO 95
<211> LENGTH: 105
<212> TYPE: PRT
<213> ORGANISM: Artificial Sequence
<220> FEATURE:
<223> OTHER INFORMATION: Synthetic peptide

<400> SEQUENCE: 95

```
Ile Leu Glu Met Glu Glu Leu Leu Pro Thr Pro Leu Glu Met His
1               5                   10                  15

Lys Val Thr Leu His Lys Asp Pro Met Arg His Asp Phe Gly Phe Ser
            20                  25                  30

Val Ser Asp Gly Leu Leu Glu Lys Gly Val Tyr Val His Thr Val Arg
        35                  40                  45

Pro Asp Gly Pro Ala His Arg Gly Gly Leu Gln Pro Phe Asp Arg Val
    50                  55                  60

Leu Gln Val Asn His Val Arg Thr Arg Asp Phe Asp Cys Cys Leu Ala
65                  70                  75                  80

Val Pro Leu Leu Ala Glu Ala Gly Asp Val Leu Glu Leu Ile Ile Ser
                85                  90                  95

Arg Lys Pro His Thr Ala His Ser Ser
            100                 105
```

<210> SEQ ID NO 96
<211> LENGTH: 102
<212> TYPE: PRT
<213> ORGANISM: Artificial Sequence
<220> FEATURE:
<223> OTHER INFORMATION: Synthetic peptide

<400> SEQUENCE: 96

```
Ile His Thr Val Ala Asn Ala Ser Gly Pro Leu Met Val Glu Ile Val
1               5                   10                  15

Lys Thr Pro Gly Ser Ala Leu Gly Ile Ser Leu Thr Thr Thr Ser Leu
            20                  25                  30

Arg Asn Lys Ser Val Ile Thr Ile Asp Arg Ile Lys Pro Ala Ser Val
            35                  40                  45

Val Asp Arg Ser Gly Ala Leu His Pro Gly Asp His Ile Leu Ser Ile
    50                  55                  60

Asp Gly Thr Ser Met Glu His Cys Ser Leu Leu Glu Ala Thr Lys Leu
65                  70                  75                  80

Leu Ala Ser Ile Ser Glu Lys Val Arg Leu Glu Ile Leu Pro Val Pro
                85                  90                  95

Gln Ser Gln Arg Pro Leu
            100
```

<210> SEQ ID NO 97
<211> LENGTH: 84
<212> TYPE: PRT
<213> ORGANISM: Artificial Sequence
<220> FEATURE:
<223> OTHER INFORMATION: Synthetic peptide

<400> SEQUENCE: 97

```
Ile Thr Val Val Glu Leu Ile Lys Lys Glu Gly Ser Thr Leu Gly Leu
1               5                   10                  15

Thr Ile Ser Gly Gly Thr Asp Lys Asp Gly Lys Pro Arg Val Ser Asn
            20                  25                  30
```

```
Leu Arg Pro Gly Gly Leu Ala Ala Arg Ser Asp Leu Leu Asn Ile Gly
        35                  40                  45

Asp Tyr Ile Arg Ser Val Asn Gly Ile His Leu Thr Arg Leu Arg His
 50                  55                  60

Asp Glu Ile Ile Thr Leu Leu Lys Asn Val Gly Glu Arg Val Val Leu
 65                  70                  75                  80

Glu Val Glu Tyr

<210> SEQ ID NO 98
<211> LENGTH: 103
<212> TYPE: PRT
<213> ORGANISM: Artificial Sequence
<220> FEATURE:
<223> OTHER INFORMATION: Synthetic peptide

<400> SEQUENCE: 98

Ile Gln Ile Val His Thr Glu Thr Thr Glu Val Val Leu Cys Gly Asp
 1               5                  10                  15

Pro Leu Ser Gly Phe Gly Leu Gln Leu Gln Gly Gly Ile Phe Ala Thr
            20                  25                  30

Glu Thr Leu Ser Ser Pro Pro Leu Val Cys Phe Ile Glu Pro Asp Ser
        35                  40                  45

Pro Ala Glu Arg Cys Gly Leu Leu Gln Val Gly Asp Arg Val Leu Ser
 50                  55                  60

Ile Asn Gly Ile Ala Thr Glu Asp Gly Thr Met Glu Glu Ala Asn Gln
 65                  70                  75                  80

Leu Leu Arg Asp Ala Ala Leu Ala His Lys Val Val Leu Glu Val Glu
                85                  90                  95

Phe Asp Val Ala Glu Ser Val
            100

<210> SEQ ID NO 99
<211> LENGTH: 92
<212> TYPE: PRT
<213> ORGANISM: Artificial Sequence
<220> FEATURE:
<223> OTHER INFORMATION: Synthetic peptide

<400> SEQUENCE: 99

Ile Leu Asp Val Ser Leu Tyr Lys Glu Gly Asn Ser Phe Gly Phe Val
 1               5                  10                  15

Leu Arg Gly Gly Ala His Glu Asp Gly His Lys Ser Arg Pro Leu Val
            20                  25                  30

Leu Thr Tyr Val Arg Pro Gly Gly Pro Ala Asp Arg Glu Gly Ser Leu
        35                  40                  45

Lys Val Gly Asp Arg Leu Leu Ser Val Asp Gly Ile Pro Leu His Gly
 50                  55                  60

Ala Ser His Ala Thr Ala Leu Ala Thr Leu Arg Gln Cys Ser His Glu
 65                  70                  75                  80

Ala Leu Phe Gln Val Glu Tyr Asp Val Ala Thr Pro
                85                  90

<210> SEQ ID NO 100
<211> LENGTH: 102
<212> TYPE: PRT
<213> ORGANISM: Artificial Sequence
<220> FEATURE:
<223> OTHER INFORMATION: Synthetic peptide

<400> SEQUENCE: 100
```

```
Gln Phe Asp Val Ala Glu Ser Val Ile Pro Ser Ser Gly Thr Phe His
1               5                   10                  15

Val Lys Leu Pro Lys Lys Arg Ser Val Glu Leu Gly Ile Thr Ile Ser
                20                  25                  30

Ser Ala Ser Arg Lys Arg Gly Glu Pro Leu Ile Ile Ser Asp Ile Lys
            35                  40                  45

Lys Gly Ser Val Ala His Arg Thr Gly Thr Leu Glu Pro Gly Asp Lys
50                  55                  60

Leu Leu Ala Ile Asp Asn Ile Arg Leu Asp Asn Cys Pro Met Glu Asp
65                  70                  75                  80

Ala Val Gln Ile Leu Arg Gln Cys Glu Asp Leu Val Lys Leu Lys Ile
                85                  90                  95

Arg Lys Asp Glu Asp Asn
            100

<210> SEQ ID NO 101
<211> LENGTH: 91
<212> TYPE: PRT
<213> ORGANISM: Artificial Sequence
<220> FEATURE:
<223> OTHER INFORMATION: Synthetic peptide

<400> SEQUENCE: 101

Met Ala Leu Thr Val Asp Val Ala Gly Pro Ala Pro Trp Gly Phe Arg
1               5                   10                  15

Ile Thr Gly Gly Arg Asp Phe His Thr Pro Ile Met Val Thr Lys Val
                20                  25                  30

Ala Glu Arg Gly Lys Ala Lys Asp Ala Asp Leu Arg Pro Gly Asp Ile
            35                  40                  45

Ile Val Ala Ile Asn Gly Glu Ser Ala Glu Gly Met Leu His Ala Glu
50                  55                  60

Ala Gln Ser Lys Ile Arg Gln Ser Pro Ser Pro Leu Arg Leu Gln Leu
65                  70                  75                  80

Asp Arg Ser Gln Ala Thr Ser Pro Gly Gln Thr
                85                  90

<210> SEQ ID NO 102
<211> LENGTH: 84
<212> TYPE: PRT
<213> ORGANISM: Artificial Sequence
<220> FEATURE:
<223> OTHER INFORMATION: Synthetic peptide

<400> SEQUENCE: 102

Ser Asn Tyr Ser Val Ser Leu Val Gly Pro Ala Pro Trp Gly Phe Arg
1               5                   10                  15

Leu Gln Gly Gly Lys Asp Phe Asn Met Pro Leu Thr Ile Ser Ser Leu
                20                  25                  30

Lys Asp Gly Gly Lys Ala Ala Gln Ala Asn Val Arg Ile Gly Asp Val
            35                  40                  45

Val Leu Ser Ile Asp Gly Ile Asn Ala Gln Gly Met Thr His Leu Glu
50                  55                  60

Ala Gln Asn Lys Ile Lys Gly Cys Thr Gly Ser Leu Asn Met Thr Leu
65                  70                  75                  80

Gln Arg Ala Ser

<210> SEQ ID NO 103
```

```
<211> LENGTH: 133
<212> TYPE: PRT
<213> ORGANISM: Artificial Sequence
<220> FEATURE:
<223> OTHER INFORMATION: Synthetic peptide

<400> SEQUENCE: 103

Thr Leu Val Glu His Ser Lys Leu Tyr Cys Gly His Cys Tyr Tyr Gln
1               5                   10                  15

Thr Val Val Thr Pro Val Ile Glu Gln Ile Leu Pro Asp Ser Pro Gly
            20                  25                  30

Ser His Leu Pro His Thr Val Thr Leu Val Ser Ile Pro Ala Ser Ser
        35                  40                  45

His Gly Lys Arg Gly Leu Ser Val Ser Ile Asp Pro Pro His Gly Pro
    50                  55                  60

Pro Gly Cys Gly Thr Glu His Ser His Thr Val Arg Val Gln Gly Val
65                  70                  75                  80

Asp Pro Gly Cys Met Ser Pro Val Lys Asn Ser Ile His Val Gly
                85                  90                  95

Asp Arg Ile Leu Glu Ile Asn Gly Thr Pro Ile Arg Asn Val Pro Leu
            100                 105                 110

Asp Glu Ile Asp Leu Leu Ile Gln Glu Thr Ser Arg Leu Leu Gln Leu
        115                 120                 125

Thr Leu Glu His Asp
        130

<210> SEQ ID NO 104
<211> LENGTH: 92
<212> TYPE: PRT
<213> ORGANISM: Artificial Sequence
<220> FEATURE:
<223> OTHER INFORMATION: Synthetic peptide

<400> SEQUENCE: 104

Pro Tyr Ser Val Thr Leu Ile Ser Met Pro Ala Thr Thr Glu Gly Arg
1               5                   10                  15

Arg Gly Phe Ser Val Ser Val Glu Ser Ala Cys Ser Asn Tyr Ala Thr
            20                  25                  30

Thr Val Gln Val Lys Glu Val Asn Arg Met His Ile Ser Pro Asn Asn
        35                  40                  45

Arg Asn Ala Ile His Pro Gly Asp Arg Ile Leu Glu Ile Asn Gly Thr
    50                  55                  60

Pro Val Arg Thr Leu Arg Val Glu Glu Val Glu Asp Ala Ile Ser Gln
65                  70                  75                  80

Thr Ser Gln Thr Leu Gln Leu Leu Ile Glu His Asp
                85                  90

<210> SEQ ID NO 105
<211> LENGTH: 82
<212> TYPE: PRT
<213> ORGANISM: Artificial Sequence
<220> FEATURE:
<223> OTHER INFORMATION: Synthetic peptide

<400> SEQUENCE: 105

Ile His Ser Val Thr Leu Arg Gly Pro Ser Pro Trp Gly Phe Arg Leu
1               5                   10                  15

Val Gly Arg Asp Phe Ser Ala Pro Leu Thr Ile Ser Arg Val His Ala
            20                  25                  30
```

-continued

```
Gly Ser Lys Ala Ser Leu Ala Ala Leu Cys Pro Gly Asp Leu Ile Gln
        35                  40                  45

Ala Ile Asn Gly Glu Ser Thr Glu Leu Met Thr His Leu Glu Ala Gln
50                  55                  60

Asn Arg Ile Lys Gly Cys His Asp His Leu Thr Leu Ser Val Ser Arg
65                  70                  75                  80

Pro Glu

<210> SEQ ID NO 106
<211> LENGTH: 74
<212> TYPE: PRT
<213> ORGANISM: Artificial Sequence
<220> FEATURE:
<223> OTHER INFORMATION: Synthetic peptide

<400> SEQUENCE: 106

Val Cys Tyr Arg Thr Asp Asp Glu Glu Asp Leu Gly Ile Tyr Val Gly
1               5                   10                  15

Glu Val Asn Pro Asn Ser Ile Ala Ala Lys Asp Gly Arg Ile Arg Glu
                20                  25                  30

Gly Asp Arg Ile Ile Gln Ile Asn Gly Val Asp Val Gln Asn Arg Glu
        35                  40                  45

Glu Ala Val Ala Ile Leu Ser Gln Glu Glu Asn Thr Asn Ile Ser Leu
    50                  55                  60

Leu Val Ala Arg Pro Glu Ser Gln Leu Ala
65                  70

<210> SEQ ID NO 107
<211> LENGTH: 93
<212> TYPE: PRT
<213> ORGANISM: Artificial Sequence
<220> FEATURE:
<223> OTHER INFORMATION: Synthetic peptide

<400> SEQUENCE: 107

Ile Pro Ala Thr Gln Pro Glu Leu Ile Thr Val His Ile Val Lys Gly
1               5                   10                  15

Pro Met Gly Phe Gly Phe Thr Ile Ala Asp Ser Pro Gly Gly Gly Gly
                20                  25                  30

Gln Arg Val Lys Gln Ile Val Asp Ser Pro Arg Cys Arg Gly Leu Lys
        35                  40                  45

Glu Gly Asp Leu Ile Val Glu Val Asn Lys Lys Asn Val Gln Ala Leu
    50                  55                  60

Thr His Asn Gln Val Val Asp Met Leu Val Glu Cys Pro Lys Gly Ser
65                  70                  75                  80

Glu Val Thr Leu Leu Val Gln Arg Gly Gly Asn Ser Ser
                85                  90

<210> SEQ ID NO 108
<211> LENGTH: 103
<212> TYPE: PRT
<213> ORGANISM: Artificial Sequence
<220> FEATURE:
<223> OTHER INFORMATION: Synthetic peptide

<400> SEQUENCE: 108

Ile Pro Asp Tyr Gln Glu Gln Asp Ile Phe Leu Trp Arg Lys Glu Thr
1               5                   10                  15

Gly Phe Gly Phe Arg Ile Leu Gly Gly Asn Glu Pro Gly Glu Pro Ile
                20                  25                  30
```

Tyr Ile Gly His Ile Val Pro Leu Gly Ala Ala Asp Thr Asp Gly Arg
            35                  40                  45

Leu Arg Ser Gly Asp Glu Leu Ile Cys Val Asp Gly Thr Pro Val Ile
 50                  55                  60

Gly Lys Ser His Gln Leu Val Val Gln Leu Met Gln Gln Ala Ala Lys
 65                  70                  75                  80

Gln Gly His Val Asn Leu Thr Val Arg Arg Lys Val Val Phe Ala Val
                 85                  90                  95

Pro Lys Thr Glu Asn Ser Ser
            100

<210> SEQ ID NO 109
<211> LENGTH: 120
<212> TYPE: PRT
<213> ORGANISM: Artificial Sequence
<220> FEATURE:
<223> OTHER INFORMATION: Synthetic peptide

<400> SEQUENCE: 109

Ile Pro Gly Val Val Ser Thr Val Val Gln Pro Tyr Asp Val Glu Ile
1               5                   10                  15

Arg Arg Gly Glu Asn Glu Gly Phe Gly Phe Val Ile Val Ser Ser Val
            20                  25                  30

Ser Arg Pro Glu Ala Gly Thr Thr Phe Ala Gly Asn Ala Cys Val Ala
        35                  40                  45

Met Pro His Lys Ile Gly Arg Ile Ile Glu Gly Ser Pro Ala Asp Arg
 50                  55                  60

Cys Gly Lys Leu Lys Val Gly Asp Arg Ile Leu Ala Val Asn Gly Cys
 65                  70                  75                  80

Ser Ile Thr Asn Lys Ser His Ser Asp Ile Val Asn Leu Ile Lys Glu
                 85                  90                  95

Ala Gly Asn Thr Val Thr Leu Arg Ile Ile Pro Gly Asp Glu Ser Ser
            100                 105                 110

Asn Ala Glu Phe Ile Val Thr Asp
        115                 120

<210> SEQ ID NO 110
<211> LENGTH: 107
<212> TYPE: PRT
<213> ORGANISM: Artificial Sequence
<220> FEATURE:
<223> OTHER INFORMATION: Synthetic peptide

<400> SEQUENCE: 110

Ile Pro Ser Glu Leu Lys Gly Lys Phe Ile His Thr Lys Leu Arg Lys
1               5                   10                  15

Ser Ser Arg Gly Phe Gly Phe Thr Val Val Gly Gly Asp Glu Pro Asp
            20                  25                  30

Glu Phe Leu Gln Ile Lys Ser Leu Val Leu Asp Gly Pro Ala Ala Leu
        35                  40                  45

Asp Gly Lys Met Glu Thr Gly Asp Val Ile Val Ser Val Asn Asp Thr
 50                  55                  60

Cys Val Leu Gly His Thr His Ala Gln Val Val Lys Ile Phe Gln Ser
 65                  70                  75                  80

Ile Pro Ile Gly Ala Ser Val Asp Leu Glu Leu Cys Arg Gly Tyr Pro
                 85                  90                  95

Leu Pro Phe Asp Pro Asp Gly Ile His Arg Asp

<210> SEQ ID NO 111
<211> LENGTH: 91
<212> TYPE: PRT
<213> ORGANISM: Artificial Sequence
<220> FEATURE:
<223> OTHER INFORMATION: Synthetic peptide

<400> SEQUENCE: 111

Gln Ala Thr Gln Glu Gln Asp Phe Tyr Thr Val Glu Leu Glu Arg Gly
1               5                   10                  15

Ala Lys Gly Phe Gly Phe Ser Leu Arg Gly Gly Arg Glu Tyr Asn Met
            20                  25                  30

Asp Leu Tyr Val Leu Arg Leu Ala Glu Asp Gly Pro Ala Glu Arg Cys
        35                  40                  45

Gly Lys Met Arg Ile Gly Asp Glu Ile Leu Glu Ile Asn Gly Glu Thr
    50                  55                  60

Thr Lys Asn Met Lys His Ser Arg Ala Ile Glu Leu Ile Lys Asn Gly
65                  70                  75                  80

Gly Arg Arg Val Arg Leu Phe Leu Lys Arg Gly
                85                  90

<210> SEQ ID NO 112
<211> LENGTH: 104
<212> TYPE: PRT
<213> ORGANISM: Artificial Sequence
<220> FEATURE:
<223> OTHER INFORMATION: Synthetic peptide

<400> SEQUENCE: 112

Arg Glu Lys Pro Leu Phe Thr Arg Asp Ala Ser Gln Leu Lys Gly Thr
1               5                   10                  15

Phe Leu Ser Thr Thr Leu Lys Lys Ser Asn Met Gly Phe Gly Phe Thr
            20                  25                  30

Ile Ile Gly Gly Asp Glu Pro Asp Glu Phe Leu Gln Val Lys Ser Val
        35                  40                  45

Ile Pro Asp Gly Pro Ala Ala Gln Asp Gly Lys Met Glu Thr Gly Asp
    50                  55                  60

Val Ile Val Tyr Ile Asn Glu Val Cys Val Leu Gly His Thr His Ala
65                  70                  75                  80

Asp Val Val Lys Leu Phe Gln Ser Val Pro Ile Gly Gln Ser Val Asn
                85                  90                  95

Leu Val Leu Cys Arg Gly Tyr Pro
            100

<210> SEQ ID NO 113
<211> LENGTH: 93
<212> TYPE: PRT
<213> ORGANISM: Artificial Sequence
<220> FEATURE:
<223> OTHER INFORMATION: Synthetic peptide

<400> SEQUENCE: 113

His Tyr Lys Glu Leu Asp Val His Leu Arg Arg Met Glu Ser Gly Phe
1               5                   10                  15

Gly Phe Arg Ile Leu Gly Gly Asp Glu Pro Gly Gln Pro Ile Leu Ile
            20                  25                  30

Gly Ala Val Ile Ala Met Gly Ser Ala Asp Arg Asp Gly Arg Leu His
        35                  40                  45

```
Pro Gly Asp Glu Leu Val Tyr Val Asp Gly Ile Pro Val Ala Gly Lys
    50                  55                  60

Thr His Arg Tyr Val Ile Asp Leu Met His His Ala Ala Arg Asn Gly
65                  70                  75                  80

Gln Val Asn Leu Thr Val Arg Arg Lys Val Leu Cys Gly
                85                  90
```

<210> SEQ ID NO 114
<211> LENGTH: 106
<212> TYPE: PRT
<213> ORGANISM: Artificial Sequence
<220> FEATURE:
<223> OTHER INFORMATION: Synthetic peptide

<400> SEQUENCE: 114

```
Glu Gly Arg Gly Ile Ser Ser His Ser Leu Gln Thr Ser Asp Ala Val
1               5                   10                  15

Ile His Arg Lys Glu Asn Glu Gly Phe Gly Phe Val Ile Ile Ser Ser
                20                  25                  30

Leu Asn Arg Pro Glu Ser Gly Ser Thr Ile Thr Val Pro His Lys Ile
            35                  40                  45

Gly Arg Ile Ile Asp Gly Ser Pro Ala Asp Arg Cys Ala Lys Leu Lys
    50                  55                  60

Val Gly Asp Arg Ile Leu Ala Val Asn Gly Gln Ser Ile Ile Asn Met
65                  70                  75                  80

Pro His Ala Asp Ile Val Lys Leu Ile Lys Asp Ala Gly Leu Ser Val
                85                  90                  95

Thr Leu Arg Ile Ile Pro Gln Glu Glu Leu
            100                 105
```

<210> SEQ ID NO 115
<211> LENGTH: 91
<212> TYPE: PRT
<213> ORGANISM: Artificial Sequence
<220> FEATURE:
<223> OTHER INFORMATION: Synthetic peptide

<400> SEQUENCE: 115

```
Leu Ser Gly Ala Thr Gln Ala Glu Leu Met Thr Leu Thr Ile Val Lys
1               5                   10                  15

Gly Ala Gln Gly Phe Gly Phe Thr Ile Ala Asp Ser Pro Thr Gly Gln
                20                  25                  30

Arg Val Lys Gln Ile Leu Asp Ile Gln Gly Cys Pro Gly Leu Cys Glu
            35                  40                  45

Gly Asp Leu Ile Val Glu Ile Asn Gln Gln Asn Val Gln Asn Leu Ser
    50                  55                  60

His Thr Glu Val Val Asp Ile Leu Lys Asp Cys Pro Ile Gly Ser Glu
65                  70                  75                  80

Thr Ser Leu Ile Ile His Arg Gly Gly Phe Phe
                85                  90
```

<210> SEQ ID NO 116
<211> LENGTH: 98
<212> TYPE: PRT
<213> ORGANISM: Artificial Sequence
<220> FEATURE:
<223> OTHER INFORMATION: Synthetic peptide

<400> SEQUENCE: 116

```
Leu Ser Asp Tyr Arg Gln Pro Gln Asp Phe Asp Tyr Phe Thr Val Asp
1               5                   10                  15

Met Glu Lys Gly Ala Lys Gly Phe Gly Phe Ser Ile Arg Gly Gly Arg
                20                  25                  30

Glu Tyr Lys Met Asp Leu Tyr Val Leu Arg Leu Ala Glu Asp Gly Pro
            35                  40                  45

Ala Ile Arg Asn Gly Arg Met Arg Val Gly Asp Gln Ile Ile Glu Ile
    50                  55                  60

Asn Gly Glu Ser Thr Arg Asp Met Thr His Ala Arg Ala Ile Glu Leu
65                  70                  75                  80

Ile Lys Ser Gly Gly Arg Arg Val Arg Leu Leu Leu Lys Arg Gly Thr
                85                  90                  95

Gly Gln

<210> SEQ ID NO 117
<211> LENGTH: 90
<212> TYPE: PRT
<213> ORGANISM: Artificial Sequence
<220> FEATURE:
<223> OTHER INFORMATION: Synthetic peptide

<400> SEQUENCE: 117

His Glu Ser Val Ile Gly Arg Asn Pro Glu Gly Gln Leu Gly Phe Glu
1               5                   10                  15

Leu Lys Gly Gly Ala Glu Asn Gly Gln Phe Pro Tyr Leu Gly Glu Val
                20                  25                  30

Lys Pro Gly Lys Val Ala Tyr Glu Ser Gly Ser Lys Leu Val Ser Glu
            35                  40                  45

Glu Leu Leu Leu Glu Val Asn Glu Thr Pro Val Ala Gly Leu Thr Ile
    50                  55                  60

Arg Asp Val Leu Ala Val Ile Lys His Cys Lys Asp Pro Leu Arg Leu
65                  70                  75                  80

Lys Cys Val Lys Gln Gly Gly Ile His Arg
                85                  90

<210> SEQ ID NO 118
<211> LENGTH: 100
<212> TYPE: PRT
<213> ORGANISM: Artificial Sequence
<220> FEATURE:
<223> OTHER INFORMATION: Synthetic peptide

<400> SEQUENCE: 118

Ala Ser Ser Gly Ser Ser Gln Pro Glu Leu Val Thr Ile Pro Leu Ile
1               5                   10                  15

Lys Gly Pro Lys Gly Phe Gly Phe Ala Ile Ala Asp Ser Pro Thr Gly
                20                  25                  30

Gln Lys Val Lys Met Ile Leu Asp Ser Gln Trp Cys Gln Gly Leu Gln
            35                  40                  45

Lys Gly Asp Ile Ile Lys Glu Ile Tyr His Gln Asn Val Gln Asn Leu
    50                  55                  60

Thr His Leu Gln Val Val Glu Val Leu Lys Gln Phe Pro Val Gly Ala
65                  70                  75                  80

Asp Val Pro Leu Leu Ile Leu Arg Gly Gly Pro Pro Ser Pro Thr Lys
                85                  90                  95

Thr Ala Lys Met
            100
```

```
<210> SEQ ID NO 119
<211> LENGTH: 98
<212> TYPE: PRT
<213> ORGANISM: Artificial Sequence
<220> FEATURE:
<223> OTHER INFORMATION: Synthetic peptide

<400> SEQUENCE: 119

Gln Asn Leu Gly Cys Tyr Pro Val Glu Leu Glu Arg Gly Pro Arg Gly
1               5                   10                  15

Phe Gly Phe Ser Leu Arg Gly Gly Lys Glu Tyr Asn Met Gly Leu Phe
            20                  25                  30

Ile Leu Arg Leu Ala Glu Asp Gly Pro Ala Ile Lys Asp Gly Arg Ile
        35                  40                  45

His Val Gly Asp Gln Ile Val Glu Ile Asn Gly Glu Pro Thr Gln Gly
    50                  55                  60

Ile Thr His Thr Arg Ala Ile Glu Leu Ile Gln Ala Gly Gly Asn Lys
65                  70                  75                  80

Val Leu Leu Leu Arg Pro Gly Thr Gly Leu Ile Pro Asp His Gly
                85                  90                  95

Leu Ala

<210> SEQ ID NO 120
<211> LENGTH: 108
<212> TYPE: PRT
<213> ORGANISM: Artificial Sequence
<220> FEATURE:
<223> OTHER INFORMATION: Synthetic peptide

<400> SEQUENCE: 120

Leu Tyr Glu Asp Lys Pro Pro Asn Thr Lys Asp Leu Asp Val Phe Leu
1               5                   10                  15

Arg Lys Gln Glu Ser Gly Phe Gly Phe Arg Val Leu Gly Gly Asp Gly
            20                  25                  30

Pro Asp Gln Ser Ile Tyr Ile Gly Ala Ile Ile Pro Leu Gly Ala Ala
        35                  40                  45

Glu Lys Asp Gly Arg Leu Arg Ala Ala Asp Glu Leu Met Cys Ile Asp
    50                  55                  60

Gly Ile Pro Val Lys Gly Lys Ser His Lys Gln Val Leu Asp Leu Met
65                  70                  75                  80

Thr Thr Ala Ala Arg Asn Gly His Val Leu Leu Thr Val Arg Arg Lys
                85                  90                  95

Ile Phe Tyr Gly Glu Lys Gln Pro Glu Asp Asp Ser
            100                 105

<210> SEQ ID NO 121
<211> LENGTH: 102
<212> TYPE: PRT
<213> ORGANISM: Artificial Sequence
<220> FEATURE:
<223> OTHER INFORMATION: Synthetic peptide

<400> SEQUENCE: 121

Pro Ser Gln Leu Lys Gly Val Leu Val Arg Ala Ser Leu Lys Lys Ser
1               5                   10                  15

Thr Met Gly Phe Gly Phe Thr Ile Ile Gly Gly Asp Arg Pro Asp Glu
            20                  25                  30

Phe Leu Gln Val Lys Asn Val Leu Lys Asp Gly Pro Ala Ala Gln Asp
        35                  40                  45
```

```
Gly Lys Ile Ala Pro Gly Asp Val Ile Val Asp Ile Asn Gly Asn Cys
 50                  55                  60

Val Leu Gly His Thr His Ala Asp Val Val Gln Met Phe Gln Leu Val
 65                  70                  75                  80

Pro Val Asn Gln Tyr Val Asn Leu Thr Leu Cys Arg Gly Tyr Pro Leu
                 85                  90                  95

Pro Asp Asp Ser Glu Asp
            100

<210> SEQ ID NO 122
<211> LENGTH: 102
<212> TYPE: PRT
<213> ORGANISM: Artificial Sequence
<220> FEATURE:
<223> OTHER INFORMATION: Synthetic peptide

<400> SEQUENCE: 122

Pro Ala Pro Gln Glu Pro Tyr Asp Val Val Leu Gln Arg Lys Glu Asn
1               5                   10                  15

Glu Gly Phe Gly Phe Val Ile Leu Thr Ser Lys Asn Lys Pro Pro Pro
            20                  25                  30

Gly Val Ile Pro His Lys Ile Gly Arg Val Ile Glu Gly Ser Pro Ala
        35                  40                  45

Asp Arg Cys Gly Lys Leu Lys Val Gly Asp His Ile Ser Ala Val Asn
 50                  55                  60

Gly Gln Ser Ile Val Glu Leu Ser His Asp Asn Ile Val Gln Leu Ile
 65                  70                  75                  80

Lys Asp Ala Gly Val Thr Val Thr Leu Thr Val Ile Ala Glu Glu Glu
                 85                  90                  95

His His Gly Pro Pro Ser
            100

<210> SEQ ID NO 123
<211> LENGTH: 94
<212> TYPE: PRT
<213> ORGANISM: Artificial Sequence
<220> FEATURE:
<223> OTHER INFORMATION: Synthetic peptide

<400> SEQUENCE: 123

Gly Leu Arg Ser Pro Ile Thr Ile Gln Arg Ser Gly Lys Lys Tyr Gly
1               5                   10                  15

Phe Thr Leu Arg Ala Ile Arg Val Tyr Met Gly Asp Thr Asp Val Tyr
            20                  25                  30

Ser Val His His Ile Val Trp His Val Glu Gly Gly Pro Ala Gln
        35                  40                  45

Glu Ala Gly Leu Cys Ala Gly Asp Leu Ile Thr His Val Asn Gly Glu
 50                  55                  60

Pro Val His Gly Met Val His Pro Glu Val Val Glu Leu Ile Leu Lys
 65                  70                  75                  80

Ser Gly Asn Lys Val Ala Val Thr Thr Thr Pro Phe Glu Asn
                 85                  90

<210> SEQ ID NO 124
<211> LENGTH: 101
<212> TYPE: PRT
<213> ORGANISM: Artificial Sequence
<220> FEATURE:
<223> OTHER INFORMATION: Synthetic peptide
```

```
<400> SEQUENCE: 124

Ile Ser Ala Leu Gly Ser Met Arg Pro Ile Ile His Arg Ala
1               5                   10                  15

Gly Lys Lys Tyr Gly Phe Thr Leu Arg Ala Ile Arg Val Tyr Met Gly
                20                  25                  30

Asp Ser Asp Val Tyr Thr Val His His Met Val Trp His Val Glu Asp
            35                  40                  45

Gly Gly Pro Ala Ser Glu Ala Gly Leu Arg Gln Gly Asp Leu Ile Thr
        50                  55                  60

His Val Asn Gly Glu Pro Val His Gly Leu Val His Thr Glu Val Val
65                  70                  75                  80

Glu Leu Ile Leu Lys Ser Gly Asn Lys Val Ala Ile Ser Thr Thr Pro
                85                  90                  95

Leu Glu Asn Ser Ser
            100

<210> SEQ ID NO 125
<211> LENGTH: 103
<212> TYPE: PRT
<213> ORGANISM: Artificial Sequence
<220> FEATURE:
<223> OTHER INFORMATION: Synthetic peptide

<400> SEQUENCE: 125

Leu Cys Gly Ser Leu Arg Pro Pro Ile Val Ile His Ser Ser Gly Lys
1               5                   10                  15

Lys Tyr Gly Phe Ser Leu Arg Ala Ile Arg Val Tyr Met Gly Asp Ser
                20                  25                  30

Asp Val Tyr Thr Val His His Val Trp Ser Val Glu Asp Gly Ser
            35                  40                  45

Pro Ala Gln Glu Ala Gly Leu Arg Ala Gly Asp Leu Ile Thr His Ile
        50                  55                  60

Asn Gly Glu Ser Val Leu Gly Leu Val His Met Asp Val Val Glu Leu
65                  70                  75                  80

Leu Leu Lys Ser Gly Asn Lys Ile Ser Leu Arg Thr Thr Ala Leu Glu
                85                  90                  95

Asn Thr Ser Ile Lys Val Gly
            100

<210> SEQ ID NO 126
<211> LENGTH: 91
<212> TYPE: PRT
<213> ORGANISM: Artificial Sequence
<220> FEATURE:
<223> OTHER INFORMATION: Synthetic peptide

<400> SEQUENCE: 126

Pro His Gln Pro Ile Val Ile His Ser Ser Gly Lys Asn Tyr Gly Phe
1               5                   10                  15

Thr Ile Arg Ala Ile Arg Val Tyr Val Gly Asp Ser Asp Ile Tyr Thr
                20                  25                  30

Val His His Ile Val Trp Asn Val Glu Glu Gly Ser Pro Ala Cys Gln
            35                  40                  45

Ala Gly Leu Lys Ala Gly Asp Leu Ile Thr His Ile Asn Gly Glu Pro
        50                  55                  60

Val His Gly Leu Val His Thr Glu Val Ile Glu Leu Leu Leu Lys Ser
65                  70                  75                  80
```

```
Gly Asn Lys Val Ser Ile Thr Thr Thr Pro Phe
                85                  90
```

<210> SEQ ID NO 127
<211> LENGTH: 100
<212> TYPE: PRT
<213> ORGANISM: Artificial Sequence
<220> FEATURE:
<223> OTHER INFORMATION: Synthetic peptide

<400> SEQUENCE: 127

```
Pro Ala Lys Met Glu Lys Glu Glu Thr Thr Arg Glu Leu Leu Leu Pro
1               5                   10                  15

Asn Trp Gln Gly Ser Gly Ser His Gly Leu Thr Ile Ala Gln Arg Asp
                20                  25                  30

Asp Gly Val Phe Val Gln Glu Val Thr Gln Asn Ser Pro Ala Ala Arg
            35                  40                  45

Thr Gly Val Val Lys Glu Gly Asp Gln Ile Val Gly Ala Thr Ile Tyr
        50                  55                  60

Phe Asp Asn Leu Gln Ser Gly Glu Val Thr Gln Leu Leu Asn Thr Met
65                  70                  75                  80

Gly His His Thr Val Gly Leu Lys Leu His Arg Lys Gly Asp Arg Ser
                85                  90                  95

Pro Asn Ser Ser
            100
```

<210> SEQ ID NO 128
<211> LENGTH: 98
<212> TYPE: PRT
<213> ORGANISM: Artificial Sequence
<220> FEATURE:
<223> OTHER INFORMATION: Synthetic peptide

<400> SEQUENCE: 128

```
Ser Glu Asn Cys Lys Asp Val Phe Ile Glu Lys Gln Lys Gly Glu Ile
1               5                   10                  15

Leu Gly Val Val Ile Val Glu Ser Gly Trp Gly Ser Ile Leu Pro Thr
                20                  25                  30

Val Ile Ile Ala Asn Met Met His Gly Gly Pro Ala Glu Lys Ser Gly
            35                  40                  45

Lys Leu Asn Ile Gly Asp Gln Ile Met Ser Ile Asn Gly Thr Ser Leu
        50                  55                  60

Val Gly Leu Pro Leu Ser Thr Cys Gln Ser Ile Ile Lys Gly Leu Lys
65                  70                  75                  80

Asn Gln Ser Arg Val Lys Leu Asn Ile Val Arg Cys Pro Pro Val Asn
                85                  90                  95

Ser Ser
```

<210> SEQ ID NO 129
<211> LENGTH: 178
<212> TYPE: PRT
<213> ORGANISM: Artificial Sequence
<220> FEATURE:
<223> OTHER INFORMATION: Synthetic peptide

<400> SEQUENCE: 129

```
Ser Glu Asn Cys Lys Asp Val Phe Ile Glu Lys Gln Lys Gly Glu Ile
1               5                   10                  15

Leu Gly Val Val Ile Val Glu Ser Gly Trp Gly Ser Ile Leu Pro Thr
```

-continued

```
                 20                  25                  30
Val Ile Ile Ala Asn Met Met His Gly Gly Pro Ala Glu Lys Ser Gly
             35                  40                  45

Lys Leu Asn Ile Gly Asp Gln Ile Met Ser Ile Asn Gly Thr Ser Leu
     50                  55                  60

Val Gly Leu Pro Leu Ser Thr Cys Gln Ser Ile Ile Lys Gly Leu Glu
 65                  70                  75                  80

Asn Gln Ser Arg Val Lys Leu Asn Ile Val Arg Cys Pro Pro Val Thr
                 85                  90                  95

Thr Val Leu Ile Arg Arg Pro Asp Leu Arg Tyr Gln Leu Gly Phe Ser
            100                 105                 110

Val Gln Asn Gly Ile Ile Cys Ser Leu Met Arg Gly Gly Ile Ala Glu
            115                 120                 125

Arg Gly Gly Val Arg Val Gly His Arg Ile Ile Glu Ile Asn Gly Gln
        130                 135                 140

Ser Val Val Ala Thr Pro His Glu Lys Ile Val His Ile Leu Ser Asn
145                 150                 155                 160

Ala Val Gly Glu Ile His Met Lys Thr Met Pro Ala Ala Met Tyr Arg
                165                 170                 175

Leu Leu

<210> SEQ ID NO 130
<211> LENGTH: 92
<212> TYPE: PRT
<213> ORGANISM: Artificial Sequence
<220> FEATURE:
<223> OTHER INFORMATION: Synthetic peptide

<400> SEQUENCE: 130

Leu Arg Cys Pro Pro Val Thr Thr Val Leu Ile Arg Arg Pro Asp Leu
 1               5                  10                  15

Arg Tyr Gln Leu Gly Phe Ser Val Gln Asn Gly Ile Ile Cys Ser Leu
                 20                  25                  30

Met Arg Gly Gly Ile Ala Glu Arg Gly Gly Val Arg Val Gly His Arg
             35                  40                  45

Ile Ile Glu Ile Asn Gly Gln Ser Val Val Ala Thr Pro His Glu Lys
     50                  55                  60

Ile Val His Ile Leu Ser Asn Ala Val Gly Glu Ile His Met Lys Thr
 65                  70                  75                  80

Met Pro Ala Ala Met Tyr Arg Leu Leu Asn Ser Ser
                 85                  90

<210> SEQ ID NO 131
<211> LENGTH: 106
<212> TYPE: PRT
<213> ORGANISM: Artificial Sequence
<220> FEATURE:
<223> OTHER INFORMATION: Synthetic peptide

<400> SEQUENCE: 131

His Asn Gly Asp Leu Asp His Phe Ser Asn Ser Asp Asn Cys Arg Glu
 1               5                  10                  15

Val His Leu Glu Lys Arg Arg Gly Glu Gly Leu Gly Val Ala Leu Val
                 20                  25                  30

Glu Ser Gly Trp Gly Ser Leu Leu Pro Thr Ala Val Ile Ala Asn Leu
             35                  40                  45

Leu His Gly Gly Pro Ala Glu Arg Ser Gly Ala Leu Ser Ile Gly Asp
```

```
                50                  55                  60
Arg Leu Thr Ala Ile Asn Gly Thr Ser Leu Val Gly Leu Pro Leu Ala
 65                  70                  75                  80

Ala Cys Gln Ala Ala Val Arg Glu Thr Lys Ser Gln Thr Ser Val Thr
                 85                  90                  95

Leu Ser Ile Val His Cys Pro Pro Val Thr
            100                 105

<210> SEQ ID NO 132
<211> LENGTH: 90
<212> TYPE: PRT
<213> ORGANISM: Artificial Sequence
<220> FEATURE:
<223> OTHER INFORMATION: Synthetic peptide

<400> SEQUENCE: 132

Pro Val Thr Thr Ala Ile Ile His Arg Pro His Ala Arg Glu Gln Leu
  1               5                  10                  15

Gly Phe Cys Val Glu Asp Gly Ile Ile Cys Ser Leu Leu Arg Gly Gly
                 20                  25                  30

Ile Ala Glu Arg Gly Gly Ile Arg Val Gly His Arg Ile Ile Glu Ile
             35                  40                  45

Asn Gly Gln Ser Val Val Ala Thr Pro His Ala Arg Ile Ile Glu Leu
         50                  55                  60

Leu Thr Glu Ala Tyr Gly Glu Val His Ile Lys Thr Met Pro Ala Ala
 65                  70                  75                  80

Thr Tyr Arg Leu Leu Thr Gly Asn Ser Ser
                 85                  90

<210> SEQ ID NO 133
<211> LENGTH: 103
<212> TYPE: PRT
<213> ORGANISM: Artificial Sequence
<220> FEATURE:
<223> OTHER INFORMATION: Synthetic peptide

<400> SEQUENCE: 133

Leu Ser Asn Ser Asp Asn Cys Arg Glu Val His Leu Glu Lys Arg Arg
  1               5                  10                  15

Gly Glu Gly Leu Gly Val Ala Leu Val Glu Ser Gly Trp Gly Ser Leu
                 20                  25                  30

Leu Pro Thr Ala Val Ile Ala Asn Leu Leu His Gly Gly Pro Ala Glu
             35                  40                  45

Arg Ser Gly Ala Leu Ser Ile Gly Asp Arg Leu Thr Ala Ile Asn Gly
         50                  55                  60

Thr Ser Leu Val Gly Leu Pro Leu Ala Ala Cys Gln Ala Ala Val Arg
 65                  70                  75                  80

Glu Thr Lys Ser Gln Thr Ser Val Thr Leu Ser Ile Val His Cys Pro
                 85                  90                  95

Pro Val Thr Thr Ala Ile Met
            100

<210> SEQ ID NO 134
<211> LENGTH: 86
<212> TYPE: PRT
<213> ORGANISM: Artificial Sequence
<220> FEATURE:
<223> OTHER INFORMATION: Synthetic peptide

<400> SEQUENCE: 134
```

```
Arg Lys Val Arg Leu Ile Gln Phe Glu Lys Val Thr Glu Pro Met
1               5                   10                  15

Gly Ile Thr Leu Lys Leu Asn Glu Lys Gln Ser Cys Thr Val Ala Arg
                20                  25                  30

Ile Leu His Gly Gly Met Ile His Arg Gln Gly Ser Leu His Val Gly
            35                  40                  45

Asp Glu Ile Leu Glu Ile Asn Gly Thr Asn Val Thr Asn His Ser Val
    50                  55                  60

Asp Gln Leu Gln Lys Ala Met Lys Glu Thr Lys Gly Met Ile Ser Leu
65                  70                  75                  80

Lys Val Ile Pro Asn Gln
                85

<210> SEQ ID NO 135
<211> LENGTH: 89
<212> TYPE: PRT
<213> ORGANISM: Artificial Sequence
<220> FEATURE:
<223> OTHER INFORMATION: Synthetic peptide

<400> SEQUENCE: 135

Pro Val Pro Pro Asp Ala Val Arg Met Val Gly Ile Arg Lys Thr Ala
1               5                   10                  15

Gly Glu His Leu Gly Val Thr Phe Arg Val Glu Gly Gly Glu Leu Val
                20                  25                  30

Ile Ala Arg Ile Leu His Gly Gly Met Val Ala Gln Gln Gly Leu Leu
            35                  40                  45

His Val Gly Asp Ile Ile Lys Glu Val Asn Gly Gln Pro Val Gly Ser
    50                  55                  60

Asp Pro Arg Ala Leu Gln Glu Leu Leu Arg Asn Ala Ser Gly Ser Val
65                  70                  75                  80

Ile Leu Lys Ile Leu Pro Asn Tyr Gln
                85

<210> SEQ ID NO 136
<211> LENGTH: 99
<212> TYPE: PRT
<213> ORGANISM: Artificial Sequence
<220> FEATURE:
<223> OTHER INFORMATION: Synthetic peptide

<400> SEQUENCE: 136

Asn Ile Asp Glu Asp Phe Asp Glu Glu Ser Val Lys Ile Val Arg Leu
1               5                   10                  15

Val Lys Asn Lys Glu Pro Leu Gly Ala Thr Ile Arg Arg Asp Glu His
                20                  25                  30

Ser Gly Ala Val Val Ala Arg Ile Met Arg Gly Gly Ala Ala Asp
            35                  40                  45

Arg Ser Gly Leu Val His Val Gly Asp Glu Leu Arg Glu Val Asn Gly
    50                  55                  60

Ile Ala Val Leu His Lys Arg Pro Asp Glu Ile Ser Gln Ile Leu Ala
65                  70                  75                  80

Gln Ser Gln Gly Ser Ile Thr Leu Lys Ile Ile Pro Ala Thr Gln Glu
                85                  90                  95

Glu Asp Arg

<210> SEQ ID NO 137
```

```
<211> LENGTH: 100
<212> TYPE: PRT
<213> ORGANISM: Artificial Sequence
<220> FEATURE:
<223> OTHER INFORMATION: Synthetic peptide

<400> SEQUENCE: 137

Trp Glu Ala Gly Ile Gln His Ile Glu Leu Glu Lys Gly Ser Lys Gly
1               5                   10                  15

Leu Gly Phe Ser Ile Leu Asp Tyr Gln Asp Pro Ile Asp Pro Ala Ser
            20                  25                  30

Thr Val Ile Ile Ile Arg Ser Leu Val Pro Gly Gly Ile Ala Glu Lys
        35                  40                  45

Asp Gly Arg Leu Leu Pro Gly Asp Arg Leu Met Phe Val Asn Asp Val
    50                  55                  60

Asn Leu Glu Asn Ser Ser Leu Glu Glu Ala Val Ala Leu Lys Gly
65                  70                  75                  80

Ala Pro Ser Gly Thr Val Arg Ile Gly Val Ala Lys Pro Leu Pro Leu
                85                  90                  95

Ser Pro Glu Glu
            100

<210> SEQ ID NO 138
<211> LENGTH: 96
<212> TYPE: PRT
<213> ORGANISM: Artificial Sequence
<220> FEATURE:
<223> OTHER INFORMATION: Synthetic peptide

<400> SEQUENCE: 138

Leu Gln Gly Leu Arg Thr Val Glu Met Lys Lys Gly Pro Thr Asp Ser
1               5                   10                  15

Leu Gly Ile Ser Ile Ala Gly Gly Val Gly Ser Pro Leu Gly Asp Val
            20                  25                  30

Pro Ile Phe Ile Ala Met Met His Pro Thr Gly Val Ala Ala Gln Thr
        35                  40                  45

Gln Lys Leu Arg Val Gly Asp Arg Ile Val Thr Ile Cys Gly Thr Ser
    50                  55                  60

Thr Glu Gly Met Thr His Thr Gln Ala Val Asn Leu Leu Lys Asn Ala
65                  70                  75                  80

Ser Gly Ser Ile Glu Met Gln Val Val Ala Gly Gly Asp Val Ser Val
                85                  90                  95

<210> SEQ ID NO 139
<211> LENGTH: 97
<212> TYPE: PRT
<213> ORGANISM: Artificial Sequence
<220> FEATURE:
<223> OTHER INFORMATION: Synthetic peptide

<400> SEQUENCE: 139

Pro Val His Trp Gln His Met Glu Thr Ile Glu Leu Val Asn Asp Gly
1               5                   10                  15

Ser Gly Leu Gly Phe Gly Ile Ile Gly Gly Lys Ala Thr Gly Val Ile
            20                  25                  30

Val Lys Thr Ile Leu Pro Gly Gly Val Ala Asp Gln His Gly Arg Leu
        35                  40                  45

Cys Ser Gly Asp His Ile Leu Lys Ile Gly Asp Thr Asp Leu Ala Gly
    50                  55                  60
```

```
Met Ser Ser Glu Gln Val Ala Gln Val Leu Arg Gln Cys Gly Asn Arg
 65                  70                  75                  80

Val Lys Leu Met Ile Ala Arg Gly Ala Ile Glu Arg Thr Ala Pro
                 85                  90                  95

Thr

<210> SEQ ID NO 140
<211> LENGTH: 98
<212> TYPE: PRT
<213> ORGANISM: Artificial Sequence
<220> FEATURE:
<223> OTHER INFORMATION: Synthetic peptide

<400> SEQUENCE: 140

Gln Glu Ser Glu Thr Phe Asp Val Glu Leu Thr Lys Asn Val Gln Gly
  1               5                  10                  15

Leu Gly Ile Thr Ile Ala Gly Tyr Ile Gly Asp Lys Lys Leu Glu Pro
                 20                  25                  30

Ser Gly Ile Phe Val Lys Ser Ile Thr Lys Ser Ser Ala Val Glu His
             35                  40                  45

Asp Gly Arg Ile Gln Ile Gly Asp Gln Ile Ile Ala Val Asp Gly Thr
 50                  55                  60

Asn Leu Gln Gly Phe Thr Asn Gln Gln Ala Val Glu Val Leu Arg His
 65                  70                  75                  80

Thr Gly Gln Thr Val Leu Leu Thr Leu Met Arg Arg Gly Met Lys Gln
                 85                  90                  95

Glu Ala

<210> SEQ ID NO 141
<211> LENGTH: 98
<212> TYPE: PRT
<213> ORGANISM: Artificial Sequence
<220> FEATURE:
<223> OTHER INFORMATION: Synthetic peptide

<400> SEQUENCE: 141

Lys Glu Glu Val Cys Asp Thr Leu Thr Ile Glu Leu Gln Lys Lys
  1               5                  10                  15

Pro Gly Lys Gly Leu Gly Leu Ser Ile Val Gly Lys Arg Asn Asp Thr
                 20                  25                  30

Gly Val Phe Val Ser Asp Ile Val Lys Gly Gly Ile Ala Asp Ala Asp
             35                  40                  45

Gly Arg Leu Met Gln Gly Asp Gln Ile Leu Met Val Asn Gly Glu Asp
 50                  55                  60

Val Arg Asn Ala Thr Gln Glu Ala Val Ala Ala Leu Leu Lys Cys Ser
 65                  70                  75                  80

Leu Gly Thr Val Thr Leu Glu Val Gly Arg Ile Lys Ala Gly Pro Phe
                 85                  90                  95

His Ser

<210> SEQ ID NO 142
<211> LENGTH: 95
<212> TYPE: PRT
<213> ORGANISM: Artificial Sequence
<220> FEATURE:
<223> OTHER INFORMATION: Synthetic peptide

<400> SEQUENCE: 142

Leu Thr Gly Glu Leu His Met Ile Glu Leu Glu Lys Gly His Ser Gly
```

```
                1               5                  10                 15
Leu Gly Leu Ser Leu Ala Gly Asn Lys Asp Arg Ser Arg Met Ser Val
                    20                  25                  30

Phe Ile Val Gly Ile Asp Pro Asn Gly Ala Ala Gly Lys Asp Gly Arg
                    35                  40                  45

Leu Gln Ile Ala Asp Glu Leu Leu Glu Ile Asn Gly Gln Ile Leu Tyr
                    50                  55                  60

Gly Arg Ser His Gln Asn Ala Ser Ser Ile Ile Lys Cys Ala Pro Ser
 65                     70                  75                  80

Lys Val Lys Ile Ile Phe Ile Arg Asn Lys Asp Ala Val Asn Gln
                    85                  90                  95

<210> SEQ ID NO 143
<211> LENGTH: 91
<212> TYPE: PRT
<213> ORGANISM: Artificial Sequence
<220> FEATURE:
<223> OTHER INFORMATION: Synthetic peptide

<400> SEQUENCE: 143

Leu Gly Pro Pro Gln Cys Lys Ser Ile Thr Leu Glu Arg Gly Pro Asp
 1               5                  10                  15

Gly Leu Gly Phe Ser Ile Val Gly Gly Tyr Gly Ser Pro His Gly Asp
                    20                  25                  30

Leu Pro Ile Tyr Val Lys Thr Val Phe Ala Lys Gly Ala Ala Ser Glu
                    35                  40                  45

Asp Gly Arg Leu Lys Arg Gly Asp Gln Ile Ile Ala Val Asn Gly Gln
                    50                  55                  60

Ser Leu Glu Gly Val Thr His Glu Glu Ala Val Ala Ile Leu Lys Arg
 65                     70                  75                  80

Thr Lys Gly Thr Val Thr Leu Met Val Leu Ser
                    85                  90

<210> SEQ ID NO 144
<211> LENGTH: 99
<212> TYPE: PRT
<213> ORGANISM: Artificial Sequence
<220> FEATURE:
<223> OTHER INFORMATION: Synthetic peptide

<400> SEQUENCE: 144

Arg Asn Val Ser Lys Glu Ser Phe Glu Arg Thr Ile Asn Ile Ala Lys
 1               5                  10                  15

Gly Asn Ser Ser Leu Gly Met Thr Val Ser Ala Asn Lys Asp Gly Leu
                    20                  25                  30

Gly Met Ile Val Arg Ser Ile Ile His Gly Gly Ala Ile Ser Arg Asp
                    35                  40                  45

Gly Arg Ile Ala Ile Gly Asp Cys Ile Leu Ser Ile Asn Glu Glu Ser
                    50                  55                  60

Thr Ile Ser Val Thr Asn Ala Gln Ala Arg Ala Met Leu Arg Arg His
 65                     70                  75                  80

Ser Leu Ile Gly Pro Asp Ile Lys Ile Thr Tyr Val Pro Ala Glu His
                    85                  90                  95

Leu Glu Glu

<210> SEQ ID NO 145
<211> LENGTH: 95
<212> TYPE: PRT
```

```
<213> ORGANISM: Artificial Sequence
<220> FEATURE:
<223> OTHER INFORMATION: Synthetic peptide

<400> SEQUENCE: 145

Leu Pro Gly Cys Glu Thr Thr Ile Glu Ile Ser Lys Gly Arg Thr Gly
1               5                   10                  15

Leu Gly Leu Ser Ile Val Gly Gly Ser Asp Thr Leu Gly Ala Ile
            20                  25                  30

Ile Ile His Glu Val Tyr Glu Glu Gly Ala Ala Cys Lys Asp Gly Arg
            35                  40                  45

Leu Trp Ala Gly Asp Gln Ile Leu Glu Val Asn Gly Ile Asp Leu Arg
    50                  55                  60

Lys Ala Thr His Asp Glu Ala Ile Asn Val Leu Arg Gln Thr Pro Gln
65                  70                  75                  80

Arg Val Arg Leu Thr Leu Tyr Arg Asp Glu Ala Pro Tyr Lys Glu
                85                  90                  95

<210> SEQ ID NO 146
<211> LENGTH: 112
<212> TYPE: PRT
<213> ORGANISM: Artificial Sequence
<220> FEATURE:
<223> OTHER INFORMATION: Synthetic peptide

<400> SEQUENCE: 146

Leu Asn Trp Asn Gln Pro Arg Arg Val Glu Leu Trp Arg Glu Pro Ser
1               5                   10                  15

Lys Ser Leu Gly Ile Ser Ile Val Gly Gly Arg Gly Met Gly Ser Arg
            20                  25                  30

Leu Ser Asn Gly Glu Val Met Arg Gly Ile Phe Ile Lys His Val Leu
            35                  40                  45

Glu Asp Ser Pro Ala Gly Lys Asn Gly Thr Leu Lys Pro Gly Asp Arg
    50                  55                  60

Ile Val Glu Val Asp Gly Met Asp Leu Arg Asp Ala Ser His Glu Gln
65                  70                  75                  80

Ala Val Glu Ala Ile Arg Lys Ala Gly Asn Pro Val Val Phe Met Val
                85                  90                  95

Gln Ser Ile Ile Asn Arg Pro Arg Lys Ser Pro Leu Pro Ser Leu Leu
                100                 105                 110

<210> SEQ ID NO 147
<211> LENGTH: 94
<212> TYPE: PRT
<213> ORGANISM: Artificial Sequence
<220> FEATURE:
<223> OTHER INFORMATION: Synthetic peptide

<400> SEQUENCE: 147

Leu Ser Ser Phe Lys Asn Val Gln His Leu Glu Leu Pro Lys Asp Gln
1               5                   10                  15

Gly Gly Leu Gly Ile Ala Ile Ser Glu Glu Asp Thr Leu Ser Gly Val
            20                  25                  30

Ile Ile Lys Ser Leu Thr Glu His Gly Val Ala Thr Asp Gly Arg
            35                  40                  45

Leu Lys Val Gly Asp Gln Ile Leu Ala Val Asp Asp Glu Ile Val Val
    50                  55                  60

Gly Tyr Pro Ile Glu Lys Phe Ile Ser Leu Leu Lys Thr Ala Lys Met
65                  70                  75                  80
```

```
Thr Val Lys Leu Thr Ile His Ala Glu Asn Pro Asp Ser Gln
                85                  90

<210> SEQ ID NO 148
<211> LENGTH: 99
<212> TYPE: PRT
<213> ORGANISM: Artificial Sequence
<220> FEATURE:
<223> OTHER INFORMATION: Synthetic peptide

<400> SEQUENCE: 148

Gln Gly Arg His Val Glu Val Phe Glu Leu Leu Lys Pro Pro Ser Gly
1               5                   10                  15

Gly Leu Gly Phe Ser Val Val Gly Leu Arg Ser Glu Asn Arg Gly Glu
            20                  25                  30

Leu Gly Ile Phe Val Gln Glu Ile Gln Glu Gly Ser Val Ala His Arg
        35                  40                  45

Asp Gly Arg Leu Lys Glu Thr Asp Gln Ile Leu Ala Ile Asn Gly Gln
    50                  55                  60

Ala Leu Asp Gln Thr Ile Thr His Gln Gln Ala Ile Ser Ile Leu Gln
65                  70                  75                  80

Lys Ala Lys Asp Thr Val Gln Leu Val Ile Ala Arg Gly Ser Leu Pro
                85                  90                  95

Gln Leu Val

<210> SEQ ID NO 149
<211> LENGTH: 92
<212> TYPE: PRT
<213> ORGANISM: Artificial Sequence
<220> FEATURE:
<223> OTHER INFORMATION: Synthetic peptide

<400> SEQUENCE: 149

Leu Asn Tyr Glu Ile Val Val Ala His Val Ser Lys Phe Ser Glu Asn
1               5                   10                  15

Ser Gly Leu Gly Ile Ser Leu Glu Ala Thr Val Gly His His Phe Ile
            20                  25                  30

Arg Ser Val Leu Pro Glu Gly Pro Val Gly His Ser Gly Lys Leu Phe
        35                  40                  45

Ser Gly Asp Glu Leu Leu Glu Val Asn Gly Ile Thr Leu Leu Gly Glu
    50                  55                  60

Asn His Gln Asp Val Val Asn Ile Leu Lys Glu Leu Pro Ile Glu Val
65                  70                  75                  80

Thr Met Val Cys Cys Arg Arg Thr Val Pro Pro Thr
                85                  90

<210> SEQ ID NO 150
<211> LENGTH: 90
<212> TYPE: PRT
<213> ORGANISM: Artificial Sequence
<220> FEATURE:
<223> OTHER INFORMATION: Synthetic peptide

<400> SEQUENCE: 150

Ile Thr Leu Leu Lys Gly Pro Lys Gly Leu Gly Phe Ser Ile Ala Gly
1               5                   10                  15

Gly Ile Gly Asn Gln His Ile Pro Gly Asp Asn Ser Ile Tyr Ile Thr
            20                  25                  30

Lys Ile Ile Glu Gly Gly Ala Ala Gln Lys Asp Gly Arg Leu Gln Ile
```

```
                35                  40                  45

Gly Asp Arg Leu Leu Ala Val Asn Asn Thr Asn Leu Gln Asp Val Arg
         50                  55                  60

His Glu Glu Ala Val Ala Ser Leu Lys Asn Thr Ser Asp Met Val Tyr
 65                  70                  75                  80

Leu Lys Val Ala Lys Pro Gly Ser Leu Glu
                 85                  90

<210> SEQ ID NO 151
<211> LENGTH: 93
<212> TYPE: PRT
<213> ORGANISM: Artificial Sequence
<220> FEATURE:
<223> OTHER INFORMATION: Synthetic peptide

<400> SEQUENCE: 151

Ile Gln Tyr Glu Glu Ile Val Leu Glu Arg Gly Asn Ser Gly Leu Gly
  1               5                  10                  15

Phe Ser Ile Ala Gly Gly Ile Asp Asn Pro His Val Pro Asp Asp Pro
                 20                  25                  30

Gly Ile Phe Ile Thr Lys Ile Ile Pro Gly Gly Ala Ala Ala Met Asp
             35                  40                  45

Gly Arg Leu Gly Val Asn Asp Cys Val Leu Arg Val Asn Glu Val
         50                  55                  60                Glu

Val Ser Glu Val Val His Ser Arg Ala Val Glu Ala Leu Lys Glu Ala
 65                  70                  75                  80

Gly Pro Val Val Arg Leu Val Val Arg Arg Gln Asn
                 85                  90

<210> SEQ ID NO 152
<211> LENGTH: 119
<212> TYPE: PRT
<213> ORGANISM: Artificial Sequence
<220> FEATURE:
<223> OTHER INFORMATION: Synthetic peptide

<400> SEQUENCE: 152

Ile Leu Leu His Lys Gly Ser Thr Gly Leu Gly Phe Asn Ile Val Gly
  1               5                  10                  15

Gly Glu Asp Gly Glu Gly Ile Phe Val Ser Phe Ile Leu Ala Gly Gly
                 20                  25                  30

Pro Ala Asp Leu Ser Gly Glu Leu Arg Arg Gly Asp Arg Ile Leu Ser
             35                  40                  45

Val Asn Gly Val Asn Leu Arg Asn Ala Thr His Glu Gln Ala Ala Ala
 50                  55                  60

Ala Leu Lys Arg Ala Gly Gln Ser Val Thr Ile Val Ala Gln Tyr Arg
 65                  70                  75                  80

Pro Glu Glu Tyr Ser Arg Phe Glu Ser Lys Ile His Asp Leu Arg Glu
                 85                  90                  95

Gln Met Met Asn Ser Ser Met Ser Ser Gly Ser Gly Ser Leu Arg Thr
                100                 105                 110

Ser Glu Lys Arg Ser Leu Glu
        115

<210> SEQ ID NO 153
<211> LENGTH: 187
<212> TYPE: PRT
<213> ORGANISM: Artificial Sequence
<220> FEATURE:
```

<223> OTHER INFORMATION: Synthetic peptide

<400> SEQUENCE: 153

```
Tyr Glu Glu Ile Val Leu Glu Arg Gly Asn Ser Gly Leu Gly Phe Ser
1               5                   10                  15

Ile Ala Gly Gly Ile Asp Asn Pro His Val Pro Asp Pro Gly Ile
            20                  25                  30

Phe Ile Thr Lys Ile Ile Pro Gly Gly Ala Ala Ala Met Asp Gly Arg
        35                  40                  45

Leu Gly Val Asn Asp Cys Val Leu Arg Val Asn Glu Val Glu Val Ser
    50                  55                  60

Glu Val Val His Ser Arg Ala Val Glu Ala Leu Lys Glu Ala Gly Pro
65                  70                  75                  80

Val Val Arg Leu Val Arg Arg Gln Pro Pro Glu Thr Ile
                85                  90                  95

Met Glu Val Asn Leu Leu Lys Gly Pro Lys Gly Leu Gly Phe Ser Ile
            100                 105                 110

Ala Gly Gly Ile Gly Asn Gln His Ile Pro Gly Asp Asn Ser Ile Tyr
        115                 120                 125

Ile Thr Lys Ile Ile Glu Gly Gly Ala Ala Gln Lys Asp Gly Arg Leu
    130                 135                 140

Gln Ile Gly Asp Arg Leu Leu Ala Val Asn Asn Thr Asn Leu Gln Asp
145                 150                 155                 160

Val Arg His Glu Glu Ala Val Ala Ser Leu Lys Asn Thr Ser Asp Met
                165                 170                 175

Val Tyr Leu Lys Val Ala Lys Pro Gly Ser Leu
            180                 185
```

<210> SEQ ID NO 154
<211> LENGTH: 106
<212> TYPE: PRT
<213> ORGANISM: Artificial Sequence
<220> FEATURE:
<223> OTHER INFORMATION: Synthetic peptide

<400> SEQUENCE: 154

```
Arg Val Glu Arg Leu Glu Leu Phe Pro Val Glu Leu Glu Lys Asp Ser
1               5                   10                  15

Glu Gly Leu Gly Ile Ser Ile Ile Gly Met Gly Ala Gly Ala Asp Met
            20                  25                  30

Gly Leu Glu Lys Leu Gly Ile Phe Val Lys Thr Val Thr Glu Gly Gly
        35                  40                  45

Ala Ala His Arg Asp Gly Arg Ile Gln Val Asn Asp Leu Leu Val Glu
    50                  55                  60

Val Asp Gly Thr Ser Leu Val Gly Val Thr Gln Ser Phe Ala Ala Ser
65                  70                  75                  80

Val Leu Arg Asn Thr Lys Gly Arg Val Arg Cys Arg Phe Met Ile Gly
                85                  90                  95

Arg Glu Arg Pro Gly Glu Gln Ser Glu Val
            100                 105
```

<210> SEQ ID NO 155
<211> LENGTH: 90
<212> TYPE: PRT
<213> ORGANISM: Artificial Sequence
<220> FEATURE:
<223> OTHER INFORMATION: Synthetic peptide

<400> SEQUENCE: 155

Gln Pro Asn Val Ile Ser Val Arg Leu Phe Lys Arg Lys Val Gly Gly
1               5                   10                  15

Leu Gly Phe Leu Val Lys Glu Arg Val Ser Lys Pro Pro Val Ile Ile
                20                  25                  30

Ser Asp Leu Ile Arg Gly Gly Ala Ala Glu Gln Ser Gly Leu Ile Gln
            35                  40                  45

Ala Gly Asp Ile Ile Leu Ala Val Asn Gly Arg Pro Leu Val Asp Leu
        50                  55                  60

Ser Tyr Asp Ser Ala Leu Glu Val Leu Arg Gly Ile Ala Ser Glu Thr
65                  70                  75                  80

His Val Val Leu Ile Leu Arg Gly Pro Glu
                85                  90

<210> SEQ ID NO 156
<211> LENGTH: 103
<212> TYPE: PRT
<213> ORGANISM: Artificial Sequence
<220> FEATURE:
<223> OTHER INFORMATION: Synthetic peptide

<400> SEQUENCE: 156

Pro Ser Asp Thr Ser Ser Glu Asp Gly Val Arg Arg Ile Val His Leu
1               5                   10                  15

Tyr Thr Thr Ser Asp Asp Phe Cys Leu Gly Phe Asn Ile Arg Gly Gly
                20                  25                  30

Lys Glu Phe Gly Leu Gly Ile Tyr Val Ser Lys Val Asp His Gly Gly
            35                  40                  45

Leu Ala Glu Glu Asn Gly Ile Lys Val Gly Asp Gln Val Leu Ala Ala
        50                  55                  60

Asn Gly Val Arg Phe Asp Asp Ile Ser His Ser Gln Ala Val Glu Val
65                  70                  75                  80

Leu Lys Gly Gln Thr His Ile Met Leu Thr Ile Lys Glu Thr Gly Arg
                85                  90                  95

Tyr Pro Ala Tyr Lys Glu Met
            100

<210> SEQ ID NO 157
<211> LENGTH: 104
<212> TYPE: PRT
<213> ORGANISM: Artificial Sequence
<220> FEATURE:
<223> OTHER INFORMATION: Synthetic peptide

<400> SEQUENCE: 157

Glu Ala Asn Ser Asp Glu Ser Asp Ile Ile His Ser Val Arg Val Glu
1               5                   10                  15

Lys Ser Pro Ala Gly Arg Leu Gly Phe Ser Val Arg Gly Gly Ser Glu
                20                  25                  30

His Gly Leu Gly Ile Phe Val Ser Lys Val Glu Glu Gly Ser Ser Ala
            35                  40                  45

Glu Arg Ala Gly Leu Cys Val Gly Asp Lys Ile Thr Glu Val Asn Gly
        50                  55                  60

Leu Ser Leu Glu Ser Thr Thr Met Gly Ser Ala Val Lys Val Leu Thr
65                  70                  75                  80

Ser Ser Ser Arg Leu His Met Met Val Arg Arg Met Gly Arg Val Pro
                85                  90                  95

```
Gly Ile Lys Phe Ser Lys Glu Lys
            100
```

<210> SEQ ID NO 158
<211> LENGTH: 116
<212> TYPE: PRT
<213> ORGANISM: Artificial Sequence
<220> FEATURE:
<223> OTHER INFORMATION: Synthetic peptide

<400> SEQUENCE: 158

```
Asp Lys Ile Lys Lys Phe Leu Thr Glu Ser His Asp Arg Gln Ala Lys
1               5                   10                  15

Gly Lys Ala Ile Thr Lys Lys Tyr Ile Gly Ile Arg Met Met Ser
            20                  25                  30

Leu Thr Ser Ser Lys Ala Lys Glu Leu Lys Asp Arg His Arg Asp Phe
        35                  40                  45

Pro Asp Val Ile Ser Gly Ala Tyr Ile Ile Glu Val Ile Pro Asp Thr
    50                  55                  60

Pro Ala Glu Ala Gly Gly Leu Lys Glu Asn Asp Val Ile Ile Ser Ile
65                  70                  75                  80

Asn Gly Gln Ser Val Val Ser Ala Asn Asp Val Ser Asp Val Ile Lys
                85                  90                  95

Arg Glu Ser Thr Leu Asn Met Val Val Arg Arg Gly Asn Glu Asp Ile
            100                 105                 110

Met Ile Thr Val
        115
```

<210> SEQ ID NO 159
<211> LENGTH: 98
<212> TYPE: PRT
<213> ORGANISM: Artificial Sequence
<220> FEATURE:
<223> OTHER INFORMATION: Synthetic peptide

<400> SEQUENCE: 159

```
Tyr Arg Pro Arg Asp Asp Ser Phe His Val Ile Leu Asn Lys Ser Ser
1               5                   10                  15

Pro Glu Glu Gln Leu Gly Ile Lys Leu Val Arg Lys Val Asp Glu Pro
            20                  25                  30

Gly Val Phe Ile Phe Asn Ala Leu Asp Gly Gly Val Ala Tyr Arg His
        35                  40                  45

Gly Gln Leu Glu Glu Asn Asp Arg Val Leu Ala Ile Asn Gly His Asp
    50                  55                  60

Leu Arg Tyr Gly Ser Pro Glu Ser Ala Ala His Leu Ile Gln Ala Ser
65                  70                  75                  80

Glu Arg Arg Val His Leu Val Val Ser Arg Gln Val Arg Gln Arg Ser
                85                  90                  95

Pro Asp
```

<210> SEQ ID NO 160
<211> LENGTH: 100
<212> TYPE: PRT
<213> ORGANISM: Artificial Sequence
<220> FEATURE:
<223> OTHER INFORMATION: Synthetic peptide

<400> SEQUENCE: 160

```
Pro Thr Ile Thr Cys His Glu Lys Val Val Asn Ile Gln Lys Asp Pro
1               5                   10                  15
```

Gly Glu Ser Leu Gly Met Thr Val Ala Gly Ala Ser His Arg Glu
            20                  25                  30

Trp Asp Leu Pro Ile Tyr Val Ile Ser Val Glu Pro Gly Gly Val Ile
            35                  40                  45

Ser Arg Asp Gly Arg Ile Lys Thr Gly Asp Ile Leu Leu Asn Val Asp
50                  55                  60

Gly Val Glu Leu Thr Glu Val Ser Arg Ser Glu Ala Val Ala Leu Leu
65                  70                  75                  80

Lys Arg Thr Ser Ser Ser Ile Val Leu Lys Ala Leu Glu Val Lys Glu
                85                  90                  95

Tyr Glu Pro Gln
            100

<210> SEQ ID NO 161
<211> LENGTH: 97
<212> TYPE: PRT
<213> ORGANISM: Artificial Sequence
<220> FEATURE:
<223> OTHER INFORMATION: Synthetic peptide

<400> SEQUENCE: 161

Pro Asp Gly Glu Ile Thr Ser Ile Lys Ile Asn Arg Val Asp Pro Ser
1               5                   10                  15

Glu Ser Leu Ser Ile Arg Leu Val Gly Gly Ser Glu Thr Pro Leu Val
            20                  25                  30

His Ile Ile Ile Gln His Ile Tyr Arg Asp Gly Val Ile Ala Arg Asp
            35                  40                  45

Gly Arg Leu Leu Pro Arg Asp Ile Ile Leu Lys Val Asn Gly Met Asp
    50                  55                  60

Ile Ser Asn Val Pro His Asn Tyr Ala Val Arg Leu Leu Arg Gln Pro
65                  70                  75                  80

Cys Gln Val Leu Trp Leu Thr Val Met Arg Glu Gln Lys Phe Arg Ser
                85                  90                  95

Arg

<210> SEQ ID NO 162
<211> LENGTH: 99
<212> TYPE: PRT
<213> ORGANISM: Artificial Sequence
<220> FEATURE:
<223> OTHER INFORMATION: Synthetic peptide

<400> SEQUENCE: 162

Pro Arg Cys Leu Tyr Asn Cys Lys Asp Ile Val Leu Arg Arg Asn Thr
1               5                   10                  15

Ala Gly Ser Leu Gly Phe Cys Ile Val Gly Gly Tyr Glu Glu Tyr Asn
            20                  25                  30

Gly Asn Lys Pro Phe Phe Ile Lys Ser Ile Val Glu Gly Thr Pro Ala
            35                  40                  45

Tyr Asn Asp Gly Arg Ile Arg Cys Gly Asp Ile Leu Leu Ala Val Asn
        50                  55                  60

Gly Arg Ser Thr Ser Gly Met Ile His Ala Cys Leu Ala Arg Leu Leu
65                  70                  75                  80

Lys Glu Leu Lys Gly Arg Ile Thr Leu Thr Ile Val Ser Trp Pro Gly
                85                  90                  95

Thr Phe Leu

<210> SEQ ID NO 163
<211> LENGTH: 101
<212> TYPE: PRT
<213> ORGANISM: Artificial Sequence
<220> FEATURE:
<223> OTHER INFORMATION: Synthetic peptide

<400> SEQUENCE: 163

```
Leu Leu Thr Glu Glu Ile Asn Leu Thr Arg Gly Pro Ser Gly Leu
1               5                   10                  15

Gly Phe Asn Ile Val Gly Gly Thr Asp Gln Gln Tyr Val Ser Asn Asp
            20                  25                  30

Ser Gly Ile Tyr Val Ser Arg Ile Lys Glu Asn Gly Ala Ala Ala Leu
        35                  40                  45

Asp Gly Arg Leu Gln Glu Gly Asp Lys Ile Leu Ser Val Asn Gly Gln
    50                  55                  60

Asp Leu Lys Asn Leu Leu His Gln Asp Ala Val Asp Leu Phe Arg Asn
65                  70                  75                  80

Ala Gly Tyr Ala Val Ser Leu Arg Val Gln His Arg Leu Gln Val Gln
                85                  90                  95

Asn Gly Ile His Ser
            100
```

<210> SEQ ID NO 164
<211> LENGTH: 94
<212> TYPE: PRT
<213> ORGANISM: Artificial Sequence
<220> FEATURE:
<223> OTHER INFORMATION: Synthetic peptide

<400> SEQUENCE: 164

```
Pro Val Asp Ala Ile Arg Ile Leu Gly Ile His Lys Arg Ala Gly Glu
1               5                   10                  15

Pro Leu Gly Val Thr Phe Arg Val Glu Asn Asn Asp Leu Val Ile Ala
            20                  25                  30

Arg Ile Leu His Gly Gly Met Ile Asp Arg Gln Gly Leu Leu His Val
        35                  40                  45

Gly Asp Ile Ile Lys Glu Val Asn Gly His Glu Val Gly Asn Asn Pro
    50                  55                  60

Lys Glu Leu Gln Glu Leu Leu Lys Asn Ile Ser Gly Ser Val Thr Leu
65                  70                  75                  80

Lys Ile Leu Pro Ser Tyr Arg Asp Thr Ile Thr Pro Gln Gln
                85                  90
```

<210> SEQ ID NO 165
<211> LENGTH: 94
<212> TYPE: PRT
<213> ORGANISM: Artificial Sequence
<220> FEATURE:
<223> OTHER INFORMATION: Synthetic peptide

<400> SEQUENCE: 165

```
Gly Lys Arg Leu Asn Ile Gln Leu Lys Lys Gly Thr Glu Gly Leu Gly
1               5                   10                  15

Phe Ser Ile Thr Ser Arg Asp Val Thr Ile Gly Gly Ser Ala Pro Ile
            20                  25                  30

Tyr Val Lys Asn Ile Leu Pro Arg Gly Ala Ala Ile Gln Asp Gly Arg
        35                  40                  45

Leu Lys Ala Gly Asp Arg Leu Ile Glu Val Asn Gly Val Asp Leu Val
```

```
                    50                  55                  60
Gly Lys Ser Gln Glu Glu Val Val Ser Leu Leu Arg Ser Thr Lys Met
 65                  70                  75                  80

Glu Gly Thr Val Ser Leu Leu Val Phe Arg Gln Glu Asp Ala
                 85                  90

<210> SEQ ID NO 166
<211> LENGTH: 106
<212> TYPE: PRT
<213> ORGANISM: Artificial Sequence
<220> FEATURE:
<223> OTHER INFORMATION: Synthetic peptide

<400> SEQUENCE: 166

Ile Pro Asn Phe Ser Leu Asp Asp Met Val Lys Leu Val Glu Val Pro
  1               5                  10                  15

Asn Asp Gly Gly Pro Leu Gly Ile His Val Val Pro Phe Ser Ala Arg
                 20                  25                  30

Gly Gly Arg Thr Leu Gly Leu Leu Val Lys Arg Leu Glu Lys Gly Gly
             35                  40                  45

Lys Ala Glu His Glu Asn Leu Phe Arg Glu Asn Asp Cys Ile Val Arg
 50                  55                  60

Ile Asn Asp Gly Asp Leu Arg Asn Arg Arg Phe Glu Gln Ala Gln His
 65                  70                  75                  80

Met Phe Arg Gln Ala Met Arg Thr Pro Ile Ile Trp Phe His Val Val
                 85                  90                  95

Pro Ala Ala Asn Lys Glu Gln Tyr Glu Gln
            100                 105

<210> SEQ ID NO 167
<211> LENGTH: 113
<212> TYPE: PRT
<213> ORGANISM: Artificial Sequence
<220> FEATURE:
<223> OTHER INFORMATION: Synthetic peptide

<400> SEQUENCE: 167

Pro Arg Glu Phe Leu Thr Phe Glu Val Pro Leu Asn Asp Ser Gly Ser
  1               5                  10                  15

Ala Gly Leu Gly Val Ser Val Lys Gly Asn Arg Ser Lys Glu Asn His
                 20                  25                  30

Ala Asp Leu Gly Ile Phe Val Lys Ser Ile Ile Asn Gly Gly Ala Ala
             35                  40                  45

Ser Lys Asp Gly Arg Leu Arg Val Asn Asp Gln Leu Ile Ala Val Asn
 50                  55                  60

Gly Glu Ser Leu Leu Gly Lys Thr Asn Gln Asp Ala Met Glu Thr Leu
 65                  70                  75                  80

Arg Arg Ser Met Ser Thr Glu Gly Asn Lys Arg Gly Met Ile Gln Leu
                 85                  90                  95

Ile Val Ala Ser Arg Ile Ser Lys Cys Asn Glu Leu Lys Ser Asn Ser
            100                 105                 110

Ser

<210> SEQ ID NO 168
<211> LENGTH: 99
<212> TYPE: PRT
<213> ORGANISM: Artificial Sequence
<220> FEATURE:
<223> OTHER INFORMATION: Synthetic peptide
```

```
<400> SEQUENCE: 168

Ile Ser Asn Lys Asn Ala Lys Lys Ile Lys Ile Asp Leu Lys Lys Gly
1               5                   10                  15

Pro Glu Gly Leu Gly Phe Thr Val Val Thr Arg Asp Ser Ser Ile His
            20                  25                  30

Gly Pro Gly Pro Ile Phe Val Lys Asn Ile Leu Pro Lys Gly Ala Ala
        35                  40                  45

Ile Lys Asp Gly Arg Leu Gln Ser Gly Asp Arg Ile Leu Glu Val Asn
50                  55                  60

Gly Arg Asp Val Thr Gly Arg Thr Gln Glu Glu Leu Val Ala Met Leu
65                  70                  75                  80

Arg Ser Thr Lys Gln Gly Glu Thr Ala Ser Leu Val Ile Ala Arg Gln
                85                  90                  95

Glu Gly His

<210> SEQ ID NO 169
<211> LENGTH: 106
<212> TYPE: PRT
<213> ORGANISM: Artificial Sequence
<220> FEATURE:
<223> OTHER INFORMATION: Synthetic peptide

<400> SEQUENCE: 169

Ile Thr Ser Glu Gln Leu Thr Phe Glu Ile Pro Leu Asn Asp Ser Gly
1               5                   10                  15

Ser Ala Gly Leu Gly Val Ser Leu Lys Gly Asn Lys Ser Arg Glu Thr
            20                  25                  30

Gly Thr Asp Leu Gly Ile Phe Ile Lys Ser Ile Ile His Gly Gly Ala
        35                  40                  45

Ala Phe Lys Asp Gly Arg Leu Arg Met Asn Asp Gln Leu Ile Ala Val
50                  55                  60

Asn Gly Glu Ser Leu Leu Gly Lys Ser Asn His Glu Ala Met Glu Thr
65                  70                  75                  80

Leu Arg Arg Ser Met Ser Met Glu Gly Asn Ile Arg Gly Met Ile Gln
                85                  90                  95

Leu Val Ile Leu Arg Arg Pro Glu Arg Pro
            100                 105

<210> SEQ ID NO 170
<211> LENGTH: 104
<212> TYPE: PRT
<213> ORGANISM: Artificial Sequence
<220> FEATURE:
<223> OTHER INFORMATION: Synthetic peptide

<400> SEQUENCE: 170

Ile Pro Arg Thr Lys Asp Thr Leu Ser Asp Met Thr Arg Thr Val Glu
1               5                   10                  15

Ile Ser Gly Glu Gly Gly Pro Leu Gly Ile His Val Val Pro Phe Phe
            20                  25                  30

Ser Ser Leu Ser Gly Arg Ile Leu Gly Leu Phe Ile Arg Gly Ile Glu
        35                  40                  45

Asp Asn Ser Arg Ser Lys Arg Glu Gly Leu Phe His Glu Asn Glu Cys
50                  55                  60

Ile Val Lys Ile Asn Asn Val Asp Leu Val Asp Lys Thr Phe Ala Gln
65                  70                  75                  80
```

Ala Gln Asp Val Phe Arg Gln Ala Met Lys Ser Pro Ser Val Leu Leu
            85                  90                  95

His Val Leu Pro Pro Gln Asn Arg
            100

<210> SEQ ID NO 171
<211> LENGTH: 104
<212> TYPE: PRT
<213> ORGANISM: Artificial Sequence
<220> FEATURE:
<223> OTHER INFORMATION: Synthetic peptide

<400> SEQUENCE: 171

Pro Glu Thr His Arg Arg Val Arg Leu His Lys His Gly Ser Asp Arg
1               5                   10                  15

Pro Leu Gly Phe Tyr Ile Arg Asp Gly Met Ser Val Arg Val Ala Pro
            20                  25                  30

Gln Gly Leu Glu Arg Val Pro Gly Ile Phe Ile Ser Arg Leu Val Arg
        35                  40                  45

Gly Gly Leu Ala Glu Ser Thr Gly Leu Leu Ala Val Ser Asp Glu Ile
    50                  55                  60

Leu Glu Val Asn Gly Ile Glu Val Ala Gly Lys Thr Leu Asp Gln Val
65                  70                  75                  80

Thr Asp Met Met Val Ala Asn Ser His Asn Leu Ile Val Thr Val Lys
                85                  90                  95

Pro Ala Asn Gln Arg Asn Asn Val
            100

<210> SEQ ID NO 172
<211> LENGTH: 120
<212> TYPE: PRT
<213> ORGANISM: Artificial Sequence
<220> FEATURE:
<223> OTHER INFORMATION: Synthetic peptide

<400> SEQUENCE: 172

Ile Pro Val Ser Ser Ile Ile Asp Val Asp Leu Pro Glu Thr His
1               5                   10                  15

Arg Arg Val Arg Leu Tyr Lys Tyr Gly Thr Glu Lys Pro Leu Gly Phe
            20                  25                  30

Tyr Ile Arg Asp Gly Ser Ser Val Arg Val Thr Pro His Gly Leu Glu
        35                  40                  45

Lys Val Pro Gly Ile Phe Ile Ser Arg Leu Val Pro Gly Gly Leu Ala
    50                  55                  60

Gln Ser Thr Gly Leu Leu Ala Val Asn Asp Glu Val Leu Glu Val Asn
65                  70                  75                  80

Gly Ile Glu Val Ser Gly Lys Ser Leu Asp Gln Val Thr Asp Met Met
                85                  90                  95

Ile Ala Asn Ser Arg Asn Leu Ile Ile Thr Val Arg Pro Ala Asn Gln
            100                 105                 110

Arg Asn Asn Arg Ile His Arg Asp
        115                 120

<210> SEQ ID NO 173
<211> LENGTH: 111
<212> TYPE: PRT
<213> ORGANISM: Artificial Sequence
<220> FEATURE:
<223> OTHER INFORMATION: Synthetic peptide -continued

<400> SEQUENCE: 173

Ile Asp Val Asp Leu Val Pro Glu Thr His Arg Arg Val Arg Leu His
1               5                   10                  15

Arg His Gly Cys Glu Lys Pro Leu Gly Phe Tyr Ile Arg Asp Gly Ala
            20                  25                  30

Ser Val Arg Val Thr Pro His Gly Leu Glu Lys Val Pro Gly Ile Phe
        35                  40                  45

Ile Ser Arg Met Val Pro Gly Leu Ala Glu Ser Thr Gly Leu Leu
    50                  55                  60

Ala Val Asn Asp Glu Val Leu Glu Val Asn Gly Ile Glu Val Ala Gly
65                  70                  75                  80

Lys Thr Leu Asp Gln Val Thr Asp Met Met Ile Ala Asn Ser His Asn
                85                  90                  95

Leu Ile Val Thr Val Lys Pro Ala Asn Gln Arg Asn Asn Val Val
            100                 105                 110

<210> SEQ ID NO 174
<211> LENGTH: 103
<212> TYPE: PRT
<213> ORGANISM: Artificial Sequence
<220> FEATURE:
<223> OTHER INFORMATION: Synthetic peptide

<400> SEQUENCE: 174

Pro Glu Gln Ile Met Gly Lys Asp Val Arg Leu Leu Arg Ile Lys Lys
1               5                   10                  15

Glu Gly Ser Leu Asp Leu Ala Leu Glu Gly Gly Val Asp Ser Pro Ile
            20                  25                  30

Gly Lys Val Val Val Ser Ala Val Tyr Glu Arg Gly Ala Ala Glu Arg
        35                  40                  45

His Gly Gly Ile Val Lys Gly Asp Glu Ile Met Ala Ile Asn Gly Lys
    50                  55                  60

Ile Val Thr Asp Tyr Thr Leu Ala Glu Ala Asp Ala Ala Leu Gln Lys
65                  70                  75                  80

Ala Trp Asn Gln Gly Gly Asp Trp Ile Asp Leu Val Val Ala Val Cys
                85                  90                  95

Pro Pro Lys Glu Tyr Asp Asp
            100

<210> SEQ ID NO 175
<211> LENGTH: 102
<212> TYPE: PRT
<213> ORGANISM: Artificial Sequence
<220> FEATURE:
<223> OTHER INFORMATION: Synthetic peptide

<400> SEQUENCE: 175

Ile Pro Gly Asn Arg Glu Asn Lys Glu Lys Val Phe Ile Ser Leu
1               5                   10                  15

Val Gly Ser Arg Gly Leu Gly Cys Ser Ile Ser Ser Gly Pro Ile Gln
            20                  25                  30

Lys Pro Gly Ile Phe Ile Ser His Val Lys Pro Gly Ser Leu Ser Ala
        35                  40                  45

Glu Val Gly Leu Glu Ile Gly Asp Gln Ile Val Glu Val Asn Gly Val
    50                  55                  60

Asp Phe Ser Asn Leu Asp His Lys Glu Ala Val Asn Val Leu Lys Ser
65                  70                  75                  80

```
Ser Arg Ser Leu Thr Ile Ser Ile Val Ala Ala Ala Gly Arg Glu Leu
            85                  90                  95

Phe Met Thr Asp Glu Phe
            100

<210> SEQ ID NO 176
<211> LENGTH: 100
<212> TYPE: PRT
<213> ORGANISM: Artificial Sequence
<220> FEATURE:
<223> OTHER INFORMATION: Synthetic peptide

<400> SEQUENCE: 176

Arg Ser Arg Lys Leu Lys Glu Val Arg Leu Asp Arg Leu His Pro Glu
1               5                   10                  15

Gly Leu Gly Leu Ser Val Arg Gly Gly Leu Glu Phe Gly Cys Gly Leu
            20                  25                  30

Phe Ile Ser His Leu Ile Lys Gly Gly Gln Ala Asp Ser Val Gly Leu
            35                  40                  45

Gln Val Gly Asp Glu Ile Val Arg Ile Asn Gly Tyr Ser Ile Ser Ser
        50                  55                  60

Cys Thr His Glu Glu Val Ile Asn Leu Ile Arg Thr Lys Lys Thr Val
65                  70                  75                  80

Ser Ile Lys Val Arg His Ile Gly Leu Ile Pro Val Lys Ser Ser Pro
                85                  90                  95

Asp Glu Phe His
            100

<210> SEQ ID NO 177
<211> LENGTH: 92
<212> TYPE: PRT
<213> ORGANISM: Artificial Sequence
<220> FEATURE:
<223> OTHER INFORMATION: Synthetic peptide

<400> SEQUENCE: 177

Arg Leu Cys Tyr Leu Val Lys Glu Gly Gly Ser Tyr Gly Phe Ser Leu
1               5                   10                  15

Lys Thr Val Gln Gly Lys Lys Gly Val Tyr Met Thr Asp Ile Thr Pro
            20                  25                  30

Gln Gly Val Ala Met Arg Ala Gly Val Leu Ala Asp Asp His Leu Ile
            35                  40                  45

Glu Val Asn Gly Glu Asn Val Glu Asp Ala Ser His Glu Glu Val Val
        50                  55                  60

Glu Lys Val Lys Lys Ser Gly Ser Arg Val Met Phe Leu Leu Val Asp
65                  70                  75                  80

Lys Glu Thr Asp Lys Arg Glu Phe Ile Val Thr Asp
                85                  90

<210> SEQ ID NO 178
<211> LENGTH: 112
<212> TYPE: PRT
<213> ORGANISM: Artificial Sequence
<220> FEATURE:
<223> OTHER INFORMATION: Synthetic peptide

<400> SEQUENCE: 178

Gln Phe Lys Arg Glu Thr Ala Ser Leu Lys Leu Leu Pro His Gln Pro
1               5                   10                  15

Arg Ile Val Glu Met Lys Lys Gly Ser Asn Gly Tyr Gly Phe Tyr Leu
```

```
                    20                  25                  30
Arg Ala Gly Ser Glu Gln Lys Gly Gln Ile Ile Lys Asp Ile Asp Ser
            35                  40                  45

Gly Ser Pro Ala Glu Glu Ala Gly Leu Lys Asn Asn Asp Leu Val Val
        50                  55                  60

Ala Val Asn Gly Glu Ser Val Glu Thr Leu Asp His Asp Ser Val Val
65                  70                  75                  80

Glu Met Ile Arg Lys Gly Gly Asp Gln Thr Ser Leu Leu Val Val Asp
                85                  90                  95

Lys Glu Thr Asp Asn Met Tyr Arg Leu Ala Glu Phe Ile Val Thr Asp
            100                 105                 110
```

<210> SEQ ID NO 179
<211> LENGTH: 324
<212> TYPE: PRT
<213> ORGANISM: Artificial Sequence
<220> FEATURE:
<223> OTHER INFORMATION: Synthetic peptide

<400> SEQUENCE: 179

```
Arg Leu Cys Tyr Leu Val Lys Glu Gly Gly Ser Tyr Gly Phe Ser Leu
1               5                   10                  15

Lys Thr Val Gln Gly Lys Lys Gly Val Tyr Met Thr Asp Ile Thr Pro
            20                  25                  30

Gln Gly Val Ala Met Arg Ala Gly Val Leu Ala Asp Asp His Leu Ile
            35                  40                  45

Glu Val Asn Gly Glu Asn Val Glu Asp Ala Ser His Glu Lys Val Val
        50                  55                  60

Glu Lys Val Lys Lys Ser Gly Ser Arg Val Met Phe Leu Leu Val Asp
65                  70                  75                  80

Lys Glu Thr Asp Lys Arg His Val Glu Gln Lys Ile Gln Phe Lys Arg
                85                  90                  95

Glu Thr Ala Ser Leu Lys Leu Leu Pro His Gln Pro Arg Ile Val Glu
            100                 105                 110

Met Lys Lys Gly Ser Asn Gly Tyr Gly Phe Tyr Leu Arg Ala Gly Ser
            115                 120                 125

Glu Gln Lys Gly Gln Ile Ile Lys Asp Ile Asp Ser Gly Ser Pro Ala
        130                 135                 140

Glu Glu Ala Gly Leu Lys Asn Asn Asp Leu Val Val Ala Val Asn Gly
145                 150                 155                 160

Glu Ser Val Glu Thr Leu Asp His Asp Ser Val Val Glu Met Ile Arg
                165                 170                 175

Lys Gly Gly Asp Gln Thr Ser Leu Leu Val Val Asp Lys Glu Thr Asp
            180                 185                 190

Asn Met Tyr Arg Leu Ala His Phe Ser Pro Phe Leu Tyr Tyr Gln Ser
        195                 200                 205

Gln Glu Leu Pro Asn Gly Ser Val Lys Glu Ala Pro Ala Pro Thr Pro
    210                 215                 220

Thr Ser Leu Glu Val Ser Ser Pro Asp Thr Thr Glu Glu Val Asp
225                 230                 235                 240

His Lys Pro Lys Leu Cys Arg Leu Ala Lys Gly Glu Asn Gly Tyr Gly
                245                 250                 255

Phe His Leu Asn Ala Ile Arg Gly Leu Pro Gly Ser Phe Ile Lys Glu
            260                 265                 270

Val Gln Lys Gly Gly Pro Ala Asp Leu Ala Gly Leu Glu Asp Glu Asp
```

```
                275                 280                 285
Val Ile Ile Glu Val Asn Gly Val Asn Val Leu Asp Glu Pro Tyr Glu
    290                 295                 300

Lys Val Val Asp Arg Ile Gln Ser Ser Gly Lys Asn Val Thr Leu Leu
305                 310                 315                 320

Val Cys Gly Lys

<210> SEQ ID NO 180
<211> LENGTH: 94
<212> TYPE: PRT
<213> ORGANISM: Artificial Sequence
<220> FEATURE:
<223> OTHER INFORMATION: Synthetic peptide

<400> SEQUENCE: 180

Pro Asp Thr Thr Glu Glu Val Asp His Lys Pro Lys Leu Cys Arg Leu
1               5                   10                  15

Ala Lys Gly Glu Asn Gly Tyr Gly Phe His Leu Asn Ala Ile Arg Gly
            20                  25                  30

Leu Pro Gly Ser Phe Ile Lys Glu Val Gln Lys Gly Gly Pro Ala Asp
        35                  40                  45

Leu Ala Gly Leu Glu Asp Glu Asp Val Ile Ile Glu Val Asn Gly Val
    50                  55                  60

Asn Val Leu Asp Glu Pro Tyr Glu Lys Val Val Asp Arg Ile Gln Ser
65                  70                  75                  80

Ser Gly Lys Asn Val Thr Leu Leu Val Gly Lys Asn Ser Ser
                85                  90

<210> SEQ ID NO 181
<211> LENGTH: 101
<212> TYPE: PRT
<213> ORGANISM: Artificial Sequence
<220> FEATURE:
<223> OTHER INFORMATION: Synthetic peptide

<400> SEQUENCE: 181

Leu Thr Ser Thr Phe Asn Pro Arg Glu Cys Lys Leu Ser Lys Gln Glu
1               5                   10                  15

Gly Gln Asn Tyr Gly Phe Phe Leu Arg Ile Glu Lys Asp Thr Glu Gly
            20                  25                  30

His Leu Val Arg Val Val Glu Lys Cys Ser Pro Ala Glu Lys Ala Gly
        35                  40                  45

Leu Gln Asp Gly Asp Arg Val Leu Arg Ile Asn Gly Val Phe Val Asp
    50                  55                  60

Lys Glu Glu His Met Gln Val Val Asp Leu Val Arg Lys Ser Gly Asn
65                  70                  75                  80

Ser Val Thr Leu Leu Val Leu Asp Gly Asp Ser Tyr Glu Lys Ala Gly
                85                  90                  95

Ser His Glu Pro Ser
            100

<210> SEQ ID NO 182
<211> LENGTH: 99
<212> TYPE: PRT
<213> ORGANISM: Artificial Sequence
<220> FEATURE:
<223> OTHER INFORMATION: Synthetic peptide

<400> SEQUENCE: 182
```

```
Leu Gly Ile Pro Thr Val Pro Gly Lys Val Thr Leu Gln Lys Asp Ala
1               5                   10                  15

Gln Asn Leu Ile Gly Ile Ser Ile Gly Gly Ala Gln Tyr Cys Pro
            20                  25                  30

Cys Leu Tyr Ile Val Gln Val Phe Asp Asn Thr Pro Ala Ala Leu Asp
            35                  40                  45

Gly Thr Val Ala Ala Gly Asp Glu Ile Thr Val Asn Gly Arg Ser
50                  55                  60

Ile Lys Gly Lys Thr Lys Val Glu Val Ala Lys Met Ile Gln Glu Val
65                  70                  75                  80

Lys Gly Glu Val Thr Ile His Tyr Asn Lys Leu Gln Ala Asp Pro Lys
                85                  90                  95

Gln Gly Met

<210> SEQ ID NO 183
<211> LENGTH: 98
<212> TYPE: PRT
<213> ORGANISM: Artificial Sequence
<220> FEATURE:
<223> OTHER INFORMATION: Synthetic peptide

<400> SEQUENCE: 183

Ser Gln Gly Val Gly Pro Ile Arg Lys Val Leu Leu Lys Glu Asp
1               5                   10                  15

His Glu Gly Leu Gly Ile Ser Ile Thr Gly Gly Lys Glu His Gly Val
            20                  25                  30

Pro Ile Leu Ile Ser Glu Ile His Pro Gly Gln Pro Ala Asp Arg Cys
            35                  40                  45

Gly Gly Leu His Val Gly Asp Ala Ile Leu Ala Val Asn Gly Val Asn
50                  55                  60

Leu Arg Asp Thr Lys His Lys Glu Ala Val Thr Ile Leu Ser Gln Gln
65                  70                  75                  80

Arg Gly Glu Ile Glu Phe Glu Val Val Tyr Val Ala Pro Glu Val Asp
                85                  90                  95

Ser Asp

<210> SEQ ID NO 184
<211> LENGTH: 98
<212> TYPE: PRT
<213> ORGANISM: Artificial Sequence
<220> FEATURE:
<223> OTHER INFORMATION: Synthetic peptide

<400> SEQUENCE: 184

Thr Ala Glu Ala Thr Val Cys Thr Val Thr Leu Glu Lys Met Ser Ala
1               5                   10                  15

Gly Leu Gly Phe Ser Leu Glu Gly Gly Lys Gly Ser Leu His Gly Asp
            20                  25                  30

Lys Pro Leu Thr Ile Asn Arg Ile Phe Lys Gly Ala Ala Ser Glu Gln
            35                  40                  45

Ser Glu Thr Val Gln Pro Gly Asp Glu Ile Leu Gln Leu Gly Gly Thr
50                  55                  60

Ala Met Gln Gly Leu Thr Arg Phe Glu Ala Trp Asn Ile Ile Lys Ala
65                  70                  75                  80

Leu Pro Asp Gly Pro Val Thr Ile Val Ile Arg Arg Lys Ser Leu Gln
                85                  90                  95

Ser Lys
```

<210> SEQ ID NO 185
<211> LENGTH: 97
<212> TYPE: PRT
<213> ORGANISM: Artificial Sequence
<220> FEATURE:
<223> OTHER INFORMATION: Synthetic peptide

<400> SEQUENCE: 185

```
Ile His Val Thr Ile Leu His Lys Glu Glu Gly Ala Gly Leu Gly Phe
1               5                   10                  15

Ser Leu Ala Gly Gly Ala Asp Leu Glu Asn Lys Val Ile Thr Val His
            20                  25                  30

Arg Val Phe Pro Asn Gly Leu Ala Ser Gln Glu Gly Thr Ile Gln Lys
        35                  40                  45

Gly Asn Glu Val Leu Ser Ile Asn Gly Lys Ser Leu Lys Gly Thr Thr
    50                  55                  60

His His Asp Ala Leu Ala Ile Leu Arg Gln Ala Arg Glu Pro Arg Gln
65                  70                  75                  80

Ala Val Ile Val Thr Arg Lys Leu Thr Pro Glu Glu Phe Ile Val Thr
                85                  90                  95

Asp
```

<210> SEQ ID NO 186
<211> LENGTH: 214
<212> TYPE: PRT
<213> ORGANISM: Artificial Sequence
<220> FEATURE:
<223> OTHER INFORMATION: Synthetic peptide

<400> SEQUENCE: 186

```
Ile His Val Thr Ile Leu His Lys Glu Glu Gly Ala Gly Leu Gly Phe
1               5                   10                  15

Ser Leu Ala Gly Gly Ala Asp Leu Glu Asn Lys Val Ile Thr Val His
            20                  25                  30

Arg Val Phe Pro Asn Gly Leu Ala Ser Gln Glu Gly Thr Ile Gln Lys
        35                  40                  45

Gly Asn Glu Val Leu Ser Ile Asn Gly Lys Ser Leu Lys Gly Thr Thr
    50                  55                  60

His His Asp Ala Leu Ala Ile Leu Arg Gln Ala Arg Glu Pro Arg Gln
65                  70                  75                  80

Ala Val Ile Val Thr Arg Lys Leu Thr Pro Glu Ala Met Pro Asp Leu
                85                  90                  95

Asn Ser Ser Thr Asp Ser Ala Ala Ser Ala Ser Ala Ala Ser Asp Val
                100                 105                 110

Ser Val Glu Ser Thr Ala Glu Ala Thr Val Cys Thr Val Thr Leu Glu
            115                 120                 125

Lys Met Ser Ala Gly Leu Gly Phe Ser Leu Glu Gly Gly Lys Gly Ser
        130                 135                 140

Leu His Gly Asp Lys Pro Leu Thr Ile Asn Arg Ile Phe Lys Gly Ala
145                 150                 155                 160

Ala Ser Glu Gln Ser Glu Thr Val Gln Pro Gly Asp Glu Ile Leu Gln
                165                 170                 175

Leu Gly Gly Thr Ala Met Gln Gly Leu Thr Arg Phe Glu Ala Trp Asn
                180                 185                 190

Ile Ile Lys Ala Leu Pro Asp Gly Pro Val Thr Ile Val Ile Arg Arg
            195                 200                 205
```

Lys Ser Leu Gln Ser Lys
    210

<210> SEQ ID NO 187
<211> LENGTH: 162
<212> TYPE: PRT
<213> ORGANISM: Artificial Sequence
<220> FEATURE:
<223> OTHER INFORMATION: Synthetic peptide

<400> SEQUENCE: 187

Ile Arg Glu Ala Lys Tyr Ser Gly Val Leu Ser Ile Gly Lys Ile
1               5                  10                  15

Phe Lys Glu Glu Gly Leu Leu Gly Phe Phe Val Gly Leu Ile Pro His
                20                  25                  30

Leu Leu Gly Asp Val Val Phe Leu Trp Gly Cys Asn Leu Leu Ala His
            35                  40                  45

Phe Ile Asn Ala Tyr Leu Val Asp Asp Ser Val Ser Asp Thr Pro Gly
        50                  55                  60

Gly Leu Gly Asn Asp Gln Asn Pro Gly Ser Gln Phe Ser Gln Ala Leu
65                  70                  75                  80

Ala Ile Arg Ser Tyr Thr Lys Phe Val Met Gly Ile Ala Val Ser Met
                85                  90                  95

Leu Thr Tyr Pro Phe Leu Leu Val Gly Asp Leu Met Ala Val Asn Asn
                100                 105                 110

Cys Gly Leu Gln Ala Gly Leu Pro Pro Tyr Ser Pro Val Phe Lys Ser
            115                 120                 125

Trp Ile His Cys Trp Lys Tyr Leu Ser Val Gln Gly Gln Leu Phe Arg
        130                 135                 140

Gly Ser Ser Leu Leu Phe Arg Arg Val Ser Ser Gly Ser Cys Phe Ala
145                 150                 155                 160

Leu Glu

<210> SEQ ID NO 188
<211> LENGTH: 338
<212> TYPE: PRT
<213> ORGANISM: Artificial Sequence
<220> FEATURE:
<223> OTHER INFORMATION: Synthetic peptide

<400> SEQUENCE: 188

Glu Gly Glu Met Glu Tyr Glu Glu Ile Thr Leu Glu Arg Gly Asn Ser
1               5                  10                  15

Gly Leu Gly Phe Ser Ile Ala Gly Gly Thr Asp Asn Pro His Ile Gly
                20                  25                  30

Asp Asp Pro Ser Ile Phe Ile Thr Lys Ile Ile Pro Gly Gly Ala Ala
            35                  40                  45

Ala Gln Asp Gly Arg Leu Arg Val Asn Asp Ser Ile Leu Phe Val Asn
        50                  55                  60

Glu Val Asp Val Arg Glu Val Thr His Ser Ala Ala Val Glu Ala Leu
65                  70                  75                  80

Lys Glu Ala Gly Ser Ile Val Arg Leu Tyr Val Met Arg Arg Lys Pro
                85                  90                  95

Pro Ala Glu Lys Val Met Glu Ile Lys Leu Ile Lys Gly Pro Lys Gly
                100                 105                 110

Leu Gly Phe Ser Ile Ala Gly Gly Val Gly Asn Gln His Ile Pro Gly
            115                 120                 125

```
Asp Asn Ser Ile Tyr Val Thr Lys Ile Ile Glu Gly Gly Ala Ala His
        130                 135                 140

Lys Asp Gly Arg Leu Gln Ile Gly Asp Lys Ile Leu Ala Val Asn Ser
145                 150                 155                 160

Val Gly Leu Glu Asp Val Met His Glu Asp Ala Val Ala Ala Leu Lys
                165                 170                 175

Asn Thr Tyr Asp Val Val Tyr Leu Lys Val Ala Lys Pro Ser Asn Ala
            180                 185                 190

Tyr Leu Ser Asp Ser Tyr Ala Pro Pro Asp Ile Thr Thr Ser Tyr Ser
        195                 200                 205

Gln His Leu Asp Asn Glu Ile Ser His Ser Ser Tyr Leu Gly Thr Asp
    210                 215                 220

Tyr Pro Thr Ala Met Thr Pro Thr Ser Pro Arg Arg Tyr Ser Pro Val
225                 230                 235                 240

Ala Lys Asp Leu Leu Gly Glu Glu Asp Ile Pro Arg Glu Pro Arg Arg
                245                 250                 255

Ile Val Ile His Arg Gly Ser Thr Gly Leu Gly Phe Asn Ile Val Gly
            260                 265                 270

Gly Glu Asp Gly Glu Gly Ile Phe Ile Ser Phe Ile Leu Ala Gly Gly
        275                 280                 285

Pro Ala Asp Leu Ser Gly Glu Leu Arg Lys Gly Asp Gln Ile Leu Ser
    290                 295                 300

Val Asn Gly Val Asp Leu Arg Asn Ala Ser His Glu Gln Ala Ala Ile
305                 310                 315                 320

Ala Leu Lys Asn Ala Gly Gln Thr Val Thr Ile Ile Ala Gln Tyr Lys
                325                 330                 335

Pro Glu

<210> SEQ ID NO 189
<211> LENGTH: 105
<212> TYPE: PRT
<213> ORGANISM: Artificial Sequence
<220> FEATURE:
<223> OTHER INFORMATION: Synthetic peptide

<400> SEQUENCE: 189

His Val Met Arg Arg Lys Pro Pro Ala Glu Lys Val Met Glu Ile Lys
1               5                   10                  15

Leu Ile Lys Gly Pro Lys Gly Leu Gly Phe Ser Ile Ala Gly Gly Val
            20                  25                  30

Gly Asn Gln His Ile Pro Gly Asp Asn Ser Ile Tyr Val Thr Lys Ile
        35                  40                  45

Ile Glu Gly Gly Ala Ala His Lys Asp Gly Arg Leu Gln Ile Gly Asp
    50                  55                  60

Lys Ile Leu Ala Val Asn Ser Val Gly Leu Glu Asp Val Met His Glu
65                  70                  75                  80

Asp Ala Val Ala Ala Leu Lys Asn Thr Tyr Asp Val Val Tyr Leu Lys
                85                  90                  95

Val Ala Lys Pro Ser Asn Ala Tyr Leu
            100                 105

<210> SEQ ID NO 190
<211> LENGTH: 97
<212> TYPE: PRT
<213> ORGANISM: Artificial Sequence
<220> FEATURE:
```

<223> OTHER INFORMATION: Synthetic peptide

<400> SEQUENCE: 190

```
Arg Glu Asp Ile Pro Arg Glu Pro Arg Arg Ile Val Ile His Arg Gly
1               5                   10                  15

Ser Thr Gly Leu Gly Phe Asn Ile Val Gly Gly Glu Asp Gly Glu Gly
            20                  25                  30

Ile Phe Ile Ser Phe Ile Leu Ala Gly Gly Pro Ala Asp Leu Ser Gly
        35                  40                  45

Glu Leu Arg Lys Gly Asp Gln Ile Leu Ser Val Asn Gly Val Asp Leu
    50                  55                  60

Arg Asn Ala Ser His Glu Gln Ala Ala Ile Ala Leu Lys Asn Ala Gly
65                  70                  75                  80

Gln Thr Val Thr Ile Ile Ala Gln Tyr Lys Pro Glu Phe Ile Val Thr
                85                  90                  95

Asp
```

<210> SEQ ID NO 191
<211> LENGTH: 99
<212> TYPE: PRT
<213> ORGANISM: Artificial Sequence
<220> FEATURE:
<223> OTHER INFORMATION: Synthetic peptide

<400> SEQUENCE: 191

```
Leu Glu Tyr Glu Glu Ile Thr Leu Glu Arg Gly Asn Ser Gly Leu Gly
1               5                   10                  15

Phe Ser Ile Ala Gly Gly Thr Asp Asn Pro His Ile Gly Asp Asp Pro
            20                  25                  30

Ser Ile Phe Ile Thr Lys Ile Ile Pro Gly Gly Ala Ala Ala Gln Asp
        35                  40                  45

Gly Arg Leu Arg Val Asn Asp Ser Ile Leu Phe Val Asn Glu Val Asp
    50                  55                  60

Val Arg Glu Val Thr His Ser Ala Ala Val Glu Ala Leu Lys Glu Ala
65                  70                  75                  80

Gly Ser Ile Val Arg Leu Tyr Val Met Arg Arg Lys Pro Pro Ala Glu
                85                  90                  95

Asn Ser Ser
```

<210> SEQ ID NO 192
<211> LENGTH: 88
<212> TYPE: PRT
<213> ORGANISM: Artificial Sequence
<220> FEATURE:
<223> OTHER INFORMATION: Synthetic peptide

<400> SEQUENCE: 192

```
Arg Asp Met Ala Glu Ala His Lys Glu Ala Met Ser Arg Lys Leu Gly
1               5                   10                  15

Gln Ser Glu Ser Gln Gly Pro Pro Arg Ala Phe Ala Lys Val Asn Ser
            20                  25                  30

Ile Ser Pro Gly Ser Pro Ala Ser Ile Ala Gly Leu Gln Val Asp Asp
        35                  40                  45

Glu Ile Val Glu Phe Gly Ser Val Asn Thr Gln Asn Phe Gln Ser Leu
    50                  55                  60

His Asn Ile Gly Ser Val Val Gln His Ser Glu Gly Ala Leu Ala Pro
65                  70                  75                  80
```

```
Thr Ile Leu Leu Ser Val Ser Met
            85
```

<210> SEQ ID NO 193
<211> LENGTH: 102
<212> TYPE: PRT
<213> ORGANISM: Artificial Sequence
<220> FEATURE:
<223> OTHER INFORMATION: Synthetic peptide

<400> SEQUENCE: 193

```
Gln Asn Asp Asn Gly Asp Ser Tyr Leu Val Leu Ile Arg Ile Thr Pro
1               5                   10                  15

Asp Glu Asp Gly Lys Phe Gly Phe Asn Leu Lys Gly Gly Val Asp Gln
            20                  25                  30

Lys Met Pro Leu Val Val Ser Arg Ile Asn Pro Glu Ser Pro Ala Asp
        35                  40                  45

Thr Cys Ile Pro Lys Leu Asn Glu Gly Asp Gln Ile Val Leu Ile Asn
    50                  55                  60

Gly Arg Asp Ile Ser Glu His Thr His Asp Gln Val Val Met Phe Ile
65                  70                  75                  80

Lys Ala Ser Arg Glu Ser His Ser Arg Glu Leu Ala Leu Val Ile Arg
                85                  90                  95

Arg Arg Ala Val Arg Ser
            100
```

<210> SEQ ID NO 194
<211> LENGTH: 88
<212> TYPE: PRT
<213> ORGANISM: Artificial Sequence
<220> FEATURE:
<223> OTHER INFORMATION: Synthetic peptide

<400> SEQUENCE: 194

```
Ile Arg Met Lys Pro Asp Glu Asn Gly Arg Phe Gly Phe Asn Val Lys
1               5                   10                  15

Gly Gly Tyr Asp Gln Lys Met Pro Val Ile Val Ser Arg Val Ala Pro
            20                  25                  30

Gly Thr Pro Ala Asp Leu Cys Val Pro Arg Leu Asn Glu Gly Asp Gln
        35                  40                  45

Val Val Leu Ile Asn Gly Arg Asp Ile Ala Glu His Thr His Asp Gln
    50                  55                  60

Val Val Leu Phe Ile Lys Ala Ser Cys Glu Arg His Ser Gly Glu Leu
65                  70                  75                  80

Met Leu Leu Val Arg Pro Asn Ala
                85
```

<210> SEQ ID NO 195
<211> LENGTH: 95
<212> TYPE: PRT
<213> ORGANISM: Artificial Sequence
<220> FEATURE:
<223> OTHER INFORMATION: Synthetic peptide

<400> SEQUENCE: 195

```
Gly Asp Ile Phe Glu Val Glu Leu Ala Lys Asn Asp Asn Ser Leu Gly
1               5                   10                  15

Ile Ser Val Thr Gly Gly Val Asn Thr Ser Val Arg His Gly Gly Ile
            20                  25                  30

Tyr Val Lys Ala Val Ile Pro Gln Gly Ala Ala Glu Ser Asp Gly Arg
```

-continued

```
                35                  40                  45
Ile His Lys Gly Asp Arg Val Leu Ala Val Asn Gly Val Ser Leu Glu
 50                  55                  60

Gly Ala Thr His Lys Gln Ala Val Glu Thr Leu Arg Asn Thr Gly Gln
 65                  70                  75                  80

Val Val His Leu Leu Glu Lys Gly Gln Ser Pro Thr Ser Lys
                 85                  90                  95

<210> SEQ ID NO 196
<211> LENGTH: 106
<212> TYPE: PRT
<213> ORGANISM: Artificial Sequence
<220> FEATURE:
<223> OTHER INFORMATION: Synthetic peptide

<400> SEQUENCE: 196

Pro Glu Arg Glu Ile Thr Leu Val Asn Leu Lys Lys Asp Ala Lys Tyr
 1               5                  10                  15

Gly Leu Gly Phe Gln Ile Ile Gly Gly Glu Lys Met Gly Arg Leu Asp
                 20                  25                  30

Leu Gly Ile Phe Ile Ser Ser Val Ala Pro Gly Gly Pro Ala Asp Phe
             35                  40                  45

His Gly Cys Leu Lys Pro Gly Asp Arg Leu Ile Ser Val Asn Ser Val
 50                  55                  60

Ser Leu Glu Gly Val Ser His His Ala Ala Ile Glu Ile Leu Gln Asn
 65                  70                  75                  80

Ala Pro Glu Asp Val Thr Leu Val Ile Ser Gln Pro Lys Glu Lys Ile
                 85                  90                  95

Ser Lys Val Pro Ser Thr Pro Val His Leu
                100                 105

<210> SEQ ID NO 197
<211> LENGTH: 98
<212> TYPE: PRT
<213> ORGANISM: Artificial Sequence
<220> FEATURE:
<223> OTHER INFORMATION: Synthetic peptide

<400> SEQUENCE: 197

Glu Leu Glu Val Glu Leu Leu Ile Thr Leu Ile Lys Ser Glu Lys Ala
 1               5                  10                  15

Ser Leu Gly Phe Thr Val Thr Lys Gly Asn Gln Arg Ile Gly Cys Tyr
                 20                  25                  30

Val His Asp Val Ile Gln Asp Pro Ala Lys Ser Asp Gly Arg Leu Lys
             35                  40                  45

Pro Gly Asp Arg Leu Ile Lys Val Asn Asp Thr Asp Val Thr Asn Met
 50                  55                  60

Thr His Thr Asp Ala Val Asn Leu Leu Arg Ala Ala Ser Lys Thr Val
 65                  70                  75                  80

Arg Leu Val Ile Gly Arg Val Leu Glu Leu Pro Arg Ile Pro Met Leu
                 85                  90                  95

Pro His

<210> SEQ ID NO 198
<211> LENGTH: 104
<212> TYPE: PRT
<213> ORGANISM: Artificial Sequence
<220> FEATURE:
<223> OTHER INFORMATION: Synthetic peptide
```

```
<400> SEQUENCE: 198

Thr Glu Glu Asn Thr Phe Glu Val Lys Leu Phe Lys Asn Ser Ser Gly
1               5                   10                  15

Leu Gly Phe Ser Phe Ser Arg Glu Asp Asn Leu Ile Pro Glu Gln Ile
            20                  25                  30

Asn Ala Ser Ile Val Arg Val Lys Lys Leu Phe Ala Gly Gln Pro Ala
        35                  40                  45

Ala Glu Ser Gly Lys Ile Asp Val Gly Asp Val Ile Leu Lys Val Asn
    50                  55                  60

Gly Ala Ser Leu Lys Gly Leu Ser Gln Gln Glu Val Ile Ser Ala Leu
65                  70                  75                  80

Arg Gly Thr Ala Pro Glu Val Phe Leu Leu Cys Arg Pro Pro
                85                  90                  95

Gly Val Leu Pro Glu Ile Asp Thr
            100

<210> SEQ ID NO 199
<211> LENGTH: 94
<212> TYPE: PRT
<213> ORGANISM: Artificial Sequence
<220> FEATURE:
<223> OTHER INFORMATION: Synthetic peptide

<400> SEQUENCE: 199

Met Leu Pro His Leu Leu Pro Asp Ile Thr Leu Thr Cys Asn Lys Glu
1               5                   10                  15

Glu Leu Gly Phe Ser Leu Cys Gly Gly His Asp Ser Leu Tyr Gln Val
            20                  25                  30

Val Tyr Ile Ser Asp Ile Asn Pro Arg Ser Val Ala Ala Ile Glu Gly
        35                  40                  45

Asn Leu Gln Leu Leu Asp Val Ile His Tyr Val Asn Gly Val Ser Thr
    50                  55                  60

Gln Gly Met Thr Leu Glu Glu Val Asn Arg Ala Leu Asp Met Ser Leu
65                  70                  75                  80

Pro Ser Leu Val Leu Lys Ala Thr Arg Asn Asp Leu Pro Val
                85                  90

<210> SEQ ID NO 200
<211> LENGTH: 92
<212> TYPE: PRT
<213> ORGANISM: Artificial Sequence
<220> FEATURE:
<223> OTHER INFORMATION: Synthetic peptide

<400> SEQUENCE: 200

Val Cys Ser Glu Arg Arg Tyr Arg Gln Ile Thr Ile Pro Arg Gly Lys
1               5                   10                  15

Asp Gly Phe Gly Phe Thr Ile Cys Cys Asp Ser Pro Val Arg Val Gln
            20                  25                  30

Ala Val Asp Ser Gly Gly Pro Ala Glu Arg Ala Gly Leu Gln Gln Leu
        35                  40                  45

Asp Thr Val Leu Gln Leu Asn Glu Arg Pro Val Glu His Trp Lys Cys
    50                  55                  60

Val Glu Leu Ala His Glu Ile Arg Ser Cys Pro Ser Glu Ile Ile Leu
65                  70                  75                  80

Leu Val Trp Arg Met Val Pro Gln Val Lys Pro Gly
                85                  90
```

<210> SEQ ID NO 201
<211> LENGTH: 93
<212> TYPE: PRT
<213> ORGANISM: Artificial Sequence
<220> FEATURE:
<223> OTHER INFORMATION: Synthetic peptide

<400> SEQUENCE: 201

Arg Pro Ser Pro Pro Arg Val Arg Ser Val Glu Val Ala Arg Gly Arg
1               5                   10                  15

Ala Gly Tyr Gly Phe Thr Leu Ser Gly Gln Ala Pro Cys Val Leu Ser
            20                  25                  30

Cys Val Met Arg Gly Ser Pro Ala Asp Phe Val Gly Leu Arg Ala Gly
        35                  40                  45

Asp Gln Ile Leu Ala Val Asn Glu Ile Asn Val Lys Lys Ala Ser His
    50                  55                  60

Glu Asp Val Val Lys Leu Ile Gly Lys Cys Ser Gly Val Leu His Met
65                  70                  75                  80

Val Ile Ala Glu Gly Val Gly Arg Phe Glu Ser Cys Ser
                85                  90

<210> SEQ ID NO 202
<211> LENGTH: 124
<212> TYPE: PRT
<213> ORGANISM: Artificial Sequence
<220> FEATURE:
<223> OTHER INFORMATION: Synthetic peptide

<400> SEQUENCE: 202

Ser Glu Asp Glu Thr Phe Ser Trp Pro Gly Pro Lys Thr Val Thr Leu
1               5                   10                  15

Lys Arg Thr Ser Gln Gly Phe Gly Phe Thr Leu Arg His Phe Ile Val
            20                  25                  30

Tyr Pro Pro Glu Ser Ala Ile Gln Phe Ser Tyr Lys Asp Glu Glu Asn
        35                  40                  45

Gly Asn Arg Gly Gly Lys Gln Arg Asn Arg Leu Glu Pro Met Asp Thr
    50                  55                  60

Ile Phe Val Lys Gln Val Lys Glu Gly Gly Pro Ala Phe Glu Ala Gly
65                  70                  75                  80

Leu Cys Thr Gly Asp Arg Ile Ile Lys Val Asn Gly Glu Ser Val Ile
                85                  90                  95

Gly Lys Thr Tyr Ser Gln Val Ile Ala Leu Ile Gln Asn Ser Asp Thr
            100                 105                 110

Thr Leu Glu Leu Ser Val Met Pro Lys Asp Glu Asp
        115                 120

<210> SEQ ID NO 203
<211> LENGTH: 96
<212> TYPE: PRT
<213> ORGANISM: Artificial Sequence
<220> FEATURE:
<223> OTHER INFORMATION: Synthetic peptide

<400> SEQUENCE: 203

Ser Ala Lys Asn Arg Trp Arg Leu Val Gly Pro Val His Leu Thr Arg
1               5                   10                  15

Gly Glu Gly Gly Phe Gly Leu Thr Leu Arg Gly Asp Ser Pro Val Leu
            20                  25                  30

```
Ile Ala Ala Val Ile Pro Gly Ser Gln Ala Ala Ala Gly Leu Lys
        35                  40                  45

Glu Gly Asp Tyr Ile Val Ser Val Asn Gly Gln Pro Cys Arg Trp Trp
 50                  55                  60

Arg His Ala Glu Val Val Thr Glu Leu Lys Ala Ala Gly Glu Ala Gly
 65                  70                  75                  80

Ala Ser Leu Gln Val Val Ser Leu Leu Pro Ser Ser Arg Leu Pro Ser
                85                  90                  95

<210> SEQ ID NO 204
<211> LENGTH: 104
<212> TYPE: PRT
<213> ORGANISM: Artificial Sequence
<220> FEATURE:
<223> OTHER INFORMATION: Synthetic peptide

<400> SEQUENCE: 204

Ile Ser Phe Ser Ala Asn Lys Arg Trp Thr Pro Pro Arg Ser Ile Arg
 1               5                  10                  15

Phe Thr Ala Glu Glu Gly Asp Leu Gly Phe Thr Leu Arg Gly Asn Ala
                20                  25                  30

Pro Val Gln Val His Phe Leu Asp Pro Tyr Cys Ser Ala Ser Val Ala
            35                  40                  45

Gly Ala Arg Glu Gly Asp Tyr Ile Val Ser Ile Gln Leu Val Asp Cys
 50                  55                  60

Lys Trp Leu Thr Leu Ser Glu Val Met Lys Leu Leu Lys Ser Phe Gly
 65                  70                  75                  80

Glu Asp Glu Ile Glu Met Lys Val Val Ser Leu Leu Asp Ser Thr Ser
                85                  90                  95

Ser Met His Asn Lys Ser Ala Thr
            100

<210> SEQ ID NO 205
<211> LENGTH: 126
<212> TYPE: PRT
<213> ORGANISM: Artificial Sequence
<220> FEATURE:
<223> OTHER INFORMATION: Synthetic peptide

<400> SEQUENCE: 205

Thr Leu Asn Glu Glu His Ser His Ser Asp Lys His Pro Val Thr Trp
 1               5                  10                  15

Gln Pro Ser Lys Asp Gly Asp Arg Leu Ile Gly Arg Ile Leu Leu Asn
                20                  25                  30

Lys Arg Leu Lys Asp Gly Ser Val Pro Arg Asp Ser Gly Ala Met Leu
            35                  40                  45

Gly Leu Lys Val Val Gly Gly Lys Met Thr Glu Ser Gly Arg Leu Cys
 50                  55                  60

Ala Phe Ile Thr Lys Val Lys Lys Gly Ser Leu Ala Asp Thr Val Gly
 65                  70                  75                  80

His Leu Arg Pro Gly Asp Glu Val Leu Glu Trp Asn Gly Arg Leu Leu
                85                  90                  95

Gln Gly Ala Thr Phe Glu Glu Val Tyr Asn Ile Ile Leu Glu Ser Lys
            100                 105                 110

Pro Glu Pro Gln Val Glu Leu Val Val Ser Arg Pro Ile Gly
        115                 120                 125

<210> SEQ ID NO 206
```

<211> LENGTH: 101
<212> TYPE: PRT
<213> ORGANISM: Artificial Sequence
<220> FEATURE:
<223> OTHER INFORMATION: Synthetic peptide

<400> SEQUENCE: 206

```
Gln Glu Met Asp Arg Glu Glu Leu Glu Glu Val Asp Leu Tyr
1               5                   10                  15

Arg Met Asn Ser Gln Asp Lys Leu Gly Leu Thr Val Cys Tyr Arg Thr
            20                  25                  30

Asp Asp Glu Asp Ile Gly Ile Tyr Ile Ser Glu Ile Asp Pro Asn
        35                  40                  45

Ser Ile Ala Ala Lys Asp Gly Arg Ile Arg Glu Gly Asp Arg Ile Ile
    50                  55                  60

Gln Ile Asn Gly Ile Glu Val Gln Asn Arg Glu Glu Ala Val Ala Leu
65                  70                  75                  80

Leu Thr Ser Glu Glu Asn Lys Asn Phe Ser Leu Leu Ile Ala Arg Pro
                85                  90                  95

Glu Leu Gln Leu Asp
            100
```

<210> SEQ ID NO 207
<211> LENGTH: 107
<212> TYPE: PRT
<213> ORGANISM: Artificial Sequence
<220> FEATURE:
<223> OTHER INFORMATION: Synthetic peptide

<400> SEQUENCE: 207

```
Gln Gly Glu Glu Thr Lys Ser Leu Thr Leu Val Leu His Arg Asp Ser
1               5                   10                  15

Gly Ser Leu Gly Phe Asn Ile Ile Gly Gly Arg Pro Ser Val Asp Asn
            20                  25                  30

His Asp Gly Ser Ser Ser Glu Gly Ile Phe Val Ser Lys Ile Val Asp
        35                  40                  45

Ser Gly Pro Ala Ala Lys Glu Gly Gly Leu Gln Ile His Asp Arg Ile
    50                  55                  60

Ile Glu Val Asn Gly Arg Asp Leu Ser Arg Ala Thr His Asp Gln Ala
65                  70                  75                  80

Val Glu Ala Phe Lys Thr Ala Lys Glu Pro Ile Val Val Gln Val Leu
                85                  90                  95

Arg Arg Thr Pro Arg Thr Lys Met Phe Thr Pro
            100                 105
```

<210> SEQ ID NO 208
<211> LENGTH: 98
<212> TYPE: PRT
<213> ORGANISM: Artificial Sequence
<220> FEATURE:
<223> OTHER INFORMATION: Synthetic peptide

<400> SEQUENCE: 208

```
Ile Leu Ala His Val Lys Gly Ile Glu Lys Glu Val Asn Val Tyr Lys
1               5                   10                  15

Ser Glu Asp Ser Leu Gly Leu Thr Ile Thr Asp Asn Gly Val Gly Tyr
            20                  25                  30

Ala Phe Ile Lys Arg Ile Lys Asp Gly Gly Val Ile Asp Ser Val Lys
        35                  40                  45
```

```
Thr Ile Cys Val Gly Asp His Ile Glu Ser Ile Asn Gly Glu Asn Ile
 50                  55                  60

Val Gly Trp Arg His Tyr Asp Val Ala Lys Lys Leu Lys Glu Leu Lys
 65                  70                  75                  80

Lys Glu Glu Leu Phe Thr Met Lys Leu Ile Glu Pro Lys Lys Ala Phe
                 85                  90                  95

Glu Ile

<210> SEQ ID NO 209
<211> LENGTH: 109
<212> TYPE: PRT
<213> ORGANISM: Artificial Sequence
<220> FEATURE:
<223> OTHER INFORMATION: Synthetic peptide

<400> SEQUENCE: 209

Arg Gly Glu Lys Lys Asn Ser Ser Gly Ile Ser Gly Ser Gln Arg
 1               5                  10                  15

Arg Tyr Ile Gly Val Met Met Leu Thr Leu Ser Pro Ser Ile Leu Ala
                 20                  25                  30

Glu Leu Gln Leu Arg Glu Pro Ser Phe Pro Asp Val Gln His Gly Val
             35                  40                  45

Leu Ile His Lys Val Ile Leu Gly Ser Pro Ala His Arg Ala Gly Leu
 50                  55                  60

Arg Pro Gly Asp Val Ile Leu Ala Ile Gly Glu Gln Met Val Gln Asn
 65                  70                  75                  80

Ala Glu Asp Val Tyr Glu Ala Val Arg Thr Gln Ser Gln Leu Ala Val
                 85                  90                  95

Gln Ile Arg Arg Gly Arg Glu Thr Leu Thr Leu Tyr Val
                100                 105

<210> SEQ ID NO 210
<211> LENGTH: 110
<212> TYPE: PRT
<213> ORGANISM: Artificial Sequence
<220> FEATURE:
<223> OTHER INFORMATION: Synthetic peptide

<400> SEQUENCE: 210

Ile Leu Glu Glu Lys Thr Val Val Leu Gln Lys Lys Asp Asn Glu Gly
 1               5                  10                  15

Phe Gly Phe Val Leu Arg Gly Ala Lys Ala Asp Thr Pro Ile Glu Glu
                 20                  25                  30

Phe Thr Pro Thr Pro Ala Phe Pro Ala Leu Gln Tyr Leu Glu Ser Val
             35                  40                  45

Asp Glu Gly Gly Val Ala Trp Gln Ala Gly Leu Arg Thr Gly Asp Phe
 50                  55                  60

Leu Ile Glu Val Asn Asn Glu Asn Val Val Lys Val Gly His Arg Gln
 65                  70                  75                  80

Val Val Asn Met Ile Arg Gln Gly Gly Asn His Leu Val Leu Lys Val
                 85                  90                  95

Val Thr Val Thr Arg Asn Leu Asp Pro Asp Asp Asn Ser Ser
                100                 105                 110

<210> SEQ ID NO 211
<211> LENGTH: 113
<212> TYPE: PRT
<213> ORGANISM: Artificial Sequence
<220> FEATURE:
```

-continued

<223> OTHER INFORMATION: Synthetic peptide

<400> SEQUENCE: 211

Ile Leu Lys Glu Lys Thr Val Leu Leu Gln Lys Lys Asp Ser Glu Gly
1               5                   10                  15

Phe Gly Phe Val Leu Arg Gly Ala Lys Ala Gln Thr Pro Ile Glu Glu
            20                  25                  30

Phe Thr Pro Thr Pro Ala Phe Pro Ala Leu Gln Tyr Leu Glu Ser Val
        35                  40                  45

Asp Glu Gly Gly Val Ala Trp Arg Ala Gly Leu Arg Met Gly Asp Phe
    50                  55                  60

Leu Ile Glu Val Asn Gly Gln Asn Val Val Lys Val Gly His Arg Gln
65                  70                  75                  80

Val Val Asn Met Ile Arg Gln Gly Gly Asn Thr Leu Met Val Lys Val
                85                  90                  95

Val Met Val Thr Arg His Pro Asp Met Asp Glu Ala Val Gln Asn Ser
            100                 105                 110

Ser

<210> SEQ ID NO 212
<211> LENGTH: 110
<212> TYPE: PRT
<213> ORGANISM: Artificial Sequence
<220> FEATURE:
<223> OTHER INFORMATION: Synthetic peptide

<400> SEQUENCE: 212

Ser Asp Tyr Val Ile Asp Asp Lys Val Ala Val Leu Gln Lys Arg Asp
1               5                   10                  15

His Glu Gly Phe Gly Phe Val Leu Arg Gly Ala Lys Ala Glu Thr Pro
            20                  25                  30

Ile Glu Glu Phe Thr Pro Thr Pro Ala Phe Pro Ala Leu Gln Tyr Leu
        35                  40                  45

Glu Ser Val Asp Val Glu Gly Val Ala Trp Arg Ala Gly Leu Arg Thr
    50                  55                  60

Gly Asp Phe Leu Ile Glu Val Asn Gly Val Asn Val Val Lys Val Gly
65                  70                  75                  80

His Lys Gln Val Val Ala Leu Ile Arg Gln Gly Gly Asn Arg Leu Val
                85                  90                  95

Met Lys Val Val Ser Val Thr Arg Lys Pro Glu Glu Asp Gly
            100                 105                 110

<210> SEQ ID NO 213
<211> LENGTH: 98
<212> TYPE: PRT
<213> ORGANISM: Artificial Sequence
<220> FEATURE:
<223> OTHER INFORMATION: Synthetic peptide

<400> SEQUENCE: 213

Ser Asn Ser Pro Arg Glu Glu Ile Phe Gln Val Ala Leu His Lys Arg
1               5                   10                  15

Asp Ser Gly Glu Gln Leu Gly Ile Lys Leu Val Arg Arg Thr Asp Glu
            20                  25                  30

Pro Gly Val Phe Ile Leu Asp Leu Leu Glu Gly Gly Leu Ala Ala Gln
        35                  40                  45

Asp Gly Arg Leu Ser Ser Asn Asp Arg Val Leu Ala Ile Asn Gly His
    50                  55                  60

Asp Leu Lys Tyr Gly Thr Pro Glu Leu Ala Ala Gln Ile Ile Gln Ala
65                  70                  75                  80

Ser Gly Glu Arg Val Asn Leu Thr Ile Ala Arg Pro Gly Lys Pro Gln
                85                  90                  95

Pro Gly

<210> SEQ ID NO 214
<211> LENGTH: 104
<212> TYPE: PRT
<213> ORGANISM: Artificial Sequence
<220> FEATURE:
<223> OTHER INFORMATION: Synthetic peptide

<400> SEQUENCE: 214

Ile Gln Cys Val Thr Cys Gln Glu Lys His Ile Thr Val Lys Lys Glu
1               5                   10                  15

Pro His Glu Ser Leu Gly Met Thr Val Ala Gly Gly Arg Gly Ser Lys
                20                  25                  30

Ser Gly Glu Leu Pro Ile Phe Val Thr Ser Val Pro Pro His Gly Cys
            35                  40                  45

Leu Ala Arg Asp Gly Arg Ile Lys Arg Gly Asp Val Leu Leu Asn Ile
        50                  55                  60

Asn Gly Ile Asp Leu Thr Asn Leu Ser His Ser Glu Ala Val Ala Met
65                  70                  75                  80

Leu Lys Ala Ser Ala Ala Ser Pro Ala Val Ala Leu Lys Ala Leu Glu
                85                  90                  95

Val Gln Ile Val Glu Glu Ala Thr
            100

<210> SEQ ID NO 215
<211> LENGTH: 110
<212> TYPE: PRT
<213> ORGANISM: Artificial Sequence
<220> FEATURE:
<223> OTHER INFORMATION: Synthetic peptide

<400> SEQUENCE: 215

Met Gly Leu Gly Val Ser Ala Glu Gln Pro Ala Gly Gly Ala Glu Gly
1               5                   10                  15

Phe His Leu His Gly Val Gln Glu Asn Ser Pro Ala Gln Gln Ala Gly
                20                  25                  30

Leu Glu Pro Tyr Phe Asp Phe Ile Ile Thr Ile Gly His Ser Arg Leu
            35                  40                  45

Asn Lys Glu Asn Asp Thr Leu Lys Ala Leu Leu Lys Ala Asn Val Glu
        50                  55                  60

Lys Pro Val Lys Leu Glu Val Phe Asn Met Lys Thr Met Arg Val Arg
65                  70                  75                  80

Glu Val Glu Val Val Pro Ser Asn Met Trp Gly Gly Gln Gly Leu Leu
                85                  90                  95

Gly Ala Ser Val Arg Phe Cys Ser Phe Arg Arg Ala Ser Glu
            100                 105                 110

<210> SEQ ID NO 216
<211> LENGTH: 109
<212> TYPE: PRT
<213> ORGANISM: Artificial Sequence
<220> FEATURE:
<223> OTHER INFORMATION: Synthetic peptide

```
<400> SEQUENCE: 216

Arg Ala Ser Glu Gln Val Trp His Val Leu Asp Val Glu Pro Ser Ser
1               5                   10                  15

Pro Ala Ala Leu Ala Gly Leu Arg Pro Tyr Thr Asp Tyr Val Val Gly
                20                  25                  30

Ser Asp Gln Ile Leu Gln Glu Ser Glu Asp Phe Phe Thr Leu Ile Glu
            35                  40                  45

Ser His Glu Gly Lys Pro Leu Lys Leu Met Val Tyr Asn Ser Lys Ser
        50                  55                  60

Asp Ser Cys Arg Glu Ser Gly Met Trp His Trp Leu Trp Val Ser Thr
65                  70                  75                  80

Pro Asp Pro Asn Ser Ala Pro Gln Leu Pro Gln Glu Ala Thr Trp His
                85                  90                  95

Pro Thr Thr Phe Cys Ser Thr Thr Trp Cys Pro Thr Thr
                100                 105

<210> SEQ ID NO 217
<211> LENGTH: 101
<212> TYPE: PRT
<213> ORGANISM: Artificial Sequence
<220> FEATURE:
<223> OTHER INFORMATION: Synthetic peptide

<400> SEQUENCE: 217

Ile Ser Val Thr Asp Gly Pro Lys Phe Glu Val Lys Leu Lys Lys Asn
1               5                   10                  15

Ala Asn Gly Leu Gly Phe Ser Phe Val Gln Met Glu Lys Glu Ser Cys
                20                  25                  30

Ser His Leu Lys Ser Asp Leu Val Arg Ile Lys Arg Leu Phe Pro Gly
            35                  40                  45

Gln Pro Ala Glu Glu Asn Gly Ala Ile Ala Gly Asp Ile Ile Leu
        50                  55                  60

Ala Val Asn Gly Arg Ser Thr Glu Gly Leu Ile Phe Gln Glu Val Leu
65                  70                  75                  80

His Leu Leu Arg Gly Ala Pro Gln Glu Val Thr Leu Leu Leu Cys Arg
                85                  90                  95

Pro Pro Pro Gly Ala
            100

<210> SEQ ID NO 218
<211> LENGTH: 100
<212> TYPE: PRT
<213> ORGANISM: Artificial Sequence
<220> FEATURE:
<223> OTHER INFORMATION: Synthetic peptide

<400> SEQUENCE: 218

Gln Pro Glu Pro Leu Arg Pro Arg Leu Cys Arg Leu Val Arg Gly Glu
1               5                   10                  15

Gln Gly Tyr Gly Phe His Leu His Gly Glu Lys Gly Arg Arg Gly Gln
                20                  25                  30

Phe Ile Arg Arg Val Glu Pro Gly Ser Pro Ala Glu Ala Ala Ala Leu
            35                  40                  45

Arg Ala Gly Asp Arg Leu Val Glu Val Asn Gly Val Asn Val Glu Gly
        50                  55                  60

Glu Thr His His Gln Val Val Gln Arg Ile Lys Ala Val Glu Gly Gln
65                  70                  75                  80
```

```
Thr Arg Leu Leu Val Val Asp Gln Glu Thr Asp Glu Glu Leu Arg Arg
            85                  90                  95

Arg Asn Ser Ser
            100

<210> SEQ ID NO 219
<211> LENGTH: 99
<212> TYPE: PRT
<213> ORGANISM: Artificial Sequence
<220> FEATURE:
<223> OTHER INFORMATION: Synthetic peptide

<400> SEQUENCE: 219

Pro Leu Arg Glu Leu Arg Pro Arg Leu Cys His Leu Arg Lys Gly Pro
1               5                   10                  15

Gln Gly Tyr Gly Phe Asn Leu His Ser Asp Lys Ser Arg Pro Gly Gln
            20                  25                  30

Tyr Ile Arg Ser Val Asp Pro Gly Ser Pro Ala Ala Arg Ser Gly Leu
        35                  40                  45

Arg Ala Gln Asp Arg Leu Ile Glu Val Asn Gly Gln Asn Val Glu Gly
    50                  55                  60

Leu Arg His Ala Glu Val Val Ala Ser Ile Lys Ala Arg Glu Asp Glu
65                  70                  75                  80

Ala Arg Leu Leu Val Val Asp Pro Glu Thr Asp Glu His Phe Lys Arg
                85                  90                  95

Asn Ser Ser

<210> SEQ ID NO 220
<211> LENGTH: 92
<212> TYPE: PRT
<213> ORGANISM: Artificial Sequence
<220> FEATURE:
<223> OTHER INFORMATION: Synthetic peptide

<400> SEQUENCE: 220

Pro Gly Val Arg Glu Ile His Leu Cys Lys Asp Glu Arg Gly Lys Thr
1               5                   10                  15

Gly Leu Arg Leu Arg Lys Val Asp Gln Gly Leu Phe Val Gln Leu Val
            20                  25                  30

Gln Ala Asn Thr Pro Ala Ser Leu Val Gly Leu Arg Phe Gly Asp Gln
        35                  40                  45

Leu Leu Gln Ile Asp Gly Arg Asp Cys Ala Gly Trp Ser Ser His Lys
    50                  55                  60

Ala His Gln Val Val Lys Lys Ala Ser Gly Asp Lys Ile Val Val Val
65                  70                  75                  80

Val Arg Asp Arg Pro Phe Gln Arg Thr Val Thr Met
                85                  90

<210> SEQ ID NO 221
<211> LENGTH: 90
<212> TYPE: PRT
<213> ORGANISM: Artificial Sequence
<220> FEATURE:
<223> OTHER INFORMATION: Synthetic peptide

<400> SEQUENCE: 221

Pro Phe Gln Arg Thr Val Thr Met His Lys Asp Ser Met Gly His Val
1               5                   10                  15

Gly Phe Val Ile Lys Lys Gly Lys Ile Val Ser Leu Val Lys Gly Ser
            20                  25                  30
```

```
Ser Ala Ala Arg Asn Gly Leu Leu Thr Asn His Tyr Val Cys Glu Val
            35                  40                  45

Asp Gly Gln Asn Val Ile Gly Leu Lys Asp Lys Lys Ile Met Glu Ile
 50                  55                  60

Leu Ala Thr Ala Gly Asn Val Val Thr Leu Thr Ile Ile Pro Ser Val
 65                  70                  75                  80

Ile Tyr Glu His Ile Val Glu Phe Ile Val
                 85                  90

<210> SEQ ID NO 222
<211> LENGTH: 96
<212> TYPE: PRT
<213> ORGANISM: Artificial Sequence
<220> FEATURE:
<223> OTHER INFORMATION: Synthetic peptide

<400> SEQUENCE: 222

Ser Leu Glu Arg Pro Arg Phe Cys Leu Leu Ser Lys Glu Glu Gly Lys
 1               5                  10                  15

Ser Phe Gly Phe His Leu Gln Gln Glu Leu Gly Arg Ala Gly His Val
                 20                  25                  30

Val Cys Arg Val Asp Pro Gly Thr Ser Ala Gln Arg Gln Gly Leu Gln
            35                  40                  45

Glu Gly Asp Arg Ile Leu Ala Val Asn Asn Asp Val Val Glu His Glu
 50                  55                  60

Asp Tyr Ala Val Val Val Arg Ile Arg Ala Ser Ser Pro Arg Val
 65                  70                  75                  80

Leu Leu Thr Val Leu Ala Arg His Ala His Asp Val Ala Arg Ala Gln
                 85                  90                  95

<210> SEQ ID NO 223
<211> LENGTH: 92
<212> TYPE: PRT
<213> ORGANISM: Artificial Sequence
<220> FEATURE:
<223> OTHER INFORMATION: Synthetic peptide

<400> SEQUENCE: 223

Leu Arg Asp Arg Pro Phe Glu Arg Thr Ile Thr Met His Lys Asp Ser
 1               5                  10                  15

Thr Gly His Val Gly Phe Ile Phe Lys Asn Gly Lys Ile Thr Ser Ile
                 20                  25                  30

Val Lys Asp Ser Ser Ala Ala Arg Asn Gly Leu Leu Thr Glu His Asn
            35                  40                  45

Ile Cys Glu Ile Asn Gly Gln Asn Val Ile Gly Leu Lys Asp Ser Gln
 50                  55                  60

Ile Ala Asp Ile Leu Ser Thr Ser Gly Thr Val Val Thr Ile Thr Ile
 65                  70                  75                  80

Met Pro Ala Phe Ile Phe Glu His Met Asn Ser Ser
                 85                  90

<210> SEQ ID NO 224
<211> LENGTH: 88
<212> TYPE: PRT
<213> ORGANISM: Artificial Sequence
<220> FEATURE:
<223> OTHER INFORMATION: Synthetic peptide

<400> SEQUENCE: 224
```

```
Leu Glu Ile Lys Gln Gly Ile Arg Glu Val Ile Leu Cys Lys Asp Gln
1               5                   10                  15

Asp Gly Lys Ile Gly Leu Arg Leu Lys Ser Ile Asp Asn Gly Ile Phe
            20                  25                  30

Val Gln Leu Val Gln Ala Asn Ser Pro Ala Ser Leu Val Gly Leu Arg
        35                  40                  45

Phe Gly Asp Gln Val Leu Gln Ile Asn Gly Glu Asn Cys Ala Gly Trp
    50                  55                  60

Ser Ser Asp Lys Ala His Lys Val Leu Lys Gln Ala Phe Gly Glu Lys
65                  70                  75                  80

Ile Thr Met Arg Ile His Arg Asp
                85
```

<210> SEQ ID NO 225
<211> LENGTH: 94
<212> TYPE: PRT
<213> ORGANISM: Artificial Sequence
<220> FEATURE:
<223> OTHER INFORMATION: Synthetic peptide

<400> SEQUENCE: 225

```
Gln Arg Arg Arg Val Thr Val Arg Lys Ala Asp Ala Gly Gly Leu Gly
1               5                   10                  15

Ile Ser Ile Lys Gly Gly Arg Glu Asn Lys Met Pro Ile Leu Ile Ser
            20                  25                  30

Lys Ile Phe Lys Gly Leu Ala Ala Asp Gln Thr Glu Ala Leu Phe Val
        35                  40                  45

Gly Asp Ala Ile Leu Ser Val Asn Gly Glu Asp Leu Ser Ser Ala Thr
    50                  55                  60

His Asp Glu Ala Val Gln Val Leu Lys Lys Thr Gly Lys Glu Val Val
65                  70                  75                  80

Leu Glu Val Lys Tyr Met Lys Asp Val Ser Pro Tyr Phe Lys
                85                  90
```

<210> SEQ ID NO 226
<211> LENGTH: 88
<212> TYPE: PRT
<213> ORGANISM: Artificial Sequence
<220> FEATURE:
<223> OTHER INFORMATION: Synthetic peptide

<400> SEQUENCE: 226

```
Pro Val Arg Arg Val Arg Val Val Lys Gln Glu Ala Gly Gly Leu Gly
1               5                   10                  15

Ile Ser Ile Lys Gly Gly Arg Glu Asn Arg Met Pro Ile Leu Ile Ser
            20                  25                  30

Lys Ile Phe Pro Gly Leu Ala Ala Asp Gln Ser Arg Ala Leu Arg Leu
        35                  40                  45

Gly Asp Ala Ile Leu Ser Val Asn Gly Thr Asp Leu Arg Gln Ala Thr
    50                  55                  60

His Asp Gln Ala Val Gln Ala Leu Lys Arg Ala Gly Lys Glu Val Leu
65                  70                  75                  80

Leu Glu Val Lys Phe Ile Arg Glu
                85
```

<210> SEQ ID NO 227
<211> LENGTH: 100
<212> TYPE: PRT
<213> ORGANISM: Artificial Sequence

```
<220> FEATURE:
<223> OTHER INFORMATION: Synthetic peptide

<400> SEQUENCE: 227

Glu Pro Phe Tyr Ser Gly Glu Arg Thr Val Thr Ile Arg Arg Gln Thr
1               5                   10                  15

Val Gly Gly Phe Gly Leu Ser Ile Lys Gly Ala Glu His Asn Ile
            20                  25                  30

Pro Val Val Ser Lys Ile Ser Lys Glu Gln Arg Ala Glu Leu Ser
        35                  40                  45

Gly Leu Leu Phe Ile Gly Asp Ala Ile Leu Gln Ile Asn Gly Ile Asn
50                  55                  60

Val Arg Lys Cys Arg His Glu Glu Val Val Gln Val Leu Arg Asn Ala
65                  70                  75                  80

Gly Glu Glu Val Thr Leu Thr Val Ser Phe Leu Lys Arg Ala Pro Ala
                85                  90                  95

Phe Leu Lys Leu
            100

<210> SEQ ID NO 228
<211> LENGTH: 99
<212> TYPE: PRT
<213> ORGANISM: Artificial Sequence
<220> FEATURE:
<223> OTHER INFORMATION: Synthetic peptide

<400> SEQUENCE: 228

Ser His Gln Gly Arg Asn Arg Arg Thr Val Thr Leu Arg Arg Gln Pro
1               5                   10                  15

Val Gly Gly Leu Gly Leu Ser Ile Lys Gly Gly Ser Glu His Asn Val
            20                  25                  30

Pro Val Val Ile Ser Lys Ile Phe Glu Asp Gln Ala Ala Asp Gln Thr
        35                  40                  45

Gly Met Leu Phe Val Gly Asp Ala Val Leu Gln Val Asn Gly Ile His
            50                  55                  60

Val Glu Asn Ala Thr His Glu Glu Val Val His Leu Leu Arg Asn Ala
65                  70                  75                  80

Gly Asp Glu Val Thr Ile Thr Val Glu Tyr Leu Arg Glu Ala Pro Ala
                85                  90                  95

Phe Leu Lys

<210> SEQ ID NO 229
<211> LENGTH: 91
<212> TYPE: PRT
<213> ORGANISM: Artificial Sequence
<220> FEATURE:
<223> OTHER INFORMATION: Synthetic peptide

<400> SEQUENCE: 229

Arg Gly Glu Thr Lys Glu Val Glu Val Thr Lys Thr Glu Asp Ala Leu
1               5                   10                  15

Gly Leu Thr Ile Thr Asp Asn Gly Ala Gly Tyr Ala Phe Ile Lys Arg
            20                  25                  30

Ile Lys Glu Gly Ser Ile Ile Asn Arg Ile Glu Ala Val Cys Val Gly
        35                  40                  45

Asp Ser Ile Glu Ala Ile Asn Asp His Ser Ile Val Gly Cys Arg His
            50                  55                  60

Tyr Glu Val Ala Lys Met Leu Arg Glu Leu Pro Lys Ser Gln Pro Phe
```

```
                65                  70                  75                  80
Thr Leu Arg Leu Val Gln Pro Lys Arg Ala Phe
                85                  90

<210> SEQ ID NO 230
<211> LENGTH: 88
<212> TYPE: PRT
<213> ORGANISM: Artificial Sequence
<220> FEATURE:
<223> OTHER INFORMATION: Synthetic peptide

<400> SEQUENCE: 230

His Ser Ile His Ile Glu Lys Ser Asp Thr Ala Ala Asp Thr Tyr Gly
1               5                   10                  15

Phe Ser Leu Ser Ser Val Glu Glu Asp Gly Ile Arg Arg Leu Tyr Val
            20                  25                  30

Asn Ser Val Lys Glu Thr Gly Leu Ala Ser Lys Lys Gly Leu Lys Ala
        35                  40                  45

Gly Asp Glu Ile Leu Glu Ile Asn Asn Arg Ala Ala Asp Ala Leu Asn
    50                  55                  60

Ser Ser Met Leu Lys Asp Phe Leu Ser Gln Pro Ser Leu Gly Leu Leu
65                  70                  75                  80

Val Arg Thr Tyr Pro Glu Leu Glu
                85

<210> SEQ ID NO 231
<211> LENGTH: 97
<212> TYPE: PRT
<213> ORGANISM: Artificial Sequence
<220> FEATURE:
<223> OTHER INFORMATION: Synthetic peptide

<400> SEQUENCE: 231

Pro Leu Asn Val Tyr Asp Val Gln Leu Thr Lys Thr Gly Ser Val Cys
1               5                   10                  15

Asp Phe Gly Phe Ala Val Thr Ala Gln Val Asp Glu Arg Gln His Leu
            20                  25                  30

Ser Arg Ile Phe Ile Ser Asp Val Leu Pro Asp Gly Leu Ala Tyr Gly
        35                  40                  45

Glu Gly Leu Arg Lys Gly Asn Glu Ile Met Thr Leu Asn Gly Glu Ala
    50                  55                  60

Val Ser Asp Leu Asp Leu Lys Gln Met Glu Ala Leu Phe Ser Glu Lys
65                  70                  75                  80

Ser Val Gly Leu Thr Leu Ile Ala Arg Pro Pro Asp Thr Lys Ala Thr
                85                  90                  95

Leu

<210> SEQ ID NO 232
<211> LENGTH: 103
<212> TYPE: PRT
<213> ORGANISM: Artificial Sequence
<220> FEATURE:
<223> OTHER INFORMATION: Synthetic peptide

<400> SEQUENCE: 232

Gln Arg Val Glu Ile His Lys Leu Arg Gln Gly Glu Asn Leu Ile Leu
1               5                   10                  15

Gly Phe Ser Ile Gly Gly Gly Ile Asp Gln Asp Pro Ser Gln Asn Pro
            20                  25                  30
```

```
Phe Ser Glu Asp Lys Thr Asp Lys Gly Ile Tyr Val Thr Arg Val Ser
        35                  40                  45

Glu Gly Gly Pro Ala Glu Ile Ala Gly Leu Gln Ile Gly Asp Lys Ile
 50                  55                  60

Met Gln Val Asn Gly Trp Asp Met Thr Met Val Thr His Asp Gln Ala
 65                  70                  75                  80

Arg Lys Arg Leu Thr Lys Arg Ser Glu Val Val Arg Leu Leu Val
                 85                  90                  95

Thr Arg Gln Ser Leu Gln Lys
                100
```

<210> SEQ ID NO 233
<211> LENGTH: 86
<212> TYPE: PRT
<213> ORGANISM: Artificial Sequence
<220> FEATURE:
<223> OTHER INFORMATION: Synthetic peptide

<400> SEQUENCE: 233

```
Arg Lys Glu Val Glu Val Phe Lys Ser Glu Asp Ala Leu Gly Leu Thr
 1               5                  10                  15

Ile Thr Asp Asn Gly Ala Gly Tyr Ala Phe Ile Lys Arg Ile Lys Glu
                 20                  25                  30

Gly Ser Val Ile Asp His Ile His Leu Ile Ser Val Gly Asp Met Ile
             35                  40                  45

Glu Ala Ile Asn Gly Gln Ser Leu Leu Gly Cys Arg His Tyr Glu Val
 50                  55                  60

Ala Arg Leu Leu Lys Glu Leu Pro Arg Gly Arg Thr Phe Thr Leu Lys
 65                  70                  75                  80

Leu Thr Glu Pro Arg Lys
                 85
```

<210> SEQ ID NO 234
<211> LENGTH: 91
<212> TYPE: PRT
<213> ORGANISM: Artificial Sequence
<220> FEATURE:
<223> OTHER INFORMATION: Synthetic peptide

<400> SEQUENCE: 234

```
His Ser His Pro Arg Val Val Glu Leu Pro Lys Thr Asp Glu Gly Leu
 1               5                  10                  15

Gly Phe Asn Val Met Gly Gly Lys Glu Gln Asn Ser Pro Ile Tyr Ile
                 20                  25                  30

Ser Arg Ile Ile Pro Gly Gly Val Ala Glu Arg His Gly Gly Leu Lys
             35                  40                  45

Arg Gly Asp Gln Leu Leu Ser Val Asn Gly Val Ser Val Glu Gly Glu
 50                  55                  60

His His Glu Lys Ala Val Glu Leu Leu Lys Ala Ala Lys Asp Ser Val
 65                  70                  75                  80

Lys Leu Val Val Arg Tyr Thr Pro Lys Val Leu
                 85                  90
```

<210> SEQ ID NO 235
<211> LENGTH: 97
<212> TYPE: PRT
<213> ORGANISM: Artificial Sequence
<220> FEATURE:
<223> OTHER INFORMATION: Synthetic peptide

```
<400> SEQUENCE: 235

Leu Ser Asn Gln Lys Arg Gly Val Lys Val Leu Lys Gln Glu Leu Gly
1               5                   10                  15

Gly Leu Gly Ile Ser Ile Lys Gly Gly Lys Glu Asn Lys Met Pro Ile
                20                  25                  30

Leu Ile Ser Lys Ile Phe Lys Gly Leu Ala Ala Asp Gln Thr Gln Ala
                35                  40                  45

Leu Tyr Val Gly Asp Ala Ile Leu Ser Val Asn Gly Ala Asp Leu Arg
            50                  55                  60

Asp Ala Thr His Asp Glu Ala Val Gln Ala Leu Lys Arg Ala Gly Lys
65                  70                  75                  80

Glu Val Leu Leu Glu Val Lys Tyr Met Arg Glu Ala Thr Pro Tyr Val
                85                  90                  95

Lys

<210> SEQ ID NO 236
<211> LENGTH: 98
<212> TYPE: PRT
<213> ORGANISM: Artificial Sequence
<220> FEATURE:
<223> OTHER INFORMATION: Synthetic peptide

<400> SEQUENCE: 236

Ile Gln Arg Ser Ser Ile Lys Thr Val Glu Leu Ile Lys Gly Asn Leu
1               5                   10                  15

Gln Ser Val Gly Leu Thr Leu Arg Leu Val Gln Ser Thr Asp Gly Tyr
                20                  25                  30

Ala Gly His Val Ile Ile Glu Thr Val Ala Pro Asn Ser Pro Ala Ala
                35                  40                  45

Ile Ala Asp Leu Gln Arg Gly Asp Arg Leu Ile Ala Ile Gly Gly Val
            50                  55                  60

Lys Ile Thr Ser Thr Leu Gln Val Leu Lys Leu Ile Lys Gln Ala Gly
65                  70                  75                  80

Asp Arg Val Leu Val Tyr Tyr Glu Arg Pro Val Gly Gln Ser Asn Gln
                85                  90                  95

Gly Ala

<210> SEQ ID NO 237
<211> LENGTH: 103
<212> TYPE: PRT
<213> ORGANISM: Artificial Sequence
<220> FEATURE:
<223> OTHER INFORMATION: Synthetic peptide

<400> SEQUENCE: 237

Ile Leu Thr Leu Thr Ile Leu Arg Gln Thr Gly Gly Leu Gly Ile Ser
1               5                   10                  15

Ile Ala Gly Gly Lys Gly Ser Thr Pro Tyr Lys Gly Asp Asp Glu Gly
                20                  25                  30

Ile Phe Ile Ser Arg Val Ser Glu Glu Gly Pro Ala Ala Arg Ala Gly
                35                  40                  45

Val Arg Val Gly Asp Lys Leu Leu Glu Val Asn Gly Val Ala Leu Gln
            50                  55                  60

Gly Ala Glu His His Glu Ala Val Gly Ala Leu Arg Gly Ala Gly Thr
65                  70                  75                  80

Ala Val Gln Met Arg Val Trp Arg Glu Arg Met Val Glu Pro Glu Asn
                85                  90                  95
```

```
Ala Glu Phe Ile Val Thr Asp
            100
```

```
<210> SEQ ID NO 238
<211> LENGTH: 105
<212> TYPE: PRT
<213> ORGANISM: Artificial Sequence
<220> FEATURE:
<223> OTHER INFORMATION: Synthetic peptide

<400> SEQUENCE: 238

Arg Glu Leu Cys Ile Gln Lys Ala Pro Gly Glu Arg Leu Gly Ile Ser
1               5                   10                  15

Ile Arg Gly Gly Ala Arg Gly His Ala Gly Asn Pro Arg Asp Pro Thr
            20                  25                  30

Asp Glu Gly Ile Phe Ile Ser Lys Val Ser Pro Thr Gly Ala Ala Gly
        35                  40                  45

Arg Asp Gly Arg Leu Arg Val Gly Leu Arg Leu Glu Val Asn Gln
    50                  55                  60

Gln Ser Leu Leu Gly Leu Thr His Gly Glu Ala Val Gln Leu Leu Arg
65                  70                  75                  80

Ser Val Gly Asp Thr Leu Thr Val Leu Val Cys Asp Gly Phe Glu Ala
                85                  90                  95

Ser Thr Asp Ala Ala Leu Glu Val Ser
            100                 105
```

```
<210> SEQ ID NO 239
<211> LENGTH: 105
<212> TYPE: PRT
<213> ORGANISM: Artificial Sequence
<220> FEATURE:
<223> OTHER INFORMATION: Synthetic peptide

<400> SEQUENCE: 239

Leu Glu Gly Pro Tyr Pro Val Glu Glu Ile Arg Leu Pro Arg Ala Gly
1               5                   10                  15

Gly Pro Leu Gly Leu Ser Ile Val Gly Gly Ser Asp His Ser Ser His
            20                  25                  30

Pro Phe Gly Val Gln Glu Pro Gly Val Phe Ile Ser Lys Val Leu Pro
        35                  40                  45

Arg Gly Leu Ala Ala Arg Ser Gly Leu Arg Val Gly Asp Arg Ile Leu
    50                  55                  60

Ala Val Asn Gly Gln Asp Val Arg Asp Ala Thr His Gln Glu Ala Val
65                  70                  75                  80

Ser Ala Leu Leu Arg Pro Cys Leu Glu Leu Ser Leu Leu Val Arg Arg
                85                  90                  95

Asp Pro Ala Glu Phe Ile Val Thr Asp
            100                 105
```

```
<210> SEQ ID NO 240
<211> LENGTH: 97
<212> TYPE: PRT
<213> ORGANISM: Artificial Sequence
<220> FEATURE:
<223> OTHER INFORMATION: Synthetic peptide

<400> SEQUENCE: 240

Pro Leu Arg Gln Arg His Val Ala Cys Leu Ala Arg Ser Glu Arg Gly
1               5                   10                  15
```

```
Leu Gly Phe Ser Ile Ala Gly Gly Lys Gly Ser Thr Pro Tyr Arg Ala
            20                  25                  30

Gly Asp Ala Gly Ile Phe Val Ser Arg Ile Ala Glu Gly Gly Ala Ala
        35                  40                  45

His Arg Ala Gly Thr Leu Gln Val Gly Asp Arg Val Leu Ser Ile Asn
 50                  55                  60

Gly Val Asp Val Thr Glu Ala Arg His Asp His Ala Val Ser Leu Leu
65                  70                  75                  80

Thr Ala Ala Ser Pro Thr Ile Ala Leu Leu Leu Glu Arg Glu Ala Gly
                85                  90                  95

Gly

<210> SEQ ID NO 241
<211> LENGTH: 114
<212> TYPE: PRT
<213> ORGANISM: Artificial Sequence
<220> FEATURE:
<223> OTHER INFORMATION: Synthetic peptide

<400> SEQUENCE: 241

Thr Leu Thr Ile Leu Arg Gln Thr Gly Gly Leu Gly Ile Ser Ile Ala
1               5                   10                  15

Gly Gly Lys Gly Ser Thr Pro Tyr Lys Gly Asp Asp Glu Gly Ile Phe
            20                  25                  30

Ile Ser Arg Val Ser Glu Glu Gly Pro Ala Ala Arg Ala Gly Val Arg
        35                  40                  45

Val Gly Asp Lys Leu Leu Glu Gly Ile Phe Val Ser Arg Ile Ala Glu
    50                  55                  60

Gly Gly Ala Ala His Arg Ala Gly Thr Leu Gln Val Gly Asp Arg Val
65                  70                  75                  80

Leu Ser Ile Asn Gly Val Asp Val Thr Glu Ala Arg His Asp His Ala
                85                  90                  95

Val Ser Leu Leu Thr Ala Ala Ser Pro Thr Ile Ala Leu Leu Leu Glu
            100                 105                 110

Arg Glu

<210> SEQ ID NO 242
<211> LENGTH: 95
<212> TYPE: PRT
<213> ORGANISM: Artificial Sequence
<220> FEATURE:
<223> OTHER INFORMATION: Synthetic peptide

<400> SEQUENCE: 242

Ile Pro Pro Val Thr Thr Val Leu Ile Lys Arg Pro Asp Leu Lys Tyr
1               5                   10                  15

Gln Leu Gly Phe Ser Val Gln Asn Gly Ile Ile Cys Ser Leu Met Arg
            20                  25                  30

Gly Gly Ile Ala Glu Arg Gly Gly Val Arg Val Gly His Arg Ile Ile
        35                  40                  45

Glu Ile Asn Gly Gln Ser Val Val Ala Thr Ala His Glu Lys Ile Val
    50                  55                  60

Gln Ala Leu Ser Asn Ser Val Gly Glu Ile His Met Lys Thr Met Pro
65                  70                  75                  80

Ala Ala Met Phe Arg Leu Leu Thr Gly Gln Glu Asn Ser Ser Leu
                85                  90                  95
```

```
<210> SEQ ID NO 243
<211> LENGTH: 110
<212> TYPE: PRT
<213> ORGANISM: Artificial Sequence
<220> FEATURE:
<223> OTHER INFORMATION: Synthetic peptide

<400> SEQUENCE: 243

Ile His Phe Ser Asn Ser Glu Asn Cys Lys Glu Leu Gln Leu Glu Lys
1               5                   10                  15

His Lys Gly Glu Ile Leu Gly Val Val Val Glu Ser Gly Trp Gly
            20                  25                  30

Ser Ile Leu Pro Thr Val Ile Leu Ala Asn Met Met Asn Gly Gly Pro
        35                  40                  45

Ala Ala Arg Ser Gly Lys Leu Ser Ile Gly Asp Gln Ile Met Ser Ile
    50                  55                  60

Asn Gly Thr Ser Leu Val Gly Leu Pro Leu Ala Thr Cys Gln Gly Ile
65                  70                  75                  80

Ile Lys Gly Leu Lys Asn Gln Thr Gln Val Lys Leu Asn Ile Val Ser
                85                  90                  95

Cys Pro Pro Val Thr Thr Val Leu Ile Lys Arg Asn Ser Ser
            100                 105                 110

<210> SEQ ID NO 244
<211> LENGTH: 101
<212> TYPE: PRT
<213> ORGANISM: Artificial Sequence
<220> FEATURE:
<223> OTHER INFORMATION: Synthetic peptide

<400> SEQUENCE: 244

Ile Trp Glu Gln His Thr Val Thr Leu His Arg Ala Pro Gly Phe Gly
1               5                   10                  15

Phe Gly Ile Ala Ile Ser Gly Gly Arg Asp Asn Pro His Phe Gln Ser
            20                  25                  30

Gly Glu Thr Ser Ile Val Ile Ser Asp Val Leu Lys Gly Gly Pro Ala
        35                  40                  45

Glu Gly Gln Leu Gln Glu Asn Asp Arg Val Ala Met Val Asn Gly Val
    50                  55                  60

Ser Met Asp Asn Val Glu His Ala Phe Ala Val Gln Gln Leu Arg Lys
65                  70                  75                  80

Ser Gly Lys Asn Ala Lys Ile Thr Ile Arg Arg Lys Lys Lys Val Gln
                85                  90                  95

Ile Pro Asn Ser Ser
            100

<210> SEQ ID NO 245
<211> LENGTH: 95
<212> TYPE: PRT
<213> ORGANISM: Artificial Sequence
<220> FEATURE:
<223> OTHER INFORMATION: Synthetic peptide

<400> SEQUENCE: 245

Ile Ser Ser Gln Pro Ala Lys Pro Thr Lys Val Thr Leu Val Lys Ser
1               5                   10                  15

Arg Lys Asn Glu Glu Tyr Gly Leu Arg Leu Ala Ser His Ile Phe Val
            20                  25                  30

Lys Glu Ile Ser Gln Asp Ser Leu Ala Ala Arg Asp Gly Asn Ile Gln
        35                  40                  45
```

```
Glu Gly Asp Val Val Leu Lys Ile Asn Gly Thr Val Thr Glu Asn Met
 50                  55                  60

Ser Leu Thr Asp Ala Lys Thr Leu Ile Glu Arg Ser Lys Gly Lys Leu
 65                  70                  75                  80

Lys Met Val Val Gln Arg Asp Arg Ala Thr Leu Leu Asn Ser Ser
                 85                  90                  95
```

<210> SEQ ID NO 246
<211> LENGTH: 90
<212> TYPE: PRT
<213> ORGANISM: Artificial Sequence
<220> FEATURE:
<223> OTHER INFORMATION: Synthetic peptide

<400> SEQUENCE: 246

```
Ile Arg Met Lys Leu Val Lys Phe Arg Lys Gly Asp Ser Val Gly Leu
 1               5                  10                  15

Arg Leu Ala Gly Gly Asn Asp Val Gly Ile Phe Val Ala Gly Val Leu
                 20                  25                  30

Glu Asp Ser Pro Ala Ala Lys Glu Gly Leu Glu Glu Gly Asp Gln Ile
             35                  40                  45

Leu Arg Val Asn Asn Val Asp Phe Thr Asn Ile Ile Arg Glu Glu Ala
 50                  55                  60

Val Leu Phe Leu Leu Asp Leu Pro Lys Gly Glu Val Thr Ile Leu
 65                  70                  75                  80

Ala Gln Lys Lys Lys Asp Val Phe Ser Asn
                 85                  90
```

<210> SEQ ID NO 247
<211> LENGTH: 99
<212> TYPE: PRT
<213> ORGANISM: Artificial Sequence
<220> FEATURE:
<223> OTHER INFORMATION: Synthetic peptide

<400> SEQUENCE: 247

```
Ile Gln His Thr Val Thr Leu His Arg Ala Pro Gly Phe Gly Phe Gly
 1               5                  10                  15

Ile Ala Ile Ser Gly Gly Arg Asp Asn Pro His Phe Gln Ser Gly Glu
                 20                  25                  30

Thr Ser Ile Val Ile Ser Asp Val Leu Lys Gly Gly Pro Ala Glu Gly
             35                  40                  45

Gln Leu Gln Glu Asn Asp Arg Val Ala Met Val Asn Gly Val Ser Met
 50                  55                  60

Asp Asn Val Glu His Ala Phe Ala Val Gln Gln Leu Arg Lys Ser Gly
 65                  70                  75                  80

Lys Asn Ala Lys Ile Thr Ile Arg Arg Lys Lys Lys Val Gln Ile Pro
                 85                  90                  95

Asn Ser Ser
```

<210> SEQ ID NO 248
<211> LENGTH: 90
<212> TYPE: PRT
<213> ORGANISM: Artificial Sequence
<220> FEATURE:
<223> OTHER INFORMATION: Synthetic peptide

<400> SEQUENCE: 248

```
His Ala Pro Asn Thr Lys Met Val Arg Phe Lys Lys Gly Asp Ser Val
```

```
                1               5                  10                 15
Gly Leu Arg Leu Ala Gly Gly Asn Asp Val Gly Ile Phe Val Ala Gly
            20                  25                 30

Ile Gln Glu Gly Thr Ser Ala Glu Gln Glu Gly Leu Gln Glu Gly Asp
            35                  40                 45

Gln Ile Leu Lys Val Asn Thr Gln Asp Phe Arg Gly Leu Val Arg Glu
            50                  55                 60

Asp Ala Val Leu Tyr Leu Leu Glu Ile Pro Lys Gly Glu Met Val Thr
65                  70                  75                     80

Ile Leu Ala Gln Ser Arg Ala Asp Val Tyr
                85                  90

<210> SEQ ID NO 249
<211> LENGTH: 79
<212> TYPE: PRT
<213> ORGANISM: Artificial Sequence
<220> FEATURE:
<223> OTHER INFORMATION: Synthetic peptide

<400> SEQUENCE: 249

Arg Val Leu Leu Met Lys Ser Arg Ala Asn Glu Glu Tyr Gly Leu Arg
1               5                   10                 15

Leu Gly Ser Gln Ile Phe Val Lys Glu Met Thr Arg Thr Gly Leu Ala
            20                  25                  30

Thr Lys Asp Gly Asn Leu His Glu Gly Asp Ile Ile Leu Lys Ile Asn
            35                  40                  45

Gly Thr Val Thr Glu Asn Met Ser Leu Thr Asp Ala Arg Lys Leu Ile
        50                  55                  60

Glu Lys Ser Arg Gly Lys Leu Gln Leu Val Val Leu Arg Asp Ser
65                  70                  75

<210> SEQ ID NO 250
<211> LENGTH: 104
<212> TYPE: PRT
<213> ORGANISM: Artificial Sequence
<220> FEATURE:
<223> OTHER INFORMATION: Synthetic peptide

<400> SEQUENCE: 250

Arg Gly Tyr Ser Pro Asp Thr Arg Val Val Arg Phe Leu Lys Gly Lys
1               5                   10                 15

Ser Ile Gly Leu Arg Leu Ala Gly Gly Asn Asp Val Gly Ile Phe Val
            20                  25                  30

Ser Gly Val Gln Ala Gly Ser Pro Ala Asp Gly Gln Gly Ile Gln Glu
            35                  40                  45

Gly Asp Gln Ile Leu Gln Val Asn Asp Val Pro Phe Gln Asn Leu Thr
        50                  55                  60

Arg Glu Glu Ala Val Gln Phe Leu Leu Gly Leu Pro Pro Gly Glu Glu
65                  70                  75                     80

Met Glu Leu Val Thr Gln Arg Lys Gln Asp Ile Phe Trp Lys Met Val
            85                  90                  95

Gln Ser Glu Phe Ile Val Thr Asp
                100

<210> SEQ ID NO 251
<211> LENGTH: 106
<212> TYPE: PRT
<213> ORGANISM: Artificial Sequence
<220> FEATURE:
```

<223> OTHER INFORMATION: Synthetic peptide

<400> SEQUENCE: 251

```
Ile Pro Gly Asn Ser Thr Ile Trp Glu Gln His Thr Ala Thr Leu Ser
1               5                   10                  15

Lys Asp Pro Arg Arg Gly Phe Gly Ile Ala Ile Ser Gly Gly Arg Asp
            20                  25                  30

Arg Pro Gly Gly Ser Met Val Val Ser Asp Val Val Pro Gly Gly Pro
        35                  40                  45

Ala Glu Gly Arg Leu Gln Thr Gly Asp His Ile Val Met Val Asn Gly
    50                  55                  60

Val Ser Met Glu Asn Ala Thr Ser Ala Phe Ala Ile Gln Ile Leu Lys
65                  70                  75                  80

Thr Cys Thr Lys Met Ala Asn Ile Thr Val Lys Arg Pro Arg Arg Ile
                85                  90                  95

His Leu Pro Ala Glu Phe Ile Val Thr Asp
            100                 105
```

<210> SEQ ID NO 252
<211> LENGTH: 98
<212> TYPE: PRT
<213> ORGANISM: Artificial Sequence
<220> FEATURE:
<223> OTHER INFORMATION: Synthetic peptide

<400> SEQUENCE: 252

```
Gln Asp Val Gln Met Lys Pro Val Lys Ser Val Leu Val Lys Arg Arg
1               5                   10                  15

Asp Ser Glu Glu Phe Gly Val Lys Leu Gly Ser Gln Ile Phe Ile Lys
            20                  25                  30

His Ile Thr Asp Ser Gly Leu Ala Ala Arg His Arg Gly Leu Gln Glu
        35                  40                  45

Gly Asp Leu Ile Leu Gln Ile Asn Gly Val Ser Ser Gln Asn Leu Ser
    50                  55                  60

Leu Asn Asp Thr Arg Arg Leu Ile Glu Lys Ser Glu Gly Lys Leu Ser
65                  70                  75                  80

Leu Leu Val Leu Arg Asp Arg Gly Gln Phe Leu Val Asn Ile Pro Asn
                85                  90                  95

Ser Ser
```

<210> SEQ ID NO 253
<211> LENGTH: 5
<212> TYPE: PRT
<213> ORGANISM: Artificial Sequence
<220> FEATURE:
<223> OTHER INFORMATION: Synthetic peptide

<400> SEQUENCE: 253

```
Gly Ile Pro Gly Asn
1               5
```

<210> SEQ ID NO 254
<211> LENGTH: 5
<212> TYPE: PRT
<213> ORGANISM: Artificial Sequence
<220> FEATURE:
<223> OTHER INFORMATION: Synthetic peptide

<400> SEQUENCE: 254

Gly Gly Gly Gly Ser

```
1               5

<210> SEQ ID NO 255
<211> LENGTH: 14
<212> TYPE: PRT
<213> ORGANISM: Artificial Sequence
<220> FEATURE:
<223> OTHER INFORMATION: Synthetic peptide

<400> SEQUENCE: 255

Glu Gly Lys Ser Ser Gly Ser Gly Ser Glu Ser Lys Val Asp
1               5                   10

<210> SEQ ID NO 256
<211> LENGTH: 18
<212> TYPE: PRT
<213> ORGANISM: Artificial Sequence
<220> FEATURE:
<223> OTHER INFORMATION: Synthetic peptide

<400> SEQUENCE: 256

Lys Glu Ser Gly Ser Val Ser Ser Glu Gln Leu Ala Gln Phe Arg Ser
1               5                   10                  15

Leu Asp

<210> SEQ ID NO 257
<211> LENGTH: 11
<212> TYPE: PRT
<213> ORGANISM: Artificial Sequence
<220> FEATURE:
<223> OTHER INFORMATION: Synthetic peptide

<400> SEQUENCE: 257

Tyr Gly Arg Lys Lys Arg Arg Gln Arg Arg Arg
1               5                   10

<210> SEQ ID NO 258
<211> LENGTH: 20
<212> TYPE: PRT
<213> ORGANISM: Artificial Sequence
<220> FEATURE:
<223> OTHER INFORMATION: Synthetic peptide

<400> SEQUENCE: 258

Tyr Gly Arg Lys Lys Arg Arg Gln Arg Arg Arg Ser Thr Asn Ser Val
1               5                   10                  15

Arg Leu Met Leu
            20

<210> SEQ ID NO 259
<211> LENGTH: 11
<212> TYPE: PRT
<213> ORGANISM: Artificial Sequence
<220> FEATURE:
<223> OTHER INFORMATION: Synthetic peptide

<400> SEQUENCE: 259

Arg Arg Ser Thr Asn Ser Val Arg Leu Met Leu
1               5                   10

<210> SEQ ID NO 260
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 260

Ser Thr Asn Ser Val Arg Leu Met Leu
1               5

<210> SEQ ID NO 261
<211> LENGTH: 20
<212> TYPE: PRT
<213> ORGANISM: Artificial Sequence
<220> FEATURE:
<223> OTHER INFORMATION: Synthetic peptide

<400> SEQUENCE: 261

Tyr Gly Arg Lys Lys Arg Arg Gln Arg Arg Ala Val Ala Ala Thr
1               5                   10                  15

Ser Ile Asn Leu
            20

<210> SEQ ID NO 262
<211> LENGTH: 20
<212> TYPE: PRT
<213> ORGANISM: Artificial Sequence
<220> FEATURE:
<223> OTHER INFORMATION: Synthetic peptide

<400> SEQUENCE: 262

Tyr Gly Arg Lys Lys Arg Arg Gln Arg Arg Ala Arg Ser Asp Arg
1               5                   10                  15

Thr Ile Trp Ala
            20

<210> SEQ ID NO 263
<211> LENGTH: 20
<212> TYPE: PRT
<213> ORGANISM: Artificial Sequence
<220> FEATURE:
<223> OTHER INFORMATION: Synthetic peptide

<400> SEQUENCE: 263

Tyr Gly Arg Lys Lys Arg Arg Gln Arg Arg Ala Arg Ser Asp Arg
1               5                   10                  15

Thr Ile Ile Ala
            20

<210> SEQ ID NO 264
<211> LENGTH: 20
<212> TYPE: PRT
<213> ORGANISM: Artificial Sequence
<220> FEATURE:
<223> OTHER INFORMATION: Synthetic peptide

<400> SEQUENCE: 264

Tyr Gly Arg Lys Lys Arg Arg Gln Arg Arg Ser Arg Thr Asp Arg
1               5                   10                  15

Lys Tyr Trp Ala
            20

<210> SEQ ID NO 265
<211> LENGTH: 20
<212> TYPE: PRT
<213> ORGANISM: Artificial Sequence
<220> FEATURE:
<223> OTHER INFORMATION: Synthetic peptide

<400> SEQUENCE: 265
```

```
Tyr Gly Arg Lys Lys Arg Arg Gln Arg Arg Ala Arg Gly Asp Arg
1               5                   10                  15

Lys Ile Arg Val
            20

<210> SEQ ID NO 266
<211> LENGTH: 20
<212> TYPE: PRT
<213> ORGANISM: Artificial Sequence
<220> FEATURE:
<223> OTHER INFORMATION: Synthetic peptide

<400> SEQUENCE: 266

Tyr Gly Arg Lys Lys Arg Arg Gln Arg Arg Ala Arg Thr Asp Arg
1               5                   10                  15

Lys Val Glu Val
            20

<210> SEQ ID NO 267
<211> LENGTH: 20
<212> TYPE: PRT
<213> ORGANISM: Artificial Sequence
<220> FEATURE:
<223> OTHER INFORMATION: Synthetic peptide

<400> SEQUENCE: 267

Tyr Gly Arg Lys Lys Arg Arg Gln Arg Arg Ala Arg Gly Asp Arg
1               5                   10                  15

Lys Tyr Ile Val
            20

<210> SEQ ID NO 268
<211> LENGTH: 20
<212> TYPE: PRT
<213> ORGANISM: Artificial Sequence
<220> FEATURE:
<223> OTHER INFORMATION: Synthetic peptide

<400> SEQUENCE: 268

Tyr Gly Arg Lys Lys Arg Arg Gln Arg Arg Ser Arg Thr Asp Arg
1               5                   10                  15

Lys Tyr Gln Ile
            20

<210> SEQ ID NO 269
<211> LENGTH: 20
<212> TYPE: PRT
<213> ORGANISM: Artificial Sequence
<220> FEATURE:
<223> OTHER INFORMATION: Synthetic peptide

<400> SEQUENCE: 269

Tyr Gly Arg Lys Lys Arg Arg Gln Arg Arg Ala Arg Gly Asp Arg
1               5                   10                  15

Lys Val Pro Val
            20

<210> SEQ ID NO 270
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 270

Tyr Gly Arg Lys Lys Arg Arg Gln Arg Arg Gln Asp Glu Arg
1               5                   10                  15

Leu Ile Val Leu
            20

<210> SEQ ID NO 271
<211> LENGTH: 20
<212> TYPE: PRT
<213> ORGANISM: Artificial Sequence
<220> FEATURE:
<223> OTHER INFORMATION: Synthetic peptide

<400> SEQUENCE: 271

Tyr Gly Arg Lys Lys Arg Arg Gln Arg Arg Ala Arg Gly Asp Arg
1               5                   10                  15

Leu Val Ser Leu
            20

<210> SEQ ID NO 272
<211> LENGTH: 20
<212> TYPE: PRT
<213> ORGANISM: Artificial Sequence
<220> FEATURE:
<223> OTHER INFORMATION: Synthetic peptide

<400> SEQUENCE: 272

Tyr Gly Arg Lys Lys Arg Arg Gln Arg Arg Ala Arg Gly Thr Arg
1               5                   10                  15

Leu Val Trp Val
            20

<210> SEQ ID NO 273
<211> LENGTH: 20
<212> TYPE: PRT
<213> ORGANISM: Artificial Sequence
<220> FEATURE:
<223> OTHER INFORMATION: Synthetic peptide

<400> SEQUENCE: 273

Tyr Gly Arg Lys Lys Arg Arg Gln Arg Arg Ala Arg Gly Asp Arg
1               5                   10                  15

Tyr Arg Ile Val
            20

<210> SEQ ID NO 274
<211> LENGTH: 20
<212> TYPE: PRT
<213> ORGANISM: Artificial Sequence
<220> FEATURE:
<223> OTHER INFORMATION: Synthetic peptide

<400> SEQUENCE: 274

Tyr Gly Arg Lys Lys Arg Arg Gln Arg Arg Ser Arg Thr Asp Arg
1               5                   10                  15

Leu Glu Tyr Val
            20

<210> SEQ ID NO 275
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 275

Tyr Gly Arg Lys Lys Arg Arg Gln Arg Arg Arg Ala Arg Gly Asp Arg
1               5                   10                  15

Thr Ile Ile Tyr
            20

<210> SEQ ID NO 276
<211> LENGTH: 20
<212> TYPE: PRT
<213> ORGANISM: Artificial Sequence
<220> FEATURE:
<223> OTHER INFORMATION: Synthetic peptide

<400> SEQUENCE: 276

Tyr Gly Arg Lys Lys Arg Arg Gln Arg Arg Arg Lys Asn Lys Asp Lys
1               5                   10                  15

Glu Tyr Tyr Val
            20

<210> SEQ ID NO 277
<211> LENGTH: 20
<212> TYPE: PRT
<213> ORGANISM: Artificial Sequence
<220> FEATURE:
<223> OTHER INFORMATION: Synthetic peptide

<400> SEQUENCE: 277

Tyr Gly Arg Lys Lys Arg Arg Gln Arg Arg Ala Arg Gly Arg Arg
1               5                   10                  15

Glu Thr Trp Val
            20

<210> SEQ ID NO 278
<211> LENGTH: 20
<212> TYPE: PRT
<213> ORGANISM: Artificial Sequence
<220> FEATURE:
<223> OTHER INFORMATION: Synthetic peptide

<400> SEQUENCE: 278

Tyr Gly Arg Lys Lys Arg Arg Gln Arg Arg Glu Lys His Phe Arg
1               5                   10                  15

Glu Thr Glu Val
            20

<210> SEQ ID NO 279
<211> LENGTH: 20
<212> TYPE: PRT
<213> ORGANISM: Artificial Sequence
<220> FEATURE:
<223> OTHER INFORMATION: Synthetic peptide

<400> SEQUENCE: 279

Ala Ala Gly Gly Arg Ser Ala Arg Gly Gly Arg Leu Gln Gly Arg Arg
1               5                   10                  15

Glu Thr Ala Leu
            20

<210> SEQ ID NO 280
<211> LENGTH: 20
<212> TYPE: PRT
<213> ORGANISM: Artificial Sequence
<220> FEATURE:
```

<223> OTHER INFORMATION: Synthetic peptide

<400> SEQUENCE: 280

Ala Thr Asp Tyr Leu Val Gln Pro Phe Met Asp Gln Leu Ala Phe His
1               5                   10                  15

Gln Phe Tyr Ile
            20

<210> SEQ ID NO 281
<211> LENGTH: 20
<212> TYPE: PRT
<213> ORGANISM: Artificial Sequence
<220> FEATURE:
<223> OTHER INFORMATION: Synthetic peptide

<400> SEQUENCE: 281

Ala Val Gly Gly Arg Pro Ala Arg Gly Gly Arg Leu Gln Gly Arg Arg
1               5                   10                  15

Gln Thr Gln Val
            20

<210> SEQ ID NO 282
<211> LENGTH: 20
<212> TYPE: PRT
<213> ORGANISM: Artificial Sequence
<220> FEATURE:
<223> OTHER INFORMATION: Synthetic peptide

<400> SEQUENCE: 282

Asp Phe Arg Pro Ser Phe Lys His Ile Leu Phe Arg Arg Ala Arg Arg
1               5                   10                  15

Gly Phe Arg Gln
            20

<210> SEQ ID NO 283
<211> LENGTH: 20
<212> TYPE: PRT
<213> ORGANISM: Artificial Sequence
<220> FEATURE:
<223> OTHER INFORMATION: Synthetic peptide

<400> SEQUENCE: 283

Asp Gly Gly Ala Arg Thr Glu Asp Glu Val Gln Ser Tyr Pro Ser Lys
1               5                   10                  15

His Asp Tyr Val
            20

<210> SEQ ID NO 284
<211> LENGTH: 20
<212> TYPE: PRT
<213> ORGANISM: Artificial Sequence
<220> FEATURE:
<223> OTHER INFORMATION: Synthetic peptide

<400> SEQUENCE: 284

Asp Thr Leu Leu Leu Thr Glu Asn Glu Gly Asp Lys Thr Glu Glu Gln
1               5                   10                  15

Val Ser Tyr Val
            20

<210> SEQ ID NO 285
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 285

Glu Leu Leu Gln Phe Cys Arg Thr Pro Asn Pro Ala Leu Lys Asn Gly
1               5                   10                  15

Gln Tyr Trp Val
            20

<210> SEQ ID NO 286
<211> LENGTH: 20
<212> TYPE: PRT
<213> ORGANISM: Artificial Sequence
<220> FEATURE:
<223> OTHER INFORMATION: Synthetic peptide

<400> SEQUENCE: 286

Glu Asn Leu Glu Leu Pro Val Asn Pro Ser Ser Val Val Ser Glu Arg
1               5                   10                  15

Ile Ser Ser Val
            20

<210> SEQ ID NO 287
<211> LENGTH: 20
<212> TYPE: PRT
<213> ORGANISM: Artificial Sequence
<220> FEATURE:
<223> OTHER INFORMATION: Synthetic peptide

<400> SEQUENCE: 287

Phe His Ser Lys Thr Ala Gly Ala Asn Thr Thr Asp Lys Glu Leu Glu
1               5                   10                  15

Val Leu Ser Leu
            20

<210> SEQ ID NO 288
<211> LENGTH: 20
<212> TYPE: PRT
<213> ORGANISM: Artificial Sequence
<220> FEATURE:
<223> OTHER INFORMATION: Synthetic peptide

<400> SEQUENCE: 288

Phe Asn Gly Ser Ser Asn Gly His Val Tyr Glu Lys Leu Ser Ser Ile
1               5                   10                  15

Glu Ser Asp Val
            20

<210> SEQ ID NO 289
<211> LENGTH: 20
<212> TYPE: PRT
<213> ORGANISM: Artificial Sequence
<220> FEATURE:
<223> OTHER INFORMATION: Synthetic peptide

<400> SEQUENCE: 289

Gly Arg Trp Thr Gly Arg Ala Met Ser Ala Trp Lys Pro Thr Arg Arg
1               5                   10                  15

Glu Thr Glu Val
            20

<210> SEQ ID NO 290
<211> LENGTH: 20
<212> TYPE: PRT
```

<213> ORGANISM: Artificial Sequence
<220> FEATURE:
<223> OTHER INFORMATION: Synthetic peptide

<400> SEQUENCE: 290

His Ala Met Asn Ala Ala Pro Arg Ala Met Glu Asn Ala Pro Ala Leu
1               5                   10                  15

Arg Thr Ser His
            20

<210> SEQ ID NO 291
<211> LENGTH: 20
<212> TYPE: PRT
<213> ORGANISM: Artificial Sequence
<220> FEATURE:
<223> OTHER INFORMATION: Synthetic peptide

<400> SEQUENCE: 291

His Asp Phe Arg Arg Ala Phe Lys Lys Ile Leu Ala Arg Gly Asp Arg
1               5                   10                  15

Lys Arg Ile Val
            20

<210> SEQ ID NO 292
<211> LENGTH: 20
<212> TYPE: PRT
<213> ORGANISM: Artificial Sequence
<220> FEATURE:
<223> OTHER INFORMATION: Synthetic peptide

<400> SEQUENCE: 292

His His Leu Val Ala Gln Arg Asp Ile Arg Gln Phe Gln Leu Gln His
1               5                   10                  15

Trp Leu Ala Ile
            20

<210> SEQ ID NO 293
<211> LENGTH: 20
<212> TYPE: PRT
<213> ORGANISM: Artificial Sequence
<220> FEATURE:
<223> OTHER INFORMATION: Synthetic peptide

<400> SEQUENCE: 293

His Ser Cys Cys Asn Arg Ala Arg Gln Glu Arg Leu Gln Arg Arg Arg
1               5                   10                  15

Glu Thr Gln Val
            20

<210> SEQ ID NO 294
<211> LENGTH: 20
<212> TYPE: PRT
<213> ORGANISM: Artificial Sequence
<220> FEATURE:
<223> OTHER INFORMATION: Synthetic peptide

<400> SEQUENCE: 294

Ile Leu Asn Ser Ile Gln Val Met Arg Ala Gln Met Asn Gln Ile Gln
1               5                   10                  15

Ser Val Glu Val
            20

<210> SEQ ID NO 295
<211> LENGTH: 20

```
<212> TYPE: PRT
<213> ORGANISM: Artificial Sequence
<220> FEATURE:
<223> OTHER INFORMATION: Synthetic peptide

<400> SEQUENCE: 295

Lys Ala Gly Tyr Arg Ala Pro Arg Ser Tyr Pro Lys Ser Asn Ser Ser
1               5                   10                  15

Lys Glu Tyr Val
            20

<210> SEQ ID NO 296
<211> LENGTH: 20
<212> TYPE: PRT
<213> ORGANISM: Artificial Sequence
<220> FEATURE:
<223> OTHER INFORMATION: Synthetic peptide

<400> SEQUENCE: 296

Lys His Ser Arg Lys Ser Ser Ser Tyr Ser Ser Ser Ser Thr Thr Val
1               5                   10                  15

Lys Thr Ser Tyr
            20

<210> SEQ ID NO 297
<211> LENGTH: 23
<212> TYPE: PRT
<213> ORGANISM: Artificial Sequence
<220> FEATURE:
<223> OTHER INFORMATION: Synthetic peptide

<400> SEQUENCE: 297

Lys Lys Lys Lys Gln Pro Gly Asn Ser Thr Lys Glu Ser Glu Ser Thr
1               5                   10                  15

Asn Ser Val Arg Leu Met Leu
            20

<210> SEQ ID NO 298
<211> LENGTH: 20
<212> TYPE: PRT
<213> ORGANISM: Artificial Sequence
<220> FEATURE:
<223> OTHER INFORMATION: Synthetic peptide

<400> SEQUENCE: 298

Lys Thr Met Pro Ala Ala Met Phe Arg Leu Leu Thr Gly Gln Glu Thr
1               5                   10                  15

Pro Leu Tyr Ile
            20

<210> SEQ ID NO 299
<211> LENGTH: 20
<212> TYPE: PRT
<213> ORGANISM: Artificial Sequence
<220> FEATURE:
<223> OTHER INFORMATION: Synthetic peptide

<400> SEQUENCE: 299

Lys Thr Met Pro Ala Ala Met Tyr Arg Leu Leu Thr Ala Gln Glu Gln
1               5                   10                  15

Pro Val Tyr Ile
            20

<210> SEQ ID NO 300
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 300

Lys Thr Met Pro Ala Ala Thr Tyr Arg Leu Leu Thr Gly Gln Glu Gln
1               5                   10                  15

Pro Val Tyr Leu
            20

<210> SEQ ID NO 301
<211> LENGTH: 20
<212> TYPE: PRT
<213> ORGANISM: Artificial Sequence
<220> FEATURE:
<223> OTHER INFORMATION: Synthetic peptide

<400> SEQUENCE: 301

Lys Tyr Ser Ala Pro Arg Arg Pro Thr Ala Thr Gly Asp Tyr Asp Lys
1               5                   10                  15

Lys Asn Tyr Val
            20

<210> SEQ ID NO 302
<211> LENGTH: 20
<212> TYPE: PRT
<213> ORGANISM: Artificial Sequence
<220> FEATURE:
<223> OTHER INFORMATION: Synthetic peptide

<400> SEQUENCE: 302

Leu Ala Ser Lys Ser Ala Glu Glu Gly Lys Gln Ile Pro Asp Ser Leu
1               5                   10                  15

Ser Thr Asp Leu
            20

<210> SEQ ID NO 303
<211> LENGTH: 20
<212> TYPE: PRT
<213> ORGANISM: Artificial Sequence
<220> FEATURE:
<223> OTHER INFORMATION: Synthetic peptide

<400> SEQUENCE: 303

Leu Ala Val Leu Ala Tyr Ser Ile Thr Leu Val Met Leu Trp Ser Ile
1               5                   10                  15

Trp Gln Tyr Ala
            20

<210> SEQ ID NO 304
<211> LENGTH: 20
<212> TYPE: PRT
<213> ORGANISM: Artificial Sequence
<220> FEATURE:
<223> OTHER INFORMATION: Synthetic peptide

<400> SEQUENCE: 304

Leu Glu Arg Thr Ser Ser Val Ser Pro Ser Thr Ala Glu Pro Glu Leu
1               5                   10                  15

Ser Ile Val Phe
            20
```

```
<210> SEQ ID NO 305
<211> LENGTH: 20
<212> TYPE: PRT
<213> ORGANISM: Artificial Sequence
<220> FEATURE:
<223> OTHER INFORMATION: Synthetic peptide

<400> SEQUENCE: 305

Leu Asn Ser Cys Ser Asn Arg Arg Val Tyr Lys Lys Met Pro Ser Ile
1               5                   10                  15

Glu Ser Asp Val
            20

<210> SEQ ID NO 306
<211> LENGTH: 20
<212> TYPE: PRT
<213> ORGANISM: Artificial Sequence
<220> FEATURE:
<223> OTHER INFORMATION: Synthetic peptide

<400> SEQUENCE: 306

Leu Gln Phe His Arg Gly Ser Arg Ala Gln Ser Phe Leu Gln Thr Glu
1               5                   10                  15

Thr Ser Val Ile
            20

<210> SEQ ID NO 307
<211> LENGTH: 20
<212> TYPE: PRT
<213> ORGANISM: Artificial Sequence
<220> FEATURE:
<223> OTHER INFORMATION: Synthetic peptide

<400> SEQUENCE: 307

Asn Tyr Lys Leu Asn Thr Asp His Ala Gly Ser Asn Asp Asn Ile Ala
1               5                   10                  15

Leu Leu Val Gln
            20

<210> SEQ ID NO 308
<211> LENGTH: 20
<212> TYPE: PRT
<213> ORGANISM: Artificial Sequence
<220> FEATURE:
<223> OTHER INFORMATION: Synthetic peptide

<400> SEQUENCE: 308

Pro Gly Gln Pro Pro Lys Val Lys Ser Glu Phe Asn Ser Tyr Ser Leu
1               5                   10                  15

Thr Gly Tyr Val
            20

<210> SEQ ID NO 309
<211> LENGTH: 20
<212> TYPE: PRT
<213> ORGANISM: Artificial Sequence
<220> FEATURE:
<223> OTHER INFORMATION: Synthetic peptide

<400> SEQUENCE: 309

Pro Ile Pro Ala Gly Gly Cys Thr Phe Ser Gly Ile Phe Pro Thr Leu
1               5                   10                  15

Thr Ser Pro Leu
            20
```

<210> SEQ ID NO 310
<211> LENGTH: 20
<212> TYPE: PRT
<213> ORGANISM: Artificial Sequence
<220> FEATURE:
<223> OTHER INFORMATION: Synthetic peptide

<400> SEQUENCE: 310

Pro Ser Ser Arg Ala Ser Ser Arg Ala Ser Ser Arg Pro Arg Pro Asp
1               5                   10                  15

Asp Leu Glu Ile
            20

<210> SEQ ID NO 311
<211> LENGTH: 20
<212> TYPE: PRT
<213> ORGANISM: Artificial Sequence
<220> FEATURE:
<223> OTHER INFORMATION: Synthetic peptide

<400> SEQUENCE: 311

Pro Tyr Ser Glu Leu Asn Tyr Glu Thr Ser His Tyr Pro Ala Ser Pro
1               5                   10                  15

Asp Ser Trp Val
            20

<210> SEQ ID NO 312
<211> LENGTH: 20
<212> TYPE: PRT
<213> ORGANISM: Artificial Sequence
<220> FEATURE:
<223> OTHER INFORMATION: Synthetic peptide

<400> SEQUENCE: 312

Gln Asp Phe Arg Arg Ala Phe Arg Arg Ile Leu Ala Arg Pro Trp Thr
1               5                   10                  15

Gln Thr Ala Trp
            20

<210> SEQ ID NO 313
<211> LENGTH: 19
<212> TYPE: PRT
<213> ORGANISM: Artificial Sequence
<220> FEATURE:
<223> OTHER INFORMATION: Synthetic peptide

<400> SEQUENCE: 313

Gln Gly Asp Pro Ala Leu Gln Asp Ala Gly Asp Ser Ser Arg Lys Glu
1               5                   10                  15

Tyr Phe Ile

<210> SEQ ID NO 314
<211> LENGTH: 20
<212> TYPE: PRT
<213> ORGANISM: Artificial Sequence
<220> FEATURE:
<223> OTHER INFORMATION: Synthetic peptide

<400> SEQUENCE: 314

Gln Ile Ser Pro Gly Gly Leu Glu Pro Pro Ser Glu Lys His Phe Arg
1               5                   10                  15

Glu Thr Glu Val
            20

```
<210> SEQ ID NO 315
<211> LENGTH: 20
<212> TYPE: PRT
<213> ORGANISM: Artificial Sequence
<220> FEATURE:
<223> OTHER INFORMATION: Synthetic peptide

<400> SEQUENCE: 315

Arg Glu Leu Val Asp Arg Gly Glu Val Arg Gln Phe Thr Leu Arg His
1               5                   10                  15

Trp Leu Lys Val
            20

<210> SEQ ID NO 316
<211> LENGTH: 20
<212> TYPE: PRT
<213> ORGANISM: Artificial Sequence
<220> FEATURE:
<223> OTHER INFORMATION: Synthetic peptide

<400> SEQUENCE: 316

Arg Arg Arg Arg Arg Arg Arg Gly Asn Thr Thr Asp Lys Glu Leu Glu
1               5                   10                  15

Val Leu Ser Leu
            20

<210> SEQ ID NO 317
<211> LENGTH: 20
<212> TYPE: PRT
<213> ORGANISM: Artificial Sequence
<220> FEATURE:
<223> OTHER INFORMATION: Synthetic peptide

<400> SEQUENCE: 317

Arg Arg Arg Arg Arg Arg Arg Gly Thr Asn Pro Ala Val Ala Ala Thr
1               5                   10                  15

Ser Ala Asn Leu
            20

<210> SEQ ID NO 318
<211> LENGTH: 20
<212> TYPE: PRT
<213> ORGANISM: Artificial Sequence
<220> FEATURE:
<223> OTHER INFORMATION: Synthetic peptide

<400> SEQUENCE: 318

Arg Ser Gly Ala Thr Ile Pro Leu Val Gly Gln Asp Ile Ile Asp Leu
1               5                   10                  15

Gln Thr Glu Val
            20

<210> SEQ ID NO 319
<211> LENGTH: 20
<212> TYPE: PRT
<213> ORGANISM: Artificial Sequence
<220> FEATURE:
<223> OTHER INFORMATION: Synthetic peptide

<400> SEQUENCE: 319

Ser Leu Ile Gly Pro Val Gln Lys Glu Tyr Gln Arg Glu Leu Gly Lys
1               5                   10                  15

Leu Ser Ser Pro
            20
```

```
<210> SEQ ID NO 320
<211> LENGTH: 19
<212> TYPE: PRT
<213> ORGANISM: Artificial Sequence
<220> FEATURE:
<223> OTHER INFORMATION: Synthetic peptide

<400> SEQUENCE: 320

Ser Ser Lys Ser Lys Ser Ser Glu Glu Ser Gln Thr Phe Phe Gly Leu
1               5                   10                  15

Tyr Lys Leu

<210> SEQ ID NO 321
<211> LENGTH: 20
<212> TYPE: PRT
<213> ORGANISM: Artificial Sequence
<220> FEATURE:
<223> OTHER INFORMATION: Synthetic peptide

<400> SEQUENCE: 321

Ser Ser Pro Asp Ser Ser Tyr Gln Gly Lys Gly Phe Val Met Ser Arg
1               5                   10                  15

Ala Met Tyr Val
            20

<210> SEQ ID NO 322
<211> LENGTH: 20
<212> TYPE: PRT
<213> ORGANISM: Artificial Sequence
<220> FEATURE:
<223> OTHER INFORMATION: Synthetic peptide

<400> SEQUENCE: 322

Ser Ser Ser Arg Arg Asp Ser Ser Trp Ser Glu Thr Ser Glu Ala Ser
1               5                   10                  15

Tyr Ser Gly Leu
            20

<210> SEQ ID NO 323
<211> LENGTH: 20
<212> TYPE: PRT
<213> ORGANISM: Artificial Sequence
<220> FEATURE:
<223> OTHER INFORMATION: Synthetic peptide

<400> SEQUENCE: 323

Ser Thr Asp Asn Leu Val Arg Pro Phe Met Asp Thr Leu Ala Ser His
1               5                   10                  15

Gln Leu Tyr Ile
            20

<210> SEQ ID NO 324
<211> LENGTH: 20
<212> TYPE: PRT
<213> ORGANISM: Artificial Sequence
<220> FEATURE:
<223> OTHER INFORMATION: Synthetic peptide

<400> SEQUENCE: 324

Thr Glu Gly Asn Glu Ser Ser Glu Ala Thr Ser Pro Val Asn Ala Ile
1               5                   10                  15

Tyr Ser Leu Ala
            20
```

```
<210> SEQ ID NO 325
<211> LENGTH: 20
<212> TYPE: PRT
<213> ORGANISM: Artificial Sequence
<220> FEATURE:
<223> OTHER INFORMATION: Synthetic peptide

<400> SEQUENCE: 325

Thr Phe Lys Gly Thr Pro Thr Ala Glu Asn Pro Glu Tyr Leu Gly Leu
1               5                   10                  15

Asp Val Pro Val
            20

<210> SEQ ID NO 326
<211> LENGTH: 20
<212> TYPE: PRT
<213> ORGANISM: Artificial Sequence
<220> FEATURE:
<223> OTHER INFORMATION: Synthetic peptide

<400> SEQUENCE: 326

Thr Gly Ser Ala Leu Gln Ala Trp Arg His Thr Ser Arg Gln Ala Thr
1               5                   10                  15

Glu Ser Thr Val
            20

<210> SEQ ID NO 327
<211> LENGTH: 20
<212> TYPE: PRT
<213> ORGANISM: Artificial Sequence
<220> FEATURE:
<223> OTHER INFORMATION: Synthetic peptide

<400> SEQUENCE: 327

Thr Gln Gly Phe Pro Gly Pro Ala Thr Trp Arg Arg Ile Ser Ser Leu
1               5                   10                  15

Glu Ser Glu Val
            20

<210> SEQ ID NO 328
<211> LENGTH: 19
<212> TYPE: PRT
<213> ORGANISM: Artificial Sequence
<220> FEATURE:
<223> OTHER INFORMATION: Synthetic peptide

<400> SEQUENCE: 328

Thr Thr Asn Asn Asn Pro Asn Ser Ala Val Asn Ile Lys Lys Ile Phe
1               5                   10                  15

Thr Asp Val

<210> SEQ ID NO 329
<211> LENGTH: 20
<212> TYPE: PRT
<213> ORGANISM: Artificial Sequence
<220> FEATURE:
<223> OTHER INFORMATION: Synthetic peptide

<400> SEQUENCE: 329

Val Asp Pro Asn Ser Pro Ala Ala Lys Lys Lys Tyr Val Ser Tyr Asn
1               5                   10                  15

Asn Leu Val Ile
            20
```

```
<210> SEQ ID NO 330
<211> LENGTH: 20
<212> TYPE: PRT
<213> ORGANISM: Artificial Sequence
<220> FEATURE:
<223> OTHER INFORMATION: Synthetic peptide

<400> SEQUENCE: 330

Val His Asp Ala Glu Ser Ser Asp Glu Asp Gly Tyr Asp Trp Gly Pro
1               5                   10                  15

Ala Thr Asp Leu
            20

<210> SEQ ID NO 331
<211> LENGTH: 20
<212> TYPE: PRT
<213> ORGANISM: Artificial Sequence
<220> FEATURE:
<223> OTHER INFORMATION: Synthetic peptide

<400> SEQUENCE: 331

Val His Lys Val Arg Asn Lys Phe Lys Ala Lys Cys Ser Leu Cys Arg
1               5                   10                  15

Leu Tyr Ile Ile
            20

<210> SEQ ID NO 332
<211> LENGTH: 20
<212> TYPE: PRT
<213> ORGANISM: Artificial Sequence
<220> FEATURE:
<223> OTHER INFORMATION: Synthetic peptide

<400> SEQUENCE: 332

Val Pro Gly Ala Leu Asp Tyr Ala Ala Phe Ser Ser Ala Leu Tyr Gly
1               5                   10                  15

Glu Ser Asp Leu
            20

<210> SEQ ID NO 333
<211> LENGTH: 20
<212> TYPE: PRT
<213> ORGANISM: Artificial Sequence
<220> FEATURE:
<223> OTHER INFORMATION: Synthetic peptide

<400> SEQUENCE: 333

Val Pro Ser Asp Asn Ile Asp Ser Gln Gly Arg Asn Ala Ser Thr Asn
1               5                   10                  15

Asp Ser Leu Leu
            20

<210> SEQ ID NO 334
<211> LENGTH: 20
<212> TYPE: PRT
<213> ORGANISM: Artificial Sequence
<220> FEATURE:
<223> OTHER INFORMATION: Synthetic peptide

<400> SEQUENCE: 334

Tyr Gly Arg Lys Lys Arg Arg Gln Arg Arg Arg Ala Arg Gly Asp Arg
1               5                   10                  15

Lys Ile Arg Val
```

20

<210> SEQ ID NO 335
<211> LENGTH: 20
<212> TYPE: PRT
<213> ORGANISM: Artificial Sequence
<220> FEATURE:
<223> OTHER INFORMATION: Synthetic peptide

<400> SEQUENCE: 335

Tyr Gly Arg Lys Lys Arg Arg Gln Arg Arg Arg Ala Arg Gly Asp Arg
1               5                   10                  15

Lys Lys Ile Val
            20

<210> SEQ ID NO 336
<211> LENGTH: 20
<212> TYPE: PRT
<213> ORGANISM: Artificial Sequence
<220> FEATURE:
<223> OTHER INFORMATION: Synthetic peptide

<400> SEQUENCE: 336

Tyr Gly Arg Lys Lys Arg Arg Gln Arg Arg Arg Ala Arg Gly Asp Arg
1               5                   10                  15

Lys Arg Trp Ala
            20

<210> SEQ ID NO 337
<211> LENGTH: 20
<212> TYPE: PRT
<213> ORGANISM: Artificial Sequence
<220> FEATURE:
<223> OTHER INFORMATION: Synthetic peptide

<400> SEQUENCE: 337

Tyr Gly Arg Lys Lys Arg Arg Gln Arg Arg Arg Ala Arg Gly Asp Arg
1               5                   10                  15

Lys Arg Trp Leu
            20

<210> SEQ ID NO 338
<211> LENGTH: 20
<212> TYPE: PRT
<213> ORGANISM: Artificial Sequence
<220> FEATURE:
<223> OTHER INFORMATION: Synthetic peptide

<400> SEQUENCE: 338

Tyr Gly Arg Lys Lys Arg Arg Gln Arg Arg Arg Ala Arg Gly Asp Arg
1               5                   10                  15

Lys Val Pro Val
            20

<210> SEQ ID NO 339
<211> LENGTH: 20
<212> TYPE: PRT
<213> ORGANISM: Artificial Sequence
<220> FEATURE:
<223> OTHER INFORMATION: Synthetic peptide

<400> SEQUENCE: 339

Tyr Gly Arg Lys Lys Arg Arg Gln Arg Arg Arg Ala Arg Gly Asp Arg
1               5                   10                  15

Lys Tyr Ile Val
            20

<210> SEQ ID NO 340
<211> LENGTH: 20
<212> TYPE: PRT
<213> ORGANISM: Artificial Sequence
<220> FEATURE:
<223> OTHER INFORMATION: Synthetic peptide

<400> SEQUENCE: 340

Tyr Gly Arg Lys Lys Arg Arg Gln Arg Arg Ala Arg Gly Asp Arg
1               5                   10                  15

Leu Glu Ile Val
            20

<210> SEQ ID NO 341
<211> LENGTH: 20
<212> TYPE: PRT
<213> ORGANISM: Artificial Sequence
<220> FEATURE:
<223> OTHER INFORMATION: Synthetic peptide

<400> SEQUENCE: 341

Tyr Gly Arg Lys Lys Arg Arg Gln Arg Arg Ala Arg Gly Asp Arg
1               5                   10                  15

Leu Val Ser Leu
            20

<210> SEQ ID NO 342
<211> LENGTH: 20
<212> TYPE: PRT
<213> ORGANISM: Artificial Sequence
<220> FEATURE:
<223> OTHER INFORMATION: Synthetic peptide

<400> SEQUENCE: 342

Tyr Gly Arg Lys Lys Arg Arg Gln Arg Arg Ala Arg Gly Asp Arg
1               5                   10                  15

Arg Arg Ile Val
            20

<210> SEQ ID NO 343
<211> LENGTH: 20
<212> TYPE: PRT
<213> ORGANISM: Artificial Sequence
<220> FEATURE:
<223> OTHER INFORMATION: Synthetic peptide

<400> SEQUENCE: 343

Tyr Gly Arg Lys Lys Arg Arg Gln Arg Arg Ala Arg Gly Asp Arg
1               5                   10                  15

Thr Ile Ile Tyr
            20

<210> SEQ ID NO 344
<211> LENGTH: 20
<212> TYPE: PRT
<213> ORGANISM: Artificial Sequence
<220> FEATURE:
<223> OTHER INFORMATION: Synthetic peptide

<400> SEQUENCE: 344

Tyr Gly Arg Lys Lys Arg Arg Gln Arg Arg Ala Arg Gly Asp Arg
1               5                   10                  15

Tyr Arg Ile Val
        20

<210> SEQ ID NO 345
<211> LENGTH: 20
<212> TYPE: PRT
<213> ORGANISM: Artificial Sequence
<220> FEATURE:
<223> OTHER INFORMATION: Synthetic peptide

<400> SEQUENCE: 345

Tyr Gly Arg Lys Lys Arg Arg Gln Arg Arg Ala Arg Gly Asp Val
1               5                   10                  15

Arg Leu Met Leu
        20

<210> SEQ ID NO 346
<211> LENGTH: 20
<212> TYPE: PRT
<213> ORGANISM: Artificial Sequence
<220> FEATURE:
<223> OTHER INFORMATION: Synthetic peptide

<400> SEQUENCE: 346

Tyr Gly Arg Lys Lys Arg Arg Gln Arg Arg Ala Arg Gly Arg Arg
1               5                   10                  15

Glu Thr Trp Val
        20

<210> SEQ ID NO 347
<211> LENGTH: 20
<212> TYPE: PRT
<213> ORGANISM: Artificial Sequence
<220> FEATURE:
<223> OTHER INFORMATION: Synthetic peptide

<400> SEQUENCE: 347

Tyr Gly Arg Lys Lys Arg Arg Gln Arg Arg Ala Arg Ser Asp Arg
1               5                   10                  15

Gly Ile Trp Ala
        20

<210> SEQ ID NO 348
<211> LENGTH: 20
<212> TYPE: PRT
<213> ORGANISM: Artificial Sequence
<220> FEATURE:
<223> OTHER INFORMATION: Synthetic peptide

<400> SEQUENCE: 348

Tyr Gly Arg Lys Lys Arg Arg Gln Arg Arg Ala Arg Ser Asp Arg
1               5                   10                  15

Lys Arg Ile Ala
        20

<210> SEQ ID NO 349
<211> LENGTH: 20
<212> TYPE: PRT
<213> ORGANISM: Artificial Sequence
<220> FEATURE:
<223> OTHER INFORMATION: Synthetic peptide

<400> SEQUENCE: 349

Tyr Gly Arg Lys Lys Arg Arg Gln Arg Arg Ala Arg Ser Asp Arg

```
1               5                   10                  15
Lys Arg Ile Val
            20

<210> SEQ ID NO 350
<211> LENGTH: 20
<212> TYPE: PRT
<213> ORGANISM: Artificial Sequence
<220> FEATURE:
<223> OTHER INFORMATION: Synthetic peptide

<400> SEQUENCE: 350

Tyr Gly Arg Lys Lys Arg Arg Gln Arg Arg Ala Arg Ser Asp Arg
1               5                   10                  15

Thr Ile Ile Ala
            20

<210> SEQ ID NO 351
<211> LENGTH: 20
<212> TYPE: PRT
<213> ORGANISM: Artificial Sequence
<220> FEATURE:
<223> OTHER INFORMATION: Synthetic peptide

<400> SEQUENCE: 351

Tyr Gly Arg Lys Lys Arg Arg Gln Arg Arg Ala Arg Ser Asp Arg
1               5                   10                  15

Thr Ile Trp Ala
            20

<210> SEQ ID NO 352
<211> LENGTH: 20
<212> TYPE: PRT
<213> ORGANISM: Artificial Sequence
<220> FEATURE:
<223> OTHER INFORMATION: Synthetic peptide

<400> SEQUENCE: 352

Tyr Gly Arg Lys Lys Arg Arg Gln Arg Arg Ala Arg Thr Asp Arg
1               5                   10                  15

Lys Val Glu Val
            20

<210> SEQ ID NO 353
<211> LENGTH: 20
<212> TYPE: PRT
<213> ORGANISM: Artificial Sequence
<220> FEATURE:
<223> OTHER INFORMATION: Synthetic peptide

<400> SEQUENCE: 353

Tyr Gly Arg Lys Lys Arg Arg Gln Arg Arg Ala Val Ala Ala Ala
1               5                   10                  15

Ser Ala Asn Leu
            20

<210> SEQ ID NO 354
<211> LENGTH: 20
<212> TYPE: PRT
<213> ORGANISM: Artificial Sequence
<220> FEATURE:
<223> OTHER INFORMATION: Synthetic peptide

<400> SEQUENCE: 354
```

```
Tyr Gly Arg Lys Lys Arg Arg Gln Arg Arg Ala Val Ala Ala Thr
1               5                   10                  15

Gly Ile Trp Ala
            20

<210> SEQ ID NO 355
<211> LENGTH: 20
<212> TYPE: PRT
<213> ORGANISM: Artificial Sequence
<220> FEATURE:
<223> OTHER INFORMATION: Synthetic peptide

<400> SEQUENCE: 355

Tyr Gly Arg Lys Lys Arg Arg Gln Arg Arg Ala Val Ala Ala Thr
1               5                   10                  15

Ser Ala Asn Leu
            20

<210> SEQ ID NO 356
<211> LENGTH: 20
<212> TYPE: PRT
<213> ORGANISM: Artificial Sequence
<220> FEATURE:
<223> OTHER INFORMATION: Synthetic peptide

<400> SEQUENCE: 356

Tyr Gly Arg Lys Lys Arg Arg Gln Arg Arg Ala Val Ala Ala Thr
1               5                   10                  15

Ser Ile Asn Leu
            20

<210> SEQ ID NO 357
<211> LENGTH: 20
<212> TYPE: PRT
<213> ORGANISM: Artificial Sequence
<220> FEATURE:
<223> OTHER INFORMATION: Synthetic peptide

<400> SEQUENCE: 357

Tyr Gly Arg Lys Lys Arg Arg Gln Arg Arg Ala Val Ala Ala Thr
1               5                   10                  15

Tyr Ser Asn Leu
            20

<210> SEQ ID NO 358
<211> LENGTH: 20
<212> TYPE: PRT
<213> ORGANISM: Artificial Sequence
<220> FEATURE:
<223> OTHER INFORMATION: Synthetic peptide

<400> SEQUENCE: 358

Tyr Gly Arg Lys Lys Arg Arg Gln Arg Arg Asp Lys Glu Leu Glu
1               5                   10                  15

Val Leu Ser Leu
            20

<210> SEQ ID NO 359
<211> LENGTH: 20
<212> TYPE: PRT
<213> ORGANISM: Artificial Sequence
<220> FEATURE:
<223> OTHER INFORMATION: Synthetic peptide

<400> SEQUENCE: 359
```

-continued

Tyr Gly Arg Lys Lys Arg Arg Gln Arg Arg Glu Lys His Phe Arg
1               5                   10                  15

Glu Thr Glu Val
            20

<210> SEQ ID NO 360
<211> LENGTH: 20
<212> TYPE: PRT
<213> ORGANISM: Artificial Sequence
<220> FEATURE:
<223> OTHER INFORMATION: Synthetic peptide

<400> SEQUENCE: 360

Tyr Gly Arg Lys Lys Arg Arg Gln Arg Arg Glu Tyr Leu Gly Leu
1               5                   10                  15

Asp Val Pro Val
            20

<210> SEQ ID NO 361
<211> LENGTH: 20
<212> TYPE: PRT
<213> ORGANISM: Artificial Sequence
<220> FEATURE:
<223> OTHER INFORMATION: Synthetic peptide

<400> SEQUENCE: 361

Tyr Gly Arg Lys Lys Arg Arg Gln Arg Arg Gly Ala Ser Ala Asp
1               5                   10                  15

Ser Thr Gln Ala
            20

<210> SEQ ID NO 362
<211> LENGTH: 20
<212> TYPE: PRT
<213> ORGANISM: Artificial Sequence
<220> FEATURE:
<223> OTHER INFORMATION: Synthetic peptide

<400> SEQUENCE: 362

Tyr Gly Arg Lys Lys Arg Arg Gln Arg Arg Gly Met Thr Ser Ser
1               5                   10                  15

Ser Ser Val Val
            20

<210> SEQ ID NO 363
<211> LENGTH: 20
<212> TYPE: PRT
<213> ORGANISM: Artificial Sequence
<220> FEATURE:
<223> OTHER INFORMATION: Synthetic peptide

<400> SEQUENCE: 363

Tyr Gly Arg Lys Lys Arg Arg Gln Arg Arg Lys Leu Ser Ser Ile
1               5                   10                  15

Glu Ser Asp Val
            20

<210> SEQ ID NO 364
<211> LENGTH: 20
<212> TYPE: PRT
<213> ORGANISM: Artificial Sequence
<220> FEATURE:
<223> OTHER INFORMATION: Synthetic peptide -continued

```
<400> SEQUENCE: 364

Tyr Gly Arg Lys Lys Arg Arg Gln Arg Arg Lys Asn Lys Asp Lys
1               5                   10                  15

Glu Tyr Tyr Val
            20

<210> SEQ ID NO 365
<211> LENGTH: 20
<212> TYPE: PRT
<213> ORGANISM: Artificial Sequence
<220> FEATURE:
<223> OTHER INFORMATION: Synthetic peptide

<400> SEQUENCE: 365

Tyr Gly Arg Lys Lys Arg Arg Gln Arg Arg Leu Gln Arg Arg
1               5                   10                  15

Glu Thr Gln Val
            20

<210> SEQ ID NO 366
<211> LENGTH: 20
<212> TYPE: PRT
<213> ORGANISM: Artificial Sequence
<220> FEATURE:
<223> OTHER INFORMATION: Synthetic peptide

<400> SEQUENCE: 366

Tyr Gly Arg Lys Lys Arg Arg Gln Arg Arg Asn Asp Asn Ile Ala
1               5                   10                  15

Leu Leu Val Gln
            20

<210> SEQ ID NO 367
<211> LENGTH: 20
<212> TYPE: PRT
<213> ORGANISM: Artificial Sequence
<220> FEATURE:
<223> OTHER INFORMATION: Synthetic peptide

<400> SEQUENCE: 367

Tyr Gly Arg Lys Lys Arg Arg Gln Arg Arg Gln Asp Glu Glu Glu
1               5                   10                  15

Gly Ile Trp Ala
            20

<210> SEQ ID NO 368
<211> LENGTH: 20
<212> TYPE: PRT
<213> ORGANISM: Artificial Sequence
<220> FEATURE:
<223> OTHER INFORMATION: Synthetic peptide

<400> SEQUENCE: 368

Tyr Gly Arg Lys Lys Arg Arg Gln Arg Arg Gln Asp Glu Glu Glu
1               5                   10                  15

Gly Ile Trp Ser
            20

<210> SEQ ID NO 369
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 369

Tyr Gly Arg Lys Lys Arg Arg Gln Arg Arg Gln Asp Glu Glu Glu
1               5                   10                  15
Thr Ile Trp Ala
            20

<210> SEQ ID NO 370
<211> LENGTH: 20
<212> TYPE: PRT
<213> ORGANISM: Artificial Sequence
<220> FEATURE:
<223> OTHER INFORMATION: Synthetic peptide

<400> SEQUENCE: 370

Tyr Gly Arg Lys Lys Arg Arg Gln Arg Arg Gln Asp Glu Arg Arg
1               5                   10                  15
Leu Ile Val Leu
            20

<210> SEQ ID NO 371
<211> LENGTH: 20
<212> TYPE: PRT
<213> ORGANISM: Artificial Sequence
<220> FEATURE:
<223> OTHER INFORMATION: Synthetic peptide

<400> SEQUENCE: 371

Tyr Gly Arg Lys Lys Arg Arg Gln Arg Arg Gln Asp Glu Arg Val
1               5                   10                  15
Glu Thr Arg Val
            20

<210> SEQ ID NO 372
<211> LENGTH: 20
<212> TYPE: PRT
<213> ORGANISM: Artificial Sequence
<220> FEATURE:
<223> OTHER INFORMATION: Synthetic peptide

<400> SEQUENCE: 372

Tyr Gly Arg Lys Lys Arg Arg Gln Arg Arg Ser Glu Gly Val Pro
1               5                   10                  15
Asp Leu Leu Val
            20

<210> SEQ ID NO 373
<211> LENGTH: 20
<212> TYPE: PRT
<213> ORGANISM: Artificial Sequence
<220> FEATURE:
<223> OTHER INFORMATION: Synthetic peptide

<400> SEQUENCE: 373

Tyr Gly Arg Lys Lys Arg Arg Gln Arg Arg Ser Arg Thr Asp Arg
1               5                   10                  15
Lys Tyr Gln Ile
            20

<210> SEQ ID NO 374
<211> LENGTH: 20
<212> TYPE: PRT
<213> ORGANISM: Artificial Sequence
<220> FEATURE:

-continued

<223> OTHER INFORMATION: Synthetic peptide

<400> SEQUENCE: 374

Tyr Gly Arg Lys Lys Arg Arg Gln Arg Arg Ser Arg Thr Asp Arg
1               5                   10                  15

Lys Tyr Trp Ala
            20

<210> SEQ ID NO 375
<211> LENGTH: 20
<212> TYPE: PRT
<213> ORGANISM: Artificial Sequence
<220> FEATURE:
<223> OTHER INFORMATION: Synthetic peptide

<400> SEQUENCE: 375

Tyr Gly Arg Lys Lys Arg Arg Gln Arg Arg Ser Arg Thr Asp Arg
1               5                   10                  15

Leu Glu Tyr Val
            20

<210> SEQ ID NO 376
<211> LENGTH: 20
<212> TYPE: PRT
<213> ORGANISM: Artificial Sequence
<220> FEATURE:
<223> OTHER INFORMATION: Synthetic peptide

<400> SEQUENCE: 376

Tyr Gly Arg Lys Lys Arg Arg Gln Arg Arg Ser Arg Thr Val Arg
1               5                   10                  15

Glu Ile Trp Ala
            20

<210> SEQ ID NO 377
<211> LENGTH: 20
<212> TYPE: PRT
<213> ORGANISM: Artificial Sequence
<220> FEATURE:
<223> OTHER INFORMATION: Synthetic peptide

<400> SEQUENCE: 377

Tyr Gly Arg Lys Lys Arg Arg Gln Arg Arg Ser Val Thr Ser Thr
1               5                   10                  15

Ser Ile Asn Leu
            20

<210> SEQ ID NO 378
<211> LENGTH: 20
<212> TYPE: PRT
<213> ORGANISM: Artificial Sequence
<220> FEATURE:
<223> OTHER INFORMATION: Synthetic peptide

<400> SEQUENCE: 378

Tyr Ser Ala Thr Tyr Ser Glu Leu Glu Asp Pro Gly Glu Met Ser Pro
1               5                   10                  15

Pro Ile Asp Leu
            20

<210> SEQ ID NO 379
<211> LENGTH: 20
<212> TYPE: PRT
<213> ORGANISM: Artificial Sequence
<220> FEATURE:
<223> OTHER INFORMATION: Synthetic peptide

<400> SEQUENCE: 379

Tyr Val Tyr Ser Arg Val Lys Asn Leu Asn Ser Ser Glu Gly Val Pro
1               5                   10                  15

Asp Leu Leu Val
            20

<210> SEQ ID NO 380
<211> LENGTH: 20
<212> TYPE: PRT
<213> ORGANISM: Artificial Sequence
<220> FEATURE:
<223> OTHER INFORMATION: Synthetic peptide

<400> SEQUENCE: 380

Tyr Gly Arg Lys Lys Arg Arg Gln Arg Arg Ala Thr Asn Ser Val
1               5                   10                  15

Arg Leu Met Leu
            20

<210> SEQ ID NO 381
<211> LENGTH: 167
<212> TYPE: DNA
<213> ORGANISM: Artificial Sequence
<220> FEATURE:
<223> OTHER INFORMATION: Viral construct

<400> SEQUENCE: 381
gaattcatat ttgcatgtcg ctatgtgttc tgggaaatca ccataaacgt gaaatgtctt      60
tggatttggg aatcttataa gttctgtatg agaccactcg gatccgagtg catgactggt     120
gaatttcaag agaattcacc agtcatgcac tcttttttgga aaagctt                 167

<210> SEQ ID NO 382
<211> LENGTH: 49
<212> TYPE: RNA
<213> ORGANISM: Artificial Sequence
<220> FEATURE:
<223> OTHER INFORMATION: misc_RNA

<400> SEQUENCE: 382
gagugcauga cuggugaauu ucaagagaau ucaccaguca ugcacucuu                 49

<210> SEQ ID NO 383
<211> LENGTH: 45
<212> TYPE: RNA
<213> ORGANISM: Artificial Sequence
<220> FEATURE:
<223> OTHER INFORMATION: misc_RNA

<400> SEQUENCE: 383
gagugcauga cuggugauuc aagagaucac cagucaugca cucuu                     45

<210> SEQ ID NO 384
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 384

Ala Thr Asn Ser Val Arg Leu Met Leu
1               5
```

METHOD OF DETERMINING INHIBITION OF BINDING TO TRPM7 PROTEIN

CROSS REFERENCE TO RELATED APPLICATION

This application claims the benefit under 35 U.S.C. §119 (e) of U.S. Provisional Patent Application No. 60/532,169 filed on Dec. 23, 2003, the disclosure of which is hereby incorporated herein by reference.

FIELD OF THE INVENTION

This invention relates to methods of reducing the damaging effect of an injury to mammalian cells by treatment with compounds which reduce cell death or dysfunction, including cellular damage following episodes of tissue ischemia, trauma, epilepsy, and acute or chronic degeneration. The invention discloses methods of treating these disorders by administering inhibitors that disrupt protein-protein interactions involved in these disorders, screening methods to identify such inhibitors and specific compositions useful for treating these disorders.

BACKGROUND

Every year, stroke and neurotrauma afflict approximately 660,000 and 350,000 North American individuals, respectively, and about 175,000 stroke and 52,000 trauma victims will die (Stroke-American Stroke Association Web Site, 2000; Centers for Disease Control and Prevention, Traumatic injury in the United States: An interim report to Congress, Centers for Disease Control and Prevention, 2001). 4.5 million people live with Alzheimer's disease, with the prevalence expected to triple by 2050 (Hebert et al. (2003) Arch. Neurol. 60:1119-1122). Epilepsy is the third most common neurological disorder after stroke and Alzheimer's disease. It affects 2.3 million Americans of all ages. Approximately 181,000 new cases of seizures and epilepsy occur each year. One in every 10 Americans will experience a seizure at some point in their lives. Three percent will eventually develop epilepsy (Epilepsy Foundation of America Web Site. Thus stroke, CNS trauma, neurodegenerative illnesses and epilepsy are each disorders of major public health significance. Moreover, cardiovascular disorders, pulmonary diseases, and endocrine illnesses such as diabetes count as among the most common causes of non-neurological morbidity and mortality worldwide. Common to all of these common illnesses is damage to cells in target tissues in the nervous, cardiovascular or endocrine system.

The public health consequences of these disorders are significant. For example, in 1998, $3.4 billion was paid in 1999 to just those Medicare beneficiaries that were discharged from short-stay hospitals, not including the long term care for >1,000,000 people that reportedly have functional limitations or difficulty with activities of daily living resulting from stroke (Heart and Stroke Statistics-2004 Update, American Heart Association, 2004). At this time, no therapeutics are available to reduce brain damage resulting from stroke, and this major disorder can be used as an example for the basis of the current invention, though the field of the invention obviously applies to other disorders involving mammalian cell injury.

Stroke is characterized by neuronal cell death in areas of ischemia, brain hemorrhage or trauma. Many lines of evidence have demonstrated that this cell death is triggered by glutamate over-excitation of neurons, leading to increased intracellular $Ca^{2+}$ and increased nitric oxide due to an increase in nNOS (neuronal nitric oxide synthase) activity. Excitotoxicity is the process by which L-glutamate, the major excitatory neurotransmitter in the mammalian CNS, damages neurons (Olney (1969) Science 164:719-721; Olney and Sharpe (1969) Science 166:386-388). It is established as a predominant neurotoxic mechanism in acute neurological disorders such as stroke, epilepsy and traumatic nervous system injuries (reviewed in Rothman and Olney (1987) TINS 10:299-302; Choi et al. (1988) Neuron 8:623-634; Coyle and Puttfarcken (1993) Science 262:689-695; Lipton and Rosenberg (1994) N. Engl. J. Med. 330:613-622; Hardingham and Bading (2003) Trends. Neurosci. 26:81-89). In brain ischemia, excitotoxic activation of postsynaptic glutamate receptors triggers downstream pathways implicated in subsequent neuronal death (reviewed in Lipton (1999) Physiol. Rev. 79:1431-1568). Of these, $Ca^{2+}$ influx through N-methyl-D-aspartate (NMDA) glutamate receptors was the process consistently revealed as a key event. In these studies, blocking NMDA receptors permitted neurons destined to die from anoxia to survive (Rothman (1983) Science 220:536-537; Goldberg et al. (1987) J. Pharmacol. Exp. Ther. 243:784-791), and animal research suggested that ischemic brain damage could be treated by this approach (Simon et al., (1984) Science 226:850-852). However, blocking NMDA receptors may be detrimental to animals and humans (Fix et al. (1993) Exp. Neurol. 123:204-215; Davis et al. (2000) Stroke 31:347-354; Ikonomidou et al. (2000) Proc. Natl. Acad. Sci. U.S.A. 97:12885-12890). Moreover, though blocking excitotoxicity was effective in laboratory models of disease, clinical trials of anti-excitotoxic therapies (AET) have generally failed to benefit patients (Davis et al., (1997) Lancet 349:32, Davis et al. (2000) Stroke 31:347:354; Morris et al. (1999) J. Neurosurg 91:737-743; Lees et al. (2000) Lancet 355:1949-1954). The reason for this, in the face of a clear role for excitotoxicity in acute neurological disorders, has remained a mystery (Birmingham (2002) Nat. Med. 8:5; Ikonomidou and Turski (2002) Lancet Neurol. 1:383-386).

The present invention relates to our discovery that processes other than excitotoxicity are responsible for neuronal damage in conditions such as stroke. In neurons exposed to oxygen glucose deprivation (OGD), AET unmasks a lethal cation current $I_{OGD}$ mediated by TRPM7, a member of the transient receptor potential (TRP) cation channel superfamily (Nadler et al. (2001) Nature 411:590-595). In OGD, $I_{OGD}$ is activated by reactive oxygen/nitrogen species (ROS), permitting $Ca^{2+}$ uptake that further stimulates ROS and $I_{OGD}$ activation. Blocking $I_{OGD}$ or suppressing TRPM7 expression prevents anoxic neuronal death even in the absence of AET, indicating that TRPM7 is an essential mediator of anoxic death. This work defines a new paradigm for understanding anoxic neuronal damage in which excitotoxicity is a subset of a larger framework of mammalian cell injury that involves TRP cation channels.

SUMMARY OF THE INVENTION

The present invention relates to the treatment of cytodestructive disorders such as tissue ischemia or brain damage resulting from stroke, epilepsy, neurodegenerative conditions or traumatic brain and spinal cord injuries by modulating specific protein:protein interactions including, but not limited to, PDZ domain:PDZ Ligand (PL) interactions that involve, directly or indirectly, members of the TRP cation channel family, and are involved in mediating these clinical disorders. Methods for identifying specific therapeutics that modulate the specific protein:protein interactions involved in these disorders are also provided. Compounds and compositions for treating these neuronal disorders are also disclosed.

Methods of identifying the cellular PDZ proteins that are bound by TRP channels and associated proteins are provided herein. Methods are also provided to identify inhibitors that are high affinity for TRP-specific interactions as well as TRP-associated protein interactions. Other methods are provided to determine selectivity of inhibition, both against the different TRP channels, TRP-associated proteins and the PDZs that can bind them. Methods for delivering peptide inhibitors to cells such as neuron cells are also disclosed.

One class of pharmaceutical compositions that are provided include a pharmaceutical composition comprising an isolated, recombinant or synthetic polypeptide inhibitor that inhibits binding between a TRP channel and a PDZ protein with a physiologically acceptable carrier, diluent or excipient, wherein the polypeptide comprises a C-terminal amino acid sequence of X-L/V/I-X-V/L/A. In certain embodiments, the C-terminal amino acid sequence of the polypeptide is XLML (SEQ ID NO: 1). These compositions can be used to inhibit binding between a TRP channel and various PDZ proteins, including, for example, but not limited to, NNOS, LIM, KIAA1095, HEMBA1003117, AIPC, KIAA1526, DVL1, DVL2, DVL3, PTPL1, ZO-1, ZO-2, ZO-3, KIAA1719, Mupp1, INADL, Shank 3, MINT1, MINT2, MAGI1, MAGI2, MAGI3, NeDLG, syntenin, PSD-95, hDLG, PAR3, MAST1, MAST2, AF6, SIP1, LIM mystique, HTRA2, TIP-1, KIAA0316, PICK1, RIM-2, INADL, Syntrophin 1 alpha, SITAC-18, PAR3L, MAST2, and NSP (novel serine protease).

The polypeptides in these compositions can be of varying lengths. In a certain embodiment such polypeptides are 3-20 amino acids in length. In other embodiments, the polypeptides are fusion polypeptides, which include the C-terminal amino acid sequence of the PL polypeptide and a segment of a transmembrane transporter sequence that is effective to facilitate transport of the polypeptide into the desired cell type, for example a neuronal cell (also known as a cell-membrane transduction domain).

Another class of pharmaceutical compositions may also include an isolated, recombinant or synthetic polypeptide and a physiologically acceptable carrier, diluent or excipient, wherein the polypeptide is 3-20 amino acids in length and inhibits binding between a TRP channel and a PDZ protein. The polypeptides in some of these compositions are 3-8 amino acids in length. Exemplary sequences of such polypeptides include LML Still other pharmaceutical compositions include a fusion polypeptide that inhibits binding between a TRP channel and a PDZ protein and a physiologically acceptable carrier, diluent or excipient. In certain embodiments, the fusion polypeptide inhibitor in these compositions is a fusion of (i) a 9 amino acid segment that has a C-terminal sequence and (ii) an amino acid segment of a transmembrane transporter that is effective to transport the polypeptide into a neuron or other affected cell. In other embodiments the fusion polypeptide inhibitor comprises (i) a 3-8 amino acid segment that has a C-terminal sequence and (ii) an amino acid segment of a transmembrane transporter that is effective to transport the polypeptide into a neuron or other affected cell. In yet other embodiments the fusion polypeptide inhibitor comprises (i) a 9-20 amino acid segment that has a C-terminal sequence and (ii) an amino acid segment of a transmembrane transporter that is effective to transport the polypeptide into a neuron or other affected cell.

The polypeptide inhibitors in the foregoing pharmaceutical compositions can be used in a variety of therapies, including treatment of a number of neurological disorders. Examples of such disorders include, but are not limited to, stroke, ischemia, myocardial ischemia, glaucoma, Parkinson's disease, Huntington's disease, Alzheimer's disease, epilepsy and inherited ataxias. The inhibitors can also be used in the preparation of medicaments for use in the treatment of neurological disorders.

Still other pharmaceutical compositions include small inhibitory RNA ("siRNA") sequences that can specifically reduce the activity of a TRP cation channel family member and protect against cell death from OGD. Specific inhibitory sequences and methods of identifying siRNA sequences are described within.

Also provided are methods for determining whether a test compound modulates binding between a PDZ protein and a TRP channel. Certain of these methods involve contacting a PDZ-domain containing polypeptide and a PDZ-Ligand ("PL") containing peptide having at least the C-terminal 3 amino acids of the TRP channel in the presence of the test compound. In certain embodiments, the PDZ proteins in these screening methods may be selected from the group consisting of DLG1, DLG2, KIAA0973, NeDLG, Outer-membrane protein, Syntrophin alpha 1, TIP1, TIP2, INADL, KIAA0807, KIAA1634, Lim-Mystique, LIM-RIL, MAGI1, MAGI2, NH-ERF1, NH-ERF2, Syntrophin beta-1 and Syntrophin gamma-1, RIM-2, Mint 1, Syntrophin 1 alpha, SITAC-18, ZO-1, PAR3L, MAST2, PAR3, and NSP [novel serine protease]. The amount of complex formed between the PDZ-domain polypeptide and the PL peptide is then determined. The test compound is identified as a potential inhibitor of binding between the PDZ protein and the TRP channel if a lower amount of the complex is detected in the presence of the test compound relative to the concentration of the complex in the absence of the test compound. Another assay can be conducted using compounds identified in the initial screen to determine whether the identified compound mitigates against a condition associated with a neuronal or ischemic disorder. Examples of such assays include necrosis assays, apoptosis assays, caspase assays, cytochrome c assays and cell lysis assays.

These and other embodiments, features and advantages of the present invention will become apparent with reference to the following description and drawings.

BRIEF DESCRIPTION OF THE DRAWINGS

FIGS. 3A, 3B, 3C, and 3D demonstrate that siRNA knock-down of TRPM7 reduces Reactive Oxygen Species (ROS) production, calcium uptake and cell death under prolonged oxygen-glucose deprivation (OGD).

FIGS. 9A, 9B, 9C, AND 9D show the results of titrations of the Tat-TRPM7 peptide with RIM-2 d2, INADL d3, ZO-1 d2, and Par3 d3.

FIG. 11 shows the adenoviral construct (SEQ ID NO:381). The TRPM7 siRNA-pAdTrack.sup.(1) (containing the hairpin under the H1 promoter and GFP under a CMV promoter as well as adeno recombination sequences was cotransfected with pAdEasy (containing viral sequences) into HEK cells and the cells selected with kanamycin. Recombined virus containing the TRPM7 siRNA hairpin (SEQ ID NO:S:382-383) and GFP sequences was then be produced from these cells. (Reference (1): T. C. He, S. Zhou, L. T. da Costa, J. Yu, K. W. Kiniler, and B. Vogelstein. A simplified system for generating recombinant adenoviruses. Proc. Natl. Acad. Sci. U.S.A 95 (5):2509-2514, 1998).

FIG. 14 shows the effect of treating the cultures with Tat-9cTRPM7. The sequence of Tat-9cTRPM7 is: [Tyr-Gly-Arg-Lys-Lys-Arg-Arg-Gln-Arg-Arg-Arg-Ser-Thr-Asn-Ser-Val-Arg-Leu-Met-Leu] or [YGRKKRRQRRR-STNSVRLML] (SEQ ID NO:258), whereby the first 11 residues correspond to the cell membrane transduction domain of the human immunodeficiency virus type 1 (HIV-1) Tat protein and the last 9 residues correspond to the last 9 amino acids of the C-terminus of human TRPM7 (accession Q96QT4). We predict similar results with a Tat-conjugated peptide encoding the last 9 residues of the mouse TRPM7 C-terminus (YGRKKRRQRRR-ATNSVRLML (SEQ ID NO:380); accession Q923J1). (A) Neuronal survival at 20 h in the indicated concentrations of Tat-9cTRPM7 in the absence of excitotoxic challenge. (B) Neuronal survival 20 h after challenging the cultures for 1 h with the indicated concentration of NMDA. Tat-9cTRPM7 was applied immediately after the NMDA challenge.

BRIEF DESCRIPTION OF THE TABLES

Figure 1:
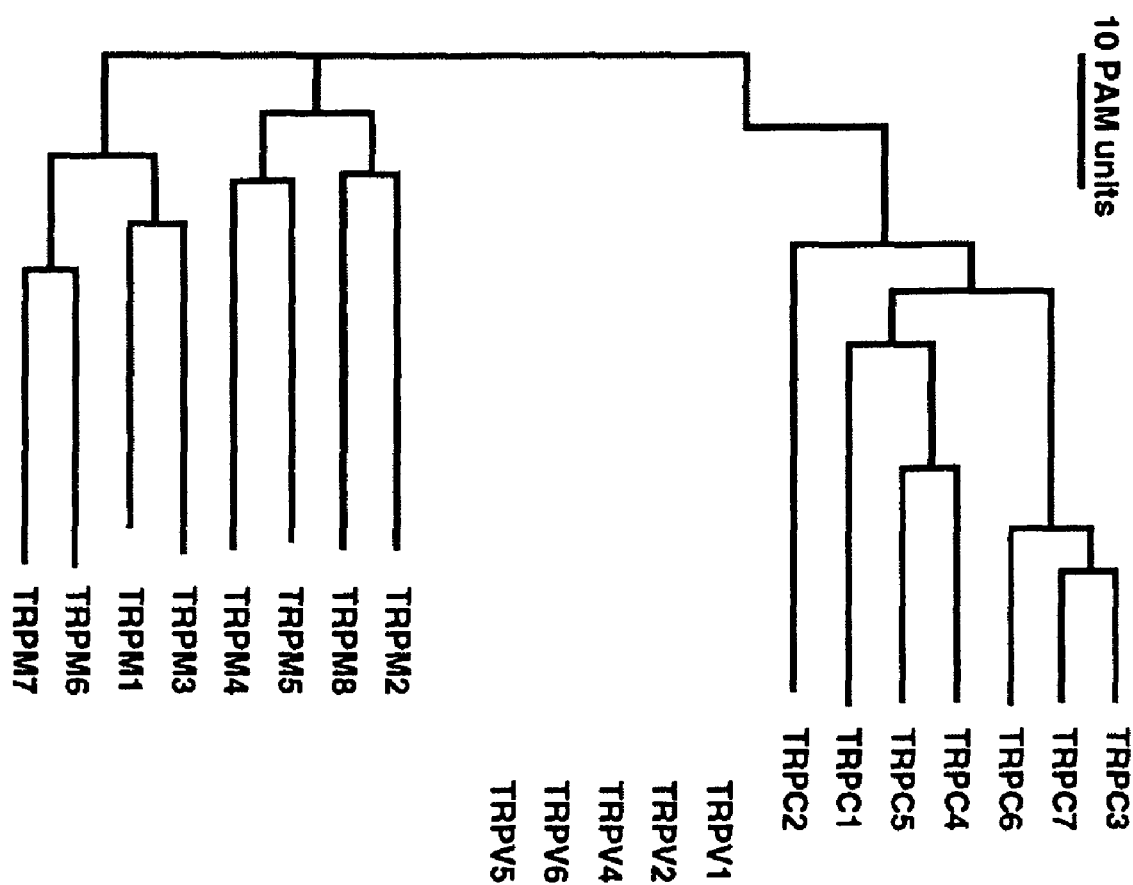
FIG. 1 shows a phylogenetic tree of TRP channels

TABLE 1 shows classifications of genetically encoded and non-encoded amino acids. Column 1 shows the classification, column 2 shows genetically encoded amino acids, and column 3 genetically non-encoded amino acids.

TABLE 2 shows glutamate receptors with PL sequences. Column 1 shows the names of the receptor, column 2 shows the GenBank number, column 3 shows the C-terminal 20mer sequence, column 4 shows the C-terminal 4mer sequence, column 5 shows which sequences are PLs, and column 6 shows internal PL ID.

TABLE 3 shows the number of TRP genes in *C. elegans, Drosophila melangaster*, mice, and humans. Column 1 shows the subfamily, column 2 shows the number in *C. elegans*, column 3 shows the number in *Drosophila melanogaster*, column 4 shows the number in mice, and column 5 shows the number in humans.

TABLE 4 shows the nomenclature of the mammalian TRP superfamily. Column 1 shows the name of the protein, column 2 shows the group number, column 3 shows former names of the protein, and column 4 shows the GenBank accession numbers.

TABLE 5 shows the sequences of PDZ domains cloned to produce GST-PDZ fusion proteins. Column 1 shows the gene name, column 2 shows the GenBank GI or Accession number, column 3 shows the domain number, and column 4 shows the sequence fused to the GST construct.

TABLE 6 shows PDZs predicted to interact with TRPM7

TABLE 7 shows PDZs demonstrated to interact with specific PL proteins.

TABLE 8 shows PDZ domains which bind the Tat-TRPM7 peptide in G0 or G3 assays. Column 1 shows the name of the PDZ protein, column 2 shows the domain number, column 3 shows the GenBank number for the gene encoding the PDZ protein; column 4 shows whether the literature indicates expression in the nervous system or brain, and column 5 shows the literature reference for column 5.

TABLE 9 shows the results of titrations of the Tat-TRPM7 peptide with RIM2 (177.4), Mint 1 (d1,d2) (36.5a), TIP1 d1 (54.10), Mint1 d1 (146.5), Mint1 d2 (147.2), INADL d3 (96.3), MUPP1 d3 (108.3), Syntrophin 1 alpha d1 (52.5), SITAC-18 d1 (122.2), SITAC-18 d2(123.2), LIM Mystique d1 (232.1), ZO-1 d2 (241.3), PAR3L d3 (406.1), MAST2 d1 (174.6), PAR3 d3 (278.1), and KIAA1284 d1 (191.2), Column 1 shows the PDZ protein and domain number, column 2 shows the EC50 in μM, column 3 shows the error of fit for the $EC_{in}$ in μM, and column 4 shows the $OD_{max}$ 450 nm). ND=not determined.

TABLE 10 shows the results of titration of peptides with Z0-1 d2 and INADL d3. Column 1 shows peptide #, column 2 shows peptide sequence, column 3 shows SEQ ID NO of the peptide, column 4 shows the PDZ protein and domain number, column 5 shows the EC50 in μM, column 6 shows the error of fit for the $EC_{in}$ in μM, and column 7 shows the $OD_{max}$ 450 nm). ND=not determined.

TABLE 11 shows the results of titrations or binding assays of peptides with RIM-2 d1, INADL d3, ZO-1 d2, PAR3 d3, and syntrophin1 alpha d1. Column 1 shows PDZ domain bound, Column 2 shows peptide sequence, and Column 3 shows SEQ ID NO.

DETAILED DESCRIPTION OF THE PREFERRED EMBODIMENTS

I. Definitions

"Polypeptide," "protein" and "peptide" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The polypeptide, protein and peptides may be in cyclic form or they may be in linear form (Piserchio et al. Chem. Biol. (2004) 111:469-473; Li et al., Bioorg. Med. Chem. Lett. (2004) 14:13855-1388; Baruch et al. Biochemistry (2003) 42:2797-2805; Harris et al., Biochemistry (2001) 40:5921-5930).

A "fusion protein" or "fusion polypeptide" as used herein refers to a composite protein, i.e., a single contiguous amino acid sequence, made up of two (or more) distinct, heterologous polypeptides which are not normally fused together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid methods, i.e., as a result of transcription and translation of a recombinant gene fusion product, which fusion comprises a segment encoding a polypeptide of the invention and a segment encoding a heterologous protein, or by chemical synthesis methods well known in the art.

A "fusion protein construct" as used herein is a polynucleotide encoding a fusion protein.

As used herein, the term "PDZ domain" refers to protein sequence (i.e., modular protein domain) of approximately 90 amino acids, characterized by homology to the brain synaptic protein PSD-95, the Drosophila septate junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, *Cell* 85: 1067-76).

PDZ domains are found in diverse membrane-associated proteins including members of the MAGUK family of guanylate kinase homologs, several protein phosphatases and kinases, neuronal nitric oxide synthase, and several dystrophin-associated proteins, collectively known as syntrophins.

Exemplary PDZ domain-containing proteins and PDZ domain sequences are shown in TABLE 5. The term "PDZ domain" also encompasses variants (e.g., naturally occurring variants) of the sequences of TABLE 5 (e.g., polymorphic variants, variants with conservative substitutions, and the like). Typically, PDZ domains are substantially identical to those shown in TABLE 5, e.g., at least about 70%, at least about 80%, or at least about 90% amino acid residue identity when compared and aligned for maximum correspondence.

As used herein, the term "PDZ protein" refers to a naturally occurring protein containing a PDZ domain. Exemplary PDZ proteins include, but are not limited to NNOS, LIM, KIAA1095, HEMBA1003117, AIPC, KIAA1526, DVL1, DVL2, DVL3, PTPL1, ZO-1, ZO-2, ZO-3, KIAA1719, Mupp1, INADL, Shank 3, MINT1, MINT2, MAGI1, MAGI2, MAGI3, NeDLG, syntenin, PSD-95, hDLG, PAR3, MAST1, MAST2, AF6, SIP1, LIM mystique, HTRA2, TIP-1, KIAA0316, PICK1, RIM-2, INADL, Syntrophin 1 alpha, SITAC-18, PAR3L, MAST2, and NSP [novel serine protease] and those listed in TABLE 5.

As used herein, the term "PDZ-domain polypeptide" refers to a polypeptide containing a PDZ domain, such as a fusion protein including a PDZ domain sequence, a naturally occurring PDZ protein, or an isolated PDZ domain peptide.

As used herein, the term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 4-25 residues, e.g., 8, 10, 12, 14 or 16 residues), forms such a molecular complex. The molecular complex can be observed in vitro using the A assay or G assay described infra, or in vivo. Exemplary TRP channel PL proteins listed in TABLE 4 and TRP associated proteins listed in TABLE 2 are demonstrated to bind specific PDZ proteins. This definition is not intended to include anti-PDZ antibodies and the like.

As used herein, the terms "NMDA receptor," "NMDAR," or "NMDA receptor protein" refer to a membrane associated protein that is known to interact with NMDA. The term thus includes the various subunit forms, including for example, those listed in TABLE 2. The receptor can be a non-human mammalian NMDAR (e.g., mouse, rat, rabbit, monkey) or a human NMDAR, for example.

As used herein, the term "NMDAR-PL" or "NMDA receptor-PL" refers to a NMDA receptor that forms a molecular complex with a PDZ domain or to a NMDAR protein whose carboxy-terminus, when expressed separately from the full length protein (e.g., as a peptide fragment of 4-25 residues, e.g., 8, 10, 12, 14 or 16 residues), forms such a molecular complex.

As used herein, the term "TRP channel" refers to an ion channel protein of the transient receptor potential family of proteins.

As used herein, the term "TRP associated proteins" refers to proteins that interact physically or functionally with TRP [ion] channel proteins. MT states that he will soon have data that demonstrates binding between TRPM7 and NMDAR (a TRP associated protein).

As used herein, the term "ion channel" refers to an ion channel protein, which could refer singularly or collectively to different ion channels, including TRP channels, NMDA Receptor channels, or other ion channels.

As used herein, "oxygen-glucose deprivation" or "OGD" refers to a change in the cellular environment that results in lower than normal access to oxygen and/or glucose.

As used herein, a "PL sequence" refers to the amino acid sequence of the C-terminus of a PL protein (e.g., the C-terminal 2, 3, 4, 5, 6, 7, 8, 9, 10, 12, 14, 16, 20 or 25 residues) ("C-terminal PL sequence") or to an internal sequence known to bind a PDZ domain ("internal PL sequence").

As used herein, a "PL peptide" is a peptide having a sequence from, or based on, the sequence of the C-terminus of a PL protein. Exemplary PL peptides (biotinylated) are listed in TABLE 2 and TABLE 4.

As used herein, a "PL fusion protein" is a fusion protein that has a PL sequence as one domain, typically as the C-terminal domain of the fusion protein. An exemplary PL fusion protein is a tat-PL sequence fusion.

As used herein, the term "PL inhibitor peptide sequence" refers to PL peptide amino acid sequence that (in the form of a peptide or PL fusion protein) inhibits the interaction between a PDZ domain polypeptide and a PL peptide (e.g., in an A assay or a G assay).

As used herein, a "PDZ-domain encoding sequence" means a segment of a polynucleotide encoding a PDZ domain. In various embodiments, the polynucleotide is DNA, RNA, single stranded or double stranded.

As used herein, the terms "antagonist" and "inhibitor," when used in the context of modulating a binding interaction (such as the binding of a PDZ domain sequence to a PL sequence), are used interchangeably and refer to an agent that reduces the binding of the, e.g., PL sequence (e.g., PL peptide) and the, e.g., PDZ domain sequence (e.g., PDZ protein, PDZ domain peptide).

As used herein, the terms "agonist" and "enhancer," when used in the context of modulating a binding interaction (such as the binding of a PDZ domain sequence to a PL sequence), are used interchangeably and refer to an agent that increases the binding of the, e.g., PL sequence (e.g., PL peptide) and the, e.g., PDZ domain sequence (e.g., PDZ protein, PDZ domain peptide).

The terms "isolated" or "purified" means that the object species (e.g., a polypeptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species.

The term "recombinant" when used with respect to a polypeptide refers to a polypeptide that has been prepared be expressing a recombinant nucleic acid molecule in which different nucleic acid segments have been joined together using molecular biology techniques.

The term "synthesized" when used with respect to a polypeptide generally means that the polypeptide has been prepared by means other than simply purifying the polypeptide from naturally occurring sources. A synthesized polypeptide can thus be prepared by chemical synthesis, recombinant means, or by a combination of chemical synthesis and recombinant means. Segments of a synthesized polypeptide, however, may be obtained from naturally occurring sources.

The term "biological function" or "biological activity" in the context of a cell, refers to a detectable biological activity normally carried out by the cell, e.g., a phenotypic change such as proliferation, cell activation, excitotoxicity responses, neurotransmitter release, cytokine release, degranulation, tyrosine phosphorylation, ion (e.g., calcium) flux, metabolic activity, apoptosis, changes in gene expression, maintenance of cell structure, cell migration, adherence to a substrate, signal transduction, cell-cell interactions, and others described herein or known in the art.

As used herein, the terms "peptide mimetic," "peptidomimetic," and "peptide analog" are used interchangeably and refer to a synthetic chemical compound which has substantially the same structural and/or functional characteristics of a PL inhibitory or PL binding peptide of the invention. The mimetic can be either entirely composed of synthetic, non-natural analogues of amino acids, or is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or inhibitory or binding activity. As with polypeptides of the invention which are conservative variants, routine experimentation will determine whether a mimetic is within the scope of the invention, i.e., that its structure and/or function is not substantially altered. Thus, a mimetic composition is within the scope of the invention if it is capable of binding to a PDZ domain and/or inhibiting a PL-PDZ interaction.

Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N=-dicyclohexylcarbodiimide (DCC) or N,N=-diisopropylcarbodiimide (DIC). Linking groups that can be an alternative to the traditional amide bond ("peptide bond") linkages include, e.g., ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (see, e.g., Spatola (1983) in *Chemistry and Biochemistry of Amino Acids, Peptides and Proteins*, Vol. 7, pp 267-357, *A Peptide Backbone Modifications*, Marcel Dekker, N.Y.).

A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below.

Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R=—N—C—N—R=) such as, e.g., 1-cyclohexyl-3 (2-morpholinyl-(4-ethyl) carboduimide or 1-ethyl-3(4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A component of a natural polypeptide (e.g., a PL polypeptide or PDZ polypeptide) can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form.

The mimetics of the invention can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647-650; Feigl (1986) J. Amer. Chem. Soc. 108:181-182; Kahn (1988) J. Amer. Chem. Soc. 110:1638-1639; Kemp (1988) Tet. Lett. 29:5057-5060; Kahn (1988) J. Molec. Recognition 1:75-79. Beta sheet mimetic structures have been described, e.g., by Smith (1992) J. Amer. Chem. Soc. 114: 10672-10674. For example, a type VI beta turn induced by a cis amide surrogate, 1,5-disubstituted tetrazol, is described by Beusen (1995) Biopolymers 36:181-200. Incorporation of achiral omega-amino acid residues to generate polymethylene units as a substitution for amide bonds is described by Banerjee (1996) Biopolymers 39:769-777. Secondary structures of polypeptides can be analyzed by, e.g., high-field 1H NMR or 2D NMR spectroscopy, see, e.g., Higgins (1997) J. Pept. Res. 50:421-435. See also, Hruby (1997) Biopolymers 43:219-266, Balaji, et al., U.S. Pat. No. 5,612,895.

As used herein, "peptide variants" and "conservative amino acid substitutions" refer to peptides that differ from a reference peptide (e.g., a peptide having the sequence of the carboxy-terminus of a specified PL protein) by substitution of an amino acid residue having similar properties (based on size, polarity, hydrophobicity, and the like). Thus, insofar as the compounds that are encompassed within the scope of the invention are partially defined in terms of amino acid residues of designated classes, the amino acids may be generally categorized into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated electron system (aromatic group). The aromatic group may be further substituted with groups such as alkyl, alkenyl, alkynyl, hydroxyl, sulfanyl, nitro and amino groups, as well as others. Examples of genetically encoded aromatic amino acids include Phe, Tyr and Trp. Commonly encountered non-genetically encoded aromatic amino acids include phenylglycine, 2-naphthylalanine, β-2-thienylalanine, 1,2,3, 4-tetrahydroisoquinoline-3-carboxylic acid, 4-chloro-phenylalanine, 2-fluorophenyl-alanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include Gly, Pro and Met. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include Asp and Glu.

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include Arg, Lys and His. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include Asx and Glx. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include Cys. Examples of non-genetically encoded cysteine-like amino acids include homocysteine and penicillamine.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded of which the peptides and peptide analogues of the invention may be composed include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); omithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH2)); N-methyl valine (MeVal); homocysteine (hCys) and homoserine (hSer). These amino acids also fall conveniently into the categories defined above.

The classifications of the above-described genetically encoded and non-encoded amino acids are summarized in TABLE 1, below. It is to be understood that TABLE 1 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$BU |
| Polar | Q, N, S, T, Y | Cit, AcLys, MSO, hSer |
| Cysteine-Like | C | Pen, hCys, p-methyl Cys |

As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical or chemical means. Labels useful in the present invention include biotin for staining with labeled streptavidin conjugate, magnetic beads (e.g., Dynabeads™), fluorescent dyes (e.g., fluorescein, Texas red, rhodamine, green fluorescent protein, enhanced green fluorescent protein, and the like), radiolabels (e.g., $^3$H, $^{125}$I, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horseradish peroxidase, and others commonly used in ELISAs), substrates, cofactors, inhibitors, chemiluminescent groups, chromogenic agents, and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels and chemiluminescent labels may be detected using photographic film or scintillation counters, fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and colorimetric labels are detected by simply visualizing the colored label. Thus, a label is any composition detectable by spectroscopic, photochemical, biochemical, immunochemical, electrical, optical or chemical means. The label may be coupled directly or indirectly to the desired component of the assay according to methods well known in the art. Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal generating system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody. The molecules can also be conjugated directly to signal generating compounds, e.g., by conjugation with an enzyme or fluorophore. Means of detecting labels are well known to those of skill in the art. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple calorimetric labels may be detected by observing the color associated with the label. It will be appreciated that when pairs of fluorophores are used in an assay, it is often preferred that they have distinct emission patterns (wavelengths) so that they can be easily distinguished.

As used herein, the term "substantially identical" in the context of comparing amino acid sequences, means that the sequences have at least about 70%, at least about 80%, or at least about 90% amino acid residue identity when compared and aligned for maximum correspondence. An algorithm that is suitable for determining percent sequence identity and sequence similarity is the FASTA algorithm, which is described in Pearson, W. R. & Lipman, D. J., 1988, *Proc. Natl. Acad. Sci. U.S.A.* 85: 2444. See also W. R. Pearson, 1996, *Methods Enzymol.* 266: 227-258. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

As used herein, the terms "test compound" or "test agent" are used interchangeably and refer to a candidate agent that may have enhancer/agonist, or inhibitor/antagonist activity, e.g., inhibiting or enhancing an interaction such as PDZ-PL binding. The candidate agents or test compounds may be any of a large variety of compounds, both naturally occurring and synthetic, organic and inorganic, and including polymers (e.g., oligopeptides, polypeptides, oligonucleotides, and polynucleotides), small molecules, antibodies (as broadly defined herein), sugars, fatty acids, nucleotides and nucleotide analogs, analogs of naturally occurring structures (e.g., peptide mimetics, nucleic acid analogs, and the like), and numerous other compounds. In certain embodiment, test agents are prepared from diversity libraries, such as random or combinatorial peptide or non-peptide libraries. Many libraries are known in the art that can be used, e.g., chemically synthesized libraries, recombinant (e.g., phage display libraries), and in vitro translation-based libraries. Examples of chemically synthesized libraries are described in Fodor et al., 1991, *Science* 251:767-773; Houghten et al., 1991, *Nature* 354:84-86; Lam et al., 1991, *Nature* 354:82-84; Medynski, 1994, *Bio/Technology* 12:709-710; Gallop et al., 1994, *J. Medicinal Chemistry* 37(9):1233-1251; Ohlmeyer et al., 1993, *Proc. Natl. Acad. Sci. USA* 90:10922-10926; Erb et al., 1994, *Proc. Natl. Acad. Sci. USA* 91:11422-11426; Houghten et al., 1992, *Biotechniques* 13:412; Jayawickreme et al., 1994, *Proc. Natl. Acad. Sci. USA* 91:1614-1618; Salmon et al., 1993, *Proc. Natl. Acad. Sci. USA* 90:11708-11712; PCT Publication No. WO 93/20242; and Brenner and Lerner, 1992, *Proc. Natl. Acad. Sci. USA* 89:5381-5383. Examples of phage display libraries are described in Scott and Smith, 1990, *Science* 249:386-390; Devlin et al., 1990, *Science,* 249:404-406; Christian, R. B., et al., 1992, *J. Mol. Biol.* 227:711-718); Lenstra, 1992, *J. Immunol. Meth.* 152:149-157; Kay et al., 1993, *Gene* 128:59-65; and PCT Publication No. WO 94/18318 dated Aug. 18, 1994. In vitro translation-based libraries include but are not limited to those described in PCT Publication No. WO 91/05058 dated Apr. 18, 1991; and Mattheakis et al., 1994, *Proc. Natl. Acad. Sci. USA* 91:9022-9026. By way of examples of nonpeptide libraries, a benzodiazepine library (see e.g., Bunin et al., 1994, *Proc. Natl. Acad. Sci. USA* 91:4708-4712) can be adapted for use. Peptdid libraries (Simon et al., 1992, *Proc. Natl. Acad. Sci. USA* 89:9367-9371) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138-11142).

As used herein, a "plurality" of PDZ proteins (or corresponding PDZ domains or PDZ fusion polypeptides) has its usual meaning. In some embodiments, the plurality is at least 5, and often at least 25, at least 40, or at least 60 different PDZ proteins. In some embodiments, the plurality is selected from the list of PDZ polypeptides listed in TABLE 5. In some embodiments, the plurality of different PDZ proteins are from (i.e., expressed in) a particular specified tissue or a particular class or type of cell. In some embodiments, the plurality of different PDZ proteins represents a substantial fraction (e.g., typically at least 50%, more often at least 80%) of all of the PDZ proteins known to be, or suspected of being, expressed in the tissue or cell(s), e.g., all of the PDZ proteins known to be present in neurons. In some embodiments, the plurality is at least 50%, usually at least 80%, at least 90% or all of the PDZ proteins disclosed herein as being expressed in a particular cell.

As used herein, a "plurality" of PDZ proteins (or corresponding PDZ domains or PDZ fusion polypeptides) has its usual meaning. In some embodiments, (Susan our US associate has cautioned us to remove phrases such as "in one embodiment" as the applicant may be required to include all of these features as limitations in the claims. I am not sure if you agree, it is now our practice to use the phrase "in certain embodiments" OK with me the plurality is at least 5, and often at least 25, at least 40, or at least 60 different PDZ proteins. In some embodiments, the plurality is selected from the list of PDZ polypeptides listed in TABLE 5. In some embodiments, the plurality of different PDZ proteins are from (i.e., expressed in) a particular specified tissue or a particular class or type of cell. In some embodiments, the plurality of different PDZ proteins represents a substantial fraction (e.g., typically at least 50%, more often at least 80%) of all of the PDZ proteins known to be, or suspected of being, expressed in the tissue or cell(s), e.g., all of the PDZ proteins known to be present in neurons. In some embodiments, the plurality is at least 50%, usually at least 80%, at least 90% or all of the PDZ proteins disclosed herein as being expressed in a particular cell.

When referring to PL peptides (or the corresponding proteins, e.g., corresponding to those listed in TABLE 2, or elsewhere herein) a "plurality" may refer to at least 5, at least 10, and often at least 25 PLs such as those specifically listed herein, or to the classes and percentages set forth supra for PDZ domains.

The term "cytodestructive disorder" generally refers to a disorder in which an injury to a tissue is sustained that results in the destruction or dysfunction of cells. Specific examples of such disorders include, but are not limited to, tissue ischemia, thermal burns, electrical burns, burns sustained from contact with caustic solutions, poisonings, endocrine and metabolic derangements, nutritional deficiencies, exposure to solar or ionizing radiation, malignant transformation, and mechanical tissue deformation such as might occur in tissue trauma.

The term "neurological disorder," "neurological injury", "neurological disease" and other related terms generally refers to a disorder correlated with some type neuronal insult or neuronal cell death. Specific examples of such disorders include, but are not limited to, stroke, ischemic stroke, glaucoma, retinal ischemia, Parkinson's disease, Huntington's disease, Alzheimer's disease, epilepsy, inherited ataxias and motor neuron diseases. Further examples of such disorders include, but are not limited to, disorders of synaptic transmission in the brain, such disorders resulting in impairments of learning, memory, neuropsychatric and mood disorders, and congenital disorders of mentation.

A "stroke" has the meaning normally accepted in the art and generally refers to neurological injury resulting from impaired blood flow regardless of cause. Potential causes include, but are not limited to, embolism, hemorrhage and thrombosis. An "ischemic stroke" refers more specifically to a type of stroke that is of limited-extent and caused due to blockage of blood flow.

A difference in general is typically considered to be "statistically significant" if the difference is less than experimental error. Thus a difference is considered statistically significant if the probability of the observed difference occurring by chance (the p-value) is less than some predetermined level. As used herein a "statistically significant difference" can refer to a p-value that is <0.05, preferably <0.01 and most preferably <0.001.

II. General

The present inventors have identified interactions between PDZ proteins and proteins that contain a PL motif that are involved in various biological functions in different types of cells. Some of these interactions involve PDZ:PL protein interactions between proteins that have important roles in neuronal cells. As such, modulation of these interactions has direct implications for the treatment of various disorders of mammalian cell injury, including, but not limited to, neurological disorders such as stroke and brain ischemia.

The inventors have identified distinct strategies for treating various neurological disorders based on PDZ:PL interations. One strategy is based upon the finding that disrupting the activity of a member of the TRP cation channel family, is protective for cellular damage induced by OGD (oxygen-glucose deprivation) or anoxia. The inventors have determined common structural features of a class of polypeptides that are effective in disrupting the interaction between a member of the TRP cation channel family and PDZ domain-containing polypeptides. These polypeptides are thus useful in treating disorders associated with OGD. The second strategy is based upon the recognition that several types of ion channels can be grouped and regulated by PDZ proteins, and that disruption of these interactions can modulate the structure of these complexes and provide protection against damage resulting from OGD.

The current inventors have thus identified compounds that inhibit the interactions between these different proteins, as well as developed methods for designing additional compounds. One general class of inhibitors is those that mimic the carboxy terminus of a PL protein and thus interfere with the ability of the carboxy terminus of the PL protein to bind its cognate PDZ protein. Another general class of inhibitors includes the PDZ domain from a PDZ protein that is involved in an interaction that is to be disrupted. These inhibitors bind the PL protein that is the cognate ligand for the PDZ protein of interest and thus prevent binding between the PL protein and PDZ protein. Because the PDZ:PL protein interactions that are described herein are involved in the biological activity of mammalian, and especially neuronal cells, the inhibitors that are provided can be used to inhibit PDZ:PL protein interactions for the treatment of neurological disorders such as stroke, ischemia, Parkinson's disease, Huntington's disease, Alzheimer's disease, epilepsy, inherited ataxias, motor neuron diseases as well as myocardial ischemia, retinal ischemia and glaucoma. Methods for determining whether a test compound acts a modulator of a particular PDZ protein and PL protein binding pair are also described.

For those PDZ proteins containing multiple PDZ domains, the methods that are provided can be utilized to determine to which specific domain(s) a particular PL protein of interest binds. The methods can thus be utilized to identify or design inhibitors that have increased selectivity for a particular PDZ domain. The methods that are disclosed can also be used to identify inhibitors with high binding affinity. Because TRP channels play a key regulatory role in many cell types, an initial set of studies were undertaken to determine which PDZ proteins bind to the PL of TRPM7. These analyses were conducted using the A and G assays described in detail below. Without intending to be limiting, the PDZ proteins identified as being able to bind TRPM7 are listed in TABLE 6.

The C-terminal sequences of the various TRP channels that contain a PL sequence are listed in TABLE 4. Because the C-terminal region of the PL protein is the most common region that binds to PDZ proteins, agents that include similar amino acid motifs can be used to inhibit binding between TRP proteins and the PDZ proteins that bind to them. As described in greater detail below, for example, certain classes of peptide inhibitors typically include at least 2 contiguous amino acids from the C-terminus of the TRP proteins listed in TABLE 4, but can include 3-20 or more contiguous amino acids from the C-terminus.

Additional studies identify the structural motifs common to the polypeptides capable of inhibiting the interaction between TRPM7 and PDZ domains. One class of compounds are polypeptides that have the following characteristics: 1) a length of about 3-20 amino acids (although somewhat longer polypeptides can be used), and 2) a C-terminal consensus sequence of X-L/I/V-X-V/L/A (the slash separates different amino acids that can appear at a given position). These polypeptides also typically have IC50 values of less than 50 µM.

The inventors have also found that the C-termini of several MAGUK (membrane associated Guanylate Kinases) are themselves PL sequences and thus can bind PDZ proteins. Accordingly, another class of inhibitors are those that disrupt binding between the PL sequences of these PDZ proteins and their PDZ binding partners. These proteins are involved in organizing signaling complexes associated with excitotoxic, anoxic or cytodestructive cellular death. Interactions of this type thus provide another therapeutic target for treatment of various neurological diseases.

Although the foregoing classes of inhibitors are based upon the C-terminal sequences of PL proteins that bind a PDZ protein, as alluded to above, another class of inhibitors includes polypeptides that include all or a part of a PDZ domain that binds to the PL sequence of a TRP channel protein or TRP associated protein. Because inhibitors in this class typically include most or the entire PDZ domain, polypeptide inhibitors in this class typically are at least 50-70 amino acids in length.

The various classes of polypeptide inhibitors just described can also be fusion proteins. These generally include a PL inhibitor peptide sequence such as those just listed that is fused to another sequence that encodes a separate protein domain. One specific example of an inhibitory fusion protein is one in which a PL sequence (e.g., it might simply be easier to reinsert the list cite Table 10 and Table 11) is coupled to a transmembrane transporter peptide. As described in greater detail infra, a variety of different transmembrane transporter peptides can be utilized.

Although certain classes of inhibitors such as those just described are polypeptides, other inhibitors are peptide mimetics or variants of these polypeptides as described in greater detail infra. Regardless of type, the inhibitors typically had IC50 values less than 50 μM, 25 μM, 10 μM, 0.1 μM or 0.01 μM. In general the inhibitors typically have an IC50 value of between 0.1-1 μM. These inhibitors can be formulated as pharmaceutical compositions and then used in the treatment of various neurological disorders such as those listed above.

The following sections provide additional details regarding the identification of PDZ:PL interactions in neuron cells, the structural characteristics of inhibitors that disrupt these interactions and treatment methods utilizing such inhibitors.

III. Identification of Candidate PL Protein and Synthesis of Peptides

A PL protein (short for PDZ Ligand protein), such as the TRP proteins described herein, is a protein (or a C-terminal fragment thereof) that can bind PDZ proteins via its carboxy terminus. PDZ proteins, in turn, are proteins with PDZ domains, which are domains common to three prototypical proteins: post synaptic density protein –95 (PSD-95), *Drosophila* large disc protein and Zonula Occludin 1 protein (see, e.g., Gomperts et al., 1996, Cell 84:659-662; see also, Songyang et al., 1997, Science 275:73; and Doyle et al., 1996, Cell 88:1067-1076). Certain classes of PDZ proteins contain three PDZ domains, one SH3 domain and one guanylate kinase domain. As described in greater detail herein, PL proteins have certain carboxy terminal motifs that enable these proteins to functions as ligands to PDZ proteins. When these carboxy terminal regions are referred to, the positioning of the carboxy terminal residues are sometimes referred to herein by a numbered position, which is illustrated in the following scheme:

Position: –3 –2 –1 0 (C-terminal)

Certain PDZ domains are bound by the C-terminal residues of PDZ-binding proteins. To identify TRP channels and TRP associated proteins containing a PL motif, the C-terminal residues of sequences were visually inspected to identify sequences that bind to PDZ-domain containing proteins (see, e.g., Doyle et al., 1996, Cell 85, 1067; Songyang et al., 1997, Science 275, 73). TABLES 2 and 4 list these proteins, and provide corresponding C-terminal sequences and GenBank accession numbers.

TABLE 2

Glutamate Receptors with PL Sequences

| Name | GI# | PL | internal PL ID |
|---|---|---|---|
| NMDAR1 | 307302 | X | AA216 |
| NMDAR1-1 | 292282 | X | AA216 |
| NMDAR1-4 | 472845 | X | AA216 |
| NMDAR1-3b | 2343286 | X | AA216 |
| NMDAR1-4b | 2343288 | X | AA216 |
| NMDAR1-2 | 11038634 | | |
| NMDAR1-3 | 11038636 | | |
| NMDAR2C | 6006004 | X | AA180 |
| NMDAR3 | 560546 | X | AA34.1 |
| NMDAR3A | 17530176 | | |
| NMDAR2B | 4099612 | X | |
| NMDAR2A | 558748 | X | AA34.2 |
| NMDAR2D | 4504130 | X | |
| GluR2 | 3287973 | X | |
| GluR3 | 481504 | X | |
| GluR1 | 1169961 | X | |
| GluR5 | 729597 | X | |
| GluR6 | 2492627 | X | |
| GluR7 | 12729188 | X | |

A. Preparation of Peptides

1) Chemical Synthesis

Technique for the preparation of peptides and peptide analogues of the current invention are well known in the art. For example, the peptides may be prepared in linear form using conventional solution or solid phase peptide syntheses and cleaved from the resin followed by purification procedures (Creighton, 1983, *Protein Structures And Molecular Principles*, W.H. Freeman and Co., N.Y.). Suitable procedures for synthesizing the peptides described herein are well known in the art. The composition of the synthetic peptides may be confirmed by amino acid analysis or sequencing (e.g., the Edman degradation procedure and mass spectroscopy).

In addition, analogues and derivatives of the peptides can be chemically synthesized. The linkage between each amino acid of the peptides of the invention may be an amide, a substituted amide or an isostere of amide. Nonclassical amino acids or chemical amino acid analogues can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general. Furthermore, the amino acid can be D (dextrorotary) or L (levorotary).

Synthetic peptides of defined sequence (e.g., corresponding to the carboxyl-termini of the indicated proteins) can be synthesized by any standard resin-based method (see, e.g., U.S. Pat. No. 4,108,846; see also, Caruthers et al., 1980, Nucleic Acids Res. Symp. Ser., 215-223; Horn et al., 1980, Nucleic Acids Res. Symp. Ser., 225-232; Roberge, et al., 1995, Science 269:202). The peptides used in the assays described herein were prepared by the FMOC (see, e.g., Guy and Fields, 1997, Meth. Enz. 289:67-83; Wellings and Atherton, 1997, Meth. Enz. 289:44-67). In some cases (e.g., for use in the A and G assays of the invention), peptides were labeled with biotin at the amino-terminus by reaction with a four-fold excess of biotin methyl ester in dimethylsulfoxide with a catalytic amount of base. The peptides were cleaved from the resin using a halide containing acid (e.g. trifluoroacetic acid) in the presence of appropriate antioxidants (e.g. ethanedithiol) and excess solvent lyophilized.

2) Recombinant Synthesis

If the peptide is composed entirely of gene-encoded amino acids, or a portion of it is so composed, the peptide or the relevant portion may also be synthesized using conventional recombinant genetic engineering techniques. For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Maniatis et al., 1989, Molecular Cloning A Laboratory Manual, Cold-Spring Harbor Laboratory, N.Y.; and Ausubel et al., 1989, Current Protocols in Molecular Biology, Greene Publishing Associates and Wiley Interscience, N.Y.).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224:838-843) or heat shock promoters, e.g., soybean hsp17.5-E or hsp17.3-B (Gurley et al., 1986, Mol. Cell. Biol. 6:559-565) may be used. These constructs can be introduced into planleukocytes using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, NY, Section VIII, pp. 421-463; and Grierson & Corey, 1988, Plant Molecular Biology, 2d Ed., Blackie, London, Ch. 7-9.

In one insect expression system that may be used to produce the peptides of the invention, *Autographa califomica* nuclear polyhidrosis virus (AcNPV) is used as a vector to express the foreign genes. The virus grows in Spodoptera frugiperda cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, J. Virol. 46:584; Smith, U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, Proc. Natl. Acad. Sci. USA 81:3655-3659). Alternatively, the vaccinia 7.5 K promoter may be used, (see, e.g., Mackett et al., 1982, Proc. Natl. Acad. Sci. USA 79:7415-7419; Mackett et al., 1984, J. Virol. 49:857-864; Panicali et al., 1982, Proc. Natl. Acad. Sci. USA 79:4927-4931).

Other expression systems for producing linear peptides of the invention will be apparent to those having skill in the art.

B. Purification of Peptides and Peptide Analogues

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art. The purified peptides can be identified by assays based on their physical or functional properties, including radioactive labeling followed by gel electrophoresis, radioimmuno-assays, ELISA, bioassays, and the like.

For affinity chromatography purification, any antibody which specifically binds the peptides or peptide analogues may be used. For the production of antibodies, various host animals, including but not limited to rabbits, mice, rats, etc., may be immunized by injection with a peptide. The peptide may be attached to a suitable carrier, such as BSA or KLH, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, 1975, Nature 256:495-497, the human B-cell hybridoma technique, Kosbor et al., 1983, Immunology Today 4:72; Cote et al., 1983, Proc. Natl. Acad. Sci. U.S.A. 80:2026-2030 and the EBV-hybridoma technique (Cole et al., 1985, Monoclonal Antibodies and Cancer Therapy, Alan R. Liss, Inc., pp. 77-96 (1985)). In addition, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce peptide-specific single chain antibodies.

Antibody fragments which contain deletions of specific binding sites may be generated by known techniques. For example, such fragments include but are not limited to F(ab')2 fragments, which can be produced by pepsin digestion of the antibody molecule and Fab fragments, which can be generated by reducing the disulfide bridges of the F(ab')2 fragments. Alternatively, Fab expression libraries may be constructed (Huse et al., 1989, Science 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides of the invention. See, Scopes, 1984, Protein Purification: Principles and Practice, Springer-Verlag New York, Inc., NY, Livingstone, 1974, Methods Enzymology: Immunoaffinity Chromatography of Proteins 34:723-731.

For the peptides used in the present invention, cleavage from resin and lyophilization was followed by peptides being redissolved and purified by reverse phase high performance liquid chromatography (HPLC). One appropriate HPLC solvent system involves a Vydac C-18 semi-preparative column running at 5 ml per minute with increasing quantities of acetonitrile plus 0.1% trifluoroacetic acid in a base solvent of water plus 0.1% trifluoroacetic acid. After HPLC purification, the identities of the peptides are confirmed by MALDI cation-mode mass spectrometry. As noted, exemplary biotinylated peptides are provided in TABLE 2.

IV. Trp Channels A. Nomenclature (Taken from C. Montell, et al. a Unified Nomenclature for the Superfamily of Trp Cation Channels. *Mol. Cell* 9 (2):229-231, 2002.)

The TRP superfamily includes a diversity of non-voltage-gated cation channels that vary significantly in their selectivity and mode of activation. Nevertheless, members of the TRP superfamily share significant sequence homology and predicted structural similarities. Until recently most of the genes and proteins that comprise the TRP superfamily have had multiple names and, in at least one instance, two distinct genes belonging to separate subfamilies have the same name. Moreover, there are many cases in which highly related proteins that belong to the same subfamily have unrelated names. Therefore, to minimize confusion, a unified nomenclature has been accepted for the TRP superfamily.

The unified TRP nomenclature focuses on three subfamilies (TRPC, TRPV, and TRPM) that bear significant similarities to the founding member of this superfamily, Drosophila TRP, and which include highly related members in worms, flies, mice, and humans (TABLE 3). Members of the three subfamilies contain six transmembrane segments, a pore loop separating the final two transmembrane segments, and similarity in the lengths of the cytoplasmic and extracellular loops. In addition, the charged residues in the S4 segment that appear to contribute to the voltage sensor in voltage-gated ion channels are not conserved. The TRP-Canonical (TRPC) subfamily (formerly short-TRPs or STRPs) is comprised of those proteins that are the most highly related to Drosophila TRP. The TRPV subfamily (formerly OTRPC), is so named based on the original designation, Vanilloid Receptor 1 (VR1), for the first mammalian member of this subfamily (now TRPV1). The name for the TRPM subfamily (formerly long-TRPs or LTRPs) is derived from the first letter of Melastatin, the former name (now TRPM1) of the founding member of this third subfamily of TRP-related proteins. Based on amino acid homologies, the mammalian members of these three subfamilies can be subdivided into several groups each (TABLE 4 and FIG. 1).

TABLE 3

Number of TRP Genes in Worms (*C. elegans*), Flies (*Drosophila melanogaster*), Mice, and Humans

| Subfamily | Worms | Flies | Mice | Humans |
| --- | --- | --- | --- | --- |
| TRPC | 3 | 3 | 7 | 6[a] |
| TRPV | 5 | 2 | 5 | 5 |
| TRPM | 4 | 1 | 8 | 8 |

[a]TRPC2 is a pseudogene and is not counted.

TABLE 4

Nomenclature of the Mammalian TRP Superfamily

| Name | Group | Former Names | Accession Numbers |
|---|---|---|---|
| TRPC Subfamily | | | |
| TRPC1 | 1 | TRP1 TRPC1 | (CAA61447), (AAA93252) |
| TRPC2 | 2 | TRP2 TRPC2 | (X89067), (AAD17195), (AAD17196), (AAG29950), (AAG29951), (AAD31453), (CAA06964) |
| TRPC3 | 3 | TRP3 TRPC3 | (AAC51653) |
| TRPC4 | 4 | TRP4 TRPC4 | (CAA68125), (BAA23599) |
| TRPC5 | 4 | TRP5 TRPC5 | (AAC13550), (CAA06911), (CAA06912) |
| TRPC6 | 3 | TRP6 TRPC6 | NP_038866 |
| TRPC7 | 3 | TRP7 TRPC7 | (AAD42069), NP_065122 |
| TRPV Subfamily | | | |
| TRPV1 | 1 | VR1 OTRPC1 | (AAC53398) |
| TRPV2 | 1 | VRL-1 OTRPC2 GRC | (AAD26363), (AAD26364), (BAA78478) |
| TRPV3 (not assigned) | | | |
| TRPV4 | 2 | OTRPC4 VR-OAC TRP12 VRL-2 | (AAG17543), (AAG16127), (AAG28027), (AAG28028), (AAG28029), (CAC20703) |
| TRPV5 | 3 | ECaC1 CaT2 | (CAB40138) |
| TRPV6 | 3 | CaT1 ECaC2 CaT-L | (AAD47636) (CAC20416) (CAC20417) |
| TRPM Subfamily | | | |
| TRPM1 | 1 | Melastatin | (AAC13683), (AAC80000) |
| TRPM2 | 2 | TRPC7 LTRPC2 | (BAA34700) |
| TRPM3 | 1 | KIAA1616 LTRPC3 | (AAO38185) |
| TRPM4 | 3 | TRPM4 LTRPC4 | (H18835) |
| TRPM5 | 3 | MTR1 LTRPC5 | (AAF26288) |
| TRPM6 | 4 | Chak2 | (AF350881) |
| TRPM7 | 4 | TRP-PLIK Chak1 LTRPC7 | (AAF73131), (AY032951) |
| TRPM8 | 2 | TRP-p8 | (AC005538) |

Figure 2:
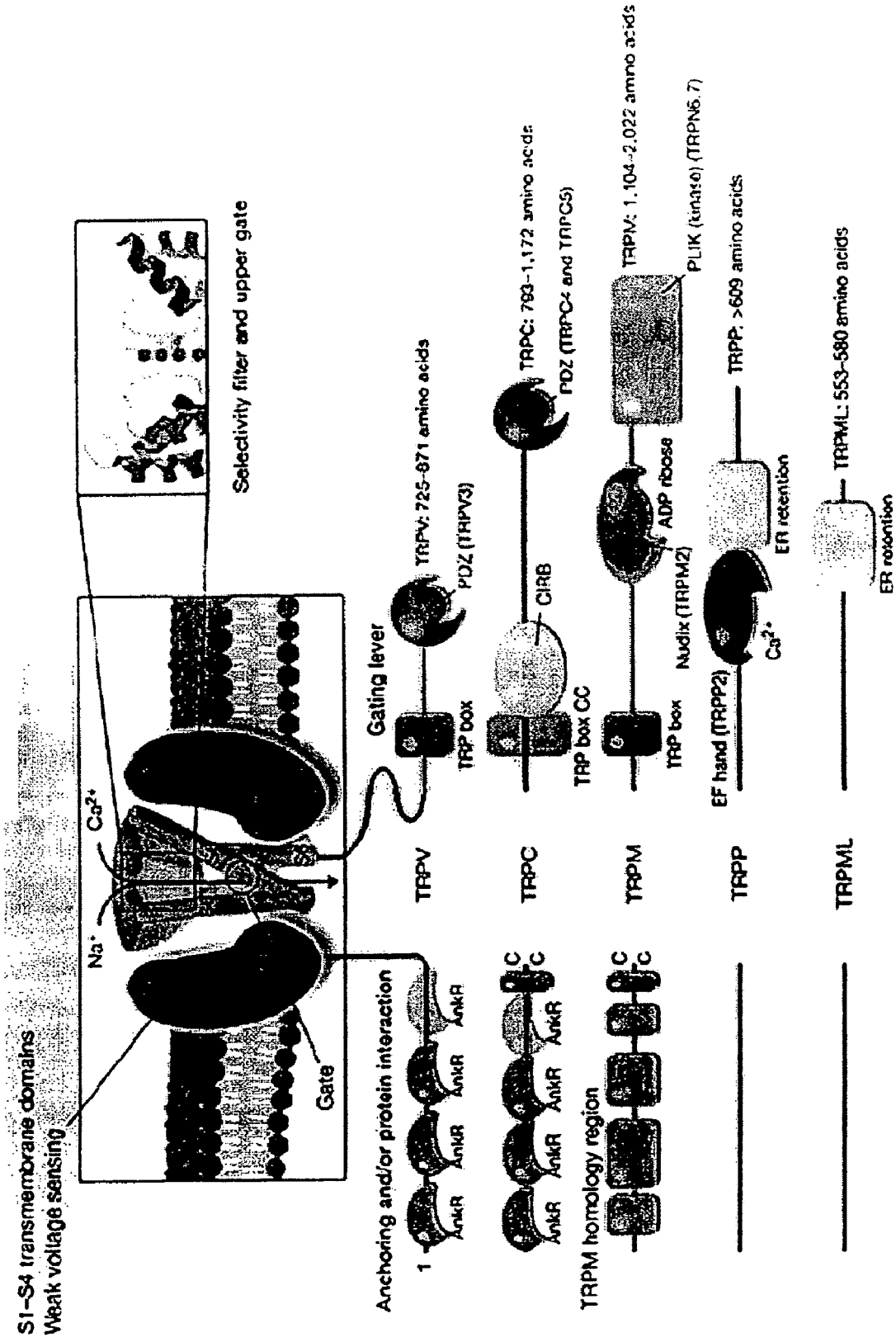
FIG. 2. shows the domain structures of different TRP channel sub-families
Figure 4:
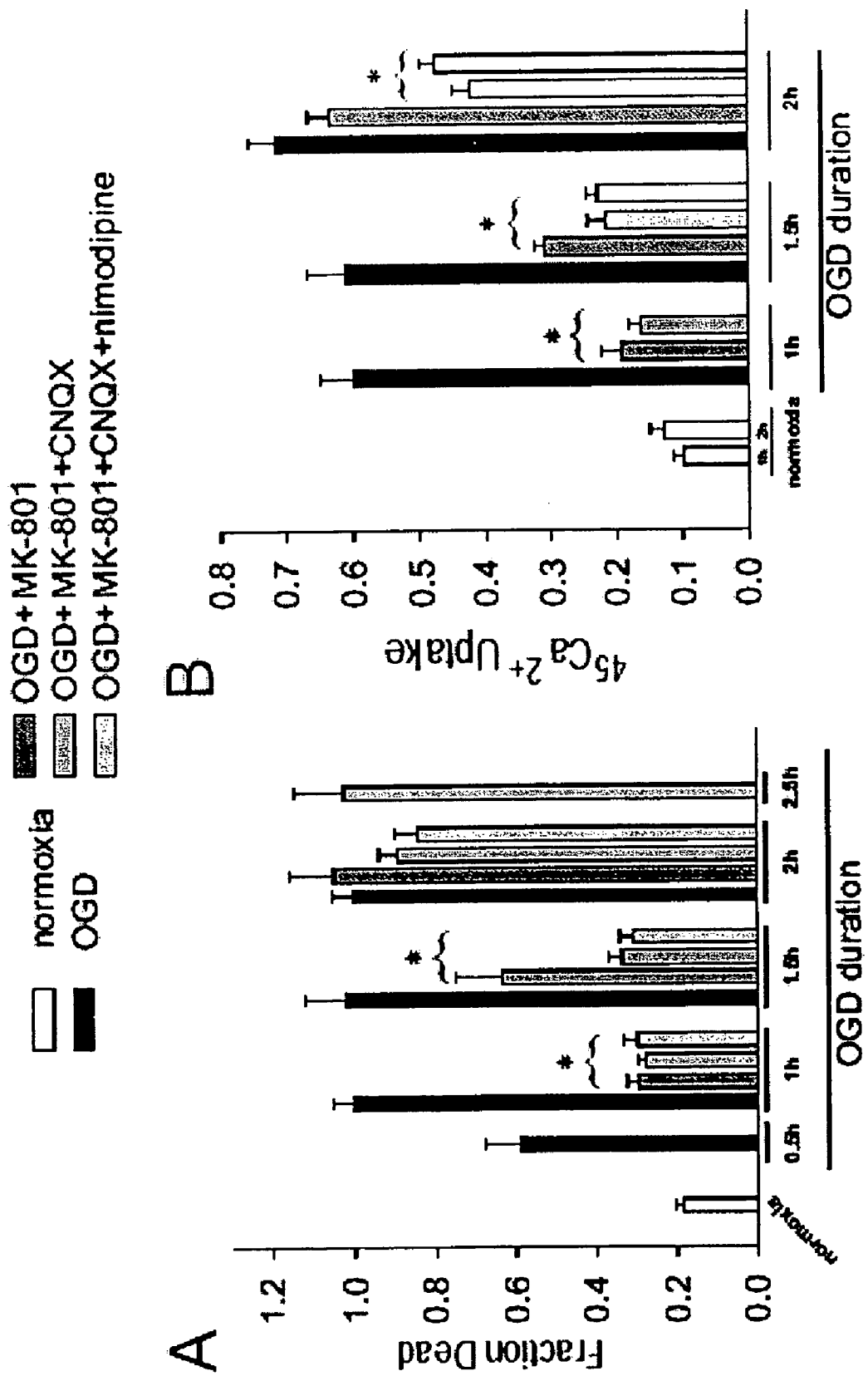
FIG. 4 shows the loss of neuroprotection and blockage of $Ca^{2+}$ accumulation by glutamate and $Ca^{2+}$ channel inhibitors with extended OGD.
Figure 5:
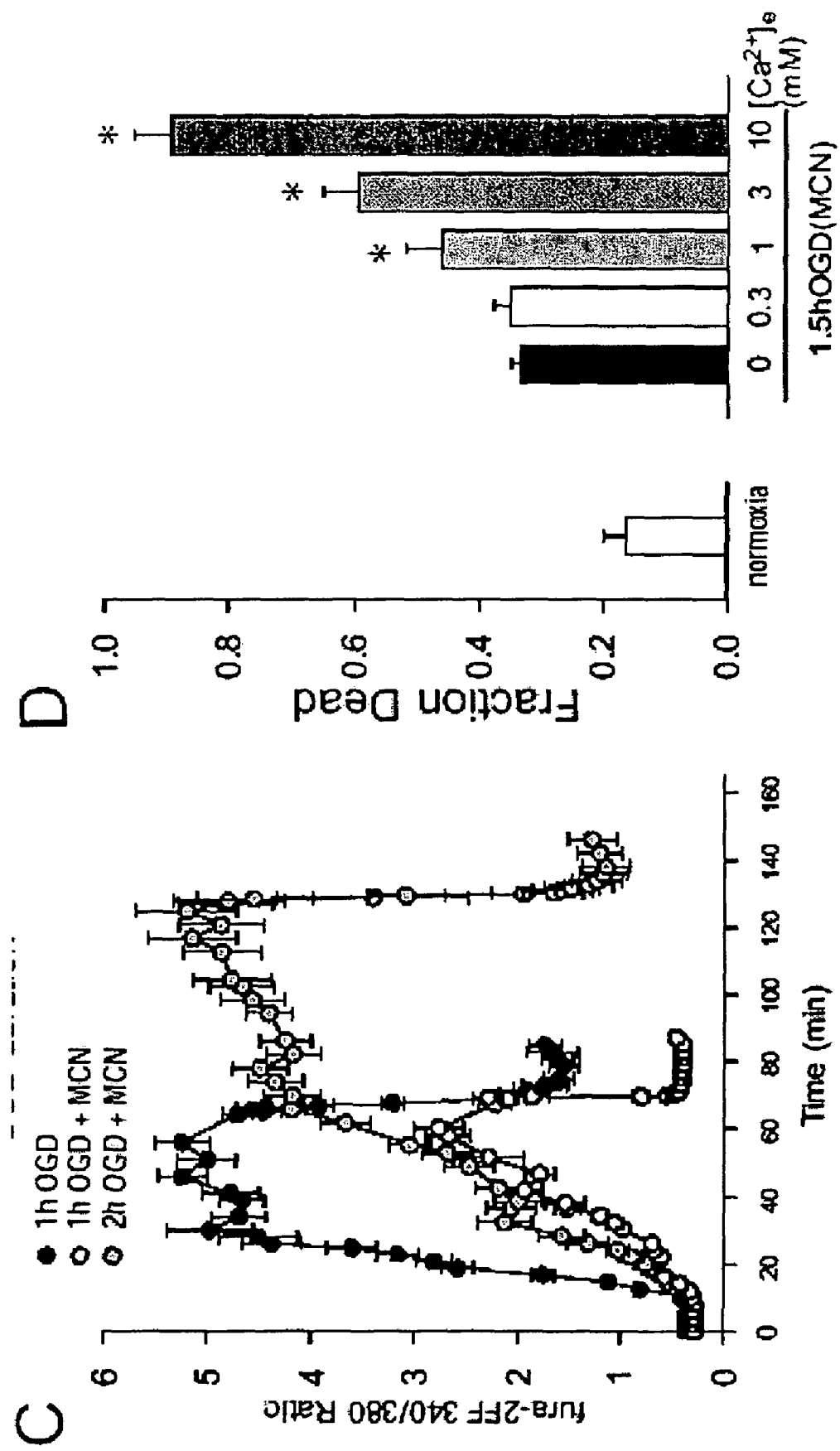
FIG. 5 shows the delay of calcium uptake in the presence of glutamate and $Ca^{2+}$ channel inhibitors and the effect of extracellular calcium concentration on OGD survival.
Figure 6:
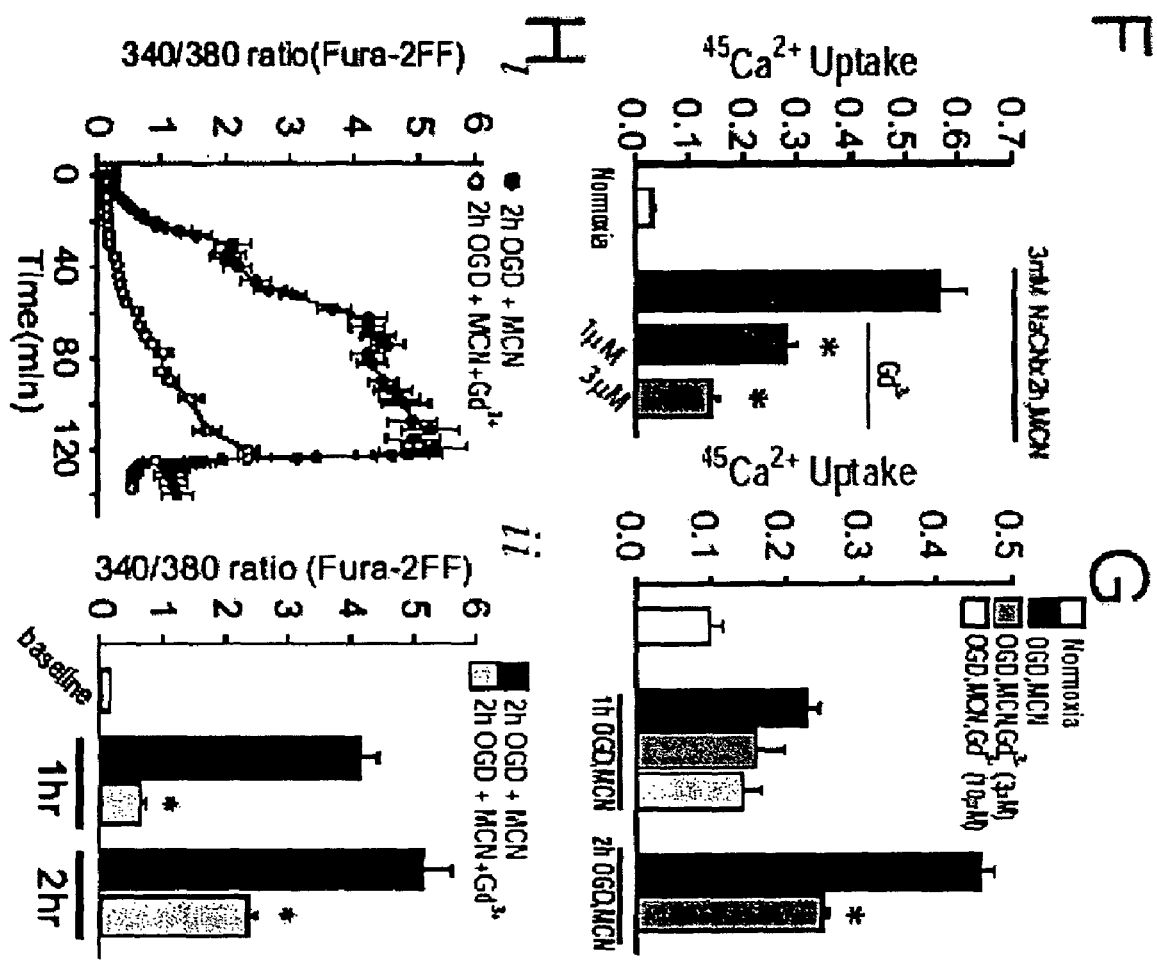
FIG. 6 shows the effect of $Gd^{3+}$ on calcium uptake in the presence of glutamate and $Ca^{2+}$ channel inhibitors FIG. 7 demonstrates that $Gd^{3+}$ can permit survival of neurons destined to die from prolonged OGD, and that superoxide and nNOS inhibition are synergistic while inhibitors of ROS pathways outside of superoxide and nitric oxide show no benefit in OGD survival.
Figure 7:
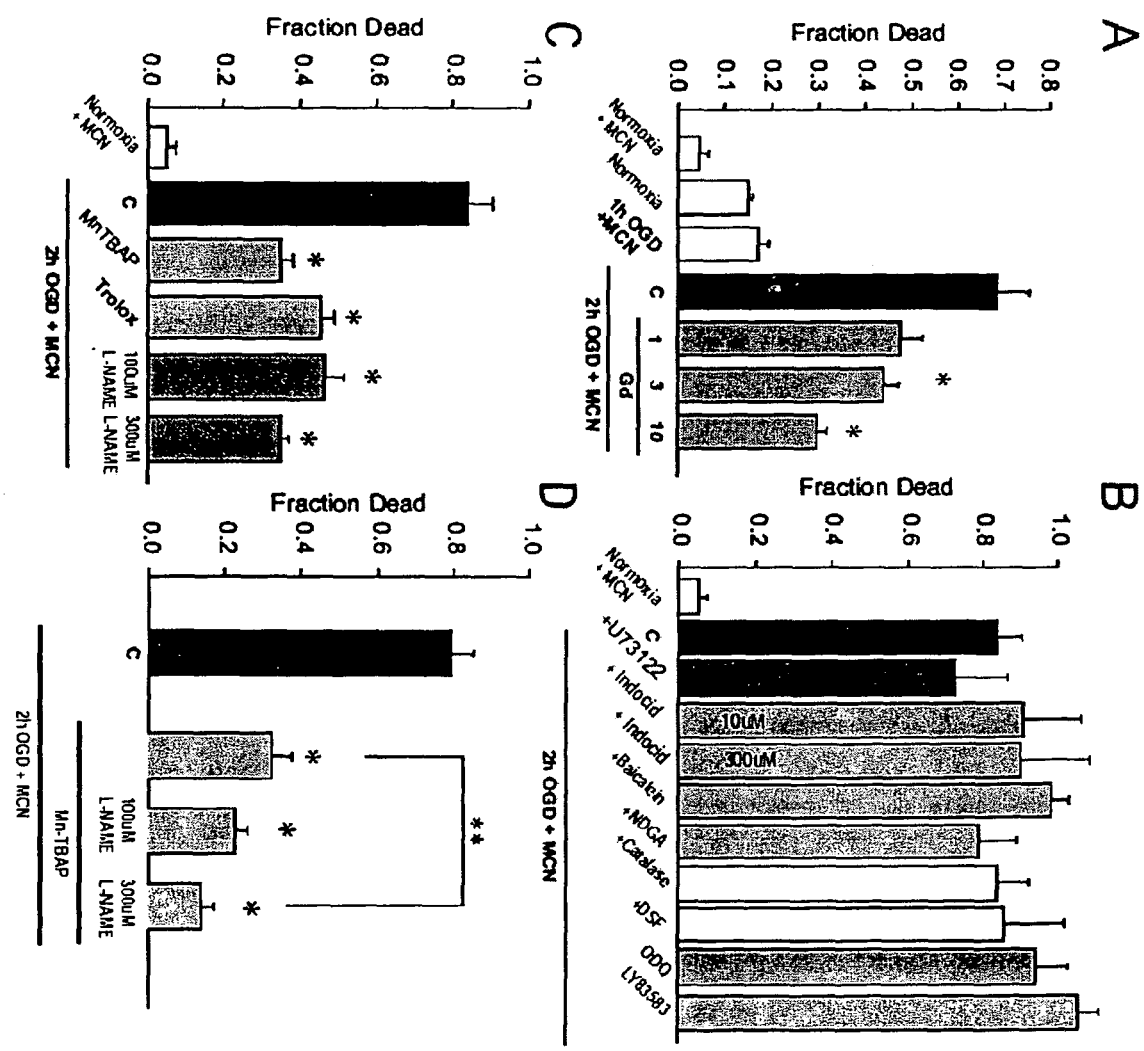

The numbering system for the mammalian TRPC, TRPV, and TRPM proteins takes into account the order of their discovery and, in as many cases as possible, the number that has already been assigned to the genes and proteins (TABLE 4). In the case of the TRPV proteins, the numbering system is also based in part on the groupings of the TRPV proteins. New members of each subfamily will maintain the same root name and, with the exception of TRPV3, will be assigned the next number in the sequence. Currently, TRPV3 is unassigned to maintain the TRPV1/TRPV2 and TRPV5/TRPV6 groupings and so that the former OTRPC4 could be renamed TRPV4. The next TRPV protein will be designated TRPV3. B. Current Knowledge on TRP channel function. (Taken directly from Clapham (2003) Nature 426:517-524, Transient receptor potential (TRP) channels were first described in *Drosophila*, where photoreceptors carrying trp gene mutations exhibited a transient voltage response to continuous light. They have been called store-operated channels (SOCs), but this description is theoretical and related to a poorly understood phenomenon. All TRP channels are putative six-transmembrane (6TM) polypeptide subunits that assemble as tetramers to form cation permeable pores (FIG. 2). In general, they are almost ubiquitously expressed and most have splice variants. So most cells have a number of TRP channel proteins.

FIG. 2 emphasizes the diversity of TRP cytoplasmic domains. The selectivity filter (light blue and inset) is formed by amino acids that dip into the bilayer (pore loops), one contributed from each of the four subunits. S5 has been removed to emphasize the link between the S6 gating helix and the TRP C-terminal polypeptide chain. The TRP box is EWKFAR (SEQ ID NO:2) in TRPC, but is less conserved in TRPV and TRPM. CC indicates a coiled-coil domain. Ankyrin repeats (AnkR) range from 0 to 14 in number (3 or 4 in TRPV and TRPC, 14 in ANKTM; not shown). Numbers on the right indicate range in length. CIRB, putative calmodulin- and IP3R-binding domain; EF hand, canonical helix-loop-helix $Ca^{2+}$-binding domain; PDZ, amino acids binding PDZ domains; PLIK, phospholipase-C-interacting kinase, an atypical protein kinase intrinsic to the TRPM6 and TRPM7 polypeptide chains; Nudix, NUDT9 hydrolase protein homologue binding ADP ribose.

The TRPC (Canonical TRP) Subfamily

All mammalian TRPC proteins appear to be analogous to the TRP involved in Drosophila phototransduction, in that they function as receptor-operated channels. They are activated by stimulation of G-protein-coupled receptors (GPCRs) and receptor tyrosine kinases.

TRPC1, the first mammalian TRP reported, forms heteromeric channels with TRPC4 and/or TRPC5. The properties of the heteromultimers are distinct from those of TRPC4 and TRPC5 homomultimers. TRPC5, but not TRPC1, is present in hippocampal growth cones and modulates neurite extension. Mice lacking TRPC4 have defects in agonist-induced vasoregulation and lung microvascular permeability.

TRPC3, TRPC6 and TRPC7 proteins share 75% identity, have relatively low selectivity for $Ca^{2+}$ over $Na^+$, and are sensitive to the intracellular concentration of $Ca^{2+}$ ($[Ca^{2+}]i$). Diacylglycerol (DAG) analogs potentiate their activity, but not through protein kinase C activation. TRPC3 has been investigated extensively as a putative inositol-1,4,5-trisphosphate (InsP3) receptor (IP3R)-binding SOC, with conflicting results. All of the TPRC3, TRPC6 and TRPC7 subfamily are highly expressed in smooth and cardiac muscle cells, making them candidates for the receptor-activated nonselective cation channels known to exist in these sites. In support of this idea, TRPC6 is an essential part of the 1-adrenoreceptor-activated cation channel in rabbit portal vein myocytes. They may also have roles in the regulation of vascular tone, airway resistance and cardiac function. TRPC2 appears to be a pseudogene in humans, but its rat orthologue encodes an important sensor localized to neuronal microvilli in the vomeronasal organ. Trpc2-deficient mice display abnormal mating behavior, consistent with a role for this channel in pheromone signaling.

The TRPV (Vanilloid Receptor, Osm9-Like) Subfamily

TRPV1 was identified by expression cloning using the 'hot' pepper-derived vanilloid compound capsaicin as a ligand. TRPV1 is a $Ca^{2+}$-permeant channel that is potentiated by heat (>43° C.) and decreased pH, and inhibited by intracellular phosphatidylinositol-4,5-bisphosphate (PIP2). Its thermal sensitivity is enhanced by bradykinin and nerve growth factor, which appear to act via phospholipase C (PLC) to hydrolyse PIP2, releasing inhibition of the channel. Trpv1−/− mice are defective in nociceptive, inflammatory and hypothermic responses to vanilloid compounds, supporting the interpretation that TRPV1 contributes to acute thermal nociception and hyperalgesia after tissue injury. TRPV1 also participates in mechanically evoked purinergic signaling by the bladder urothelium.

TRPV2, which is 50% identical to TRPV1, may mediate high-threshold (>52° C.) noxious heat sensation, perhaps through lightly myelinated A nociceptors. Interestingly, TRPV2 translocates from intracellular pools upon insulin growth factor stimulation of transfected cells. Stretch reportedly increases TRPV2 translocation, and cardiac-specific transgene expression of TRPV2 results in $Ca^{2+}$-overload-induced cardiomyopathy. But it is not surprising that overexpression of a $Ca^{2+}$-permeant channel induces cardiomyopathy, because such TRP channels are deleterious to many cells, including neurons. In fact, the mechanism of pain-relieving topical capsaicin is due, in part, to neuronal cell death.

Increased temperature also activates TRPV3 (>31° C.) and TRPV4 (>25° C.). The neuronal distribution of TRPV3 overlaps with TRPV1, raising the interesting possibility that they may heteromultimerize. TRPV3 is also highly expressed in skin, tongue and the nervous system, possibly explaining the activity of 'warm-sensitive' neurons. The effect of temperature on rates of biological processes is expressed as the 10° C. temperature coefficient1: Q10=rate(T+10° C.)/rate(T). Most ion channels and enzymes have gating Q10 values of 3-5, but the Q10 of TRPV3 gating is >20, and for TRPV1 and TRPV4 it is estimated to be 10-20. TRPV4 current is potentiated by hypotonicity (cell swelling). Trpv4−/− mice have a marginally impaired renal response to hypertonicity, probably due to abnormal central control of antidiuretic hormone secretion. Hypotonicity increases TRPV4-mediated current in primary afferent nociceptive nerve fibers, an effect that is enhanced by the hyperalgesic inflammatory mediator prostaglandin E2. Expressed TRPV4 may be gated by epoxyeicosatrienoic acids.

TRPV5 and TRPV6 comprise a subfamily of homomeric and heteromeric channels found in transporting epithelia of the kidney and intestine. They show strong inwardly rectifying currents and are the most Ca2+-selective TRP channels (permeability ratio PCa/PNa>100), suggesting that they mediate Ca2+ uptake. Both are inactivated by [Ca2+]I; TRPV6 shows voltage-dependent intracellular Mg2+ blockade.

The TRPM (Melastatin) Subfamily and TRPA

TRPM1 (melastatin) was initially identified as a transcript that showed decreased expression in highly metastatic versus non-metastatic melanoma cells.

TRPM2 forms a Ca2+-permeant channel that is gated by binding of ADP ribose (EC50 100 μM) and nicotinamide adenine dinucleotide (NAD; 1 mM) to a carboxy-terminal NUDT9 Nudix hydrolase domain. ADP ribose is a breakdown product of NAD, CD38, cyclic ADP ribose (a Ca2+-release messenger) and protein de-acetylation (O-acetylated ADP ribose), but the TRPM2 domain itself is an ineffective hydrolase. The channel is regulated by signaling pathways responsive to H2O2 and tumor-necrosis factor, suggesting that it may act as a sensor of intracellular oxidation/reduction, possibly during the oxidative burst of neutrophils.

TRPM3 forms a Ca2+-permeant nonselective channel that is constitutively active when heterologously expressed. Its activity is increased by hypotonicity (200 mOsm per liter). TRPM3 is expressed primarily in kidney distal-collecting-duct epithelium and in the central nervous system.

TRPM4 and TRPM5 are the only monovalent-selective ion channels of the TRP family. They are widely distributed and may account for observed Ca2+-activated 20-30 pS nonselective channel activities. They are activated through GPCRs coupled to PLC-dependent endoplasmic reticular Ca2+ release, perhaps by direct Ca2+ binding to the channel. However, relatively high [Ca2+]i is required to activate these channels, suggesting that they localize close to sites of Ca2+ release or that other modulators are important. Although their instantaneous I-V relationships are linear, the fraction of open channels increases at positive potentials. This voltage dependence is not mediated by divalent cation binding, suggesting an intrinsic voltage-sensing mechanism.

TRPM5 is found in cells expressing taste receptors. In an in vivo study in TrpM5−/− mice, it was shown that taste receptors T1R and T2R share a common signaling pathway involving PLC2 and TRPM5, to produce sweet, umami and bitter taste sensations. The authors concluded that InsP3, Ca2+ and thapsigargin-mediated store depletion did not activate TRPM5. However, it is possible that PIP2 or other molecules modulate its sensitivity to [Ca2+]i.

TRPM6 and TRPM7 are unique among ion channels because they also contain functional kinase domains. TRPM7 passes little inward current under physiological conditions, is permeant to both Ca2+ and Mg2+, and is inhibited by 0.6 mM intracellular free Mg2+. In contrast to other GPCR-activated TRP channels, TRPM7 current increases slowly under whole-cell recording conditions and is inactivated by PIP2 hydrolysis by PLCbeta or PLCgamma. The function of the kinase domain is poorly understood and its substrates have not been identified. The kinase domain, in contrast to original reports, is not required for channel activation. The catalytic core of the kinase domain is similar to that of other eukaryotic protein kinases and to enzymes with ATP-grasp domains. The sensitivity of TRPM7 to physiological Mg-ATP levels has been suggested to have a central role in metabolic sensing or to serve as a mechanism to adjust cellular Mg2+ homeostasis. But a spontaneous human mutation in TRPM6 results in familial hypomagnesaemia with secondary hypocalcemia, suggesting that TRPM6 may be important for Mg2+ uptake in the kidney and intestine.

TRPM8 was identified as a messenger RNA that was upregulated in prostatic and other cancers. Its sensory role was recognized when it was isolated by expression cloning of a menthol receptor from trigeminal neurons. TRPM8 is a nonselective, outwardly rectifying channel that can be activated by cold (8-28° C.) and enhanced by 'cooling' compounds such as menthol and icilin. TRPM8 is widely expressed, but thought to function specifically as a thermosensor in TrkA+, small-diameter primary sensory neurons.

ANKTM1, a Ca2+-permeant, nonselective channel homologous to Drosophila painless, is distinguished by 14 amino-terminal ankyrin repeats. It is activated by noxious cold temperature (<15° C.) but bears little similarity to menthol-sensitive TRPM8. It is found in a subset of nociceptive sensory dorsal root ganglion neurons, in the company of capsaicin-sensitive TRPV1, but not TRPM8. Interestingly, the Drosophila orthologue of ANKTM1 responds to warming (>27° C.) rather than to cooling when expressed in Xenopus oocytes. These observations are consistent with sensitivity to the surrounding membrane environment, but might also be reconciled if the lowest energy state of the mammalian channel is the open configuration. Other TRP channels have not been systematically tested for temperature sensitivity, but such a comparison would clarify this issue.

The TRPP (Polycystin) and TRPML (Mucolipin) Subfamilies

Polycystic kidney disease proteins PKD2, PKD2L1 and PKD2L2 are 6TM Ca2+-permeant channels called TRPP2, TRPP3 and TRPP5, respectively. The much larger TRPP1, polycystin-REJ and polycystin-1L1 proteins are 11TM proteins that contain a C-terminal 6TM TRP-like channel domain. TRPP1 is not known to form a channel by itself, but it complexes with TRPP2 to form a Ca2+-permeable nonselective cation channel70. Autosomal dominant polycystic kidney disease is caused by mutations in TRPP1 or TRPP2, leading to alterations in the polarization and function of cyst-lining epithelial cells. Trpp1−/− and Trpp2−/− mice die in utero with cardiac septal defects and cystic changes in nephrons and pancreatic ducts. The mouse ortholog of TRPP3 is deleted in krd mice, resulting in defects in the kidney and retina.

TRPP proteins have another role in development. Normal body asymmetry appears to arise from leftward extracellular flow generated by motor-protein-dependent rotation of monocilia on the ventral surface of the embryonic node. Motile monocilia generate nodal flow, and non-motile TRPP2-containing cilia sense nodal flow, initiating an asymmetric Ca2+ signal at the left nodal border. TRPP1 and TRPP2 both appear to be targeted to primary cilia cells of renal epithelia, where the channel complex is gated by fluid flow.

The mucolipins (MCOLN1, MCOLN2 and MCOLN3) are 6TM channels that are probably restricted to intracellular vesicles. Mutations in MCOLN1 (TRPML1) are associated with mucolipidosis type IV, a neurodegenerative lysosomal storage disorder. The defect appears to be in sorting or transport in the late endocytic pathway. Mutations in a Caenorhabditis elegans TRPML1 homologue, cup-5, cause excess lysosome formation and apoptosis in all cell types. TRPML3 is present in the cytoplasm of hair cells and the plasma membrane of stereocilia. TRPML3 is mutated in the varitint-waddler mouse, resulting in deafness and pigmentation defects.

TRP Channel Related Disorders

Modulation of TRP channel protein levels, protein interactions, and function may be used to treat disorders including, but not intended to be limit to:

Defects in osmoregulation, including brain edema, abdominal ascites, pulmonary effusion, pericardial effusion and bruising Defects in olfaction Defects in taste sensation Defects in hearing Peripheral pain syndromes, including painful neuromas, denervation pain, and pain due to averrent innervation Central pain syndromes, including thalamic pain, denervation pain, hyperpathia, and hyperalgesia Defect in thermoregulation and thermal sensation (nociception)

Visual defects, including defects in phototransduction, glaucoma, retinal ischemia, idiopathic retinopathies, and macular degeneration Defects of vascular tone, including hypertension, orthostatic hypotension and defects of microvascular regulation including pulmonary, brain, myocardial edemas, and abdominal ascites Defects of airway resistance, including asthma Defects of myocardial function, including cardiomyopathies, myocardial ischemia, and cardiac arrhythmias Defects of bladder and ureteral function Defects of renal function.

Defects of the immune system and inflammatory response

Defects of tissue senescence/aging

Defects of the endocrine system and metabolism, including familial hypomagnesemia with secondary hypocalcemia, diabetes and mucolipidosis type IV Cancer, including prostate (cancer) and melanoma Congenital malformations, including atrial septal defects, polycystic kidneys, congenital retinopathies and congenital deafness Defects in skin pigmentation V. PDZ Protein and PL Protein Interactions TABLES 6, 7, and 8 list PDZ proteins and other PL proteins which the current inventors have identified as binding to one another. This column provides the gene name for the PDZ portion of the GST-PDZ fusion that interacts with the PDZ-ligand to the left. Many of the genes listed in TABLE 5 express more than one amino acid sequence, depending on alternative exon splicing and single amino acid changes. It is understood in the art that many alternatively spliced and point mutated forms of the same gene may exist in nature. As indicated supra, all peptides were biotinylated at the amino terminus and the amino acid sequences correspond to the C-terminal sequence of the gene name listed in column 1.

TABLE 5 lists the sequences of the PDZ domains cloned into a vector (PGEX-3X vector) for production of GST-PDZ fusion proteins (Pharmacia). More specifically, the first column (left to right) entitled "Gene Name" lists the name of the gene containing the PDZ domain. The second column labeled "GI or Acc#" is a unique Genbank identifier for the gene used to design primers for PCR amplification of the listed sequence. The next column labeled "Domain#" indicates the Pfam-predicted PDZ domain number, as numbered from the amino-terminus of the gene to the carboxy-terminus. The last column entitled "Sequence fused to GST Construct" (SEQ ID NO:s) provides the actual amino acid sequence inserted into the GST-PDZ expression vector as determined by DNA sequencing of the constructs.

TABLE 5

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| AF6 | 430993 | 1 | LRKEPEIITVTLKKQNGMGLSIVAAKGAGQDKLGIYVKS VVKGGAADVDGRLAAGDQLLSVDGRSLVGLSQERAAE LMTRTSSWTLEVAKQG | 3 |
| AIPC | 12751451 | 1 | LIRPSVISIIGLYKEKGKGLGFSIAGGRDCIRGQMGIFVK TIFPNGSAAEDGRLKEGDEILDVNGIPIKGLTFQEAIHTF KQIRSGLFVLTVRTKLVSPSLTNSS | 4 |
| AIPC | 12751451 | 3 | QSENEEDVCFIVLNRKEGSGLGFSVAGGTDVEPKSITV HRVFSQGAASQEGTMNRGDFLLSVNGASLAGLAHGN VLKVLHQAQLHKDALWIKKGMDQPRPSNSS | 5 |
| AIPC | 12751451 | 2 | GISSLGRKTPGPKDRIVMEVTLNKEPRVGLGIGACCLAL ENSPPGIYIHSLAPGSVAKMESNLSRGDQILEVNSVNV RHAALSKVHAILSKCPPGPVRLVIGRHPNPKVSEQEMD EVIARSTYQESKEANSS | 6 |
| AIPC | 12751451 | 4 | LGRSVAVHDALCVEVLKTSAGLGLSLDGGKSSVTGDG PLVIKRVYKGGAAEQAGIIEAGDEILAINGKPLVGLMHFD AWNIMKSVPEGPVQLLIRKHRNSS | 7 |
| ALP | 2773059 | 1 | REEGGMPQTVILPGPAPWGFRLSGGIDFNQPLVITRITP GSKAAAANLCPGDVILAIDGFGTESMTHADAQDRIKAA AHQLCLKIDRGETHLWSPNSS | 8 |
| APXL1 | 13651263 | 1 | ILVEVQLSGGAPWGFTLKGGREHGEPLVITKIEEGSKAA AVDKLLAGDEIVGINDIGLSGFRQEAICLVKGSHKTLKLV VKRNSS | 9 |
| CARD11 | 12382772 | 1 | SVGHVRGPGPSVQHTTLNGDSLTSQLTLLGGNARGSF VHSVKPGSLAEKAGLREGHQLLLLEGCIRGERQSVPLD TCTKEEAHWTIQRCSGPVTLHYKVNHEGYRK | 10 |
| CARD14 | 13129123 | 1 | RRPARRILSQVTMLAFQGDALLEQISVIGGNLTGIFIHRV TPGSAADQMALRPGTQIVMVDYEASEPLFKAVLEDTTL EEAVGLLRRVDGFCCLSVKVNTDGYKR | 11 |
| CARD14 | 13129123 | 1 | ILSQVTMLAFQGDALLEQISVIGGNLTGIFIHRVTPGSAA DQMALRPGTQIVMVDYEASEPLFKAVLEDTTLEEAVGL LRRVDGFCCLSVKVNTDGYKRL | 12 |
| CASK | 3087815 | 1 | TRVRLVQFQKNTDEPMGITLKMNELNHCIVARIMHGGM IHRQGTLHVGDEIREINGISVANQTVEQLQKMLREMRG SITFKIVPSYRTQS | 13 |
| CNK1 | 3930780 | 1 | LEQKAVLEQVQLDSPLGLEIHTTSNCQHFVSQVDTQVP TDSRLQIQPGDEWQINEQWVGWPRKNMVRELLREP AGLSLVLKKIPIP | 14 |
| Cytohesin binding Protein | 3192908 | 1 | QRKLVTVEKQDNETFGFEIQSYRPQNQNACSSEMFTLI CKIQEDSPAHCAGLQAGDVLANINGVSTEGFTYKQWD LIRSSGNLLTIETLNG | 15 |
| Densin | 16755892 | 1 | RCLIQTKGQRSMDGYPEQFCVRIEKNPGLGFSISGGIS GQGNPFKPSDKGIFVTRVQPDGPASNLLQPGDKILQAN GHSFVHMEHEKAVLLLKSFQNTVDLVIQRELTV | 16 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| DLG 6 splice variant 2 | AB053303 | 1 | PTSPEIQELRQMLQAPHFKGATIKRHEMTGDILVARIIH GGLAERSGLLYAGDKLVEVNGVSVEGLDPEQVIHILAM SRGTIMFKVVPVSDPPVNSS | 17 |
| DLG 6, splice variant 1 | 14647140 | 1 | PTSPEIQELRQMLQAPHFKALLSAHDTIAQKDFEPLLPP LPDNIPESEEAMRIVCLVKNQQPLGATIKRHEMTGDILV ARIIHGGLAERSGLLYAGDKLVEVNGVSVEGLDPEQVIH ILAMSRGTIMFKWPVSDPPVNSS | 18 |
| DLG1 | 475816 | 1 | IQVNGTDADYEYEEITLERGNSGLGFSIAGGTDNPHIGD DSSIFITKIITGGAAAQDGRLRVNDCILQVNEVDVRDVTH SKAVEALKEAGSIVRLYVKRRN | 19 |
| DLG1 | 475816 | 2 | IQLIKGPKGLGFSIAGGVGNQHIPGDNSIYVTKIIEGGAA HKDGKLQIGDKLLAVNNVCLEEVTHEEAVTALKNTSDF VYLKVAKPTSMYMNDGN | 20 |
| DLG1 | 475816 | 1,2 | VNGTDADYEYEEITLERGNSGLGFSIAGGTDNPHIGDD SSIFITKIITGGAAAQDGRLRVNDCILQVNEVDVRDVTHS KAVEALKEAGSIVRLYVKRRKPVSEKIMEIKLIKGPKGLG FSIAGGVGNQHIPGDNSIYVTKIIEGGAAHKDGKLQIGD KLLAVNNVCLEEVTHEEAVTALKNTSDFVYLKVAKPTS MYMNDGYA | 21 |
| DLG1 | 475816 | 3 | ILHRGSTGLGFNIVGGEDGEGIFISFILAGGPADLSGELR KGDRIISVNSVDLRAASHEQAAAALKNAGQAVTIVAQY RPEEYSR | 22 |
| DLG2 | 12736552 | 3 | IEGRGILEGEPRKVVLHKGSTGLGFNIVGGEDGEGIFVS FILAGGPADLSGELQRGDQILSVNGIDLRGASHEQAAA ALKGAGQTVTIIAQHQPEDYARFEAKIHDLNSS | 23 |
| DLG2 | 12736552 | 1 | ISYVNGTEIEYEFEEITLERGNSGLGFSIAGGTDNPHIGD DPGIFITKIIPGGAAAEDGRLRVNDCILRVNEVDVSEVSH SKAVEALKEAGSIVRLYVRRR | 24 |
| DLG2 | 12736552 | 2 | IPILETWEIKLFKGPKGLGFSIAGGVGNQHIPGDNSIYV TKIIDGGAAQKDGRLQVGDRLLMVNNYSLEEVTHEEAV AILKNTSEWYLKVGKPTTIYMTDPYGPPNSSLTD | 25 |
| DLG5 | 3650451 | 1 | GIPYVEEPRHVKVQKGSEPLGISIVSGEKGGIYVSKVTV GSIAHQAGLEYGDQLLEFNGINLRSATEQQARLIIGQQC DTITILAQYNPHVHQLRNSSLTD | 26 |
| DLG5 | 3650451 | 2 | GILAGDANKKTLEPRWFIKKSQLELGVHLCGGNLHGV FVAEVEDDSPAKGPDGLVPGDLILEYGSLDVRNKTVEE VYVEMLKPRDGVRLKVQYRPEEFIVTD | 27 |
| DVL1 | 2291005 | 1 | LNIVTVTLNMERHHFLGISIVGQSNDRGDGGIYIGSIMKG GAVAADGRIEPGDMLLQVNDVNFENMSNDDAVRVLRE IVSQTGPISLTVAKCW | 28 |
| DVL2 | 2291007 | 1 | LNIITVTLNMEKYNFLGISIVGQSNERGDGGIYIGSIMKG GAVAADGRIEPGDMLLQVNDMNFENMSNDDAVRVLRD IVHKPGPIVLTVAKCWDPSPQNS | 29 |
| DVL3 | 6806886 | 1 | IITVTLNMEKYNFLGISIVGQSNERGDGGIYIGSIMKGGA VAADGRIEPGDMLLQVNEINFENMSNDDAVRVLREIVH KPGPITLTVAKCWDPSP | 30 |
| EBP50 | 3220018 | 2 | QQRELRPRLCTMKKGPSGYGFNLHSDKSKPGQFIRSV DPDSPAEASGLRAQDRIVEVNGVCMEGKQHGDWSAI RAGGDETKLLWDRETDEFFKNSS | 31 |
| EBP50 | 3220018 | 1 | GIQMSADAAAGAPLPRLCCLEKGPNGYGFHLHGEKGK LGQYIRLVEPGSPAEKAGLLAGDRLVEVNGENVEKETH QQWSRIRAALNAVRLLWDPETDEQLQKLGVQVREEL LRAQEAPGQAEPPAAAEVQGAGNENEPREADKSHPE QRELRN | 32 |
| EBP50 | 3220018 | 1,2 | GIQMSADAAAGAPLPRLCCLEKGPNGYGFHLHGEKGK LGQYIRLVEPGSPAEKAGLLAGDRLVEVNGENVEKETH | 33 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| | | | QQWSRIRAALNAVRLLWDPETDEQLQKLGVQVREEL LRAQEAPGQAEPPAAAEVQGAGNENEPREADKSHPE QRELRPRLCTMKKGPSGYGFNLHSDKSKPGQFIRSVD PDSPAEASGLRAQDRIVEVNGVCMEGKQHGDWSAIR AGGDETKLLWDRETDEFFK | |
| EBP50 | 3220018 | 1 | QMSADAAAGAPLPRLCCLEKGPNGYGFHLHGEKGKLG QYIRLVEPGSPAEKAGLLAGDRLVEVNGENVEKETHQ QWSRIRAALNAVRLLWDPETDEQLQKLGVQVREELL RAQEAPGQAEPPAAAEVQGAGNENEPREADKSHPEQ RELRNSS | 34 |
| ELFIN 1 | 2957144 | 1 | LTTQQIDLQGPGPWGFRLVGGKDFEQPLAISRVTPGSK AALANLCIGDVITAIDGENTSNMTHLEAQNRIKGCTDNL TLTVARSEHKVWSPLVTNSSW | 35 |
| ENIGMA | 561636 | 1 | IFMDSFKWLEGPAPWGFRLQGGKDFNVPLSISRLTPG GKAAQAGVAVGDWVLSIDGENAGSLTHIEAQNKIRACG ERLSLGLSRAQPV | 36 |
| ERBIN | 8923908 | 1 | QGHELAKQEIRVRVEKDPELGFSISGGVGGRGNPFRP DDDGIFVTRVQPEGPASKLLQPGDKIIQANGYSFINIEH GQAVSLLKTFQNTVELIIVREVSS | 37 |
| FLJ00011 | 10440352 | 1 | KNPSGELKTVTLSKMKQSLGISISGGIESKVQPMVKIEKI FPGGAAFLSGALQAGFELVAVDGENLEQVTHQRAVDTI RRAYRNKAREPMELVVRVPGPSPRPSPSD | 38 |
| FLJ11215 | 11436365 | 1 | EGHSHPRWELPKTEEGLGFNIMGGKEQNSPIYISRIIP GGIADRHGGLKRGDQLLSVNGVSVEGEHHEKAVELLK AAQGKVKLWRYTPKVLEEME | 39 |
| FLJ12428 | BC012040 | 1 | PGAPYARKTFTIVGDAVGWGFWRGSKPCHIQAVDPS GPAAAAGMKVCQFVVSVNGLNVLHVDYRTVSNLILTGP RTIVMEVMEELEC | 40 |
| FLJ12615 | 10434209 | 1 | GQYGGETVKIVRIEKARDIPLGATVRNEMDSVIISRIVKG GAAEKSGLLHEGDEVLEINGIEIRGKDVNEVFDLLSDMH GTLTFVLIPSQQIKPPPA | 41 |
| FLJ21687 | 10437836 | 1 | KPSQASGHFSVELVRGYAGFGLTLGGGRDVAGDTPLA VRGLLKDGPAQRCGRLEVGDLVLHINGESTQGLTHAQ AVERIRAGGPQLHLVIRRPLETHPGKPRGV | 42 |
| FLJ31349 | AK05591 | 1 | PVMSQCACLEEVHLPNIKPGEGLGMYIKSTYDGLHVIT GTTENSPADRSQKIHAGDEVTQVNQQTVVGWQLKNLV KKLRENPTGWLLLKKRPTGSFNFTP | 43 |
| FLJ32798 | AK057360 | 1 | IDDEEDSVKIIRLVKNREPLGATIKKDEQTGAIIVARIMRG GAADRSGLIHVGDELREVNGIPVEDKRPEEIIQILAQSQ GAITFKIIPGSKEETPS | 44 |
| GORASP 2 | 13994253 | 1,2 | MGSSQSVEIPGGGTEGYHVLRVQENSPGHRAGLEPFF DFIVSINGSRLNKDNDTLKDLLKANVEKPVKMLIYSSKTL ELRETSVTPSNLWGGQGLLGVSIRFCSFDGANENVWH VLEVESNSPAALAGLRPHSDYIIGADTVMNESEDLESLI ETHEAKPLKLYVYNTDTDNCREVIITPNSAWGGEGSLG CGIGYGYLHRIPTRPFEEGKKISLPGQMAGTPITPLKDG FTEVQLSSVNPPSLSPPGTTGIEQSLTGLSISSTPPAVS SVLSTGVPTVPLLPPQVNQSLTSVPPMNPATTLPGLMP LPAGLPNLPNLNLNLPAPHIMPGVGLPELVNPGLPPLPS MPPRNLPGIAPLPLPSEFLPSFPLVPESSSAASSGELLS SLPPTSNAPSDPATTTAKADAASSLTVDVTPPTAKAPTT VEDRVGDSTPVSEKPVSAAVDANASESP | 45 |
| GORASP 2 | 13994253 | 2 | NENVWHVLEVESNSPAALAGLRPHSDYIIGADTVMNES EDLFSLIETHEAKPLKLYVYNTDTDNCREVIITPNSAWG GEGSLGCGIGYGYLHRIPTR | 46 |
| GORASP 2 | 13994253 | 1 | MGSSQSVEIPGGGTEGYHVLRVQENSPGHRAGLEPFF DFIVSINGSRLNKDNDTLKDLLKANVEKPVKMLIYSSKTL ELRETSVTPSNLWGGQGLLGVSIRFCSFDGANE | 47 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| GORASP 1 | 29826292 | 2 | RASEQVWHVLDVEPSSPAALAGLRPYTDYVVGSDQIL QESEDFFTLIESHEGKPLKLMVYNSKSDSCREVTVTPN AAWGGEGSLGCGIGYGYLHRIPTQ | 48 |
| GORASP 1 | 29826292 | 1 | MGLGVSAEQPAGGAEGFHLHGVQENSPAQQAGLEPY FDFIITIGHSRLNKENDTLKALLKANVEKPVKLEVFNMKT MRVREVEWPSNMWGGQGLLGASVRFCSFRRASE | 49 |
| GORASP 1 | 29826292 | 1,2 | MGLGVSAEQPAGGAEGFHLHGVQENSPAQQAGLEPY FDFIITIGHSRLNKENDTLKALLKANVEKPVKLEVFNMKT MRVREVEWPSNMWGGQGLLGASVRFCSFRRASEQV WHVLDVEPSSPAALAGLRPYTDYVVGSDQILQESEDFF TLIESHEGKPLKLMVYNSKSDSCREVTVTPNAAWGGE GSLGCGIGYGYLHRIPTQPPSYHKKPPGTPPPSALPLG APPPDALPPGPTPEDSPSLETGSRQSDYMEALLQAPG SSMEDPLPGPGSPSHSAPDPDGLPHFMETPLQPPPPV QRVMDPGFLDVSGISLLDNSNASVWPSLPSSTELTTTA VSTSGPEDICSSSSSHERGGEATWSGSEFEVSFLDSP GAQAQADHLPQLTLPDSLTSAASPEDGLSAELLEAQAE EEPASTEGLDTGTEAEGLDSQAQISTTE | 50 |
| GRIP 1 | 4539083 | 6 | IYTVELKRYGGPLGITISGTEEPFDPIIISSLTKGGLAERT GAIHIGDRILAINSSSLKGKPLSEAIHLLQMAGETVTLKIK KQTDAQSA | 51 |
| GRIP 1 | 4539083 | 1 | WELMKKEGTTLGLTVSGGIDKDGKPRVSNLRQGGIAA RSDQLDVGDYIKAVNGINLAKFRHDEIISLLKNVGERVV LEVEYE | 52 |
| GRIP 1 | 4539083 | 3 | HVATASGPLLVEVAKTPGASLGVALTTSMCCNKQVIVID KIKSASIADRCGALHVGDHILSIDGTSMEYCTLAEATQFL ANTTDQVKLEILPHHQTRLALKGPNSS | 53 |
| GRIP 1 | 4539083 | 7 | IMSPTPVELHKVTLYKDSDMEDFGFSVADGLLEKGVYV KNIRPAGPGDLGGLKPYDRLLQVNHVRTRDFDCCLVV PLIAESGNKLDLVISRNPLA | 54 |
| GRIP 1 | 4539083 | 4 | IYTVELKRYGGPLGITISGTEEPFDPIIISSLTKGGLAERT GAIHIGDRILAINSSSLKGKPLSEAIHLLQMAGETVTLKIK KQTDAQSA | 55 |
| GRIP 1 | 4539083 | 5 | IMSPTPVELHKVTLYKDSDMEDFGFSVADGLLEKGVYV KNIRPAGPGDLGGLKPYDRLLQVNHVRTRDFDCCLVV PLIAESGNKLDLVISRNPLA | 56 |
| GTPase activating enzyme | 2389008 | 1 | SRGCETRELALPRDGQRLGFEVDAEGFVTHVERFTF AETAGLRPGARLLRVCGQTLPSLRPEAAAQLLRSAPKV CVTVLPPDESGRP | 57 |
| Guanine exchange factor | 6650765 | 1 | CSVMIFEWEQAGAIILEDGQELDSWYVILNGTVEISHP DGKVENLFMGNSFGITPTLDKQYMHGIVRTKVDDCQFV CIAQQDYWRILNHVEKNTHKVEEEGEIVMVH | 58 |
| HEMBA 1000505 | 10436367 | 2 | PRETVKIPDSADGLGFQIRGFGPSVVHAVGRGTVAAAA GLHPGQCIIKVNGINVSKETHASVIAHVTACRKYRRPTK QDSIQ | 59 |
| HEMBA 1000505 | 10436367 | 1 | LENVIAKSLLIKSNEGSYGFGLEDKNKVPIIKLVEKGSNA EMAGMEVGKKIFAINGDLVFMRPFNEVDCFLKSCLNSR KPLRVLVSTKP | 60 |
| HEMBA 1003117 | 7022001 | 1 | EDFCYVFTVELERGPSGLGMGLIDGMHTHLGAPGLYIQ TLLPGSPAAADGRLSLGDRILEVNGSSLLGLGYLRAVDL IRHGGKKMRFLVAKSDVETAKKI | 61 |
| hShroom | 18652858 | 1 | IYLEAFLEGGAPWGFTLKGGLEHGEPLIISKVEEGGKAD TLSSKLQAGDEWHINEVTLSSSRKEAVSLVKGSYKTLR LWRRDVCTDPGH | 62 |
| HSPC227 | 7106843 | 1 | NNELTQFLPRTITLKKPPGAQLGFNIRGGKASQLGIFISK VIPDSDAHRAGLQEGDQVLAVNDVDFQDIEHSKAVEIL KTAREISMRVRFFPYNYHRQKE | 63 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| HTRA 3 | AY040094 | 1 | FLTEFQDKQIKDWKKRFIGIRMRTITPSLVDELKASNPD FPEVSSGIYVQEVAPNSPSQRGGIQDGDIIVKVNGRPLV DSSELQEAVLTESPLLLEVRRGNDDLLFS | 64 |
| HTRA 4 | AL576444 | 1 | NKKYLGLQMLSLTVPLSEELKMHYPDFPDVSSGVYVCK VVEGTAAQSSGLRDHDVIVNINGKPITTTTDWKALDSD SLSMAVLRGKDNLLLTV | 65 |
| INADL | 2370148 | 3 | PGSDSSLFETYNVELVRKDGQSLGIRIVGYVGTSHTGE ASGIYVKSIIPGSAAYHNGHIQVNDKIVAVDGVNIQGFAN HDWEVLRNAGQWHLTLVRRKTSSSTSRIHRD | 66 |
| INADL | 2370148 | 8 | PATCPIVPGQEMIIEISKGRSGLGLSIVGGKDTPLNAIVIH EVYEEGAAARDGRLWAGDQILEVNGVDLRNSSHEEAIT ALRQTPQKVRLVVY | 67 |
| INADL | 2370148 | 2 | LPETVCWGHVEEVELINDGSGLGFGIVGGKTSGVVVRT IVPGGLADRDGRLQTGDHILKIGGTNVQGMTSEQVAQV LRNCGNSVRMLVARDPAGDIQSPI | 68 |
| INADL | 2370148 | 6 | PNFSHWGPPRIVEIFREPNVSLGISIVVGQTVIKRLKNG EELKGIFIKQVLEDSPAGKTNALKTGDKILEVSGVDLQN ASHSEAVEAIKNAGNPVVFIVQSLSSTPRVIPNVHNKAN SS | 69 |
| INADL | 2370148 | 7 | PGELHIIELEKDKNGLGLSLAGNKDRSRMSIFVVGINPE GPAAADGRMRIGDELLEINNQILYGRSHQNASAIIKTAP SKVKLVFIRNEDAVNQMANSS | 70 |
| INADL | 2370148 | 5 | LSSPEVKIVELVKDCKGLGFSILDYQDPLDPTRSVIVIRS LVADGVAERSGGLLPGDRLVSVNEYCLDNTSLAEAVEI LKAVPPGLVHLGICKPLVEFIVTD | 71 |
| INADL | 2370148 | 1 | IWQIEYIDIERPSTGGLGFSVVALRSQNLGKVDIFVKDV QPGSVADRDQRLKENDQILAINHTPLDQNISHQQAIALL QQTTGSLRLIVAREPVHTKSSTSSSE | 72 |
| INADL | 2370148 | 4 | NSDDAELQKYSKLLPIHTLRLGVEVDSFDGHHYISSIVS GGPVDTLGLLQPEDELLEVNGMQLYGKSRREAVSFLK EVPPPFTLVCCRRLFDDEAS | 73 |
| KIAA0313 | 76572601 | 1 | HLRLLNIACAAKAKRRLMTLTKPSREAPLPFILLGGSEK GFGIFVDSVDSGSKATEAGLKRGDQILEVNGQNFENIQ LSKAMEILRNNTHLSITVKTNLFVFKELLTRLSEEKRNGA P | 74 |
| KIAA0316 | 6683123 | 1 | IPPAPRKVEMRRDPVLGFGFVAGSEKPWVRSVTPGG PSEGKLIPGDQIVMINDEPVSAAPRERVIDLVRSCKESIL LTVIQPYPSPK | 75 |
| KIAA0340 | 2224620 | 1 | LNKRTTMPKDSGALLGLKWGGKMTDLGRLGAFITKVK KGSLADVVGHLRAGDEVLEWNGKPLPGATNEEVYNIIL ESKSEPQVEIIVSRPIGDIPRIHRD | 76 |
| KIAA0380 | 2224700 | 1 | RCVIIQKDQHGFGFTVSGDRIVLVQSVRPGGAAMKAGV KEGDRIIKVNGTMVTNSSHLEWKLIKSGAYVALTLLGS | 77 |
| KIAA0382 | 7662087 | 1 | ILVQRCVIIQKDDNGFGLTVSGDNPVFVQSVKEDGAAM RAGVQTGDRIIKVNGTLVTHSNHLEWKLIKSGSYVALT VQGRPPGNSS | 78 |
| KIAA0440 | 2662160 | 1 | SVEMTLRRNGLGQLGFHVNYEGIVADVEPYGYAWQAG LRQGSRLVEICKVAVATLSHEQMIDLLRTSVTVKVVIIPP H | 79 |
| KIAA0545 | 14762850 | 1 | LKVMTSGWETVDMTLRRNGLGQLGFHVKYDGTVAEVE DYGFAWQAGLRQGSRLVEICKVAVVTLTHDQMIDLLRT SVTVKWIIPPFEDGTPRRGW | 80 |
| KIAA0559 | 3043641 | 1 | HYIFPHARIKITRDSKDHTVSGNGLGIRIVGGKEIPGHSG EIGAYIAKILPGGSAEQTGKLMEGMQVLEWNGIPLTSKT YEEVQSIISQQSGEAEICVRLDLNML | 81 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| KIAA0613 | 3327039 | 1 | SYSVTLTGPGPWGFRLQGGKDFNMPLTISRITPGSKAA QSQLSQGDLVVAIDGVNTDTMTHLEAQNKIKSASYNLS LTLQKSKNSS | 82 |
| KIAA0858 | 4240204 | 1 | FSDMRISINQTPGKSLDFGFTIKWDIPGIFVASVEAGSPA EFSQLQVDDEIIAINNTKFSYNDSKEWEEAMAKAQETG HLVMDVRRYGKAGSPE | 83 |
| KIAA0902 | 4240292 | 1 | QSAHLEVIQLANIKPSEGLGMYIKSTYDGLHVITGTTEN SPADRCKKIHAGDEVIQVNHQTWGWQLKNLVNALRE DPSGVILTLKKRPQSMLTSAPA | 84 |
| KIAA0967 | 4589577 | 1 | ILTQTLIPVRHTVKIDKDTLLQDYGFHISESLPLTVVAVTA GGSAHGKLFPGDQILQMNNEPAEDLSWERAVDILREA EDSLSITVVRCTSGVPKSSNSS | 85 |
| KIAA1202 | 6330421 | 1 | RSFQYVPVQLQGGAPWGFTLKGGLEHCEPLTVSKIED GGKAALSQKMRTGDELVNINGTPLYGSRQEALILIKGSF RILKLIVRRRNAPVS | 86 |
| KIAA1222 | 6330610 | 1 | ILEKLELFPVELEKDEDGLGISIIGMGVGADAGLEKLGIF VKTVTEGGAAQRDGRIQVNDQIVEVDGISLVGVTQNFA ATVLRNTKGNVRFVIGREKPGQVSE | 87 |
| KIAA1284 | 6331369 | 1 | KDVNVYVNPKKLTVIKAKEQLKLLEVLVGIIHQTKWSWR RTGKQGDGERLVVHGLLPGGSAMKSGQVLIGDVLVAV NDVDVTTENIERVLSCIPGPMQVKLTFENAYDVKRET | 88 |
| KIAA1389 | 7243158 | 1 | TRGCETVEMTLRRNGLGQLGFHVNFEGIVADVEPFGF AWKAGLRQGSRLVEICKVAVATLTHEQMIDLLRTSVTV KVVIIQPHDDGSPRR | 89 |
| KIAA1415 | 7243210 | 1 | VENILAKRLLILPQEEDYGFDIEEKNKAVVVKSVQRGSL AEVAGLQVGRKIYSINEDLVFLRPFSEVESILNQSFCSR RPLRLLVATKAKEIIKIP | 90 |
| KIAA1526 | 5817166 | 1 | PDSAGPGEVRLVSLRRAKAHEGLGFSIRGGSEHGVGIY VSLVEPGSLAEKEGLRVGDQILRVNDKSLARVTHAEAV KALKGSKKLVLSVYSAGRIPGGYVTNH | 91 |
| KIAA1526 | 5817166 | 2 | LQGGDEKKVNLVLGDGRSLGLTIRGGAEYGLIGIYITGV DPGSEAEGSGLKVGDQIIEVNGRSFLNILHDEAVRLLK SSRHLILTVKDVGRLPHARTTVDE | 92 |
| KIAA1620 | 10047316 | 1 | LRRAELVEIIVETEAQTGVSGINVAGGGKEGIFVRELRE DSPAARSLSLQEGDQLLSARVFFENFKYEDALRLLQCA EPYKVSFCLKRTVPTGDLALR | 93 |
| KIAA1719 | 1267982 | 5 | IQTTGAVSYTVELKRYGGPLGITISGTEEPFDPIVISGLT KRGLAERTGAIHVGDRILAINNVSLKGRPLSEAIHLLQVA GETVTLKIKKQLDR | 94 |
| KIAA1719 | 1267982 | 6 | ILEMEELLLPTPLEMHKVTLHKDPMRHDFGFSVSDGLL EKGVYVHTVRPDGPAHRGGLQPFDRVLQVNHVRTRDF DCCLAVPLLAEAGDVLELIISRKPHTAHSS | 95 |
| KIAA1719 | 1267982 | 2 | IHTVANASGPLMVEIVKTPGSALGISLTTTSLRNKSVITID RIKPASWDRSGALHPGDHILSIDGTSMEHCSLLEATKL LASISEKVRLEILPVPQSQRPL | 96 |
| KIAA1719 | 1267982 | 1 | ITVVELIKKEGSTLGLTISGGTDKDGKPRVSNLRPGGLA ARSDLLNIGOYIRSVNGIHLTRLRHDEIITLLKNVGERVV LEVEY | 97 |
| KIAA1719 | 1267982 | 3 | IQIVHTETTEVVLCGDPLSGFGLQLQGGIFATETLSSPPL VCFIEPDSPAERCGLLQVGDRVLSINGIATEDGTMEEA NQLLRDAALAHKWLEVEFDVAESV | 98 |
| KIAA1719 | 1267982 | 1 | ILDVSLYKEGNSFGFVLRGGAHEDGHKSRPLVLTYVRP GGPADREGSLKVGDRLLSVDGIPLHGASHATALATLRQ CSHEALFQVEYDVATP | 99 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| KIAA1719 | 1267982 | 4 | QFDVAESVIPSSGTFHVKLPKKRSVELGITISSASRKRG EPLIISDIKKGSVAHRTGTLEPGDKLLAIDNIRLDNCPME DAVQILRQCEDLVKLKIRKDEDN | 100 |
| LIM mystique | 12734250 | 1 | MALTVDVAGPAPWGFRITGGRDFHTPIMVTKVAERGK AKDADLRPGDIIVAINGESAEGMLHAEAQSKIRQSPSPL RLQLDRSQATSPGQT | 101 |
| LIM protein | 3108092 | 1 | SNYSVSLVGPAPWGFRLQGGKDFNMPLTISSLKDGGK AAQANVRIGDWLSIDGINAQGMTHLEAQNKIKGCTGSL NMTLQRAS | 102 |
| LIMK1 | 4587498 | 1 | TLVEHSKLYCGHCYYQTVVTPVIEQILPDSPGSHLPHTV TLVSIPASSHGKRGLSVSIDPPHGPPGCGTEHSHTVRV QGVDPGCMSPDVKNSIHVGDRILEINGTPIRNVPLDEID LLIQETSRLLQLTLEHD | 103 |
| LIMK2 | 1805593 | 1 | PYSVTLISMPATTEGRRGFSVSVESACSNYATTVQVKE VNRMHISPNNRNAIHPGDRILEINGTPVRTLRVEEVEDA ISQTSQTLQLLIEHD | 104 |
| LIM-RIL | 1085021 | 1 | IHSVTLRGPSPWGFRLVGRDFSAPLTISRVHAGSKASL AALCPGDLIQAINGESTELMTHLEAQNRIKGCHDHLTLS VSRPE | 105 |
| LU-1 | U52111 | 1 | VCYRTDDEEDLGIYVGEVNPNSIAAKDGRIREGDRIIQIN GVDVQNREEAVAILSQEENTNISLLVARPESQLA | 106 |
| MAGI 1 | 3370997 | 2 | IPATQPELITVHIVKGPMGFGFTIADSPGGGGQRVKQIV DSPRCRGLKEGDLIVEVNKKNVQALTHNQWDMLVEC PKGSEVTLLVQRGGNSS | 107 |
| MAGI 1 | 3370997 | 5 | IPDYQEQDIFLWRKETGFGFRILGGNEPGEPIYIGHIVPL GAADTDGRLRSGDELICVDGTPVIGKSHQLVVQLMQQ AAKQGHVNLTVRRKVVFAVPKTENSS | 108 |
| MAGI 1 | 3370997 | 4 | IPGWSTVVQPYDVEIRRGENEGFGFVIVSSVSRPEAG TTFAGNACVAMPHKIGRIIEGSPADRCGKLKVGDRILAV NGCSITNKSHSDIVNLIKEAGNTVTLRIIPGDESSNAEFIV TD | 109 |
| MAGI 1 | 3370997 | 1 | IPSELKGKFIHTKLRKSSRGFGFTVVGGDEPDEFLQIKS LVLDGPAALDGKMETGDVIVSVNDTCVLGHTHAQVVKI FQSIPIGASVDLELCRGYPLPFDPDGIHRD | 110 |
| MAGI 1 | 3370997 | 3 | QATQEQDFYTVELERGAKGFGFSLRGGREYNMDLYVL RLAEDGPAERCGKMRIGDEILEINGETTKNMKHSRAIEL IKNGGRRVRLFLKRG | 111 |
| Magi 2 | 2947231 | 1 | REKPLFTRDASQLKGTFLSTTLKKSNMGFGFTIIGGDEP DEFLQVKSVIPDGPAAQDGKMETGDVIVYINEVCVLGH THADVVKLFQSVPIGQSVNLVLCRGYP | 112 |
| Magi 2 | 2947231 | 3 | HYKELDVHLRRMESGFGFRILGGDEPGQPILIGAVIAMG SADRDGRLHPGDELVYVDGIPVAGKTHRYVIDLMHHAA RNGQVNLTVRRKVLCG | 113 |
| Magi 2 | 2947231 | 4 | EGRGISSHSLQTSDAVIHRKENEGFGFVIISSLNRPESG STITVPHKIGRIIDGSPADRCAKLKVGDRILAVNGQSIIN MPHADIVKLIKDAGLSVTLRIIPQEEL | 114 |
| Magi 2 | 2947231 | 2 | LSGATQAELMTLTIVKGAQGFGFTIADSPTGQRVKQILD IQGCPGLCEGDLIVEINQQNVQNLSHTEWDILKDCPIG SETSLIIHRGGFF | 115 |
| Magi 2 | 2947231 | 5 | LSDYRQPQDFDYFTVDMEKGAKGFGFSIRGGREYKMD LYVLRLAEDGPAIRNGRMRVGDQIIEINGESTRDMTHAR AIELIKSGGRRVRLLLKRGTGQ | 116 |
| Magi 2 | 2947231 | 6 | HESVIGRNPEGQLGFELKGGAENGFPYLGEVKPGKV AYESGSKLVSEELLLEVNETPVAGLTIRDVLAVIKHCKD PLRLKCVKQGGIHR | 117 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| MAGI 3 | 10047344? | 2 | ASSGSSQPELVTIPLIKGPKGFGFAIADSPTGQKVKMIL DSQWCQGLQKGDIIKEIYHQNVQNLTHLQVVEVLKQFP VGADVPLLILRGGPPSPTKTAKM | 118 |
| MAGI 3 | 10047344 | 5 | QNLGCYPVELERGPRGFGFSLRGGKEYNMGLFILRLA EDGPAIKDGRIHVGDQIVEINGEPTQGITHTRAIELIQAG GNKVLLLLRPGTGLIPDHGLA | 119 |
| MAGI 3 | 10047344 | 3 | LYEDKPPNTKDLDVFLRKQESGFGFRVLGGDGPDQSIY IGAIIPLGAAEKDGRLRAADELMCIDGIPVKGKSHKQVL DLMTTAARNGHVLLTVRRKIFYGEKQPEDDS | 120 |
| MAGI 3 | 10047344 | 1 | PSQLKGVLVRASLKKSTMGFGFTIIGGDRPDEFLQVKN VLKDGPAAQDGKIAPGDVIVDINGNCVLGHTHADVVQM FQLVPVNQYVNLTLCRGYPLPDDSED | 121 |
| MAGI 3 | 10047344 | 4 | PAPQEPYDVVLQRKENEGFGFVILTSKNKPPPGVIPHKI GRVIEGSPADRCGKLKVGDHISAVNGQSIVELSHDNIV QLIKDAGVTVTLTVIAEEEHHGPPS | 122 |
| MAST1 | 4589589 | 1 | GLRSPITIQRSGKKYGFTLRAIRVYMGDTDVYSVHHIVW HVEEGGPAQEAGLCAGDLITHVNGEPVHGMVHPEVVE LILKSGNKVAVTTTPFEN | 123 |
| MAST2 | 3882334 | 1 | ISALGSMRPPIIIHRAGKKYGFTLRAIRVYMGDSDVYTV HHMVWHVEDGGPASEAGLRQGDLITHVNGEPVHGLV HTEWELILKSGNKVAISTTPLENSS | 124 |
| MAST3 | 3043645 | 1 | LCGSLRPPIVIHSSGKKYGFSLRAIRVYMGDSDVYTVHH VVWSVEDGSPAQEAGLRAGDLITHINGESVLGLVHMD VVELLLKSGNKISLRTTALENTSIKVG | 125 |
| MAST4 | 2224546 | 1 | PHQPIVIHSSGKNYGFTIRAIRVYVGDSDIYTVHHIVWNV EEGSPACQAGLKAGDLITHINGEPVHGLVHTEVIELLLK SGNKVSITTTPF | 126 |
| MGC5395 | BC012477 | 1 | PAKMEKEETTRELLLPNWQGSGSHGLTIAQRDDGVFV QEVTQNSPAARTGVVKEGDQIVGATIYFDNLQSGEVTQ LLNTMGHHTVGLKLHRKGDRSPNSS | 127 |
| MINT1 | 2625024 | 1 | SENCKdVFIEKQKGEILGWIVESGWGSILPTVIIANMMH GGPAEKSGKLNIGDQIMSINGTSLVGLPLSTCQSIIKGLK NQSRVKLNIVRCPPVNSS | 128 |
| MINT1 | 2625024 | 1,2 | SENCKDVFIEKQKGEILGVVIVESGWGSILPTVIIANMMH GGPAEKSGKLNIGDQIMSINGTSLVGLPLSTCQSIIKGLE NQSRVKLNIVRCPPVTTVLIRRPDLRYQLGFSVQNGIIC SLMRGGIAERGGVRVGHRIIEINGQSVVATPHEKIVHILS NAVGEIHMKTMPAAMYRLL | 129 |
| MINT1 | 2625024 | 2 | LRCPPVTTVLIRRPDLRYQLGFSVQNGIICSLMRGGIAE RGGVRVGHRIIEINGQSVVATPHEKIVHILSNAVGEIHMK TMPAAMYRLLNSS | 130 |
| MINT3 | 3169808 | 1 | HNGDLDHFSNSDNCREVHLEKRRGEGLGVALVESGW GSLLPTAVIANLLHGGPAERSGALSIGDRLTAINGTSLV GLPLAACQAAVRETKSQTSVTLSIVHCPPVT | 131 |
| MINT3 | 3169808 | 2 | PVTTAIIHRPHAREQLGFCVEDGIICSLLRGGIAERGGIR VGHRIIEINGQSWATPHARIIELLTEAYGEVHIKTMPAAT YRLLTGNSS | 132 |
| MINT3 | 3169808 | 1 | LSNSDNCREVHLEKRRGEGLGVALVESGWGSLLPTAVI ANLLHGGPAERSGALSIGDRLTAINGTSLVGLPLAACQA AVRETKSQTSVTLSIVHCPPVTTAIM | 133 |
| MPP1 | 189785 | 1 | RKVRLIQFEKVTEEPMGITLKLNEKQSCTVARILHGGMI HRQGSLHVGDEILEINGTNVTNHSVDQLQKAMKETKG MISLKVIPNQ | 134 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| MPP2 | 939884 | 1 | PVPPDAVRMVGIRKTAGEHLGVTFRVEGGELVIARILH GGMVAQQGLLHVGDIIKEVNGQPVGSDPRALQELLRN ASGSVILKILPNYQ | 135 |
| MPP3 | 21536463 | 1 | NIDEDFDEESVKIVRLVKNKEPLGATIRRDEHSGAVVVA RIMRGGAADRSGLVHVGDELREVNGIAVLHKRPDEISQ ILAQSQGSITLKIIPATQEEDR | 136 |
| MUPP1 | 2104784 | 5 | WEAGIQHIELEKGSKGLGFSILDYQDPIDPASTVIIRSLV PGGIAEKDGRLLPGDRLMFVNDVNLENSSLEEAVEALK GAPSGTVRIGVAKPLPLSPEE | 137 |
| MUPP1 | 2104784 | 12 | LQGLRTVEMKKGPTDSLGISIAGGVGSPLGDVPIFIAMM HPTGVAAQTQKLRVGDRIVTICGTSTEGMTHTQAVNLL KNASGSIEMQWAGGDVSV | 138 |
| MUPP1 | 2104784 | 2 | PVHWQHMETIELVNDGSGLGFGIIGGKATGVIVKTILPG GVADQHGRLCSGDHILKIGDTDLAGMSSEQVAQVLRQ CGNRVKLMIARGAIEERTAPT | 139 |
| MUPP1 | 2104784 | 3 | QESETFDVELTKNVQGLGITIAGYIGDKKLEPSGIFVKSI TKSSAVEHDGRIQIGDQIIAVDGTNLQGFTNQQAVEVLR HTGQTVLLTLMRRGMKQEA | 140 |
| MUPP1 | 2104784 | 11 | KEEEVCDTLTIELQKKPGKGLGLSIVGKRNDTGVFVSDI VKGGIADADGRLMQGDQILMVNGEDVRNATQEAVAAL LKCSLGTVTLEVGRIKAGPFHS | 141 |
| MUPP1 | 2104784 | 8 | LTGELHMIELEKGHSGLGLSLAGNKDRSRMSVFIVGIDP NGAAGKDGRLQIADELLEINGQILYGRSHQNASSIIKCA PSKVKIIFIRNKDAVNQ | 142 |
| MUPP1 | 2104784 | 13 | LGPPQCKSITLERGPDGLGFSIVGGYGSPHGDLPIYVKT VFAKGAASEDGRLKRGDQIIAVNGQSLEGVTHEEAVAIL KRTKGTVTLMVLS | 143 |
| MUPP1 | 2104784 | 6 | RNVSKESFERTINIAKGNSSLGMTVSANKDGLGMIVRSI IHGGAISRDGRIAIGDCILSINEESTISVTNAQARAMLRR HSLIGPDIKITYVPAEHLEE | 144 |
| MUPP1 | 2104784 | 10 | LPGCETTIEISKGRTGLGLSIVGGSDTLLGAIIIHEVYEE GAACKDGRLWAGDQILEVNGIDLRKATHDEAINVLRQTP QRVRLTLYRDEAPYKE | 145 |
| MUPP1 | 2104784 | 7 | LNWNQPRRVELWREPSKSLGISIVGGRGMGSRLSNGE VMRGIFIKHVLEDSPAGKNGTLKPGDRIVEVDGMDLRD ASHEQAVEAIRKAGNPWFMVQSIINRPRKSPLPSLL | 146 |
| MUPP1 | 2104784 | 9 | LSSFKNVQHLELPKDQGGLGIAISEEDTLSGVIIKSLTEH GVAATDGRLKVGDQILAVDDEIVVGYPIEKFISLLKTAKM TVKLTIHAENPDSQ | 147 |
| MUPP1 | 2104784 | 1 | QGRHVEVFELLKPPSGGLGFSWGLRSENRGELGIFVQ EIQEGSVAHRDGRLKETDQILAINGQALDQTITHQQAISI LQKAKDTVQLVIARGSLPQLV | 148 |
| MUPP1 | 2104784 | 4 | LNYEIVVAHVSKFSENSGLGISLEATVGHHFIRSVLPEG PVGHSGKLFSGDELLEVNGITLLGENHQDVVNILKELPI EVTMVCCRRTVPPT | 149 |
| NeDLG | 10863920 | 2 | ITLLKGPKGLGFSIAGGIGNQHIPGDNSIYITKIIEGGAAQ KDGRLQIGDRLLAVNNTNLQDVRHEEAVASLKNTSDM VYLKVAKPGSLE | 150 |
| NeDLG | 10863920 | 1 | IQYEEIVLERGNSGLGFSIAGGIDNPHVPDDPGIFITKIIP GGAAAMDGRLGVNDCVLRVNEVEVSEVVHSRAVEALK EAGPVVRLVVRRRQN | 151 |
| NeDLG | 10863920 | 3 | ILLHKGSTGLGFNIVGGEDGEGIFVSFILAGGPADLSGE LRRGDRILSVNGVNLRNATHEQAAAALKRAGQSVTIVA QYRPEEYSRFESKIHDLREQMMNSSMSSGSGSLRTSE KRSLE | 152 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| NeDLG | 10863920 | 1,2 | YEEIVLERGNSGLGFSIAGGIDNPHVPDDPGIFITKIIPGG AAAMDGRLGVNDCVLRVNEVEVSEVVHSRAVEALKEA GPVVRLWRRRQPPPETIMEVNLLKGPKGLGFSIAGGI GNQHIPGDNSIYITKIIEGGAAQKDGRLQIGDRLLAVNNT NLQDVRHEEAVASLKNTSDMVYLKVAKPGSL | 153 |
| Neurabin II | AJ401189 | 1 | RVERLELFPVELEKDSEGLGISIIGMGAGADMGLEKLGI FVKTVTEGGAAHRDGRIQVNDLLVEVDGTSLVGVTQSF AASVLRNTKGRVRCRFMIGRERPGEQSEV | 154 |
| NOS1 | 642525 | 1 | QPNVISVRLFKRKVGGLGFLVKERVSKPPVIISDLIRGG AAEQSGLIQAGDIILAVNGRPLVDLSYDSALEVLRGIASE THWLILRGPE | 155 |
| novel PDZ gene | 7228177 | 2 | PSDTSSEDGVRRIVHLYTTSDDFCLGFNIRGGKEFGLGI YVSKVDHGGLAEENGIKVGDQVLAANGVRFDDISHSQ AVEVLKGQTHIMLTIKETGRYPAYKEM | 156 |
| novel PDZ gene | 7228177 | 1 | EANSDESDIIHSVRVEKSPAGRLGFSVRGGSEHGLGIF VSKVEEGSSAERAGLCVGDKITEVNGLSLESTTMGSAV KVLTSSSRLHMMVRRMGRVPGIKFSKEK | 157 |
| novel serine protease | 1621243 | 1 | OKIKKFLTESHDRQAKGKAITKKKYIGIRMMSLTSSKAK ELKDRHRDFPDVISGAYIIEVIPDTPAEAGGLKENDVIISI NGQSWSANDVSDVIKRESTLNMWRRGNEDIMITV | 158 |
| Numb BP | AK056823 | 2 | YRPRDDSFHVILNKSSPEEQLGIKLVRKVDEPGVFIFNA LDGGVAYRHGQLEENDRVLAINGHDLRYGSPESAAHLI QASERRVHLVVSRQVRQRSPD | 159 |
| Numb BP | AK056823 | 3 | PTITCHEKVVNIQKDPGESLGMTVAGGASHREWDLPIY VISVEPGGVISRDGRIKTGDILLNVDGVELTEVSRSEAV ALLKRTSSSIVLKALEVKEYEPQ | 160 |
| Numb BP | AK056823 | 1 | PDGEITSIKINRVDPSESLSIRLVGGSETPLVHIIIQHIYRD GVIARDGRLLPRDIILKVNGMDISNVPHNYAVRLLRQPC QVLWLTVMREQKFRSR | 161 |
| Numb BP | AK056823 | 4 | PRCLYNCKDIVLRRNTAGSLGFCIVGGYEEYNGNKPFFI KSIVEGTPAYNDGRIRCGDILLAVNGRSTSGMIHACLAR LLKELKGRITLTIVSWPGTFL | 162 |
| outer membrane | 7023825 | 1 | LLTEEEINLTRGPSGLGFNIVGGTDQQYVSNDSGIYVSR IKENGAAALDGRLQEGDKILSVNGQDLKNLLHQDAVDL FRNAGYAVSLRVQHRLQVQNGIHS | 163 |
| p55T | 12733367 | 1 | PVDAIRILGIHKRAGEPLGVTFRVENNDLVIARILHGGMI DRQGLLHVGDIIKEVNGHEVGNNPKELQELLKNISGSVT LKILPSYRDTITPQQ | 164 |
| PAR3 | 8037914 | 2 | GKRLNIQLKKGTEGLGFSITSRDVTIGGSAPIYVKNILPR GAAIQDGRLKAGDRLIEVNGVDLVGKSQEEVVSLLRST KMEGTVSLLVFRQEDA | 165 |
| PAR3 | 8037914 | 1 | IPNFSLDDMVKLVEVPNDGGPLGIHVVPFSARGGRTLG LLVKRLEKGGKAEHENLFRENDCIVRINDGDLRNRRFE QAQHMFRQAMRTPIIWFHVVPAANKEQYEQ | 166 |
| PAR3 | 8037914 | 3 | PREFLTFEVPLNDSGSAGLGVSVKGNRSKENHADLGIF VKSIINGGAASKDGRLRVNDQLIAVNGESLLGKTNQDA METLRRSMSTEGNKRGMIQLIVASRISKCNELKSNSS | 167 |
| PAR3L | 18874467 | 2 | ISNKNAKKIKIDLKKGPEGLGFTVVTRDSSIHGPGPIFVK NILPKGAAIKDGRLQSGDRILEVNGRDVTGRTQEELVA MLRSTKQGETASLVIARQEGH | 168 |
| PAR3L | 18874467 | 3 | ITSEQLTFEIPLNDSGSAGLGVSLKGNKSRETGTDLGIFI KSIIHGGAAFKDGRLRMNDQLIAVNGESLLGKSNHEAM ETLRRSMSMEGNIRGMIQLVILRRPERP | 169 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| PAR3L | 18874467 | 1 | IPRTKDTLSDMTRTVEISGEGGPLGIHVVPFFSSLSGRIL GLFIRGIEDNSRSKREGLFHENECIVKINNVDLVDKTFA QAQDVFRQAMKSPSVLLHVLPPQNR | 170 |
| PAR6 | 2613011 | 1 | PETHRRVRLHKHGSDRPLGFYIRDGMSVRVAPQGLER VPGIFISRLVRGGLAESTGLLAVSDEILEVNGIEVAGKTL DQVTDMMVANSHNLIVTVKPANQRNNV | 171 |
| PAR6 beta | M1353716 | 1 | IPVSSIIDVDILPETHRRVRLYKYGTEKPLGFYIRDGSSV RVTPHGLEKVPGIFISRLVPGGLAQSTGLLAVNDEVLEV NGIEVSGKSLDQVTDMMIANSRNLIITVRPANQRNNRIH RD | 172 |
| PAR6 GAMMA | 13537118 | 1 | IDVDLVPETHRRVRLHRHGCEKPLGFYIRDGASVRVTP HGLEKVPGIFISRMVPGGLAESTGLLAVNDEVLEVNGIE VAGKTLDQVTDMMIANSHNLIVTVKPANQRNNVV | 173 |
| PDZ-73 | 5031978 | 3 | PEQIMGKDVRLLRIKKEGSLDLALEGGVDSPIGKVVVSA VYERGAAERHGGIVKGDEIMAINGKIVTDYTLAEADAAL QKAWNQGGDWIDLWAVCPPKEYDD | 174 |
| PDZ-73 | 5031978 | 2 | IPGNRENKEKKVFISLVGSRGLGCSISSGPIQKPGIFISH VKPGSLSAEVGLEIGDQIVEVNGVDFSNLDHKEAVNVL KSSRSLTISIVAAAGRELFMTDEF | 175 |
| PDZ-73 | 5031978 | 1 | RSRKLKEVRLDRLHPEGLGLSVRGGLEFGCGLFISHLIK GGQADSVGLQVGDEIVRINGYSISSCTHEEVINLIRTKK TVSIKVRHIGLIPVKSSPDEFH | 176 |
| PDZK1 | 2944188 | 2 | RLCYLVKEGGSYGFSLKTVQGKKGVYMTDITPQGVAM RAGVLADDHLIEVNGENVEDASHEEWEKVKKSGSRV MFLLVDKETDKREFIVTD | 177 |
| PDZK1 | 2944188 | 3 | QFKRETASLKLLPHQPRIVEMKKGSNGYGFYLRAGSE QKGQIIKDIDSGSPAEEAGLKNNDLVVAVNGESVETLD HDSWEMIRKGGDQTSLLWDKETDNMYRLAEFIVTD | 178 |
| PDZK1 | 2944188 | 2,3,4 | RLCYLVKEGGSYGFSLKTVQGKKGVYMTDITPQGVAM RAGVLADDHLIEVNGENVEDASHEKWEKVKKSGSRV MFLLVDKETDKRHVEQKIQFKRETASLKLLPHQPRIVEM KKGSNGYGFYLRAGSEQKGQIIKDIDSGSPAEEAGLKN NDLVVAVNGESVETLDHDSWEMIRKGGDQTSLLWDK ETDNMYRLAHFSPFLYYQSQELPNGSVKEAPAPTPTSL EVSSPPDTTEEVDHKPKLCRLAKGENGYGFHLNAIRGL PGSFIKEVQKGGPADLAGLEDEDVIIEVNGVNVLDEPYE KVVDRIQSSGKNVTLLVCGK | 179 |
| PDZK1 | 2944188 | 4 | PDTTEEVDHKPKLCRLAKGENGYGFHLNAIRGLPGSFI KEVQKGGPADLAGLEDEDVIIEVNGVNVLDEPYEKVVD RIQSSGKNVTLLVGKNSS | 180 |
| PDZK1 | 2944188 | 1 | LTSTFNPRECKLSKQEGQNYGFFLRIEKDTEGHLVRVV EKCSPAEKAGLQDGDRVLRINGVFVDKEEHMQVVDLV RKSGNSVTLLVLDGDSYEKAGSHEPS | 181 |
| PICK1 | 4678411 | 1 | LGIPTVPGKVTLQKDAQNLIGISIGGGAQYCPCLYIVQVF DNTPAALDGTVAAGDEITGVNGRSIKGKTKVEVAKMIQ EVKGEVTIHYNKLQADPKQGM | 182 |
| PIST | 98374330 | 1 | SQGVGPIRKVLLLKEDHEGLGISITGGKEHGVPILISEIH PGQPADRCGGLHVGDAILAVNGVNLRDTKHKEAVTILS QQRGEIEFEWYVAPEVDSD | 183 |
| priL16 | 1478492 | 2 | TAEATVCTVTLEKMSAGLGFSLEGGKGSLHGDKPLTIN RIFKGAASEQSETVQPGDEILQLGGTAMQGLTRFEAW NIIKALPDGPVTIVIRRKSLQSK | 184 |
| prIL16 | 1478492 | 1 | IHVTILHKEEGAGLGFSLAGGADLENKVITVHRVFPNGL ASQEGTIQKGNEVLSINGKSLKGTTHHDALAILRQAREP RQAVIVTRKLTPEEFIVTD | 185 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| prIL16 | 1478492 | 1,2 | IHVTILHKEEGAGLGFSLAGGADLENKVITVHRVFPNGL ASQEGTIQKGNEVLSINGKSLKGTTHHDALAILRQAREP RQAVIVTRKLTPEAMPDLNSSTDSAASASAASDVSVES TAEATVCTVTLEKMSAGLGFSLEGGKGSLHGDKPLTIN RIFKGAASEQSETVQPGDEILQLGGTAMQGLTRFEAW NIIKALPDGPVTIVIRRKSLQSK | 186 |
| PSAP | 6409315 | 1 | IREAKYSGVLSSIGKIFKEEGLLGFFVGLIPHLLGDVVFL WGCNLLAHFINAYLVDDSVSDTPGGLGNDQNPSGQFS QALAIRSYTKFVMGIAVSMLTYPFLLVGDLMAVNNCGL QAGLPPYSPVFKSWIHCWKYLSVQGQLFRGSSLLFRR VSSGSCFALE | 187 |
| PSD95 | 3318652 | 1,2,3 | EGEMEYEEITLERGNSGLGFSIAGGTDNPHIGDDPSIFIT KIIPGGAAAQDGRLRVNDSILFVNEVDVREVTHSAAVEA LKEAGSIVRLYVMRRKPPAEKVMEIKLIKGPKGLGFSIA GGVGNQHIPGDNSIYVTKIIEGGAAHKDGRLQIGDKILA VNSVGLEDVMHEDAVAALKNTYDVVYLKVAKPSNAYLS DSYAPPDITTSYSQHLDNEISHSSYLGTDYPTAMTPTSP RRYSPVAKDLLGEEDIPREPRRIVIHRGSTGLGFNIVGG EDGEGIFISFILAGGPADLSGELRKGDQILSVNGVDLRN ASHEQAAIALKNAGQTVTIIAQYKPE | 188 |
| PSD95 | 3318652 | 2 | HVMRRKPPAEKVMEIKLIKGPKGLGFSIAGGVGNQHIP GDNSIYVTKIIEGGAAHKDGRLQIGDKILAVNSVGLEDV MHEDAVAALKNTYDVVYLKVAKPSNAYL | 189 |
| PSD95 | 3318652 | 3 | REDIPREPRRIVIHRGSTGLGFNIVGGEDGEGIFISFILAG GPADLSGELRKGDQILSVNGVDLRNASHEQAAIALKNA GQTVTIIAQYKPEFIVTD | 190 |
| PSD95 | 3318652 | 1 | LEYEeITLERGNSGLGFSIAGGTDNPHIGDDPSIFITKIIP GGAAAQDGRLRVNDSILFVNEVDVREVTHSAAVEALKE AGSIVRLYVMRRKPPAENSS | 191 |
| PSMD9 | 9184389 | 1 | RDMAEAHKEAMSRKLGQSESQGPPRAFAKVNSISPGS PASIAGLQVDDEIVEFGSVNTQNFQSLHNIGSWQHSE GALAPTILLSVSM | 192 |
| PTN-3 | 179912 | 1 | QNDNGDSYLVLIRITPDEDGKFGFNLKGGVDQKMPLVV SRINPESPADTCIPKLNEGDQIVLINGRDISEHTHDQVV MFIKASRESHSRELALVIRRRAVRS | 193 |
| PTN-4 | 190747 | 1 | IRMKPDENGRFGFNVKGGYDQKMPVIVSRVAPGTPAD LCVPRLNEGDQWLINGRDIAEHTHDQWLFIKASCERH SGELMLLVRPNA | 194 |
| PTPL1 | 515030 | 2 | GDIFEVELAKNDNSLGISVTGGVNTSVRHGGIYVKAVIP QGAAESDGRIHKGDRVLAVNGVSLEGATHKQAVETLR NTGQVVHLLLEKGQSPTSK | 195 |
| PTPL1 | 515030 | 1 | PEREITLVNLKKDAKYGLGFQIIGGEKMGRLDLGIFISSV APGGPADFHGCLKPGDRLISVNSVSLEGVSHHAAIEILQ NAPEDVTLVISQPKEKISKVPSTPVHL | 196 |
| PTPL1 | 515030 | 4 | ELEVELLITLIKSEKASLGFTVTKGNQRIGCYVHDVIQDP AKSDGRLKPGDRLIKVNDTDVTNMTHTDAVNLLRAASK TVRLVIGRVLELPRIPMLPH | 197 |
| PTPL1 | 515030 | 3 | TEENTFEVKLFKNSSGLGFSFSREDNLIPEQINASIVRV KKLFAGQPAAESGKIDVGDVILKVNGASLKGLSQQEVIS ALRGTAPEVFLLLCRPPPGVLPEIDT | 198 |
| PTPL1 | 515030 | 5 | MLPHLLPDITLTCNKEELGFSLCGGHDSLYQVVYISDIN PRSVAAIEGNLQLLDVIHYVNGVSTQGMTLEEVNRALD MSLPSLVLKATRNDLPV | 199 |
| RGS 3 | 18644735 | 1 | VCSERRYRQITIPRGKDFGFTICCDSPVRVQAVDSGG PAERAGLQQLDTVLQLNERPVEHWKCVELAHEIRSCP SEIILLVWRMVPQVKPG | 200 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| RGS12 | 3290015 | 1 | RPSPPRVRSVEVARGRAGYGFTLSGQAPCVLSCVMR GSPADFVGLRAGDQILAVNEINVKKASHEDWKLIGKCS GVLHMVIAEGVGRFESCS | 201 |
| Rho-GAP 10 | 50345878 | 1 | SEDETFSWPGPKTVTLKRTSQGFGFTLRHFIVYPPESAI QFSYKDEENGNRGGKQRNRLEPMDTIFVKQVKEGGPA FEAGLCTGDRIIKVNGESVIGKTYSQVIALIQNSDTTLEL SVMPKDED | 202 |
| Rhophilin | AY082588 | 1 | SAKNRWRLVGPVHLTRGEGGFGLTLRGDSPVLIAAVIP GSQAAAAGLKEGDYIVSVNGQPCRWWRHAEVVTELK AAGEAGASLQVVSLLPSSRLPS | 203 |
| Rhophilin-like | AF268032 | 1 | ISFSANKRWTPPRSIRFTAEEGDLGFTLRGNAPVQVHF LDPYCSASVAGAREGDYIVSIQLVDCKWLTLSEVMKLL KSFGEDEIEMKVVSLLDSTSSMHNKSAT | 204 |
| RIM2 | 12734165 | 1 | TLNEEHSHSDKHPVTWQPSKDGDRLIGRILLNKRLKDG SVPRDSGAMLGLKVVGGKMTESGRLCAFITKVKKGSL ADTVGHLRPGDEVLEWNGRLLQGATFEEVYNIILESKP EPQVELVVSRPIG | 205 |
| SEMCAP 3 | 5889526 | 2 | QEMDREELELEEVDLYRMNSQDKLGLTVCYRTDDEDD IGIYISEIDPNSIAAKDGRIREGDRIIQINGIEVQNREEAVA LLTSEENKNFSLLIARPELQLD | 206 |
| SEMCAP 3 | 5889526 | 1 | QGEETKSLTLVLHRDSGSLGFNIIGGRPSVDNHDGSSS EGIFVSKIVDSGPAAKEGGLQIHDRIIEVNGRDLSRATH DQAVEAFKTAKEPIVVQVLRRTPRTKMFTP | 207 |
| semcap2 | 7019938 | 1 | ILAHVKGIEKEVNVYKSEDSLGLTITDNGVGYAFIKRIKD GGVIDSVKTICVGDHIESINGENIVGWRHYDVAKKLKEL KKEELFTMKLIEPKKAFEI | 208 |
| serine protease | 2738914 | 1 | RGEKKNSSSGISGSQRRYIGVMMLTLSPSILAELQLREP SFPDVQHGVLIHKVILGSPAHRAGLRPGDVILAIGEQMV QNAEDVYEAVRTQSQLAVQIRRGRETLTLYV | 209 |
| Shank 1 | 6049185 | 1 | ILEEKTVVLQKKDNEGFGFVLRGAKADTPIEEFTPTAF PALQYLESVDEGGVAWQAGLRTGDFLIEVNNENVVKV GHRQVVNMIRQGGNHLVLKVVTVTRNLDPDDNSS | 210 |
| Shank 2 | 7025450 | 1 | ILKEKTVLLQKKDSEGFGFVLRGAKAQTPIEEFTPTAF PALQYLESVDEGGVAWRAGLRMGDFLIEVNGQNVVKV GHRQVVNMIRQGGNTLMVKVVMVTRHPDMDEAVQNS S | 211 |
| Shank 3 | * | 1 | SDYVIDDKVAVLQKRDHEGFGFVLRGAKAETPIEEFTPT PAPPALQYLESVDVEGVAWRAGLRTGDFLIEVNGVNVV KVGHKQVVALIRQGGNRLVMKVVSVTRKPEEDG | 212 |
| sim to lig of numb px2 | 22477649 | 2 | SNSPREEIFQVALHKRDSGEQLGIKLVRRTDEPGVFILD LLEGGLAAQDGRLSSNDRVLAINGHDLKYGTPELAAQII QASGERVNLTIARPGKPQPG | 213 |
| sim to lig of numb px2 | 22477649 | 3 | IQCVTCQEKHITVKKEPHESLGMTVAGGRGSKSGELPI FVTSVPPHGCLARDGRIKRGDVLLNINGIDLTNLSHSEA VAMLKASAASPAVALKALEVQIVEEAT | 214 |
| Similar to GRASP65 | 14286261 | 1 | MGLGVSAEQPAGGAEGFHLHGVQENSPAQQAGLEPY FDFIITIGHSRLNKENDTLKALLKANVEKPVKLEVFNMKT MRVREVEVVPSNMWGGQGLLGASVRFCSFRRASE | 215 |
| Similar to GRASP65 | 14286261 | 2 | RASEQVWHVLDVEPSSPAALAGLRPYTDYVVGSDQIL QESEDEETLIESHEGKPLKLMVYNSKSDSCRESGMWH WLWVSTPDPNSAPQLPQEATWHPTTFCSTTWCPTT | 216 |
| Similar to Protein-Tyrosine-Phosphatase Homolog | 21595065 | 1 | ISVTDGPKFEVKLKKNANGLGFSFVQMEKESCSHLKSD LVRIKRLFPGQPAEENGAIAAGDIILAVNGRSTEGLIFQE VLHLLRGAPQEVTLLLCRPPPGA | 217 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| SIP1 | 2047327 | 1 | QPEPLRPRLCRLVRGEQGYGFHLHGEKGRRGQFIRRV EPGSPAEAAALRAGDRLVEVNGVNVEGETHHQVVQRI KAVEGQTRLLVVDQETDEELRRRNSS | 218 |
| SIP1 | 2047327 | 2 | PLRELRPRLCHLRKGPQGYGFNLHSDKSRPGQYIRSV DPGSPAARSGLRAQDRLIEVNGQNVEGLRHAEVVASIK AREDEARLLVVDPETDEHFKRNSS | 219 |
| SITAC 18 | 8886071 | 1 | PGVREIHLCKDERGKTGLRLRKVDQGLFVQLVQANTPA SLVGLRFGDQLLQIDGRDCAGWSSHKAHQWKKASGD KIVVVVRDRPFQRTVTM | 220 |
| SITAC 18 | 8886071 | 2 | PFQRTVTMHKDSMGHVGFVIKKGKIVSLVKGSSAARN GLLTNHYVCEVDGQNVIGLKDKKIMEILATAGNVVTLTII PSVIYEHIVEFIV | 221 |
| SNPC IIa | 20809633 | 1 | SLERPRFCLLSKEEGKSFGFHLQQELGRAGHVVCRVD PGTSAQRQGLQEGDRILAVNNDVVEHEDYAVVVRRIR ASSPRVLLTVLARHAHDVARAQ | 222 |
| SYNTENIN | 2795862 | 2 | LRDRPFERTITMHKDSTGHVGFIFKNGKITSIVKDSSAA RNGLLTEHNICEINGQNVIGLKDSQIADILSTSGTVVTITI MPAFIFEHMNSS | 223 |
| SYNTENIN | 2795862 | 1 | LEIKQGIREVILCKDQDGKIGLRLRKSIDNGIFVQLVQANS PASLVGLRFGDQVLQINGENCAGWSSDKAHKVLKQAF GEKITMRIHRD | 224 |
| Syntrophin 1 alpha | 1145727 | 1 | QRRRVTVRKADAGGLGISIKGGRENKMPILISKIFKGLA ADQTEALFVGDAILSVNGEDLSSATHDEAVQVLKKTGK EVVLEVKYMKDVSPYFK | 225 |
| Syntrophin beta 2 | 476700 | 1 | PVRRRVVVKQEAGGLGISIKGGRENRMPILISKIFPGLA ADQSRALRLGDAILSVNGTDLRQATHDQAVQALKRAG KEVLLEVKFIRE | 226 |
| Syntrophin gamma 1 | 9507162 | 1 | EPFYSGERTVTIRRQTVGGFGLSIKGGAEHNIPVVVSKI SKEQRAELSGLLFIGDAILQINGINVRKCRHEEVVQVLR NAGEEVTLTVSFLKRAPAFLKL | 227 |
| Syntrophin gamma 2 | 9507164 | 1 | SHQGRNRRTVTLRRQPVGGLGLSIKGGSEHNVPVVISK IFEDQAADQTGMLFVGDAVLQVNGIHVENATHEEVVHL LRNAGDEVTITVEYLREAPAFLK | 228 |
| TAX2-like protein | 3253116 | 1 | RGETKEVEVTKTEDALGLTITDNGAGYAFIKRIKEGSIIN RIEAVCVGDSIEAINDHSIVGCRHYEVAKMLRELPKSQP FTLRLVQPKRAF | 229 |
| TIAM1 | 4507500 | 1 | HSIHIEKSDTAADTYGFSLSSVEEDGIRRLYVNSVKETG LASKKGLKAGDEILEINNRAADALNSSMLKDFLSQPSLG LLVRTYPELE | 230 |
| TIAM2 | 6912703 | 1 | PLNVYDVQLTKTGSVCDFGFAVTAQVDERQHLSRIFIS DVLPDGLAYGEGLRKGNEIMTLNGEAVSDLDLKQMEAL FSEKSVGLTLIARPPDTKATL | 231 |
| TIP1 | 2613001 | 1 | QRVEIHKLRQGENLILGFSIGGGIDQDPSQNPFSEDKTD KGIYVTRVSEGGPAEIAGLQIGDKIMQVNGWDMTMVTH DQARKRLTKRSEEVVRLLVTRQSLQK | 232 |
| TIP2 | 2613003 | 1 | RKEVEVFKSEDALGLTITDNGAGYAFIKRIKEGSIVDIHH LISVGDMIEAINGQSLLGCRHYEVARLLKELPRGRTFTL KLTEPRK | 233 |
| TIP33 | 2613007 | 1 | HSHPRWELPKTDEGLGFNVMGGKEQNSPIYISRIIPGG VAERHGGLKRGDQLLSVNGVSVEGEHHEKAVELLKAA KDSVKLVVRYTPKVL | 234 |
| TIP43 | 2613011 | 1 | LSNQKRGVKVLKQELGGLGISIKGGKENKMPILISKIFKG LAADQTQALYVGDAILSVNGADLRDATHDEAVQALKRA GKEVLLEVKYMREATPYVK | 235 |

TABLE 5-continued

Sequences of PDZ Domains Cloned to Produce GST-PDZ Fusions

| Gene Name | GI or Acc. | Domain # | Sequence fused to GST Construct | SEQ ID NO: |
|---|---|---|---|---|
| Unknown PDZ | 22382223 | 1 | IQRSSIKTVELIKGNLQSVGLTLRLVQSTDGYAGHVIIET VAPNSPAAIADLQRGDRLIAIGGVKITSTLQVLKLIKQAG DRVLVYYERPVGQSNQGA | 236 |
| Vartul | 1469875 | 1 | ILTLTILRQTGGLGISIAGGKGSTPYKGDDEGIFISRVSEE GPAARAGVRVGDKLLEVNGVALQGAEHHEAVEALRGA GTAVQMRVWRERMVEPENAEFIVTD | 237 |
| Vartul | 1469875 | 4 | RELCIQKAPGERLGISIRGGARGHAGNPRDPTDEGIFIS KVSPTGAAGRDGRLRVGLRLLEVNQQSLLGLTHGEAV QLLRSVGDTLTVLVCDGFEASTDAALEVS | 238 |
| Vartul | 1469875 | 3 | LEGPYPVEEIRLPRAGGPLGLSIVGGSDHSSHPFGVQE PGVFISKVLPRGLAARSGLRVGDRILAVNGQDVRDATH QEAVSALLRPCLELSLLVRRDPAEFIVTD | 239 |
| Vartul | 1469875 | 2 | PLRQRHVACLARSERGLGFSIAGGKGSTPYRAGDAGIF VSRIAEGGAAHRAGTLQVGDRVLSINGVDVTEARHDHA VSLLTAASPTIALLLEREAGG | 240 |
| Vartul | 1469875 | 1,2 | TLTILRQTGGLGISIAGGKGSTPYKGDDEGIFISRVSEEG PAARAGVRVGDKLLEGIFVSRIAEGGAAHRAGTLQVGD RVLSINGVDVTEARHDHAVSLLTAASPTIALLLERE | 241 |
| X-11 beta | 3005559 | 2 | IPPVTTVLIKRPDLKYQLGFSVQNGIICSLMRGGIAERGG VRVGHRIIEINGQSWATAHEKIVQALSNSVGEIHMKTM PAAMFRLLTGQENSSL | 242 |
| X-11 beta | 3005559 | 1 | IHFSNSENCKELQLEKHKGEILGVVVVESGWGSILPTVI LANMMNGGPAARSGKLSIGDQIMSINGTSLVGLPLATC OGIIKGLKNQTQVKLNIVSCPPVTTVLIKRNSS | 243 |
| ZO-1 | 292937 | 1 | IWEQHTVTLHRAPGFGFGIAISGGRDNPHFQSGETSIVI SDVLKGGPAEGQLQENDRVAMVNGVSMDNVEHAFAV QQLRKSGKNAKITIRRKKKVQIPNSS | 244 |
| ZO-1 | 292937 | 2 | ISSQPAKPTKVTLVKSRKNEEYGLRLASHIFVKEISQDSL AARDGNIQEGDWLKINGTVTENMSLTDAKTLIERSKGK LKMVVQRDRATLLNSS | 245 |
| ZO-1 | 292937 | 3 | IRMKLVKFRKGDSVGLRLAGGNDVGIFVAGVLEDSPAA KEGLEEGDQILRVNNVDFTNIIREEAVLFLLDLPKGEEVT ILAQKKKDVFSN | 246 |
| ZO-2 | 12734763 | 1 | IQHTVTLHRAPGFGFGIAISGGRDNPHFQSGETSIVISD VLKGGPAEGQLQENDRVAMVNGVSMDNVEHAFAVQQ LRKSGKNAKITIRRKKKVQIPNSS | 247 |
| ZO-2 | 12734763 | 3 | HAPNTKMVRFKKGDSVGLRLAGGNDVGIFVAGIQEGT SAEQEGLQEGDQILKVNTQDFRGLVREDAVLYLLEIPK GEMVTILAQSRADVY | 248 |
| ZO-2 | 12734763 | 2 | RVLLMKSRANEEYGLRLGSQIFVKEMTRTGLATKDGNL HEGDIILKINGTVTENMSLTDARKLIEKSRGKLQLVVLRD S | 249 |
| ZO-3 | 10092690 | 3 | RGYSPDTRWRFLKGKSIGLRLAGGNDVGIFVSGVQAG SPADGQGIQEGDQILQVNDVPFQNLTREEAVQFLLGLP PGEEMELVTQRKQDIFWKMVQSEFIVTD | 250 |
| ZO-3 | 10092690 | 1 | IPGNSTIWEQHTATLSKDPRRGFGIAISGGRDRPGGSM VVSDVVPGGPAEGRLQTGOHIVMVNGVSMENATSAFA IQILKTCTKMANITVKRPRRIHLPAEFIVTD | 251 |
| ZO-3 | 10092690 | 2 | QDVQMKPVKSVLVKRRDSEEFGVKLGSQIFIKHITDSGL AARHRGLQEGDLILQINGVSSQNLSLNDTRRLIEKSEGK LSLLVLRDRGQFLVNIPNSS | 252 |

*: No GI number for this PDZ domain containing protein. It was computer cloned at Arbor Vita Corporation using rat Shank3 seq against human genomic clone AC000036. In silico spliced together nt6400-6496, 6985-7109, 7211-7400 to create hypothetical human Shank3.

As discussed in detail herein, the PDZ proteins listed in TABLE 5 are naturally occurring proteins containing a PDZ domain. Thus, one aspect of the present invention is directed to the detection and modulation of interactions between a PDZ protein and PL protein pair listed in TABLE 6 or 7 or 8. As used herein the phrase "protein pair" or "protein binding pair" when used in reference to a PDZ protein and PL protein refers to a PL protein and PDZ protein such as those listed in TABLES 6 or 7 or 8 which bind to one another. It should be understood that TABLES 6, 7, and 8 are set up to show that certain PL proteins bind to a plurality of PDZ proteins.

The interactions like those summarized in TABLES 6, 7, and 8 can occur in a wide variety of cell types. Examples of such cells include neuronal, hematopoietic, stem, muscle, epidermal, epithelial, endothelial, and cells from essentially any tissue such as liver, lung, placenta, uterus, kidney, ovaries, testes, stomach, colon and intestine. Because the interactions disclosed herein can occur in such a wide variety of cell types, these interactions can also play an important role in a variety of biological functions.

Thus, for example, in certain embodiments of the invention, the PL proteins and/or the PDZ protein to which it binds are expressed in the nervous system (e.g., neurons). In an embodiment, the PL proteins of the invention bind a PDZ protein that is expressed in neurons. In various embodiments, the PL protein is highly expressed in neuronal cells. In still other instances the PL proteins and/or the PDZ protein to which it binds are expressed in non-neural cells (e.g., in hematopoietic cells).

In various embodiments of the invention, the PL protein is expressed or up-regulated upon cell activation (e.g., in stimulated neurons), upon entry into mitosis (e.g., up-regulation in rapidly proliferating cell populations), or in association with cell death.

A. Detection of PDZ Domain-Containing Proteins

As noted supra, the present inventors have identified a number of PDZ protein and NMDAR PL protein interactions and a number of PDZ protein and TRP PL protein interactions that can play a role in modulation of a number of biological functions in a variety of cell types. A comprehensive list of PDZ domain-containing proteins was retrieved from the Sanger Centre database (Pfam) searching for the keyword, "PDZ". The corresponding cDNA sequences were retrieved from GenBank using the NCBI "entrez" database (hereinafter, "GenBank PDZ protein cDNA sequences"). The DNA portion encoding PDZ domains was identified by alignment of cDNA and protein sequence using CLUSTALW. Based on the DNA/protein alignment information, primers encompassing the PDZ domains were designed. The expression of certain PDZ-containing proteins in cells was detected by polymerase chain reaction ("PCR") amplification of cDNAs obtained by reverse transcription ("RT") of cell-derived RNA (i.e., "RT-PCR"). PCR, RT-PCR and other methods for analysis and manipulation of nucleic acids are well known and are described generally in Sambrook et al., (1989) Molecular Cloning: A Laboratory Manual, 2nd Ed., Vols. 1-3, Cold Spring Harbor Laboratory hereinafter, "Sambrook"); and Ausubel et al., Current Protocols in Molecular Biology, Greene Publishing and Wiley-Interscience, New York (1997), as supplemented through January 1999 (hereinafter "Ausubel").

Samples of cDNA for those sequences identified through the foregoing search were obtained and then amplified. In general a sample of the cDNA (typically, ⅕ of a 20 µl reaction) was used to conduct PCR. PCR was conducted using primers designed to amplify specifically PDZ domain-containing regions of PDZ proteins of interest. Oligonucleotide primers were designed to amplify one or more PDZ-encoding domains. The DNA sequences encoding the various PDZ domains of interest were identified by inspection (i.e., conceptual translation of the PDZ protein cDNA sequences obtained from GenBank, followed by alignment with the PDZ domain amino acid sequence). TABLE 5 shows the PDZ-encoded domains amplified, and the GenBank accession number of the polynucleotides encoding the PDZ-domain containing proteins. To facilitate subsequent cloning of PDZ domains, the PCR primers included endonuclease restriction sequences at their ends to allow ligation with pGEX-3X cloning vector (Pharmacia, GenBank XXI13852) in frame with glutathione-S transferase (GST). TABLE 5 lists the proteins isolated for use in the aforementioned assays.

B. Production of Fusion Proteins Containing PDZ-Domains

GST-PDZ domain fusion proteins were prepared for use in the assays of the invention. PCR products containing PDZ encoding domains (as described supra) were subcloned into an expression vector to permit expression of fusion proteins containing a PDZ domain and a heterologous domain (i.e., a glutathione-S transferase sequence, "GST"). PCR products (i.e., DNA fragments) representing PDZ domain encoding DNA was extracted from agarose gels using the "sephaglas" gel extraction system (Pharmacia) according to the manufacturer's recommendations.

As noted supra, PCR primers were designed to include endonuclease restriction sites to facilitate ligation of PCR fragments into a GST gene fusion vector (pGEX-3X; Pharmacia, GenBank accession # XXU13852) in-frame with the glutathione-S transferase coding sequence. This vector contains a IPTG inducible lacZ promoter. The pGEX-3X vector was linearized using Bam HI and Eco RI or, in some cases, Eco RI or Sma I, and dephosphorylated. For most cloning approaches, double digestion with Bam HI and Eco RI was performed, so that the ends of the PCR fragments to clone were Bam HI and Eco RI. In some cases, restriction endonuclease combinations used were Bgl II and Eco RI, Bam HI and Mfe I, or Eco RI only, Sma I only, or BamHI only. When more than one PDZ domain was cloned, the DNA portion cloned represents the PDZ domains and the cDNA portion located between individual domains. DNA linker sequences between the GST portion and the PDZ domain containing DNA portion vary slightly, dependent on which of the above described cloning sites and approaches were used. As a consequence, the amino acid sequence of the GST-PDZ fusion protein varies in the linker region between GST and PDZ domain. Protein linker sequences corresponding to different cloning sites/approaches are shown below. Linker sequences (vector DNA encoded) are bold, PDZ domain containing gene derived sequences are in italics.

```
1)    GST-BamHI/BamHI-PDZ domain insert
      Gly-Ile-PDZ domain insert

2)    GST-BamHI/BglII-PDZ domain insert
      Gly-Ile-PDZ domain insert
```

-continued

```
                                       (SEQ ID NO: 253)
3)   GST-EcoRI/EcoI-PDZ domain insert
     Gly-Ile-Pro-Gly-Asn-PDZ domain insert 4)   GST-SmaI/SmaI-PDZ domain insert
     Gly-Ile-Pro-PDZ domain insert
```

The PDZ-encoding PCR fragment and linearized pGEX-3X vector were ethanol precipitated and resuspended in 10 μl standard ligation buffer. Ligation was performed for 4-10 hours at 7° C. using T4 DNA ligase. It will be understood that some of the resulting constructs include very short linker sequences and that, when multiple PDZ domains were cloned, the constructs included some DNA located between individual PDZ domains.

The ligation products were transformed in DH5α or BL-21 E. coli bacteria strains. Colonies were screened for presence and identity of the cloned PDZ domain containing DNA as well as for correct fusion with the glutathione S-transferase encoding DNA portion by PCR and by sequence analysis. Positive clones were tested in a small scale assay for expression of the GST/PDZ domain fusion protein and, if expressing, these clones were subsequently grown up for large scale preparations of GST/PDZ fusion protein.

GST-PDZ domain fusion protein was overexpressed following addition of IPTG to the culture medium and purified. Detailed procedure of small scale and large scale fusion protein expression and purification are described in "GST Gene Fusion System" (second edition, revision 2; published by Pharmacia). In brief, a small culture (3-5 ml) containing a bacterial strain (DH5α, BL21 or JM109) with the fusion protein construct was grown overnight in LB-media at 37° C. with the appropriate antibiotic selection (100 μg/ml ampicillin; a.k.a. LB-amp). The overnight culture was poured into a fresh preparation of LB-amp (typically 250-500 ml) and grown until the optical density (OD) of the culture was between 0.5 and 0.9 (approximately 2.5 hours). IPTG (isopropyl β-D-thiogalactopyranoside) was added to a final concentration of 1.0 mM to induce production of GST fusion protein, and culture was grown an additional 1.5-2.5 hours. Bacteria were collect by centrifugation (4500 g) and resuspended in Buffer A-(50 mM Tris, pH 8.0, 50 mM dextrose, 1 mM EDTA, 200 μM phenylmethylsulfonylfluoride). An equal volume of Buffer A+ (Buffer A-, 4 mg/ml lysozyme) was added and incubated on ice for 3 min to lyse bacteria. An equal volume of Buffer B (10 mM Tris, pH 8.0, 50 mM KCl, 1 mM EDTA, 0.5% Tween-20, 0.5% NP40 (a.k.a. IGEPAL CA-630), 200 μM phenylmethylsulfonylfluoride) was added and incubated for an additional 20 minutes. The bacterial cell lysate was centrifuged (×20,000 g), and supernatant was added to glutathione SEPHAROSE 4B beads (Pharmacia, Cat. # 17-0765-01) previously swelled (rehydrated) in 1× phosphate-buffered saline (PBS). The supernatant-glutathione SEPHAROSE bead slurry was poured into a column and washed with at least 20 bed volumes of 1×PBS. GST fusion protein was eluted off the glutathione SEPHAROSE beads by applying 0.5-1.0 ml aliquots of 5 mM glutathione and collected as separate fractions. Concentrations of fractions were determined using BioRad Protein Assay (Cat. #500-0006) according to manufacturer's specifications. Those fractions containing the highest concentration of fusion protein were pooled and dialyzed against 1×PBS/35% glycerol. Fusion proteins were assayed for size and quality by SDS gel electrophoresis (PAGE) as described in "Sambrook." Fusion protein aliquots were stored at minus 80° C. and at minus 20° C.

C. Classification of PDZ Domain-Containing Proteins

The PDZ proteins identified herein as interacting with particular PL proteins can be grouped into a number of different categories. Thus, as described in greater detail below, the methods and reagents that are provided herein can be utilized to modulate PDZ interactions, and thus biological functions, that are regulated or otherwise involve the following classes of proteins. It should be recognized, however, that modulation of the interactions that are identified herein can be utilized to affect biological functions involving other protein classes.

1) Protein Kinases

A number of protein kinases contain PDZ domains. Protein kinases are widely involved in cellular metabolism and regulation of protein activity through phosphorylation of amino acids on proteins. An example of this is the regulation of signal transduction pathways such as T cell activation through the T cell Receptor, where ZAP-70 kinase function is required for transmission of the activation signal to downstream effector molecules. These molecules include, but are not limited to KIAA0303, KIAA0561, KIAA0807, KIAA0973, and CASK.

2) Guanalyte Kinases

A number of guanalyte kinases contain PDZ domains. These molecules include, but are not limited to Atrophin 1, CARD11, CARD14, DLG1, DLG2, DLG5, FLJ12615, MPP1, MPP2, NeDLG, p55T, PSD95, ZO-1, ZO-2, and ZO-3.

3) Guanine Exchange Factors

A number of guanine exchange factors contain PDZ domains. Guanine exchange factors regulate signal transduction pathways and other biological processes through facilitating the exchange of differently phosphorylated guanine residues. These molecules include, but are not limited to GTPase, Guanine Exchange, KIAA0313, KIAA0380, KIAA0382, KIAA1389, KIAA1415, TIAM1, and TIAM2.

4) LIM PDZ's

A number of LIM proteins contain PDZ domains. These molecules include, but are not limited to α-Actinin 2, ELFIN1, ENIGMA, HEMBA 1003117, KIAA0613, KIAA0858, KIAA0631, LIM Mystique, LIM protein, LIMRIL, LIMK1, LIMK2, and LU-1.

5) Proteins Containing Only PDZ Domains

A number of proteins contain PDZ domains without any other predicted functional domains. These include, but are not limited to 26s subunit p27, AIPC, Cytohesion Binding Protein, EZRIN Binding Protein, FLJ00011, FLJ20075, FLJ21687, GRIP1, HEMBA1000505, KIAA0545, KIAA0967, KIAA1202, KIAA1284, KIAA1526, KIAA1620, KIAA1719, MAGI1, Novel PDZ gene, Outer Membrane, PAR3, PAR6, PAR6γ, PDZ-73, PDZK1, PICK1, PIST, prIL16, Shank1, SIP1, SITAC-18, Syntenin, Syntrophin γ2, TIP1, TIP2, and TIP43.

6) Tyrosine Phosphatases

A number of tyrosine phosphatases contain PDZ domains. Tyrosine phosphatases regulate biological processes such as signal transduction pathways through removal of phosphate groups required for function of the target protein. Examples of such enzymes include, but are not limited to PTN-3, PTN-4, and PTPL1.

7) Serine Proteases

A number of serine proteases contain PDZ domains. Proteases affect biological molecules by cleaving them to either activate or repress their functional ability. These enzymes have a variety of functions, including roles in digestion, blood coagulation and lysis of blood clots. These include, but are not limited to Novel Serine Protease and Serine Protease.

8) Viral Oncogene Interacting Proteins that Contain PDZ Domains

A number of TAX interacting proteins contain PDZ domains. Many of these also bind to multiple viral oncoproteins such as Adenovirus E4, Papillomavirus E6, and HBV protein X. These TAX interacting proteins include, but are not limited to AIPC, Connector Enhancer, DLG1, DLG2, ERBIN, FLJ00011, FLJ11215, HEMBA1003117, INADL, KIAA0147, KIAA0807, KIAA1526, KIAA1634, LIMK1, LIM Mystique, LIM-RIL, MUPP1, NeDLG, Outer Membrane, PSD95, PTN-4, PTPL-1, Syntrophin γ1, Syntrophin γ2, TAX2-like protein, TIP2, TIP1, TIP33, and TIP43.

9) Other PDZ-Domain Containing Proteins

A number of proteins containing RA and/or RHA and/or DIL and/or IGFBP and/or WW and/or L27 and/or SAM and/or PH and/or DIX and/or DIP and/or Dishevelled and/or LRR and/or Hormone 3 and/or C2 and/or RPH3A and/or zf-TRAF and/or zf-C3HC4 and/or PID and/or NO_Synthase and/or Flavodoxin and/or FAD binding and/or NAD binding and/or Kazal and/or Trypsin and/or RBD and/or RGS and/or GoLoco and/or HR1 and/or BR01 domains contain PDZ domains. These include, but are not limited to AF6, APXL-1, MAGI1, DVL1, DVL2, DVL3, KIAA0417, KIAA0316, KIAA0340, KIAA0559, KIAA0751, KIAA0902, KIAA1095, KIAA1222, KIAA1634, MINT1, NOS1, RGS12, Rhophilin-like, Shank 3, Syntrophin 1α, Syntrophin β2, and X11β.

D. Assays for Detection of Interactions Between PDZ-Domain Polypeptides and TRP PL Proteins and TRP Associated Proteins Two complementary assays, termed A and G, were developed to detect binding between a PDZ-domain polypeptide and candidate PDZ ligand. In each of the two different assays, binding is detected between a peptide having a sequence corresponding to the C-terminus of a protein anticipated to bind to one or more PDZ domains (i.e. a candidate PL peptide) and a PDZ-domain polypeptide (typically a fusion protein containing a PDZ domain). In the A assay, the candidate PL peptide is immobilized and binding of a soluble PDZ-domain polypeptide to the immobilized peptide is detected (the A assay is named for the fact that in one embodiment an avidin surface is used to immobilize the peptide). In the G assay, the PDZ-domain polypeptide is immobilized and binding of a soluble PL peptide is detected (The G assay is named for the fact that in one embodiment a GST-binding surface is used to immobilize the PDZ-domain polypeptide). Preferred embodiments of these assays are described in detail infra. However, it will be appreciated by ordinarily skilled practitioners that these assays can be modified in numerous ways while remaining useful for the purposes of the present invention.

1) A Assay Detection of PDZ-Ligand Binding Using Immobilized PL Peptide.

In one aspect, the invention provides an assay in which biotinylated candidate PL peptides are immobilized on an avidin coated surface. The binding of PDZ-domain fusion protein to this surface is then measured. In a preferred embodiment, the PDZ-domain fusion protein is a GST/PDZ fusion protein and the assay is carried out as follows:

(1) Avidin is bound to a surface, e.g. a protein binding surface. In one embodiment, avidin is bound to a polystyrene 96 well plate (e.g., Nunc Polysorb (Cat. #475094) by addition of 100 μl per well of 20 μg/ml of avidin (Pierce) in phosphate buffered saline without calcium and magnesium, pH 7.4 ("PBS", GibcoBRL) at 4° C. for 12 hours. The plate is then treated to block nonspecific interactions by addition of 200 μl per well of PBS containing 2 g per 100 ml protease-free bovine serum albumin ("PBS/BSA") for 2 hours at 4° C. The plate is then washed 3 times with PBS by repeatedly adding 200 μl per well of PBS to each well of the, plate and then dumping the contents of the plate into a waste container and tapping the plate gently on a dry surface.

(2) Biotinylated PL peptides (or candidate PL peptides, e.g. see TABLE 2 and TABLE 4) are immobilized on the surface of wells of the plate by addition of 50 μl per well of 0.4 μM peptide in PBS/BSA for 30 minutes at 4° C. Usually, each different peptide is added to at least eight different wells so that multiple measurements (e.g. duplicates and also measurements using different (GST/PDZ-domain fusion proteins and a GST alone negative control) can be made, and also additional negative control wells are prepared in which no peptide is immobilized. Following immobilization of the PL peptide on the surface, the plate is washed 3 times with PBS.

(3) GST/PDZ-domain fusion protein (prepared as described supra) is allowed to react with the surface by addition of 50 μl per well of a solution containing 5 μg/ml GST/PDZ-domain fusion protein in PBS/BSA for 2 hours at 4° C. As a negative control, GST alone (i.e. not a fusion protein) is added to specified wells, generally at least 2 wells (i.e. duplicate measurements) for each immobilized peptide. After the 2 hour reaction, the plate is washed 3 times with PBS to remove unbound fusion protein.

(4) The binding of the GST/PDZ-domain fusion protein to the avidin-biotinylated peptide surface can be detected using a variety of methods, and detectors known in the art. In one embodiment, 50 μl per well of an anti-GST antibody in PBS/BSA (e.g. 2.5 μg/ml of polyclonal goat-anti-GST antibody, Pierce) is added to the plate and allowed to react for 20 minutes at 4° C. The plate is washed 3 times with PBS and a second, detectably labeled antibody is added. In one embodiment, 50 μl per well of 2.5 μg/ml of horseradish peroxidase (HRP)-conjugated polyclonal rabbit anti-goat immunoglobulin antibody is added to the plate and allowed to react for 20 minutes at 4° C. The plate is washed 5 times with 50 mM Tris pH 8.0 containing 0.2% Tween 20, and developed by addition of 100 μl per well of HRP-substrate solution (TMB, Dako) for 20 minutes at room temperature (RT). The reaction of the HRP and its substrate is terminated by the addition of 100 μl per well of 1 M sulfuric acid and the optical density (O.D.) of each well of the plate is read at 450 nm.

(5) Specific binding of a PL peptide and a PDZ-domain polypeptide is detected by comparing the signal from the well(s) in which the PL peptide and PDZ domain polypeptide are combined with the background signal(s). The background signal is the signal found in the negative controls. Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g. a T-test) comparing repeated measurements of the signal with repeated measurements of the background will result in a p-value <0.05, more typically a p-value <0.01, and most typically a p-value <0.001 or less.

As noted, in an embodiment of the A assay, the signal from binding of a GST/PDZ-domain fusion protein to an avidin surface not exposed to (i.e. not covered with) the PL peptide is one suitable negative control (sometimes referred to as B1).

The signal from binding of GST polypeptide alone (i.e. not a fusion protein) to an avidin-coated surface that has been exposed to (i.e. covered with) the PL peptide is a second suitable negative control (sometimes referred to as B2. Because all measurements are done in multiples (i.e. at least duplicate) the arithmetic mean (or, equivalently, average) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the plate-bound PL peptide is determined by comparing the mean signal ("mean S") and standard error of the signal ("SE") for a particular PL-PDZ combination with the mean B1 and/or mean B2.

2) G Assay-Detection of PDZ-Ligand Binding Using Immobilized PDZ-Domain Fusion Polypeptide In one aspect, the invention provides an assay in which a GST/PDZ fusion protein is immobilized on a surface (G assay). The binding of labeled PL peptide (e.g., as listed in TABLE 2 and TABLE 4) to this surface is then measured. In a preferred embodiment, the assay is carried out as follows:

(1) A PDZ-domain polypeptide is bound to a surface, e.g. a protein binding surface. In a preferred embodiment, a GST/PDZ fusion protein containing one or more PDZ domains is bound to a polystyrene 96-well plate. The GST/PDZ fusion protein can be bound to the plate by any of a variety of standard methods known to one of skill in the art, although some care must be taken that the process of binding the fusion protein to the plate does not alter the ligand-binding properties of the PDZ domain. In one embodiment, the GST/PDZ fusion protein is bound via an anti-GST antibody that is coated onto the 96-well plate. Adequate binding to the plate can be achieved when:

a. 100 μl per well of 5 μg/ml goat anti-GST polyclonal antibody (Pierce) in PBS is added to a polystyrene 96-well plate (e.g., Nunc Polysorp) at 4° C. for 12 hours.
b. The plate is blocked by addition of 200 μl per well of PBS/BSA for 2 hours at 4° C.
c. The plate is washed 3 times with PBS.
d. 50 μl per well of 5 μg/ml GST/PDZ fusion protein) or, as a negative control, GST polypeptide alone (i.e. not a fusion protein) in PBS/BSA is added to the plate for 2 hours at 4° C.
e. the plate is again washed 3 times with PBS.

(2) Biotinylated PL peptides are allowed to react with the surface by addition of 50 μl per well of 20 μM solution of the biotinylated peptide in PBS/BSA for 10 minutes at 4° C., followed by an additional 20 minute incubation at 25° C. The plate is washed 3 times with ice cold PBS.

(3) The binding of the biotinylated peptide to the GST/PDZ fusion protein surface can be detected using a variety of methods and detectors known to one of skill in the art. In one embodiment, 100 μl per well of 0.5 μg/ml streptavidin-horseradish peroxidase (HRP) conjugate dissolved in BSA/PBS is added and allowed to react for 20 minutes at 4° C. The plate is then washed 5 times with 50 mM Tris pH 8.0 containing 0.2% Tween 20, and developed by addition of 100 μl per well of HRP-substrate solution (TMB, Dako) for 20 minutes at room temperature (RT). The reaction of the HRP and its substrate is terminated by addition of 100 μl per well of 1 M sulfuric acid, and the optical density (O.D.) of each well of the plate is read at 450 um.

(4) Specific binding of a PL peptide and a PDZ domain polypeptide is determined by comparing the signal from the well(s) in which the PL peptide and PDZ domain polypeptide are combined, with the background signal(s). The background signal is the signal found in the negative control(s). Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g. a T-test) comparing repeated measurements of the signal with repeated measurements of the background will result in a p-value <0.05, more typically a p-value <0.01, and most typically a p-value <0.001 or less. As noted, in an embodiment of the G assay, the signal from binding of a given PL peptide to immobilized (surface bound) GST polypeptide alone is one suitable negative control (sometimes referred to as B1). Because all measurement are done in multiples (i.e. at least duplicate) the arithmetic mean (or, equivalently, average.) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the platebound peptide is determined by comparing the mean signal ("mean S") and standard error of the signal ("SE") for a particular PL-PDZ combination with the mean B1.

I) G1 Assay, G2 Assay, and G3 Assay

Three specific modifications of the specific conditions described supra for the G assay are particularly useful. The modified assays use lesser quantities of labeled PL peptide and have slightly different biochemical requirements for detection of PDZ-ligand binding compared to the specific assay conditions described supra. For convenience, the assay conditions described in this section are referred to as the G1 assay, the G2 assay, and the G3 assay, with the specific conditions described in the preceding section on G assays being referred to as the G0 assay. The G1 assay is identical to the G0 assay except at step (2) the peptide concentration is 10 μM instead of 20 μM. This results in slightly lower sensitivity for detection of interactions with low affinity and/or rapid dissociation rate. Correspondingly, it slightly increases the certainty that detected interactions are of sufficient affinity and half-life to be of biological importance and useful therapeutic targets.

The G2 assay is identical to the G0 assay except that at step (2) the peptide concentration is 1 μM instead of 20 μM and the incubation is performed for 60 minutes at 25° C. (rather than, e.g., 10 minutes at 4° C. followed by 20 minutes at 25° C.). This results in lower sensitivity for interactions of low affinity, rapid dissociation rate, and/or affinity that is less at 25° C. than at 4° C. Interactions will have lower affinity at 25° C. than at 4° C. if (as have found to be generally true for PDZ-ligand binding) the reaction entropy is negative (i.e. the entropy of the products is less than the entropy of the reactants). In contrast, the PDZ-PL binding signal may be similar in the G2 assay and the G0 assay for interactions of slow association and dissociation rate, as the PDZ-PL complex will accumulate during the longer incubation of the "G" assay." Thus comparison of results of the G2 assay and the G0 assay can be used to estimate the relative entropies, enthalpies, and kinetics of different PDZ-PL interactions. (Entropies and enthalpies are related to binding affinity by the equations delta G=RT ln(Kd)=delta H−T delta S where delta G, H, and S are the reaction free energy, enthalpy, and entropy respectively, T is the temperature in degrees Kelvin, R is the gas constant, and Kd is the equilibrium dissociation constant). In particular, interactions that are detected only or much more strongly in the G0 assay generally have a rapid dissociation rate at 25° C. ($t_{1/2}$<10 minutes) and a negative reaction entropy, while interactions that are detected similarly strongly in the "G" assay" generally have a slower dissociation rate at 25° C. ($t_{1/2}$>10 minutes). Rough estimation of the thermodynamics and kinetics of PDZ-PL interactions (as can be achieved via comparison of results of the G0 assay versus the G2 assay as outlined supra) can be used in the design of efficient inhibitors of the interactions. For example, a small molecule inhibitor based on the chemical structure of a PL that dissociates slowly from a given PDZ domain (as evidenced by similar binding in the G2 assay as in the G0 assay) may itself dissociate slowly and thus be of high affinity.

The G3 assay is identical to the G0 assay with the following exceptions. The peptides are typically present at 0.1 µM rather than 20 µM. The peptides are also pre-incubated with the HRP-streptavidin prior to adding to the assay plate. In the G0 assay, free peptide is incubated with the PDZ proteins prior to the addition of the HRP-streptavidin. Thus, for the G0 assay one can lose signal if the bound peptide dissociates from the PDZ protein prior to the addition of the HRP-streptavidin. In the G3 modified assay the HRP-streptavidin/peptide complex is added to the plate in one step, thus increasing the likelihood that all the bound peptide will be bound to HRP-streptavidin. The G3 modified assay increases the chance of observing weak interaactions.

In this manner, variation of the temperature and duration of step (2) of the G assay can be used to provide insight into the kinetics and thermodynamics of the PDZ-ligand binding reaction and into design of inhibitors of the reaction.

With any of the assays, peptides should be titrated to find the optimal concentration for which the signal to noise ratio is in the appropriate range over the entire collection of PDZ domains tested.

3) Assay Variations

As discussed supra, it will be appreciated that many of the steps in the above-described assays can be varied, for example, various substrates can be used for binding the PL and PDZ-containing proteins; different types of PDZ containing fusion proteins can be used; different labels for detecting PDZ/PL interactions can be employed; and different ways of detection can be used.

The PL protein used in the assay is not intended to be limited to a 20 amino acid peptide. Full length or partial protein may be used, either alone or as a fusion protein. For example, a GST-PL protein fusion may be bound to the anti-GST antibody, with PDZ protein added to the bound PL protein or peptide.

The PDZ-PL detection assays can employ a variety of surfaces to bind the PL and PDZ-containing proteins. For example, a surface can be an "assay plate" which is formed from a material (e.g. polystyrene) which optimizes adherence of either the PL protein or PDZ-containing protein thereto. Generally, the individual wells of the assay plate will have a high surface area to volume ratio and therefore a suitable shape is a flat bottom well (where the proteins of the assays are adherent). Other surfaces include, but are not limited to, polystyrene or glass beads, polystyrene or glass slides, and the like.

For example, the assay plate can be a multiwell plate. The term multiwell plate when used herein refers to a multiwell assay plate, e.g., having between about 30 to 200 individual wells, usually 96 wells. Alternatively, high density arrays can be used. Often, the individual wells of the multiwell plate will hold a maximum volume of about 250 µl. Conveniently, the assay plate is a 96 well polystyrene plate (such as that sold by Becton Dickinson Labware, Lincoln Park, N.J.), which allows for automation and high throughput screening. Other surfaces include polystyrene multiwell ELISA plates such as that sold by Nunc Maxisorp, Inter Med, Denmark. Often, about 50 µl to 300 µl, more preferably 100 µl to 200 µl, of an aqueous sample comprising buffers suspended therein will be added to each well of the assay plate.

The detectable labels of the invention can be any detectable compound or composition which is conjugated directly or indirectly with a molecule (such as described above). The label can be detectable by itself (e.g., radioisotope labels or fluorescent labels) or, in the case of an enzymatic label, can catalyze a chemical alteration of a substrate compound or composition which is detectable. The preferred label is an enzymatic one which catalyzes a color change of a non-radioactive color reagent.

Sometimes, the label is indirectly conjugated with the antibody. One of skill is aware of various techniques for indirect conjugation. For example, the antibody can be conjugated with biotin and any of the categories of labels mentioned above can be conjugated with avidin, or vice versa (see also A and G assay above). Biotin binds selectively to avidin and thus, the label can be conjugated with the antibody in this indirect manner. See, Ausubel, supra, for a review of techniques involving biotin-avidin conjugation and similar assays. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

Assay variations can include different washing steps. By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or HRP antibody) is removed therefrom. To reduce background noise, it is convenient to include a detergent (e.g., Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) can be required.

Various buffers can also be used in PDZ-PL detection assays. For example, various blocking buffers can be used to reduce assay background. The term "blocking buffer" refers to an aqueous, pH buffered solution containing at least one blocking compound which is able to bind to exposed surfaces of the substrate which are not coated with a PL or PDZ-containing protein. The blocking compound is normally a protein such as bovine serum albumin (BSA), gelatin, casein or milk powder and does not cross-react with any of the reagents in the assay. The block buffer is generally provided at a pH between about 7 to 7.5 and suitable buffering agents include phosphate and TRIS.

Various enzyme-substrate combinations can also be utilized in detecting PDZ-PL interactions. Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine

[OPD] or 3,3',5,5'-tetramethyl benzidine hydrochloride [TMB]) (as described above).

(ii) alkaline phosphatase (AP) with para-Nitrophenyl phosphate as chromogenic substrate.

(iii) β-D-galactosidase (β D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980, both of which are herein incorporated by reference.

Further, it will be appreciated that, although, for convenience, the present discussion primarily refers antagonists of PDZ-PL interactions, agonists of PDZ-PL interactions can be identified using the methods disclosed herein or readily apparent variations thereof.

E. Detecting PDZ-PL Interactions

The present inventors were able in part to identify the interactions summarized in TABLES 6, 7, and 8 by developing new high throughput screening assays which are described supra. Various other assay formats known in the art can be used to select ligands that are specifically reactive with a particular protein. For example, solid-phase ELISA immunoassays, immunoprecipitation, Biacore, Fluorescence Polarization (FP), Fluorescence Resonance Energy Transfer (FRET) and western blot assays can be used to identify peptides that specifically bind PDZ-domain polypeptides. As discussed supra, two different, complementary assays were developed to detect PDZ-PL interactions. In each, one binding partner of a PDZ-PL pair is immobilized, and the ability of the second binding partner to bind is determined. These assays, which are described supra, can be readily used to screen for hundreds to thousands of potential PDZ-ligand interactions in a few hours. Thus these assays can be used to identify yet more novel PDZ-PL interactions in neuronal cells. In addition, they can be used to identify antagonists of PDZ-PL interactions (see infra).

In various embodiments, fusion proteins are used in the assays and devices of the invention. Methods for constructing and expressing fusion proteins are well known. Fusion proteins generally are described in Ausubel et al., supra, Kroll et al., 1993, DNA Cell. Biol. 12:441, and Imai et al., 1997, Cell 91:521-30. Usually, the fusion protein includes a domain to facilitate immobilization of the protein to a solid substrate ("an immobilization domain"). Often, the immobilization domain includes an epitope tag (i.e., a sequence recognized by a antibody, typically a monoclonal antibody) such as polyhistidine (Bush et al, 1991, J. Biol Chem 266:13811-14), SEAP (Berger et al, 1988, Gene 66:1-10), or M1 and M2 flag (see, e.g., U.S. Pat. Nos. 5,011,912; 4,851,341; 4,703,004; 4,782,137). In an embodiment, the immobilization domain is a GST coding region. It will be recognized that, in addition to the PDZ-domain and the particular residues bound by an immobilized antibody, protein A, or otherwise contacted with the surface, the protein (e.g., fusion protein), will contain additional residues. In some embodiments these are residues naturally associated with the PDZ-domain (i.e., in a particular PDZ-protein) but they may include residues of synthetic (e.g., poly(alanine)) or heterologous origin (e.g., spacers of, e.g., between 10 and 300 residues).

PDZ domain-containing polypeptide used in the methods of the invention (e.g., PDZ fusion proteins) of the invention are typically made by (1) constructing a vector (e.g., plasmid, phage or phagemid) comprising a polynucleotide sequence encoding the desired polypeptide, (2) introducing the vector into an suitable expression system (e.g., a prokaryotic, insect, mammalian, or cell free expression system), (3) expressing the fusion protein and (4) optionally purifying the fusion protein.

In one embodiment, expression of the protein comprises inserting the coding sequence into an appropriate expression vector (i.e., a vector that contains the necessary elements for the transcription and translation of the inserted coding sequence required for the expression system employed, e.g., control elements including enhancers, promoters, transcription terminators, origins of replication, a suitable initiation codon (e.g., methionine), open reading frame, and translational regulatory signals (e.g., a ribosome binding site, a termination codon and a polyadenylation sequence. Depending on the vector system and host utilized, any number of suitable transcription and translation elements, including constitutive and inducible promoters, can be used.

The coding sequence of the fusion protein includes a PDZ domain and an immobilization domain as described elsewhere herein. Polynucleotides encoding the amino acid sequence for each domain can be obtained in a variety of ways known in the art; typically the polynucleotides are obtained by PCR amplification of cloned plasmids, cDNA libraries, and cDNA generated by reverse transcription of RNA, using primers designed based on sequences determined by the practitioner or, more often, publicly available (e.g., through GenBank). The primers include linker regions (e.g., sequences including restriction sites) to facilitate cloning and manipulation in production of the fusion construct. The polynucleotides corresponding to the PDZ and immobilization regions are joined in-frame to produce the fusion protein-encoding sequence.

The fusion proteins of the invention may be expressed as secreted proteins (e.g., by including the signal sequence encoding DNA in the fusion gene; see, e.g., Lui et al, 1993, PNAS USA, 90:8957-61) or as nonsecreted proteins.

In some embodiments, the PDZ-containing proteins are immobilized on a solid surface. The substrate to which the polypeptide is bound may in any of a variety of forms, e.g., a multiwell dish, a test tube, a dipstick, a microcentrifuge tube, a bead, a spinnable disk, and the like. Suitable materials include glass, plastic (e.g., polyethylene, PVC, polypropylene, polystyrene, and the like), protein, paper, carbohydrate, lipid monolayer or supported lipid bilayer, and other solid supports. Other materials that may be employed include ceramics, metals, metalloids, semiconductive materials, cements and the like.

In some embodiments, the fusion proteins are organized as an array. The term "array," as used herein, refers to an ordered arrangement of immobilized fusion proteins, in which particular different fusion proteins (i.e., having different PDZ domains) are located at different predetermined sites on the substrate. Because the location of particular fusion proteins on the array is known, binding at that location can be correlated with binding to the PDZ domain situated at that location. Immobilization of fusion proteins on beads (individually or in groups) is another particularly useful approach. In one embodiment, individual fusion proteins are immobilized on beads. In one embodiment, mixtures of distinguishable beads are used. Distinguishable beads are beads that can be separated from each other on the basis of a property such as size, magnetic property, color (e.g., using FACS) or affinity tag (e.g., a bead coated with protein A can be separated from a bead not coated with protein A by using IgG affinity methods). Binding to particular PDZ domain may be determined; similarly, the effect of test compounds (i.e., agonists and antagonists of binding) may be determined.

Methods for immobilizing proteins are known, and include covalent and non-covalent methods. One suitable immobilization method is antibody-mediated immobilization. According to this method, an antibody specific for the sequence of an "immobilization domain" of the PDZ-domain containing protein is itself immobilized on the substrate (e.g., by adsorption). One advantage of this approach is that a single antibody may be adhered to the substrate and used for immobilization of a number of polypeptides (sharing the same immobilization domain). For example, an immobilization domain consisting of poly-histidine (Bush et al, 1991, J. Biol Chem 266:13811-14) can be bound by an anti-histidine monoclonal antibody (R&D Systems, Minneapolis, Minn.); an immobilization domain consisting of secreted alkaline phosphatase ("SEAP") (Berger et al, 1988, Gene 66:1-10) can be bound by anti-SEAP (Sigma Chemical Company, St. Louis, Mo.); an immobilization domain consisting of a FLAG epitope can be bound by anti-FLAG. Other ligand-antiligand immobilization methods are also suitable (e.g., an immobilization domain consisting of protein A sequences (Harlow and Lane, 1988, Antibodies A Laboratory Manual, Cold Spring Harbor Laboratory; Sigma Chemical Co., St. Louis, Mo.) can be bound by IgG; and an immobilization domain consisting of streptavidin can be bound by biotin (Harlow & Lane, supra; Sigma Chemical Co., St. Louis, Mo.). In a preferred embodiment, the immobilization domain is a GST moiety, as described herein.

When antibody-mediated immobilization methods are used, glass and plastic are especially useful substrates. The substrates may be printed with a hydrophobic (e.g., Teflon) mask to form wells. Preprinted glass slides with 3, 10 and 21 wells per 14.5 cm2 slide "working area" are available from, e.g., SPI Supplies, West Chester, Pa.; also see U.S. Pat. No. 4,011,350). In certain applications, a large format (12.4 cm×8.3 cm) glass slide is printed in a 96 well format is used; this format facilitates the use of automated liquid handling equipment and utilization of 96 well format plate readers of various types (fluorescent, colorimetric, scintillation). However, higher densities may be used (e.g., more than 10 or 100 polypeptides per cm2). See, e.g., MacBeath et al, 2000, Science 289:1760-63.

Typically, antibodies are bound to substrates (e.g., glass substrates) by adsorption. Suitable adsorption conditions are well known in the art and include incubation of 0.5-50 µg/ml (e.g., 10 µg/ml) mAb in buffer (e.g., PBS, or 50 to 300 mM Tris, MOPS, HEPES, PIPES, acetate buffers, pHs 6.5 to 8, at 4° C.) to 37° C. and from 1 hr to more than 24 hours.

Proteins may be covalently bound or noncovalently attached through nonspecific bonding. If covalent bonding between the fusion protein and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

F. Results of PDZ-PL Interaction Assays

TABLE 6 shows the predicted results of assays in which specific binding will be detected between TRPM7 and PDZ proteins using the G3 assay described herein TABLE 8 shows PDZ domains demonstrated to interact with Tat-TRPM7 peptide. TABLE 7 shows PDZs that have been demonstrated to interact with PLs involved in excitotoxicity.

TABLE 6

| PDZs predicted to interact with TRPM7 |
| --- |
| TRPM7 NNOS, LIM, KIAA1095, HEMBA1003117, AIPC, KIAA1526, DVL1, DVL2, DVL3, PTPL1, ZO-1, ZO-2, ZO-3, KIAA1719, Mupp1, INADL, Shank 3, MINT1, MINT2, MAGI1, MAGI2, MAGI3, NeDLG, syntenin, PSD-95, hDLG, PAR3, MAST1, MAST2, AF6, SIP1, LIM mystique, KIAA0751, HTRA1, HTRA2, TIP-1, KIAA0316, PICK1, |

TABLE 7

| PDZs demonstrated to interact with specific PL proteins | |
| --- | --- |
| PL | PDZs that interact |
| NMDA Receptor 2s | PSD95, DLG1, DLG2, NeDLG, KIAA0973, Outermembrane Protein, syntrophin alpha 1, TIP1, TIP2, MAGI1, MAGI2, syntrophin beta 1, syntrophin gamma1, LIM-RIL, KIAA1634, KIAA0807 |
| NMDA Receptor 1s | NeDLG, DLG1, PTPL1, PSD-95, MAGI3, |
| AMPA Rs | |
| PLC beta, gamma | EBP50, |
| NNOS internal | |

TABLE 8

| PDZ domains demonstrated to interact with Tat-TRPM7 peptide | | | | |
| --- | --- | --- | --- | --- |
| PDZ Protein | Domain | GenBank # | Nervous System/Brain Expression | Reference |
| RIM-2 | 1 | 12734165 | yes | Mukasa et al. (2004) Brain Pathol. 14: 34-42 |
| Mint 1 | 1 and 2 | 2625024 | yes | Ho et al. (2003) Proc. Natl. Acad. Sci. U.S.A. 100: 1409-1414 |
| INADL | 3 | 2370148 | yes | Philipp et al. (1997) FEBS Lett. 413: 243-248 |
| Syntrophin 1 alpha | 1 | 1145727 | yes | Connors et al. (2004) J. Biol. Chem. 279: 28387-28392 g45700023 g34455039 |
| SITAC-18 | 2 | 8886071 | yes | Borrell-Pagès et al. (2000) Mol. Biol. Cell 11: 4217-4225 |

TABLE 8-continued

PDZ domains demonstrated to interact with Tat-TRPM7 peptide

| PDZ Protein | Domain | GenBank # | Nervous System/Brain Expression | Reference |
|---|---|---|---|---|
| LIM mystique | 1 | 12734250 | no | |
| ZO-1 | 2 | 292937 | yes | Poliak et al. (2002) J. Cell Biol. 159: 361-372 |
| PAR3L | 3 | 18568347 | yes | Gao et al. (2002) Gene 294: 99-107 |
| MAST2 | 1 | 3882334 | yes | g47035747 |
| PAR3 | 3 | 8037914 | yes | Poliak et al. (2002) J. Cell Biol. 159: 361-372 |
| NSP [novel serine protease] | 1 | 1621243 | yes | g46953413 |

TABLE 9 results of titrations of the Tat-TRPM7 peptide

| PDZ | EC50, uM | error of fit, EC50, uM | ODmax (450 nm) |
|---|---|---|---|
| RIM2 (177.4) | 0.047 | 0.005 | 2.10 |
| Mint 1 (d1, d2) (36.5a) | 0.180 | 0.016 | 1.90 |
| TIP1 d1 (54.10) | <1 | ND | 1.82 |
| Mint1 d1 (146.5) | ND | ND | 0.33 |
| Mint1 d2 (147.2) | <2 uM | ND | 0.76 |
| INADL d3 (96.3) | 0.120 | 0.015 | 1.90 |
| MUPP1 d3 (108.3) | 0.290 | 0.037 | 2.06 |
| Syntrophin 1 alpha d1 (52.5) | 0.160 | 0.017 | 2.05 |
| SITAC-18 d1 (122.2) | <1 uM | ND | 1.70 |
| SITAC-18 d2 (123.2) | 0.090 | 0.013 | 1.95 |
| LIM Mystique d1 (232.1) | 0.090 | 0.015 | 2.10 |
| ZO-1 d2 (241.3) | 0.033 | 0.003 | 2.20 |
| PAR3L d3 (406.1) | 0.100 | 0.017 | 1.97 |
| MAST2 d1 (174.6) | 0.110 | 0.008 | 2.10 |
| PAR3 d3 (278.1) | 0.018 | 0.002 | 2.50 |
| KIAA1284 d1 (191.2) | >2 uM | ND | 0.63 |

ZO-1 is a PDZ protein that is known to associate with cell surface proteins, junctions and cytoskeletal proteins. TRPC4 has also been shown to colocalize with ZO-1 (Song, X. et. Al. Glia. Nov. 11, 2004, [Epub] PMID 15540229). We have demonstrated that TRPM7 interacts with the second PDZ domain of ZO-1. Without being bound by mechanism, we propose that interruption of TRPM7/ZO-1 d2 interaction may reduce the efficiency $Ca^{2+}$ pumping activity of TRPM7/TRP during oxygen/glucose deprivation or ischemia, resulting in protection from ischemia, especially neuroprotection.

MINT1 is a PDZ protein containing 2 PDZ domains and a PTB domain. MINT1 has been shown to associate with KIR2, an inward rectifying potassium channel (Leonoudakis D. et. al. J Biol. Chem. 2004 279(21):22331-46). MINT1 has also been demonstrated to affect transport of NMDA Receptor 2B to the post-synaptic density of neurons (Scorza et al. Epilepsy Res. 2003 57(1): 49-57), and to play a role in transient global ischema in the mouse hippocampus (Nishimura, H. J. Cereb. Blood Flow Metab. 2000 20(10): 1437-45). We have disclosed herein that TRPM7 binds to MINT1. Without being bound by specific mechanism, we propose that disruption of this interaction with a peptide therapeutic or small molecule will reduce excitotoxicity and result in neuroprotection from ischemic damage.

Partitioning-defective homolog 3 (PAR3) is a PDZ protein with three PDZ domains. It is known to localize to tight junctions form a complex that regulates signaling through cdc42/Rac and Protein Kinases C and A (Lin, D. Nat. Cell Biol. 2 (8), 540-547 (2000)). We have disclosed that TRPM7 interacts with PAR3. Without being bound by specific mechanism, we propose that disruption of this interaction with a peptide therapeutic or small molecule will reduce excitotoxicity and result in neuroprotection from ischemic damage.

RIM2 is a PDZ protein known to be involved with secretory vesicle exocytosis and vesicle transport (Fukuda, M. Genes Cells. 2004 September; 9(9):831-42). We have disclosed that TRPM7 interacts with RIM2. Without being bound by specific mechanism, we propose that disruption of this interaction with a peptide therapeutic or small molecule will reduce the ability of TRPM7 to function appropriately at the membrane and result in neuroprotection from ischemic damage.

INADL is a PDZ protein with multiple PDZ domains. It is known to organize proteins at the cell membrane photoreceptor complex, including the *Drosophila* TRP channel. We disclose herein that TRPM7 binds the third PDZ domain of INADL. Without being bound by specific mechanism, we propose that disruption of this interaction with a peptide therapeutic or small molecule will reduce the ability of TRPM7 to associate with necessary accessory proteins and thereby function, resulting in neuroprotection from ischemic damage.

G. Measurement of PDZ-Ligand Binding Affinity

The A and G assays of the invention can be used to determine the "apparent affinity" of binding of a PDZ ligand peptide to a PDZ-domain polypeptide. Apparent affinity is determined based on the concentration of one molecule required to saturate the binding of a second molecule (e.g., the binding of a ligand to a receptor). Two particularly useful approaches for quantitation of apparent affinity of PDZ-ligand binding are provided infra.

Approach 1:

(1) A GST/PDZ fusion protein, as well as GST alone as a negative control, are bound to a surface (e.g., a 96-well plate) and the surface blocked and washed as described supra for the G assay.

(2) 50 μl per well of a solution of biotinylated PL peptide (e.g. as shown in TABLE 2) is added to the surface in increasing concentrations in PBS/BSA (e.g. at 0.1 μM, 0.33 μM, 1 μM, 3.3 μM, 10 μM, 33 μM, and 100 μM). In one embodiment, the PL peptide is allowed to react with the bound GST/PDZ fusion protein (as well as the GST alone negative control) for 10 minutes at 4° C. followed by 20 minutes at 25° C. The plate is washed 3 times with ice cold PBS to remove unbound labeled peptide.

(3) The binding of the PL peptide to the immobilized PDZ-domain polypeptide is detected as described supra for the G assay.

(4) For each concentration of peptide, the net binding signal is determined by subtracting the binding of the peptide to GST alone from the binding of the peptide to the GST/PDZ fusion protein. The net binding signal is then plotted as a function of ligand concentration and the plot is fit (e.g. by using the Kaleidagraph Synergy Software, Reading, Pa.) software package curve fitting algorithm) to the following equation, where "Signal$_{[ligand]}$" is the net binding signal at PL peptide concentration "[ligand]," "$K_d$" is the apparent affinity of the binding event, and "Saturation Binding" is a constant determined by the curve fitting algorithm to optimize the fit to the experimental data:

$$\text{Signal}_{[ligand]} = \text{Saturation Binding} \times ([ligand]/([ligand] + K_d))$$

For reliable application of the above equation it is necessary that the highest peptide ligand concentration successfully tested experimentally be greater than, or at least similar to, the calculated $K_d$ (equivalently, the maximum observed binding should be similar to the calculated saturation binding). In cases where satisfying the above criteria proves difficult, an alternative approach (infra) can be used.

Approach 2:

(1) A fixed concentration of a PDZ-domain polypeptide and increasing concentrations of a labeled PL peptide (labeled with, for example, biotin or fluorescein, see TABLE 2 and TABLE 4 for representative peptide amino acid sequences) are mixed together in solution and allowed to react. In one embodiment, preferred peptide concentrations are 0.1 µM, 1 µM, 10 µM, 100 µM, 1 mM. In various embodiments, appropriate reaction times can range from 10 minutes to 2 days at temperatures ranging from 4° C. to 37° C. In some embodiments, the identical reaction can also be carried out using a non-PDZ domain-containing protein as a control (e.g., if the PDZ-domain polypeptide is fusion protein, the fusion partner can be used).

(2) PDZ-ligand complexes can be separated from unbound labeled peptide using a variety of methods known in the art. For example, the complexes can be separated using high performance size-exclusion chromatography (HPSEC, gel filtration) (Rabinowitz et al., 1998, Immunity 9:699), affinity chromatography (e.g. using glutathione SEPHAROSE beads), and affinity absorption (e.g., by binding to an anti-GST-coated plate as described supra).

(3) The PDZ-ligand complex is detected based on presence of the label on the peptide ligand using a variety of methods and detectors known to one of skill in the art. For example, if the label is fluorescein and the separation is achieved using HPSEC, an in-line fluorescence detector can be used. The binding can also be detected as described supra for the G assay.

(4) The PDZ-ligand binding signal is plotted as a function of ligand concentration and the plot is fit. (e.g., by using the Kaleidagraph software package curve fitting algorithm) to the following equation, where "Signal$_{[ligand]}$" is the binding signal at PL peptide concentration "[ligand]," "$K_d$" is the apparent affinity of the binding event, and "Saturation Binding" is a constant determined by the curve fitting algorithm to optimize the fit to the experimental data:

$$\text{Signal}_{[Ligand]} = \text{Saturation Binding} \times ([ligand]/([ligand] + K_d])$$

Measurement of the affinity of a labeled peptide ligand binding to a PDZ-domain polypeptide is useful because knowledge of the affinity (or apparent affinity) of this interaction allows rational design of inhibitors of the interaction with known potency. The potency of inhibitors in inhibition would be similar to (i.e. within one-order of magnitude of) the apparent affinity of the labeled peptide ligand binding to the PDZ-domain.

Thus, in one aspect, the invention provides a method of determining the apparent affinity of binding between a PDZ domain and a ligand by immobilizing a polypeptide comprising the PDZ domain and a non-PDZ domain on a surface, contacting the immobilized polypeptide with a plurality of different concentrations of the ligand, determining the amount of binding of the ligand to the immobilized polypeptide at each of the concentrations of ligand, and calculating the apparent affinity of the binding based on that data. Typically, the polypeptide comprising the PDZ domain and a non-PDZ domain is a fusion protein. In one embodiment, the e.g., fusion protein is GST-PDZ fusion protein, but other polypeptides can also be used (e.g., a fusion protein including a PDZ domain and any of a variety of epitope tags, biotinylation signals and the like) so long as the polypeptide can be immobilized in an orientation that does not abolish the ligand binding properties of the PDZ domain, e.g, by tethering the polypeptide to the surface via the non-PDZ domain via an anti-domain antibody and leaving the PDZ domain as the free end. It was discovered, for example, reacting a PDZ-GST fusion polypeptide directly to a plastic plate provided suboptimal results. The calculation of binding affinity itself can be determined using any suitable equation (e.g., as shown supra; also see Cantor and Schimmel (1980) Biophysical Chemistry WH Freeman & Co., San Francisco) or software.

Thus, in a preferred embodiment, the polypeptide is immobilized by binding the polypeptide to an immobilized immunoglobulin that binds the non-PDZ domain (e.g., an anti-GST antibody when a GST-PDZ fusion polypeptide is used). In a preferred embodiment, the step of contacting the ligand and PDZ-domain polypeptide is carried out under the conditions provided supra in the description of the G assay. It will be appreciated that binding assays are conveniently carried out in multiwell plates (e.g., 24-well, 96-well plates, or 384 well plates).

The present method has considerable advantages over other methods for measuring binding affinities PDZ-PL affinities, which typically involve contacting varying concentrations of a GST-PDZ fusion protein to a ligand-coated surface. For example, some previously described methods for determining affinity (e.g., using immobilized ligand and GST-PDZ protein in solution) did not account for oligomerization state of the fusion proteins used, resulting in potential errors of more than an order of magnitude.

Although not sufficient for quantitative measurement of PDZ-PL binding affinity, an estimate of the relative strength of binding of different PDZ-PL pairs can be made based on the absolute magnitude of the signals observed in the G assay. This estimate will reflect several factors, including biologically relevant aspects of the interaction, including the affinity and the dissociation rate. For comparisons of different ligands binding to a given PDZ domain-containing protein, differences in absolute binding signal likely relate primarily to the affinity and/or dissociation rate of the interactions of interest.

H. Assays to Identify Novel PDZ Domain Binding Moieties and to Identify Modulators of PDZ Protein-PL Protein Binding Although described supra primarily in terms of identifying interactions between PDZ-domain polypeptides and PL proteins, the assays described supra and other assays can also be used to identify the binding of other molecules (e.g., peptide mimetics, small molecules, and the like) to PDZ domain sequences. For example, using the assays disclosed herein, combinatorial and other libraries of compounds can be screened, e.g., for molecules that specifically bind to PDZ domains. Screening of libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241: 577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. Nos. 5,096,815, 5,223,409, and 5,198,346, all to Ladner et al.; Rebar and Pabo, 1993, Science 263:671-673; and PCT Publication No. WO 94/18318.

In a specific embodiment, screening can be carried out by contacting the library members with a PDZ-domain polypeptide immobilized on a solid support (e.g. as described supra in the G assay) and harvesting those library members that bind to the protein. Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited hereinabove.

In another embodiment, the two-hybrid system for selecting interacting proteins in yeast (Fields and Song, 1989, Nature 340:245-246; Chien et al., 1991, Proc. Natl. Acad. Sci. USA 88:9578-9582) can be used to identify molecules that specifically bind to a PDZ domain-containing protein. Furthermore, the identified molecules are further tested for their ability to inhibit transmembrane receptor interactions with a PDZ domain.

In one aspect of the invention, antagonists of an interaction between a PDZ protein and a PL protein are identified. In one embodiment, a modification of the A assay described supra is used to identify antagonists. In one embodiment, a modification of the G assay described supra is used to identify antagonists.

In certain embodiments, screening assays are used to detect molecules that specifically bind to PDZ domains. Such molecules are useful as agonists or antagonists of PDZ-protein-mediated cell function (e.g., cell activation, e.g., T cell activation, vesicle transport, cytokine release, growth factors, transcriptional changes, cytoskeleton rearrangement, cell movement, chemotaxis, intercellular signaling, regulation of synaptic function, neuronal excitation, cytoskeletal integrity, and neurotransmitter release). In one embodiment, such assays are performed to screen for leukocyte activation inhibitors for drug development. The invention thus provides assays to detect molecules that specifically bind to PDZ domain-containing proteins. For example, recombinant cells expressing PDZ domain-encoding nucleic acids can be used to produce PDZ domains in these assays and to screen for molecules that bind to the domains. Molecules are contacted with the PDZ domain (or fragment thereof) under conditions conducive to binding, and then molecules that specifically bind to such domains are identified. Methods that can be used to carry out the foregoing are commonly known in the art.

It will be appreciated by the ordinarily skilled practitioner that, in one embodiment, antagonists are identified by conducting the A or G assays in the presence and absence of a known or candidate antagonist. When decreased binding is observed in the presence of a compound, that compound is identified as an antagonist. Increased binding in the presence of a compound signifies that the compound is an agonist.

For example, in one assay, a test compound can be identified as an inhibitor (antagonist) of binding between a PDZ protein and a PL protein by contacting a PDZ domain polypeptide and a PL peptide or protein in the presence and absence of the test compound, under conditions in which they would (but for the presence of the test compound) form a complex, and detecting the formation of the complex in the presence and absence of the test compound. It will be appreciated that less complex formation in the presence of the test compound than in the absence of the compound indicates that the test compound is an inhibitor of a PDZ protein-PL protein binding.

In one embodiment, the G assay is used in the presence or absence of an candidate inhibitor. In one embodiment, the A assay is used in the presence or absence of a candidate inhibitor.

In one embodiment (in which a G assay is used), one or more PDZ domain-containing GST-fusion proteins are bound to the surface of wells of a 96-well plate as described supra (with appropriate controls including nonfusion GST protein). All fusion proteins are bound in multiple wells so that appropriate controls and statistical analysis can be done. A test compound in BSA/PBS (typically at multiple different concentrations) is added to wells. Immediately thereafter, 30 μl of a detectably labeled (e.g., biotinylated) PL peptide or protein known to bind to the relevant PDZ domain (see, e.g., TABLE 5) is added in each of the wells at a final concentration of, e.g., between about 2 μM and about 40 μM, typically 5 μM, 15 μM, or 25 μM. This mixture is then allowed to react with the PDZ fusion protein bound to the surface for 10 minutes at 4° C. followed by 20 minutes at 25° C. The surface is washed free of unbound PL polypeptide three times with ice cold PBS and the amount of binding of the polypeptide in the presence and absence of the test compound is determined. Usually, the level of binding is measured for each set of replica wells (e.g. duplicates) by subtracting the mean GST alone background from the mean of the raw measurement of polypeptide binding in these wells.

In an alternative embodiment, the A assay is carried out in the presence or absence of a test candidate to identify inhibitors of PL-PDZ interactions.

If assays are conducted in the presence of test compound and compared against binding in the absence of test compound, then the assay can be conducted to determine if the difference between binding in the presence and absence of the test compound is a statistically significant difference.

In certain screening assays, assays are conducted to identify compounds that can inhibit a binding interaction between a TRP channel or TRP associated protein and a PDZ listed in TABLE 5. In other screening assays involve screening to identify an inhibitor that interferes with binding between TRPM7 and a PDZ listed in TABLE 5.

In one embodiment, a test compound is determined to be a specific inhibitor of the binding of the PDZ domain (P) and a PL (L) sequence when, at a test compound concentration of less than or equal to 1 mM (e.g., less than or equal to: 500 μM, 100 μM, 10 μM, 1 μM, 100 nM or 1 nM) the binding of P to L in the presence of the test compound less than about 50% of the binding in the absence of the test compound (in various embodiments, less than about 25%, less than about 10%, or less than about 1%). Preferably, the net signal of binding of P to L in the presence of the test compound plus six (6) times the standard error of the signal in the presence of the test compound is less than the binding signal in the absence of the test compound.

In one embodiment, assays for an inhibitor are carried out using a single PDZ protein-PL protein pair (e.g., a PDZ domain fusion protein and a PL peptide or protein). In a related embodiment, the assays are carried out using a plurality of pairs, such as a plurality of different pairs listed in TABLES 2, 4 and 5.

In some embodiments, it is desirable to identify compounds that, at a given concentration, inhibit the binding of one PL-PDZ pair, but do not inhibit (or inhibit to a lesser degree) the binding of a specified second PL-PDZ pair. These antagonists can be identified by carrying out a series of assays using a candidate inhibitor and different PL-PDZ pairs (e.g., as shown in TABLE 6, 7, and 8) and comparing the results of the assays. All such pairwise combinations are contemplated by the invention (e.g., test compound inhibits binding of PL1 to PDZ1 to a greater degree than it inhibits binding of PL1 to PDZ2 or PL2 to PDZ2). Importantly, it will be appreciated that, based on the data provided in TABLE 6, 7, and 8 and disclosed herein (and additional data that can be generated using the methods described herein) inhibitors with different specificities can readily be designed.

For example, according to the invention, the Ki ("potency") of an inhibitor of a PDZ-PL interaction can be determined. Ki is a measure of the concentration of an inhibitor required to have a biological effect. For example, administration of an inhibitor of a PDZ-PL interaction in an amount sufficient to result in an intracellular inhibitor concentration of at least between about 1 and about 100 Ki is expected to inhibit the biological response mediated by the target PDZ-PL interaction. In one aspect of the invention, the Kd measurement of PDZ-PL binding as determined using the methods supra is used in determining Ki.

Thus, in one aspect, the invention provides a method of determining the potency (Ki) of an inhibitor or suspected inhibitor of binding between a PDZ domain and a ligand by immobilizing a polypeptide comprising the PDZ domain and a non-PDZ domain on a surface, contacting the immobilized polypeptide with a plurality of different mixtures of the ligand and inhibitor, wherein the different mixtures comprise a fixed amount of ligand and different concentrations of the inhibitor, determining the amount of ligand bound at the different concentrations of inhibitor, and calculating the Ki of the binding based on the amount of ligand bound in the presence of different concentrations of the inhibitor. In an embodiment, the polypeptide is immobilized by binding the polypeptide to an immobilized immunoglobulin that binds the non-PDZ domain. This method, which is based on the G assay described supra, is particularly suited for high-throughput analysis of the Ki for inhibitors of PDZ-ligand interactions. Further, using this method, the inhibition of the PDZ-ligand interaction itself is measured, without distortion of measurements by avidity effects.

Typically, at least a portion of the ligand is detectably labeled to permit easy quantitation of ligand binding.

It will be appreciated that the concentration of ligand and concentrations of inhibitor are selected to allow meaningful detection of inhibition. Thus, the concentration of the ligand whose binding is to be blocked is close to or less than its binding affinity (e.g., preferably less than the 5× Kd of the interaction, more preferably less than 2× Kd, most preferably less than 1× Kd). Thus, the ligand is typically present at a concentration of less than 2 Kd (e.g., between about 0.01 Kd and about 2 Kd) and the concentrations of the test inhibitor typically range from 1 nM to 100 µM (e.g. a 4-fold dilution series with highest concentration 10 µM or 1 mM). In a preferred embodiment, the Kd is determined using the assay disclosed supra.

The Ki of the binding can be calculated by any of a variety of methods routinely used in the art, based on the amount of ligand bound in the presence of different concentrations of the inhibitor. In an illustrative embodiment, for example, a plot of labeled ligand binding versus inhibitor concentration is fit to the equation:

$$S_{inhibitor} = S_0 * K_i / ([I] + K_i)$$

where $S_{inhibitor}$ is the signal of labeled ligand binding to immobilized PDZ domain in the presence of inhibitor at concentration [I] and $S_0$ is the signal in the absence of inhibitor (i.e., [I]=0). Typically [I] is expressed as a molar concentration.

In another aspect of the invention, an enhancer (sometimes referred to as, augmentor or agonist) of binding between a PDZ domain and a ligand is identified by immobilizing a polypeptide comprising the PDZ domain and a non-PDZ domain on a surface, contacting the immobilized polypeptide with the ligand in the presence of a test agent and determining the amount of ligand bound, and comparing the amount of ligand bound in the presence of the test agent with the amount of ligand bound by the polypeptide in the absence of the test agent. At least two-fold (often at least 5-fold) greater binding in the presence of the test agent compared to the absence of the test agent indicates that the test agent is an agent that enhances the binding of the PDZ domain to the ligand. As noted supra, agents that enhance PDZ-ligand interactions are useful for disruption (dysregulation) of biological events requiring normal PDZ-ligand function (e.g., cancer cell division and metastasis, and activation and migration of immune cells, intercellular communication, neurotransmitter release, membrane receptor turnover, second messenger signaling responsible for cell homeostasis and function).

The invention also provides methods for determining the "potency" or "Kenhancer" of an enhancer of a PDZ-ligand interaction. For example, according to the invention, the Kenhancer of an enhancer of a PDZ-PL interaction can be determined, e.g., using the Kd of PDZ-PL binding as determined using the methods described supra. Kenhancer is a measure of the concentration of an enhancer expected to have a biological effect. For example, administration of an enhancer of a PDZ-PL interaction in an amount sufficient to result in an intracellular inhibitor concentration of at least between about 0.1 and about 100 Kenhancer (e.g., between about 0.5 and about 50 Kenhancer) is expected to disrupt the biological response mediated by the target PDZ-PL interaction.

Thus, in one aspect the invention provides a method of determining the potency (Kenhancer) of an enhancer or suspected enhancer of binding between a PDZ domain and a ligand by immobilizing a polypeptide comprising the PDZ domain and a non-PDZ domain on a surface, contacting the immobilized polypeptide with a plurality of different mixtures of the ligand and enhancer, wherein the different mixtures comprise a fixed amount of ligand, at least a portion of which is detectably labeled, and different concentrations of the enhancer, determining the amount of ligand bound at the different concentrations of enhancer, and calculating the potency (Kenhancer) of the enhancer from the binding based on the amount of ligand bound in the presence of different concentrations of the enhancer. Typically, at least a portion of the ligand is detectably labeled to permit easy quantitation of ligand binding. This method, which is based on the G assay described supra, is particularly suited for high-throughput analysis of the Kenhancer for enhancers of PDZ-ligand interactions.

It will be appreciated that the concentration of ligand and concentrations of enhancer are selected to allow meaningful detection of enhanced binding. Thus, the ligand is typically present at a concentration of between about 0.01 Kd and about 0.5 Kd and the concentrations of the test agent/enhancer typically range from 1 nM to 1 mM (e.g. a 4-fold dilution series with highest concentration 10 μM or 1 mM). In a preferred embodiment, the Kd is determined using the assay disclosed supra.

The potency of the binding can be determined by a variety of standard methods based on the amount of ligand bound in the presence of different concentrations of the enhancer or augmentor. For example, a plot of labeled ligand binding versus enhancer concentration can be fit to the equation:

$$S([E])=S(0)+(S(0)*(D_{enhancer}-1)*[E]/([E]+K_{enhancer})$$

where "$K_{enhancer}$" is the potency of the augmenting compound, and "$D_{enhancer}$" is the fold-increase in binding of the labeled ligand obtained with addition of saturating amounts of the enhancing compound, [E] is the concentration of the enhancer. It will be understood that saturating amounts are the amount of enhancer such that further addition does not significantly increase the binding signal. Knowledge of "$K_{enhancer}$" is useful because it describes a concentration of the augmenting compound in a target cell that will result in a biological effect due to dysregulation of the PDZ-PL interaction. Typical therapeutic concentrations are between about 0.1 and about 100 $K_{enhancer}$.

V. Validation of Binding Assays

Compounds identified in the foregoing binding assays can be further analyzed using a variety of biological assays to confirm that the ability of the compound to inhibit a PDZ:PL protein interaction actually inhibits a cellular activity correlated with the PDZ:PL binding interaction. Alternatively, these assays can be used directly to assay the activity of a potential inhibitory compound without conducting a binding assay beforehand. These assays can be conducted using various in vitro assays, or in vivo assays using various appropriate animal model systems.

The PDZ:PL binding interactions described herein include those involved in various biological activities in neurons. As already noted, one set of cellular activities of interest are those associated with various types of neurological disorders or injury, such as cellular responses associated with stroke and ischemia. Because neurological injury is often associated with cell death, apoptosis and excitotoxicity responses, assays for each of these responses can be conducted to validate the inhibitory activity of a compound identified through a binding assay.

For example, a variety of different parameters can be monitored to assess toxicity. Examples of such parameters include, but are not limited to, cell proliferation, monitoring activation of cellular pathways for toxicological responses by gene or protein expression analysis, DNA fragmentation, changes in the composition of cellular membranes, membrane permeability, activation of components of death-receptors or downstream signaling pathways (e.g., caspases), generic stress responses, NF-kappaB activation and responses to mitogens. Related assays are used to assay for apoptosis (a programmed process of cell death) and necrosis, including cGMP formation and NO formation. The following are illustrative of the type of biological assays that can be conducted to assess whether a inhibitory agent has a protective effect against neuronal injury or disease.

A. Morphological Changes

Apoptosis in many cell types is correlated with altered morphological appearances. Examples of such alterations include, but are not limited to, plasma membrane blebbing, cell shape change, loss of substrate adhesion properties. Such changes are readily detectable with a light microscope. Cells undergoing apoptosis can also be detected by fragmentation and disintegration of chromosomes. These changes can be detected using light microscopy and/or DNA or chromatin specific dyes.

B. Altered Membrane Permeability

Often the membranes of cells undergoing apoptosis become increasingly permeable. This change in membrane properties can be readily detected using vital dyes (e.g., propidium iodide and trypan blue). Dyes can be used to detect the presence of necrotic cells. For example, certain methods utilize a green-fluorescent LIVE/DEAD Cytotoxicity Kit #2, available from Molecular Probes. The dye specifically reacts with cellular amine groups. In necrotic cells, the entire free amine content is available to react with the dye, thus resulting in intense fluorescent staining. In contrast, only the cell-surface amines of viable cells are available to react with the dye. Hence, the fluorescence intensity for viable cells is reduced significantly relative to necrotic cells, (see, e.g., Haugland, 1996 Handbook of Fluorescent Probes and Research *Chemicals*, 6th ed., Molecular Probes, Oreg.).

C. Dysfunction of Mitochondrial Membrane Potential

Mitochondria provide direct and indirect biochemical regulation of diverse cellular processes as the main energy source in cells of higher organisms. These processes include the electron transport chain activity, which drives oxidative phosphorylation to produce metabolic energy in the form of adenosine triphosphate (i.e., ATP). Altered or defective mitochondrial activity can result in mitochondrial collapse called the "permeability transition" or mitochondrial permeability transition. Proper mitochondrial functioning requires maintenance of the membrane potential established across the membrane. Dissipation of the membrane potential prevents ATP synthesis and thus halts or restricts the production of a vital biochemical energy source.

Consequently, a variety of assays designed to assess toxicity and cell death involve monitoring the effect of a test agent on mitochondrial membrane potentials or on the mitochondrial permeability transition. One approach is to utilize fluorescent indicators (see, e.g., Haugland, 1996 Handbook of Fluorescent Probes and Research Chemicals, 6th ed., Molecular Probes, Oreg., pp. 266-274 and 589-594). Various non-fluorescent probes can also be utilized (see, e.g., Kamo et al. (1979) J. Membrane Biol. 49:105). Mitochondrial membrane potentials can also be determined indirectly from mitochondrial membrane permeability (see, e.g., Quinn (1976) The Molecular Biology of Cell Membranes, University Park Press, Baltimore, Md., pp. 200-217). Further guidance on methods for conducting such assays is provided in PCT publication WO 00/19200 to Dykens et al.

D. Caspase Activation

Apoptosis is the process of programmed cell death and involves the activation of a genetic program when cells are no longer needed or have become seriously damaged. Apoptosis involves a cascade of biochemical events and is under the regulation of a number of different genes. One group of genes act as effectors of apoptosis and are referred to as the interleukin-1 beta.converting enzyme (ICE) family of genes. These genes encode a family of cysteine proteases whose activity is increased in apoptosis. The ICE family of proteases is generically referred to as caspase enzymes. The "c" in the name reflects the fact that the enzymes are cysteine proteases, while "aspase" refers to the ability of these enzymes to cleave after aspartic acid residues.

Consequently, some assays for apoptosis are based upon the observation that caspases are induced during apoptosis. Induction of these enzymes can be detected by monitoring the cleavage of specifically-recognized substrates for these enzymes. A number of naturally occurring and synthetic protein substrates are known (see, e.g., Ellerby et al. (1997) J. Neurosci. 17:6165; Kluck, et al. (1997) Science 275:1132; Nicholson et al. (1995) Nature 376:37; and Rosen and Casciola-Rosen (1997) J. Cell Biochem. 64:50). Methods for preparing a number of different substrates that can be utilized in these assays are described in U.S. Pat. No. 5,976,822. This patent also describes assays that can be conducted using whole cells that are amendable to certain of the microfluidic devices described herein. Other methods using FRET techniques are discussed in Mahajan, et al. (1999) Chem. Biol. 6:401-9; and Xu, et al. (1998) Nucl. Acids. Res. 26:2034-5.

E. Cytochrome c Release

In healthy cells, the inner mitochondrial membrane is impermeable to macromolecules. Thus, one indicator of cell apoptosis is the release or leakage of cytochrome c from the mitochondria. Detection of cytochrome c can be performed using spectroscopic methods because of the inherent absorption properties of the protein. Thus, one detection option with the present devices is to place the cells within a holding space and monitor absorbance at a characteristic absorption wavelength for cytochrome c. Alternatively, the protein can be detected using standard immunological methods (e.g., ELISA assays) with an antibody that specifically binds to cytochrome c (see, e.g., Liu et al. (1996) Cell 86:147).

F. Assays for Cell Lysis

The final stage of cell death is typically lysis of the cell. When cells die they typically release a mixture of chemicals, including nucleotides, and a variety of other substances (e.g., proteins and carbohydrates) into their surroundings. Some of the substances released include ADP and ATP, as well as the enzyme adenylate cyclase, which catalyzes the conversion of ADP to ATP in the presence of excess ADP. Thus, certain assays involve providing sufficient ADP in the assay medium to drive the equilibrium towards the generation of ATP which can subsequently be detected via a number of different means. One such approach is to utilize a luciferin/luciferase system that is well known to those of ordinary skill in the art in which the enzyme luciferase utilizes ATP and the substrate luciferin to generate a photometrically detectable signal. Further details regarding certain cell lysis assays that can be performed are set forth in PCT publication WO 00/70082, the disclosure of which is hereby incorporated by reference.

G. Ischemic Model Systems

Methods for assaying whether a compound can confer protective neurological effects against ischemia and stroke are discussed by Aarts, et al. (Science 298:846-850, 2002). In general, this assay involves subjecting rats to a middle cerebral artery occlusion (MCAO) for a relatively short period of time (e.g., about 90 minutes). MCAO can be induced using various methods, including an intraluminal suture method (see, e.g., Longa, E. Z. et al. (1989) Stroke 20:84; and Belayev, L., et al. (1996) Stroke 27:1616). A composition containing the putative inhibitor is introduced into the rat using conventional methods (e.g., via intravenous injection). To evaluate the composition's prophylactic effect, the composition is administered before performing MCAO. If the compound is to be evaluated for its ability to mitigate against an ischemic event that has already occurred, the composition with the compound is introduced after MCAO has been initiated. The extent of cerebral infarction is then evaluated using various measures of neurological function. Examples of such measures include the postural reflex test (Bederson, J. B. et al. (1986) Stroke 17:472) and the forelimb placing test (De Ryck, M. et al. (1989) Stroke 20:1383). Methods are also described in Aarts et al (supra) assessing the effects of NMDA-induced excitotoxicity using in vitro assays.

VI. Global Analysis of PDZ-PL Interactions

As described supra, the present invention provides powerful methods for analysis of PDZ-ligand interactions, including high-throughput methods such as the G assay and affinity assays described supra. In one embodiment of the invention, the affinity is determined for a particular ligand and a plurality of PDZ proteins. Typically the plurality is at least 5, and often at least 25, or at least 40 different PDZ proteins. In a preferred embodiment, the plurality of different PDZ proteins are from a particular tissue (e.g., central nervous system) or a particular class or type of cell, (e.g., a neuron) and the like. In a most preferred embodiment, the plurality of different PDZ proteins represents a substantial fraction (e.g., typically a majority, more often at least 80%) of all of the PDZ proteins known to be, or suspected of being, expressed in the tissue or cell(s), e.g., all of the PDZ proteins known to be present in neuronal cells. In an embodiment, the plurality is at least 50%, usually at least 80%, at least 90% or all of the PDZ proteins disclosed herein as being expressed in neuronal cells.

In one embodiment of the invention, the binding of a ligand to the plurality of PDZ proteins is determined. Using this method, it is possible to identify a particular PDZ domain bound with particular specificity by the ligand. The binding may be designated as "specific" if the affinity of the ligand to the particular PDZ domain is at least 2-fold that of the binding to other PDZ domains in the plurality (e.g., present in that cell type). The binding is deemed "very specific" if the affinity is at least 10-fold higher than to any other PDZ in the plurality or, alternatively, at least 10-fold higher than to at least 90%, more often 95% of the other PDZs in a defined plurality. Similarly, the binding is deemed "exceedingly specific" if it is at least 100-fold higher. For example, a ligand could bind to 2 different PDZs with an affinity of 1 µM and to no other PDZs out of a set 40 with an affinity of less than 100 µM. This would constitute specific binding to those 2 PDZs. Similar measures of specificity are used to describe binding of a PDZ to a plurality of PLs.

It will be recognized that high specificity PDZ-PL interactions represent potentially more valuable targets for achieving a desired biological effect. The ability of an inhibitor or enhancer to act with high specificity is often desirable. In particular, the most specific PDZ-ligand interactions are also the best therapeutic targets, allowing specific inhibition of the interaction.

Thus, in one embodiment, the invention provides a method of identifying a high specificity interaction between a particular PDZ domain and a ligand known or suspected of binding at least one PDZ domain, by providing a plurality of different immobilized polypeptides, each of said polypeptides comprising a PDZ domain and a non-PDZ domain; determining the affinity of the ligand for each of said polypeptides, and comparing the affinity of binding of the ligand to each of said polypeptides, wherein an interaction between the ligand and a particular PDZ domain is deemed to have high specificity when the ligand binds an immobilized polypeptide comprising the particular PDZ domain with at least 2-fold higher affinity than to immobilized polypeptides not comprising the particular PDZ domain.

In a related aspect, the affinity of binding of a specific PDZ domain to a plurality of ligands (or suspected ligands) is determined. For example, in one embodiment, the invention provides a method of identifying a high specificity interaction between a PDZ domain and a particular ligand known or suspected of binding at least one PDZ domain, by providing an immobilized polypeptide comprising the PDZ domain and a non-PDZ domain; determining the affinity of each of a plurality of ligands for the polypeptide, and comparing the affinity of binding of each of the ligands to the polypeptide, wherein an interaction between a particular ligand and the PDZ domain is deemed to have high specificity when the ligand binds an immobilized polypeptide comprising the PDZ domain with at least 2-fold higher affinity than other ligands tested. Thus, the binding may be designated as "specific" if the affinity of the PDZ to the particular PL is at least 2-fold that of the binding to other PLs in the plurality (e.g., present in that cell type). The binding is deemed "very specific" if the affinity is at least 10-fold higher than to any other PL in the plurality or, alternatively, at least 10-fold higher than to at least 90%, more often 95% of the other PLs in a defined plurality. Similarly, the binding is deemed "exceedingly specific" if it is at least 100-fold higher. Typically the plurality is at least 5 different ligands, more often at least 10.

1. Use of Array for Global Predictions

One discovery of the present inventors relates to the important and extensive roles played by interactions between PDZ proteins and PL proteins, particularly in the biological function of neuronal cells. Further, it has been discovered that valuable information can be ascertained by analysis (e.g., simultaneous analysis) of a large number of PDZ-PL interactions. In a preferred embodiment, the analysis encompasses all of the PDZ proteins expressed in a particular tissue (e.g., brain) or type or class of cell (e.g., neuron). Alternatively, the analysis encompasses at least about 5, or at least about 10, or at least about 12, or at least about 15 and often at least 50 different polypeptides, up to about 60, about 80, about 100, about 150, about 200, or even more different polypeptides; or a substantial fraction (e.g., typically a majority, more often at least 80%) of all of the PDZ proteins known to be, or suspected of being, expressed in the tissue or cell(s), (e.g., all of the PDZ proteins known to be present in neurons).

It will be recognized that the arrays and methods of the invention are directed to analyze of PDZ and PL interactions, and involve selection of such proteins for analysis. While the devices and methods of the invention may include or involve a small number of control polypeptides, they typically do not include significant numbers of proteins or fusion proteins that do not include either PDZ or PL domains (e.g., typically, at least about 90% of the arrayed or immobilized polypeptides in a method or device of the invention is a PDZ or PL sequence protein, more often at least about 95%, or at least about 99%).

It will be apparent from this disclosure that analysis of the relatively large number of different interactions preferably takes place simultaneously. In this context, "simultaneously" means that the analysis of several different PDZ-PL interactions (or the effect of a test agent on such interactions) is assessed at the same time. Typically the analysis is carried out in a high throughput (e.g., robotic) fashion. One advantage of this method of simultaneous analysis is that it permits rigorous comparison of multiple different PDZ-PL interactions. For example, as explained in detail elsewhere herein, simultaneous analysis (and use of the arrays described infra) facilitates, for example, the direct comparison of the effect of an agent (e.g., a potential interaction inhibitor) on the interactions between a substantial portion of PDZs and/or PLs in a tissue or cell.

Accordingly, in one aspect, the invention provides an array of immobilized polypeptide comprising the PDZ domain and a non-PDZ domain on a surface. Typically, the array comprises at least about 5, or at least about 10, or at least about 12, or at least about 15 and often at least 50 different polypeptides. In one preferred embodiment, the different PDZ proteins are from a particular tissue (e.g., central nervous system) or a particular class or type of cell, (e.g., a neuron) and the like. In a most preferred embodiment, the plurality of different PDZ proteins represents a substantial fraction (e.g., typically a majority, more often at least 60%, 70% or 80%) of all of the PDZ proteins known to be, or suspected of being, expressed in the tissue or cell(s), (e.g., all of the PDZ proteins known to be present in neurons).

Certain embodiments are arrays which include a plurality, usually at least 5, 10, 25, or 50 PDZ proteins present in a particular cell of interest. In this context, "array" refers to an ordered series of immobilized polypeptides in which the identity of each polypeptide is associated with its location. In some embodiments the plurality of polypeptides are arrayed in a "common" area such that they can be simultaneously exposed to a solution (e.g., containing a ligand or test agent). For example, the plurality of polypeptides can be on a slide, plate or similar surface, which may be plastic, glass, metal, silica, beads or other surface to which proteins can be immobilized. In a different embodiment, the different immobilized polypeptides are situated in separate areas, such as different wells of multi-well plate (e.g., a 24-well plate, a 96-well plate, a 384 well plate, and the like). It will be recognized that a similar advantage can be obtained by using multiple arrays in tandem.

2. Analysis of PDZ-PL Inhibition Profile

In one aspect, the invention provides a method for determining if a test compound inhibits any PDZ-ligand interaction in large set of PDZ-ligand interaction (e.g., a plurality of the PDZ-ligand interactions described in TABLE 6 and TABLE 7 and TABLE 8; a majority of the PDZ-ligands identified in a particular cell or tissue as described supra (e.g., neurons) and the like. In one embodiment, the PDZ domains of interest are expressed as GST-PDZ fusion proteins and immobilized as described herein. For each PDZ domain, a labeled ligand that binds to the domain with a known affinity is identified as described herein.

For any known or suspected modulator (e.g., inhibitor) of a PDL-PL interaction(s), it is useful to know which interactions are inhibited (or augmented). For example, an agent that inhibits all PDZ-PL interactions in a cell (e.g., a neuron) will have different uses than an agent that inhibits only one, or a small number, of specific PDZ-PL interactions. The profile of PDZ interactions inhibited by a particular agent is referred to as the "inhibition profile" for the agent, and is described in detail below. The profile of PDZ interactions enhanced by a particular agent is referred to as the "enhancement profile" for the agent. It will be readily apparent to one of skill guided by the description of the inhibition profile how to determine the enhancement profile for an agent. The present invention provides methods for determining the PDZ interaction (inhibition/enhancement) profile of an agent in a single assay.

In one aspect, the invention provides a method for determining the PDZ-PL inhibition profile of a compound by providing (i) a plurality of different immobilized polypeptides, each of said polypeptides comprising a PDZ domain and a non-PDZ domain and (ii) a plurality of corresponding ligands, wherein each ligand binds at least one PDZ domain in (i), then contacting each of said immobilized polypeptides in (i) with a corresponding ligand in (ii) in the presence and absence of a test compound, and determining for each polypeptide-ligand pair whether the test compound inhibits binding between the immobilized polypeptide and the corresponding ligand.

Typically the plurality is at least 5, and often at least 25, or at least 40 different PDZ proteins. In a preferred embodiment, the plurality of different ligands and the plurality of different PDZ proteins are from the same tissue or a particular class or type of cell, (e.g., a neuron). In a most preferred embodiment, the plurality of different PDZs represents a substantial fraction (e.g., at least 80%) of all of the PDZs known to be, or suspected of being, expressed in the tissue or cell(s), e.g., all of the PDZs known to be present in neurons (for example, at least 80%, at least 90% or all of the PDZs disclosed herein as being expressed in neuronal cells).

In one embodiment, the inhibition profile is determined as follows: A plurality (e.g., all known) PDZ domains expressed in a cell (e.g., neurons) are expressed as GST-fusion proteins and immobilized without altering their ligand binding properties as described supra. For each PDZ domain, a labeled ligand that binds to this domain with a known affinity is identified. If the set of PDZ domains expressed in neurons is denoted by {P1 ... Pn}, any given PDZ domain Pi binds a (labeled) ligand Li with affinity Kdi. To determine the inhibition profile for a test agent "compound X" the G assay (supra) can be performed as follows in 96-well plates with rows A-H and columns 1-12. Column 1 is coated with P1 and washed. The corresponding ligand L1 is added to each washed coated well of column 1 at a concentration 0.5 Kd1 with (rows B, D, F, H) or without (rows A, C, E, F) between about 1 and about 1000 µM) of test compound X. Column 2 is coated with P2, and L2 (at a concentration 0.5 Kd2) is added with or without inhibitor X. Additional PDZ domains and ligands are similarly tested.

Compound X is considered to inhibit the binding of Li to Pi if the average signal in the wells of column i containing X is less than half the signal in the equivalent wells of the column lacking X. Thus, in this single assay one determines the full set of neural PDZs that are inhibited by compound X.

In some embodiments, the test compound X is a mixture of compounds, such as the product of a combinatorial chemistry synthesis as described supra. In some embodiments, the test compound is known to have a desired biological effect, and the assay is used to determine the mechanism of action (i.e., if the biological effect is due to modulating a PDZ-PL interaction).

It will be apparent that an agent that modulates only one, or a few PDZ-PL interactions, in a panel (e.g., a panel of all known PDZs in neurons, a panel of at least 10, at least 20 or at least 50 PDZ domains) is a more specific modulator than an agent that modulate many or most interactions. Typically, an agent that modulates less than 20% of PDZ domains in a panel (e.g., TABLE 5) is deemed a "specific" inhibitor, less than 6% a "very specific" inhibitor, and a single PDZ domain a "maximally specific" inhibitor.

It will be recognized that high specificity modulators of PDZ-PL interactions represent potentially more valuable drug targets for achieving a desired biological effect. The ability of an inhibitor or enhancer to act with "maximal specificity" is most desirable.

In one embodiment, the assays of the invention can be used to determine a maximally specific modulator of the interaction between a TRP channel and a PDZ domain.

In a preferred embodiment, the assays of the invention are used to identify a maximally specific modulator of the interaction between TRPM7 and a PDZ domain.

It will also be appreciated that "compound X" may be a composition containing mixture of compounds (e.g., generated using combinatorial chemistry methods) rather than a single compound.

Several variations of this assay are contemplated:

In some alternative embodiments, the assay above is performed using varying concentrations of the test compound X, rather than fixed concentration. This allows determination of the Ki of the X for each PDZ as described above.

In an alternative embodiment, instead of pairing each PDZ Pi with a specific labeled ligand Li, a mixture of different labeled ligands is created that such that for every PDZ at least one of the ligands in the mixture binds to this PDZ sufficiently to detect the binding in the G assay. This mixture is then used for every PDZ domain.

In one embodiment, compound X is known to have a desired biological effect, but the chemical mechanism by which it has that effect is unknown. The assays of the invention can then be used to determine if compound X has its effect by binding to a PDZ domain.

In one embodiment, PDZ-domain containing proteins are classified in to groups based on their biological function, e.g. into those that regulate apoptosis versus those that regulate transcription. An optimal inhibitor of a particular function (e.g., including but not limited to an anti-apoptotic agent, an anti-T cell activation agent, cell-cycle control, vesicle transport, etc.) will inhibit multiple PDZ-ligand interactions involved in the function (e.g., apoptosis, activation) but few other interactions. Thus, the assay is used in one embodiment in screening and design of a drug that specifically blocks a particular function. For example, an agent designed to block apoptosis might be identified because, at a given concentration, the agent inhibits 2 or more PDZs involved in apoptosis but fewer than 3 other PDZs, or that inhibits PDZs involved in apoptosis with a Ki>10-fold better than for other PDZs. Thus, the invention provides a method for identifying an agent that inhibits a first selected PDZ-PL interaction or plurality of interactions but does not inhibit a second selected PDZ-PL interaction or plurality of interactions. The two (or more) sets of interactions can be selected on the basis of the known biological function of the PDZ proteins, the tissue specificity of the PDZ proteins, or any other criteria. Moreover, the assay can be used to determine effective doses (i.e., drug concentrations) that result in desired biological effects while avoiding undesirable effects.

3. Side Effects of PDZ-PL Modulator Interactions

In a related embodiment, the invention provides a method for determining likely side effects of a therapeutic that inhibits PDZ-ligand interactions. The method entails identifying those target tissues, organs or cell types that express PDZ proteins and ligands that are disrupted by a specified inhibitor. If, at a therapeutic dosage, a drug intended to have an effect in one organ system (e.g., central nervous system) disrupts PDZ-PL interactions in a different system (e.g., hematopoietic system) it can be predicted that the drug will have effects ("side effects") on the second system. It will be apparent that the information obtained from this assay will be useful in the rational design and selection of drugs that do not have the side-effect.

In one embodiment, for example, a comprehensive PDZ protein set is obtained. A "perfectly comprehensive" PDZ protein set is defined as the set of all PDZ proteins expressed in the subject animal (e.g., humans). A comprehensive set may be obtained by analysis of, for example, the human genome sequence. However, a "perfectly comprehensive" set is not required and any reasonably large set of PDZ domain proteins (e.g., the set of all known PDZ proteins; or the set listed in TABLE 5) will provide valuable information.

In one embodiment, the method involves some of all of the following steps:
a) For each PDZ protein, determine the tissues in which it is highly expressed. This can be done experimentally although the information generally will be available in the scientific literature;
b) For each PDZ protein (or as many as possible), identify the cognate PL(s) bound by the PDZ protein;
c) Determine the $K_i$ at which the test agent inhibits each PDZ-PL interaction, using the methods described supra;
d) From this information it is possible to calculate the pattern of PDZ-PL interactions disrupted at various concentrations of the test agent.

By correlating the set of PDZ-PL interactions disrupted with the expression pattern of the members of that set, it will be possible to identify the tissues likely affected by the agent.

Additional steps can also be carried out, including determining whether a specified tissue or cell type is exposed to an agent following a particular route of administration. This can be determined using basis pharmacokinetic methods and principles.

4. Modulation of Activities

The PDZ binding moieties and inhibitors described herein that disrupt PDZ:PL protein interactions can be used to modulate biological activities or functions of cells (e.g., neurons). These agents can also be utilized to treat diseases and conditions in human and nonhuman animals (e.g., experimental models). Exemplary biological activities are listed supra.

When administered to patients, the compounds of the invention (e.g., PL-PDZ interaction inhibitors) are useful for treating (ameliorating symptoms of) a variety of neurological disorders, including those associated with some type of injury to neuronal cells or the death of neurons. Such disorders include, but are not limited to, stroke, ischemia, brain traumas and chronic pain. Certain inhibitors can also be used to treat other types of neuorological disorders like Alzheimer's disease, epilepsy, Parkinson's disease, Huntington's disease, motor neuron diseases and inherited ataxias.

Some other inhibitors can be utilized to treat other disease types, including, for instance, inflammatory and humoral immune responses, e.g., inflammation, allergy (e.g., systemic anaphylaxis, hypersensitivity responses, drug allergies, insect sting allergies); infectious diseases (e.g., viral infection, such as HIV, measles, parainfluenza, virus-mediated cell fusion,), and ischemia (e.g., post-myocardial infarction complications, joint injury, kidney, scleroderma).

VII. Antagonists of PDZ-PL Interactions

As described herein, interactions between PDZ proteins and PL proteins in cells (e.g., neurons) may be disrupted or inhibited by the administration of inhibitors or antagonists. Inhibitors can be identified using screening assays described herein. In embodiment, the motifs disclosed herein are used to design inhibitors. In some embodiments, the antagonists of the invention have a structure (e.g., peptide sequence) based on the C-terminal residues of PL-domain proteins listed in TABLE 2 and TABLE 4. In some embodiments, the antagonists of the invention have a structure (e.g., peptide sequence) based on a PL motif disclosed herein.

The PDZ/PL antagonists and antagonists of the invention can be any of a large variety of compounds, both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds. Although, for convenience, the present discussion primarily refers antagonists of PDZ-PL interactions, it will be recognized that PDZ-PL interaction agonists can also be use in the methods disclosed herein.

In one aspect, the peptides and peptide mimetics or analogues of the invention contain an amino acid sequence that binds a PDZ domain in a cell of interest. In one embodiment, the antagonists comprise a peptide that has a sequence corresponding to the carboxy-terminal sequence of a PL protein listed in TABLE 2 or TABLE 4, e.g., a peptide listed TABLE 2. Typically, the peptide comprises at least the C-terminal two (3), three (3) or four (4) residues of the PL protein, and often the inhibitory peptide comprises more than four residues (e.g., at least five, six, seven, eight, nine, ten, twelve or fifteen residues) from the PL protein C-terminus.

In some embodiments, the inhibitor is a peptide, e.g., having a sequence of a PL C-terminal protein sequence.

In some embodiments, the antagonist is a fusion protein comprising such a sequence. Fusion proteins containing a transmembrane transporter amino acid sequence can be used to facilitate transport of the inhibitor into a cell.

In some embodiments, the inhibitor is conserved variant of the PL C-terminal protein sequence having inhibitory activity.

In some embodiments, the antagonist is a peptide mimetic of a PL C-terminal sequence.

In some embodiments, the inhibitor is a small molecule (i.e., having a molecular weight less than 1 kDa).

A. Polypeptide Antagonists

1. Inhibitors with a PL Sequence

One class of inhibitors or antagonists that are provided comprise a peptide that has a sequence of a PL protein carboxy-terminus listed in TABLE 4. The PL protein carboxy-terminus sequences can be considered as the "core PDZ motif sequence" because of the ability of the short sequence from the carboxy terminus to interact with the PDZ domain. For example, in some inhibitors the "core PDZ motif sequence" or simply the "PL sequence" contains the last 2, 3 or 4 C-terminus amino acids. In other instances, however, the core PDZ motif comprises more than 2-4 residues (e.g., at least 5, 6, 7, 8, 9, 10, 11, 12, 13, 14, 15, 16, 17, 18, 19, or 20 residues) from the PL protein C-terminus. For some inhibitors, the PDZ motif sequence peptide is from 4-15 amino acids in length. Other inhibitors have a PDZ motif sequence that is 6-10 amino acids in length, or 3-8 amino acids in length, or 3-7 amino acids in length. Certain inhibitors have a PDZ motif sequence that is 8 amino acids in length. Although the residues shared by the inhibitory peptide and the PL protein are often found at the C-terminus of the peptide, some inhibitors incorporate a PL sequence that is located in an internal region of a PL protein. Similarly, in some cases, the inhibitory peptide comprises residues from a PL sequence that is near, but not at the C-terminus of a PL protein (see, Gee et al., 1998, J Biol. Chem. 273:21980-87). Another set of inhibitors are based upon the identification of amino acid sequences that specifically disrupt binding between NMDAR proteins and PSD-95. This particular class of inhibitors are polypeptides that share the following characteristics: 1) a size ranging from 3-20 amino acids in length (although somewhat longer polypeptides can be used), and 2) a C-terminal consensus sequence of X-L/I/V-X-V/L/A (the slash separates different amino acids that can appear at a given position).

Specific examples of peptides which are useful as inhibitors of the interaction between TRPM7 and the PDZ domains RIM-2 d1, INADL d3, ZO-1 d2, PAR3 d3, and syntrophin1 alpha d1 are shown in TABLES 10 and 11 Variants of these peptides are which bind PDZ domains RIM-2 d1, INADL d3, ZO-1 d2, PAR3 d3, and syntrophin1 alpha d1 are also useful as inhibitors.

TABLE 10

| Peptide # | Peptide Sequence | SEQ ID NO: | PDZ domain | EC50, uM | error of fit EC50, uM | ODmax (450 nm) |
|---|---|---|---|---|---|---|
| 1791 | biotin-YGRKKRRQRRRAVAATSINL | 261 | ZO-1 d2 | <0.1 | ND | 2.50 |
| 1791 | biotin-YGRKKRRQRRRAVAATSINL | 261 | INADL d3 | ND | ND | 0.09 |
| 1829 | biotin-YGRKKRRQRRRARSDRTIWA | 262 | ZO-1 d2 | 0.007 | 0.0027 | 2.90 |
| 1829 | biotin-YGRKKRRQRRRARSDRTIWA | 262 | INADL d3 | ND | ND | 1.40 |
| 1830 | biotin-YGRKKRRQRRRARSDRTIIA | 263 | ZO-1 d2 | <0.02 | ND | 1.80 |
| 1830 | biotin-YGRKKRRQRRRARSDRTIIA | 263 | INADL d3 | <2 | ND | 1.20 |
| 1832 | biotin-YGRKKRRQRRRSRTDRKYWA | 264 | ZO-1 d2 | <0.02 | ND | 2.10 |
| 1832 | biotin-YGRKKRRQRRRSRTDRKYWA | 264 | INADL d3 | 0.20 | 0.023 | 0.60 |
| 1836 | biotin-YGRKKRRQRRRARGDRKIRV | 265 | ZO-1 d2 | <0.01 | ND | 2.60 |
| 1836 | biotin-YGRKKRRQRRRARGDRKIRV | 265 | INADL d3 | ND | ND | 0.30 |
| 1837 | biotin-YGRKKRRQRRRARTDRKVEV | 266 | ZO-1 d2 | <0.02 | ND | 1.80 |
| 1837 | biotin-YGRKKRRQRRRARTDRKVEV | 266 | INADL d3 | ND | ND | 0.37 |
| 1838 | biotin-YGRKKRRQRRRARGDRKYIV | 267 | ZO-1 d2 | <0.1 | ND | 2.60 |
| 1838 | biotin-YGRKKRRQRRRARGDRKYIV | 267 | INADL d3 | <0.1 | ND | 2.60 |
| 1839 | biotin-YGRKKRRQRRRSRTDRKYQI | 268 | ZO-1 d2 | <0.02 | ND | 2.50 |
| 1839 | biotin-YGRKKRRQRRRSRTDRKYQI | 268 | INADL d3 | 0.13 | 0.007 | 1.60 |
| 1841 | biotin-YGRKKRRQRRRARGDRKVPV | 269 | ZO-1 d2 | <0.02 | ND | 2.10 |
| 1841 | biotin-YGRKKRRQRRRARGDRKVPV | 269 | INADL d3 | ND | ND | 0.20 |
| 1842 | biotin-YGRKKRRQRRRQDERRLIVL | 270 | ZO-1 d2 | 0.035 | 0.008 | 2.30 |
| 1842 | biotin-YGRKKRRQRRRQDERRLIVL | 270 | INADL d3 | <1 | ND | 1.90 |
| 1843 | biotin-YGRKKRRQRRRARGDRLVSL | 271 | ZO-1 d2 | 0.017 | 0.003 | 2.20 |
| 1843 | biotin-YGRKKRRQRRRARGDRLVSL | 271 | INADL d3 | <2 uM | ND | 1.20 |
| 1844 | biotin-YGRKKRRQRRRARGTRLVWV | 272 | ZO-1 d2 | <0.02 | ND | 2.60 |
| 1844 | biotin-YGRKKRRQRRRARGTRLVWV | 272 | INADL d3 | <0.02 | ND | 2.40 |
| 1845 | biotin-YGRKKRRQRRRARGDRYRIV | 273 | ZO-1 d2 | <0.1 | ND | 2.30 |
| 1845 | biotin-YGRKKRRQRRRARGDRYRIV | 273 | INADL d3 | <0.1 | ND | 2.20 |
| 1846 | biotin-YGRKKRRQRRRSRTDRLEYV | 274 | INADL d3 | ND | ND | 1.50 |
| 1848 | biotin-YGRKKRRQRRRARGDRTIIY | 275 | ZO-1 d2 | <0.02 | ND | 2.20 |
| 1848 | biotin-YGRKKRRQRRRARGDRTIIY | 275 | INADL d3~<2 | ND | ND | 1.20 |
| 1852 | biotin-YGRKKRRQRRRKAKDKEYYV | 276 | ZO-1 d2 | <0.02 | ND | 2.60 |
| 1852 | biotin-YGRKKRRQRRRKNKDKEYYV | 276 | INADL d3 | <0.02 | ND | 2.40 |
| 1854 | biotin-YGRKKRRQRRPARGRRETWV | 277 | ZO-1 d2 | ND | ND | 2.80 |
| 1854 | biotin-YGRKKRRQRRRARGRRETWV | 277 | INADL d3 | <0.02 | ND | 2.10 |
| AA353 | biotin-YGRKKRRQRRREKHFRETEV | 278 | TIP1 | <0.002 | ND | 3.00 |

TABLE 11 titrations or binding assays of peptides with RIM-2 d1, INADL d3, ZO-1 d2, PAR3 d3, and syntrophin1 alpha d1

| POZ domain bound | Peptide Sequence | SEQ ID NO: |
|---|---|---|
| INADL D3 | ATDYLVQPFMDQLAFHQFYI | 280 |
| INADL D3 | DFRPSFKHILFRRARRGFRQ | 282 |
| INADL D3 | ELLQFCRTPNPALKNGQYWV | 285 |
| INADL D3 | ENLELPVNPSSWSERISSV | 286 |
| INADL D3 | FHSKTAGANTTDKELEVLSL | 287 |
| INADL D3 | GRWTGRAMSAWKPTRRETEV | 289 |
| INADL D3 | HAMNAAPRAMENAPALRTSH | 290 |
| INADL D3 | HDFRRAFKKILARGORKRIV | 291 |
| INADL D3 | HHLVAQRDIRQFQLQHWLAI | 292 |
| INADL D3 | HSCCNRARQERLQRRRETQV | 293 |
| INADL D3 | ILNSIQVMRAQMNQIQSVEV | 294 |
| INADL D3 | KHSRKSSSYSSSSTTVKTSY | 296 |
| INADL D3 | KKKKQPGNSTKESESTNSVRLML | 297 |
| INADL D3 | LASKSAEEGKQIPDSLSTDL | 302 |
| INADL D3 | LAVLAYSITLVMLWSIWQYA | 303 |
| INADL D3 | LNSCSNRRVYKKMPSIESDV | 305 |
| INADL D3 | LQFHRGSRAQSFLQTETSVI | 306 |
| INADL D3 | PGOPPKVKSEFNSYSLTGYV | 308 |
| INADL D3 | PIPAGGCTFSGIFPTLTSPL | 309 |
| INADL D3 | QDFRRAFRRILARPWTQTAW | 312 |
| INADL D3 | RELVDRGEVRQFTLRHWLKV | 315 |
| INADL D3 | RSGATIPLVGQDIIDLQTEV | 318 |
| INADL D3 | SLIGPVQKEYQRELGKLSSP | 319 |
| INADL D3 | SSKSKSSEESQTFFGLYKL | 320 |
| INADL D3 | STDNLVRPFMDTLASHQLYI | 323 |
| INADL D3 | TQGFPGPATWRRISSLESEV | 327 |
| INADL D3 | TTNNNPNSAVNIKKIFTDV | 328 |
| INADL D3 | VDPNSPAAKKKYVSYNNLVI | 329 |
| INADL D3 | VHKVRNKFKAKCSLCRLYII | 331 |
| INADL D3 | VPSDNIDSQGRNASTNDSLL | 333 |
| INADL D3 | YGRKKRRQRRRARGDRKYIV | 339 |
| INADL D3 | YGRKKRRQRRRARSDRTIIA | 350 |
| INADL D3 | YGRKKRRQRRRARSDRTIWA | 351 |
| INADL D3 | YGRKKRRQRRRAVAATSANL | 355 |
| INADL D3 | YGRKKRRQRRREYLGLDVPV | 360 |
| INADL D3 | YGRKKRRQRRRSRTORKYQI | 373 |
| INADL D3 | YGRKKRRQRRRSRTDRKYWA | 374 |
| INADL D3 | YSATYSELEDPGEMSPPIDL | 378 |
| PAR3 D3 | ATDYLVQPFMDQLAFHQFYI | 280 |
| PAR3 D3 | DFRPSFKHILFRRARRGFRQ | 282 |
| PAR3 D3 | DGGARTEDEVQSYPSKHDYV | 283 |
| PAR3 D3 | DTLLLTENEGDKTEEQVSYV | 284 |
| PAR3 D3 | ELLQFCRTPNPALKNGQYWV | 285 |
| PAR3 D3 | FHSKTAGANTTDKELEVLSL | 287 |
| PAR3 D3 | HDFRRAFKKILARGDRKRIV | 291 |
| PAR3 D3 | HHLVAQRDIRQFQLQHWLAI | 292 |
| PAR3 D3 | HSCCNRARQERLQRRRETQV | 293 |
| PAR3 D3 | ILNSIQVMRAQMNQIQSVEV | 294 |
| PAR3 D3 | KAGYRAPRSYPKSNSSKEYV | 295 |
| PAR3 D3 | KHSRKSSSYSSSSTTVKTSY | 296 |
| PAR3 D3 | KKKKQPGNSTKESESTNSVRLML | 297 |
| PAR3 D3 | KTMPAAMFRLLTGQETPLYI | 298 |
| PAR3 D3 | KTMPAAMYRLLTAQEQPVYI | 299 |
| PAR3 D3 | KTMPAATYRLLTGQEQPVYL | 300 |
| PAR3 D3 | KYSAPRRPTATGDYDKKNYV | 301 |
| PAR3 D3 | LASKSAEEGKQIPDSLSTDL | 302 |
| PAR3 D3 | LAVLAYSITLVMLWSIWQYA | 303 |
| PAR3 D3 | LERTSSVSPSTAEPELSIVF | 304 |
| PAR3 D3 | LQFHRGSRAQSFLQTETSVI | 306 |
| PAR3 D3 | PGOPPKVKSEFNSYSLTGYV | 308 |
| PAR3 D3 | PIPAGGCTFSGIFPTLTSPL | 309 |
| PAR3 D3 | QDFRRAFRRILARPWTQTAW | 312 |
| PAR3 D3 | QGDPALQDAGDSSRKEYFI | 313 |
| PAR3 D3 | RELVDRGEVRQFTLRHWLKV | 315 |
| PAR3 D3 | SSKSKSSEESQTFFGLYKL | 320 |
| PAR3 D3 | SSPDSSYQGKGFVMSRAMYV | 321 |
| PAR3 D3 | STDNLVRPFMDTLASHQLYI | 323 |
| PAR3 D3 | VDPNSPAAKKKYVSYNNLVI | 329 |
| PAR3 D3 | VHKVRNKFKAKCSLCRLYII | 331 |
| PAR3 D3 | YGRKKRRQRRRAVAATSANL | 355 |
| PAR3 D3 | YGRKKRRQRRRAVAATSINL | 356 |

TABLE 11-continued titrations or binding assays of peptides with RIM-2 d1, INADL d3, ZO-1 d2, PAR3 d3, and syntrophin1 alpha d1

| POZ domain bound | Peptide Sequence | SEQ ID NO: |
|---|---|---|
| PAR3 D3 | YGRKKRRQRRREYLGLDVPV | 360 |
| PAR3 D3 | YGRKKRRQRRRGASADSTQA | 361 |
| PAR3 D3 | YGRKKRRQRRRKLSSIESDV | 363 |
| PAR3 D3 | YGRKKRRQRRRNDNIALLVQ | 366 |
| PAR3 D3 | YGRKKRRQRRRSEGVPDLLV | 372 |
| RIM2 D1 | DFRPSFKHILFRRARRGFRQ | 282 |
| RIM2 D1 | FHSKTAGANTTDKELEVLSL | 287 |
| RIM2 D1 | HDFRRAFKKILARGQRKRIV | 291 |
| RIM2 D1 | HHLVAQRDIRQFQLQHWLAI | 292 |
| RIM2 D1 | KHSRKSSSYSSSSTTVKTSY | 296 |
| RIM2 D1 | KKKKQPGNSTKESESTNSVRLML | 297 |
| RIM2 D1 | LAVLAYSITLVMLWSIWQYA | 303 |
| RIM2 D1 | NYKLNTDHAGSNDNIALLVQ | 307 |
| RIM2 D1 | QDFRRAFRRILARPWTQTAW | 312 |
| RIM2 D1 | RELVDRGEVRQFTLRHWLKV | 315 |
| RIM2 D1 | SSKSKSSEESQTFFGLYKL | 320 |
| RIM2 D1 | SSSRRDSSWSETSEASYSGL | 322 |
| RIM2 D1 | VDPNSPAAKKKYVSYNNLVI | 329 |
| RIM2 D1 | VHKVRNKFKAKCSLCRLYII | 331 |
| RIM2 D1 | YGRKKRRQRRRARGDRKIRV | 334 |
| RIM2 D1 | YGRKKRRQRRRARGDRKKIV | 335 |
| RIM2 D1 | YGRKKRRQRRRARGDRKRIV | 335 |
| RIM2 D1 | YGRKKRRQRRRARGDRKRWA | 336 |
| RIM2 D1 | YGRKKRRQRRRARGDRKRWL | 337 |
| RIM2 D1 | YGRKKRRQRRRARGDRKVPV | 338 |
| RIM2 D1 | YGRKKRRQRRRARGDRKYIV | 339 |
| RIM2 D1 | YGRKKRRQRRRARGDRLEIV | 340 |
| RIM2 D1 | YGRKKRRQRRRARGDRLVSL | 341 |
| RIM2 D1 | YGRKKRRQRRRARGDRRRIV | 342 |
| RIM2 D1 | YGRKKRRQRRRARGDRTIIY | 343 |
| RIM2 D1 | YGRKKRRQRRRARGDRYRIV | 344 |
| RIM2 D1 | YGRKKRRQRRRARGDVRLML | 345 |
| RIM2 D1 | YGRKKRRQRRRARGRRETWV | 346 |
| RIM2 D1 | YGRKKRRQRRRARGTRLVWV | 346 |
| RIM2 D1 | YGRKKRRQRRRARSDRGIWA | 347 |
| RIM2 D1 | YGRKKRRQRRRARSDRKRIA | 348 |
| RIM2 D1 | YGRKKRRQRRRARSDRKRIV | 349 |
| RIM2 D1 | YGRKKRRQRRRARSDRTIIA | 350 |
| RIM2 D1 | YGRKKRRQRRRARSDRTIWA | 351 |
| RIM2 D1 | YGRKKRRQRRRARTDRKVEV | 352 |
| RIM2 D1 | YGRKKRRQRRRAVAAASANL | 353 |
| RIM2 D1 | YGRKKRRQRRRAVAATGIWA | 354 |
| RIM2 D1 | YGRKKRRQRRRAVAATSANL | 355 |
| RIM2 D1 | YGRKKRRQRRRAVAATSINL | 356 |
| RIM2 D1 | YGRKKRRQRRRAVAATYSNL | 357 |
| RIM2 D1 | YGRKKRRQRRREKHFRETEV | 359 |
| RIM2 D1 | YGRKKRRQRRREYLGLDVPV | 360 |
| RIM2 D1 | YGRKKRRQRRRGASADSTQA | 361 |
| RIM2 D1 | YGRKKRRQRRRGMTSSSSVV | 362 |
| RIM2 D1 | YGRKKRRQRRRKNKDKEYYV | 364 |
| RIM2 D1 | YGRKKRRQRRRLQRRRETQV | 365 |
| RIM2 D1 | YGRKKRRQRRRNDNIALLVQ | 366 |
| RIM2 D1 | YGRKKRRQRRRQDEEEGIWA | 367 |
| RIM2 D1 | YGRKKRRQRRRQDEEEGIWS | 368 |
| RIM2 D1 | YGRKKRRQRRRQDEEETIWA | 369 |
| RIM2 D1 | YGRKKRRQRRRQDERRLIVL | 370 |
| RIM2 D1 | YGRKKRRQRRRQDERVETRV | 371 |
| RIM2 D1 | YGRKKRRQRRRSRTDRKYQI | 373 |
| RIM2 D1 | YGRKKRRQRRRSRTDRKYWA | 374 |
| RIM2 D1 | YGRKKRRQRRRSRTDRLEYV | 375 |
| RIM2 D1 | YGRKKRRQRRRSRTVREIWA | 376 |
| RIM2 D1 | YGRKKRRQRRRSVTSTSINL | 377 |
| Syntrophin 1 alpha D1 | AAGGRSARGGRLQGRRETAL | 279 |
| Syntrophin 1 alpha D1 | ATDYLVQPFMDQLAFHQFYI | 280 |
| Syntrophin 1 alpha D1 | AVGGRPARGGRLQGRRQTQV | 281 |
| Syntrophin 1 alpha D1 | DFRPSFKHILFRRARRGFRQ | 282 |
| Syntrophin 1 alpha D1 | DTLLLTENEGQKTEEQVSYV | 284 |
| Syntrophin 1 alpha D1 | FNGSSNGHVYEKLSSIESDV | 288 |
| Syntrophin 1 alpha D1 | GRWTGRAMSAWKPTRRETEV | 289 |
| Syntrophin 1 alpha D1 | HDFRRAFKKILARGDRKRIV | 291 |
| Syntrophin 1 alpha D1 | HHLVAQRDIRQFQLQHWLAI | 292 |

TABLE 11-continued titrations or binding assays of peptides with RIM-2 d1, INADL d3, ZO-1 d2, PAR3 d3, and syntrophin1 alpha d1

| POZ domain bound | Peptide Sequence | SEQ ID NO: |
|---|---|---|
| Syntrophin 1 alpha D1 | HSCCNRARQERLQRRRETQV | 293 |
| Syntrophin 1 alpha D1 | ILNSIQVMRAQMNQIQSVEV | 294 |
| Syntrophin 1 alpha D1 | KKKKQPGNSTKESESTNSVRLML | 297 |
| Syntrophin 1 alpha D1 | LAVLAYSITLVMLWSIWQYA | 303 |
| Syntrophin 1 alpha D1 | PIPAGGCTFSGIFPTLTSPL | 309 |
| Syntrophin 1 alpha D1 | PYSELNYETSHYPASPDSWV | 311 |
| Syntrophin 1 alpha D1 | QDFRRAFRRILARPWTQTAW | 312 |
| Syntrophin 1 alpha D1 | QISPGGLEPPSEKHFRETEV | 314 |
| Syntrophin 1 alpha D1 | RELVDRGEVRQFTLRHWLKV | 315 |
| Syntrophin 1 alpha D1 | SSKSKSSEESQTFFGLYKL | 320 |
| Syntrophin 1 alpha D1 | TFKGTPTAENPEYLGLDVPV | 325 |
| Syntrophin 1 alpha D1 | TGSALQAWRHTSRQATESTV | 326 |
| Syntrophin 1 alpha D1 | TQGFPGPAIWRRISSLESEV | 327 |
| Syntrophin 1 alpha D1 | VHDAESSOEDGYDWGPATDL | 330 |
| Syntrophin 1 alpha D1 | VHKVRNKFKAKCSLCRLYII | 331 |
| Syntrophin 1 alpha D1 | VPGALDYAAFSSALYGESDL | 332 |
| Syntrophin 1 alpha D1 | YGRKKRRQRRRKLSSIESDV | 363 |
| Syntrophin 1 alpha D1 | YGRKKRRQRRRNDNIALLVQ | 366 |
| ZO-1 D2 | DFRPSFKHILFRRARRGFRQ | 282 |
| ZO-1 D2 | ELLQFCRTPNPALKNGQYWV | 285 |
| ZO-1 D2 | FHSKTAGANTTDKELEVLSL | 287 |
| ZO-1 D2 | HDFRRAFKKILARGDRKRIV | 291 |
| ZO-1 D2 | HHLVAQRDIRQFQLQHWLAI | 292 |
| ZO-1 D2 | HSCCNRARQERLQRRRETQV | 293 |
| ZO-1 D2 | ILNSIQVMRAQMNQIQSVEV | 294 |
| ZO-1 D2 | KHSRKSSSYSSSSTTVKTSY | 296 |
| ZO-1 D2 | KKKKQPGNSTKESESTNSVRLML | 297 |
| ZO-1 D2 | LAVLAYSITLVMLWSIWQYA | 303 |
| ZO-1 D2 | LNSCSNRRVYKKMPSIESDV | 305 |
| ZO-1 D2 | NYKLNTDHAGSNDNIALLVQ | 307 |
| ZO-1 D2 | PSSRASSRASSRPRPDDLEI | 310 |
| ZO-1 D2 | QDFRRAFRRILARPWTQTAW | 312 |
| ZO-1 D2 | RELVDRGEVRQFTLRHWLKV | 315 |
| ZO-1 D2 | RRRRRRGNTTDKELEVLSL | 316 |
| ZO-1 D2 | RRRRRRGTNPAVAATSANL | 317 |
| ZO-1 D2 | SSKSKSSEESQTFFGLYKL | 320 |
| ZO-1 D2 | SSSRRDSSWSETSEASYSGL | 322 |
| ZO-1 D2 | TEGNESSEATSPVNAIYSLA | 324 |
| ZO-1 D2 | TTNNNPNSAVNIKKIFTDV | 328 |
| ZO-1 D2 | VDPNSPAAKKKYVSYNNLVI | 329 |
| ZO-1 D2 | VHKVRNKFKAKCSLCRLYII | 331 |
| ZO-1 D2 | YGRKKRRQRRRARGDRKRIV | 335 |
| ZO-1 D2 | YGRKKRRQRRRARGDRKRWA | 336 |
| ZO-1 D2 | YGRKKRRQRRRARGDRKRWL | 337 |
| ZO-1 D2 | YGRKKRRQRRRARGDRKVPV | 338 |
| ZO-1 D2 | YGRKKRRQRRRARGDRLVSL | 341 |
| ZO-1 D2 | YGRKKRRQRRRARGDRTIIY | 343 |
| ZO-1 D2 | YGRKKRRQRRRARGDRYRIV | 344 |
| ZO-1 D2 | YGRKKRRQRRRARGRRETWV | 346 |
| ZO-1 D2 | YGRKKRRQRRRARGTRLVWV | 346 |
| ZO-1 D2 | YGRKKRRQRRRARSGRGIWA | 347 |
| ZO-1 D2 | YGRKKRRQRRRARSDRTIIA | 350 |
| ZO-1 D2 | YGRKKRRQRRRARSDRTIWA | 351 |
| ZO-1 D2 | YGRKKRRQRRRAVAAASANL | 353 |
| ZO-1 D2 | YGRKKRRQRRRAVAATSANL | 355 |
| ZO-1 D2 | YGRKKRRQRRRAVAATSINL | 356 |
| ZO-1 D2 | YGRKKRRQRRRAVAATYSNL | 357 |
| ZO-1 D2 | YGRKKRRQRRRDKELEVLSL | 358 |
| ZO-1 D2 | YGRKKRRQRRREKHFRETEV | 359 |
| ZO-1 D2 | YGRKKRRQRRREYLGLDVPV | 360 |
| ZO-1 D2 | YGRKKRRQRRGASAOSTQA | 361 |
| ZO-1 D2 | YGRKKRRQRRRKLSSIESDV | 363 |
| ZO-1 D2 | YGRKKRRQRRRKNKDKEYYV | 364 |
| ZO-1 D2 | YGRKKRRQRRRNONIALLVQ | 366 |
| ZO-1 D2 | YGRKKRRQRRRQDEEEGIWA | 367 |
| ZO-1 D2 | YGRKKRRQRRRQDERRLIVL | 370 |
| ZO-1 D2 | YGRKKRRQRRRSEGVPDLLV | 372 |
| ZO-1 D2 | YGRKKRRQRRRSRTDRKYWA | 374 |
| ZO-1 D2 | YVYSRVKNLNSSEGVPDLLV | 379 |

These specific examples should not be considered as limiting but simply illustrative of inhibitors having the general characteristics listed above.

As described in greater detail below, short PL peptides, such as just described can be used in the rational design of other small molecules with similar properties according to established techniques.

Core PDZ motif sequences/PL sequences such as those just listed can optionally be joined to additional amino acids at their amino terminus to further increase binding affinity and/or stability and/or transportability into cells. These additional sequences located at the amino terminus can be from the natural sequence of a neuronal cell surface receptor or from other sources. The PDZ motif sequence and additional N-terminal sequences can optionally be joined by a linker. The additional amino acids can also be conservatively substituted. The total peptide length (i.e., core PDZ motif sequence plus optional N-terminal segment) can be of a variety of lengths (e.g., at least 2, 3, 4, 5, 6, 8, 10, 15, 20, 25, 30, 40, 50, 60, 70, 80, 90, 100 or more amino acids). Typically, the overall length is in the range of 30-40 amino acids) For those inhibitors in which additional sequences are attached at the N-terminus of the core PDZ motif sequence (PL sequence), the overall structure is thus: N-terminal segment—core PDZ motif sequence (PL sequence), or N-terminal segment—linker—core PDZ motif sequence (PL sequence). As discussed further below, one useful class of proteins that can be fused to the core PDZ motifs or PL sequences are transmembrane transporter peptides. These peptides can be fused to the inhibitory sequences to facilitate transport into a target cell (e.g., neuron). Further details are provided below. Purification tags that are known in the art can also optionally be fused to the N-terminus of the PL sequence.

2. Inhibitors with a PDZ-Domain Polypeptide

Some of the inhibitors that are provided contain all or a portion of a PDZ binding domain rather than containing a PL sequence. The PDZ-domain sequence included in these inhibitors is selected to mimic (i.e., have similar binding characteristics) of the PDZ domain in the PDZ protein of interest (i.e., the PDZ protein whose binding interaction with a PL protein one seeks to disrupt). The PDZ-domain sequence is long enough to include at least enough of the PDZ domain such that the resulting polypeptide inhibitor can effectively bind to the cognate PL protein. This typically means that the PDZ-domain sequence is at least 50, 55, 60, 65, 70, 75, 80, 85, 90 or more amino acids long. But certain inhibitors can include the entire PDZ-domain, or even additional amino acids from the PDZ protein that extend beyond the PDZ-domain.

3. Optional Features of Inhibitors

Polypeptide inhibitors such as those just described can optionally be derivatized (e.g., acetylated, phosphorylated and/or glycoslylated) to improve the binding affinity of the inhibitor, to improve the ability of the inhibitor to be transported across a cell membrane or to improve stability. As a specific example, for inhibitors in which the third residue from the C-terminus is S, T or Y, this residue can be phosphorylated prior to the use of the peptide.

The polypeptide inhibitors can also optionally be linked directly or via a linker to a transmembrane transporter peptide. Specific examples of these sequences are described in the section on formulation and administration of the polypeptides of the invention. But certain polypeptide inhibitors do not include a transporter peptide.

B. Peptide Variants

Having identified PDZ binding peptides and PDZ-PL interaction inhibitory sequences, variations of these sequences can be made and the resulting peptide variants can be tested for PDZ domain binding or PDZ-PL inhibitory activity. In embodiments, the variants have the same or a different ability to bind a PDZ domain as the parent peptide. Typically, such amino acid substitutions are conservative, i.e., the amino acid residues are replaced with other amino acid residues having physical and/or chemical properties similar to the residues they are replacing. Preferably, conservative amino acid substitutions are those wherein an amino acid is replaced with another amino acid encompassed within the same designated class.

C. Peptide Mimetics

Having identified PDZ binding peptides and PDZ-PL interaction inhibitory sequences, peptide mimetics can be prepared using routine methods, and the inhibitory activity of the mimetics can be confirmed using the assays of the invention. Thus, in some embodiments, the antagonist is a peptide mimetic of a PL C-terminal sequence. The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

D. Small Molecules

In some embodiments, the inhibitor is a small molecule (i.e., having a molecular weight less than 1 kDa). Methods for screening small molecules are well known in the art and include those described supra.

E. Binding Affinity

Regardless of type, the inhibitors generally have an EC50 of less than 50 µm. Some inhibitors have an EC50 of less than 10 µM, others have an EC50 of 1 µM, and still others an EC50 of less than 100 nM. The inhibitors typically have an EC50 value of 20-100 nM.

VIII. Uses of PDZ Domain Binding and Antagonist Compounds

Because the inhibitors that are described herein are useful in interfering with binding between certain PDZ and PL proteins in neurons (e.g., the TRPM7/PDZ interaction), the inhibitors can be utilized in the treatment of a variety of biological processes in neuron cells. For instance, the inhibitors can be utilized to treat problems associated with excitotoxicity and apoptosis occasioned by neuronal damage. The inhibitors can also be utilized to treat various neurological diseases, including those associated with stroke and ischemia. Specific examples of neurological diseases that can be treated with certain inhibitors include, Alzheimer's disease, epilepsy, Parkinson's disease, Huntington's disease, motor neuron diseases and inherited ataxias.

Because PDZ proteins are involved in a number of biological functions besides involvement in excitotoxicity responses, some of the inhibitors that are provided can be used in the treatment of other conditions and activities correlated with the PDZ:PL protein interactions described herein. Examples of such activities include, but are not limited to, organization and regulation of multiprotein complexes, vesicular trafficking, tumor suppression, protein sorting, establishment of membrane polarity, apoptosis, regulation of immune response and organization of synapse formation. In general, PDZ proteins have a common function of facilitating the assembly of multi-protein complexes, often serving as a bridge between several proteins, or regulating the function of other proteins. Additionally, as also noted supra, these proteins are found in essentially all cell types.

Consequently, modulation of these interactions can be utilized to control a wide variety of biological conditions and physiological conditions. In particular, modulation of interactions such as those disclosed herein can be utilized to control movement of vesicles within a cell, inhibition of tumor formation, as well as in the treatment of immune disorders, neurological disorders, muscular disorders, and intestinal disorders.

Certain compounds which modulate binding of the PDZ proteins and PL proteins can be used to inhibit leukocyte activation, which is manifested in measurable events including but not limited to, cytokine production, cell adhesion, expansion of cell numbers, apoptosis and cytotoxicity. Thus, some compounds of the invention can be used to treat diverse conditions associated with undesirable leukocyte activation, including but not limited to, acute and chronic inflammation, graft-versus-host disease, transplantation rejection, hypersensitivities and autoimmunity such as multiple sclerosis, rheumatoid arthritis, peridontal disease, systemic lupus erythematosis, juvenile diabetes mellitus, non-insulin-dependent diabetes, and allergies, and other conditions listed herein.

Thus, the invention also relates to methods of using such compositions in modulating leukocyte activation as measured by, for example, cytotoxicity, cytokine production, cell proliferation, and apoptosis.

IX. Formulation and Route of Administration

A. Introduction of Antagonists (e.g., Peptides and Fusion Proteins) into Cells

The inhibitors disclosed herein or identified using the screening methods that are provided can be used in the manufacture of a medicament or pharmaceutical composition. These can then be administered according to a number of different methods.

In one aspect, the PDZ-PL antagonists of the invention are introduced into a cell to modulate (i.e., increase or decrease) a biological function or activity of the cell. Many small organic molecules readily cross the cell membranes (or can be modified by one of skill using routine methods to increase the ability of compounds to enter cells, e.g., by reducing or eliminating charge, increasing lipophilicity, conjugating the molecule to a moiety targeting a cell surface receptor such that after interacting with the receptor). Methods for introducing larger molecules, e.g., peptides and fusion proteins are also well known, including, e.g., injection, liposome-mediated fusion, application of a hydrogel, conjugation to a targeting moiety conjugate endocytozed by the cell, electroporation, and the like).

In one embodiment, the antagonist or agent is a fusion polypeptide or derivatized polypeptide. A fusion or derivatized protein may include a targeting moiety that increases the ability of the polypeptide to traverse a cell membrane or causes the polypeptide to be delivered to a specified cell type (e.g., a neuron) preferentially or cell compartment (e.g., nuclear compartment) preferentially. Examples of targeting moieties include lipid tails, amino acid sequences such as antennapoedia peptide or a nuclear localization signal (NLS; e.g., *Xenopus* nucleoplasmin Robbins et al., 1991, Cell 64:615).

In one embodiment of the invention, a peptide sequence or peptide analog determined to inhibit a PDZ domain-PL protein binding interaction as described herein is introduced into a cell by linking the sequence to an amino acid sequence that facilitates its transport through the plasma membrane (a "transmembrane transporter sequence"). The peptides of the invention may be used directly or fused to a transmembrane transporter sequence to facilitate their entry into cells. In the case of such a fusion peptide, each peptide may be fused with a heterologous peptide at its amino terminus directly or by using a flexible polylinker such as the pentamer G-G-G-G-S (SEQ ID NO:254) repeated 1 to 3 times. Such linker has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883). The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (SEQ ID NO:255) (Chaudhary et al., 1990, Proc. Natl. Acad. Sci. U.S.A. 87:1066-1070) and Lys-Glu-Ser-Gly-Ser-Val-Ser-Ser-Glu-Gln-Leu-Ala-Gln-Phe-Arg-Ser-Leu-Asp (SEQ ID NO:256) (Bird et al., 1988, Science 242:423-426).

A number of peptide sequences have been described in the art as capable of facilitating the entry of a peptide linked to these sequences into a cell through the plasma membrane (Derossi et al., 1998, Trends in Cell Biol. 8:84). For the purpose of this invention, such peptides are collectively referred to as transmembrane transporter peptides. Examples of these peptides include, but are not limited to, tat derived from HIV (Vives et al., 1997, J. Biol. Chem. 272:16010; Nagahara et al., 1998, Nat. Med. 4:1449), antennapedia from *Drosophila* (Derossi et al., 1994, J. Biol. Chem. 261:10444), VP22 from herpes simplex virus (Elliot and D'Hare, 1997, Cell 88:223-233), complementarity-determining regions (CDR) 2 and 3 of anti-DNA antibodies (Avrameas et al., 1998, Proc. Natl Acad. Sci. U.S.A., 95:5601-5606), 70 kDa heat shock protein (Fujihara, 1999, EMBO J. 18:411-419), transportan (Pooga et al., 1998, FASEB J. 12:67-77), penetratin, SynB1, SynB3, amphipathic model peptide, signal sequence-based peptides, and Arg, as described in Temsamani et al. (2004) Drug Discovery Today 9:1012-1019. In a preferred embodiment of the invention, a truncated HIV tat peptide having the sequence of YGRKKRRQRRR (SEQ ID NO:257) is used.

In some instances, a transmembrane transporter sequence is fused to a neuronal cell surface receptor carboxyl terminal sequence at its amino-terminus with or without a linker. Generally, the C-terminus of a PDZ motif sequence (PL sequence) is free to interact with a PDZ domain. The transmembrane transporter sequence can be used in whole or in part as long as it is capable of facilitating entry of the peptide into a cell.

In an alternate embodiment of the invention, a neuronal cell surface receptor C-terminal sequence can be used alone when it is delivered in a manner that allows its entry into cells in the absence of a transmembrane transporter sequence. For example, the peptide may be delivered in a liposome formulation or using a gene therapy approach by delivering a coding sequence for the PDZ motif alone or as a fusion molecule into a target cell.

The compounds of the invention can also be administered via liposomes, which serve to target the conjugates to a particular tissue, such as neural tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to, e.g., a receptor prevalent among neural cells, such as monoclonal antibodies which bind to the NMDA Receptor. Thus, liposomes filled with a desired peptide or conjugate of the invention can be directed to the site of neural cells, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to the neural cells, a ligand to be incorporated into the liposome can include, e.g., antibodies or fragments thereof specific for cell surface determinants of the desired nervous system cells. A liposome suspension containing a peptide or conjugate may be administered intravenously, locally, topically, etc. in a dose which varies according to, inter alia, the manner of administration, the conjugate being delivered, and the stage of the disease being treated.

In order to specifically deliver a PDZ motif sequence or PL sequence peptide into a specific cell type, the peptide can be linked to a cell-specific targeting moiety, which include but are not limited to, ligands for diverse neuron surface molecules such as growth factors, hormones and cytokines, neuronal receptors, ion transporters, as well as antibodies or antigen-binding fragments thereof. Since a large number of cell surface receptors have been identified in neurons, ligands or antibodies specific for these receptors may be used as cell-specific targeting moieties.

Antibodies are the most versatile cell-specific targeting moieties because they can be generated against any cell surface antigen. Monoclonal antibodies have been generated against neuron-specific markers. Antibody variable region genes can be readily isolated from hybridoma cells by methods well known in the art. However, since antibodies are assembled between two heavy chains and two light chains, it is preferred that a scFv be used as a cell-specific targeting moiety in the present invention. Such scFv are comprised of VH and VL domains linked into a single polypeptide chain by a flexible linker peptide.

The PDZ motif sequence (PL sequence) may be linked to a transmembrane transporter sequence and a cell-specific targeting moiety to produce a tri-fusion molecule. This molecule can bind to a neuron surface molecule, pass through the membrane and target PDZ domains. Alternatively, a PDZ motif sequence (PL sequence) may be linked to a cell-specific targeting moiety that binds to a surface molecule that internalizes the fusion peptide.

In another approach, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents. Also see, U.S. Pat. Nos. 5,907,030 and 6,033,884, which are incorporated herein by reference.

B. Introduction of Polynucleotides into Cells

By introducing gene sequences into cells, gene therapy can be used to treat diseased cells (e.g., neuron cells that are associated with apoptosis or an excitotoxic response due to a neuronal insult). In one embodiment, a polynucleotide that encodes a PL sequence peptide of the invention is introduced into a cell where it is expressed. The expressed peptide then inhibits the interaction of PDZ proteins and PL proteins in the cell. In another embodiment, the expression of a given protein would be suppressed, thus inhibiting its interactions with other proteins. In a specific embodiment, a polynucleotide that encoders an interfering RNA duplex is introduced into the cell. This results in RNA interference (RNAi), a process of post transcriptional gene silencing that inhibits, with high specificity, the expression of native genes in mammalian cells (Elbashir et al., 2001; Cullen, 2002). In a specific embodiment, the polynucleotides of the invention would suppress the expression of a given TRP channel such as TRPM7, or the expression of a protein with which the TRP channel interacts.

Figure 8:
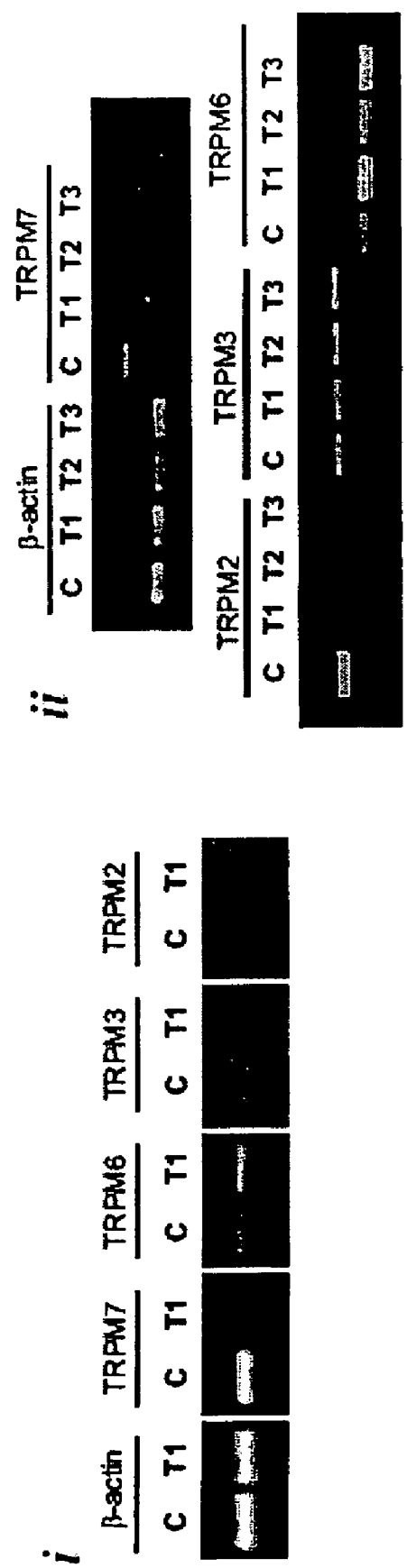
FIG. 8 shows the results of rtPCR experiments demonstrating the effect of siRNA treatment of TRPM7 on other TRPM channels using different constructs.

Examples of specific siRNAs against TRPM7 corresponded to coding regions 5152-5172, 5023-5043 and 1318-1338 (siRNATRPM7-1 to siRNATRPM7-3, respectively) relative to the first nucleotide of the start codon of murine TRPM7 (GenBank accession #AY032951). These siRNAs can reduce the expression levels of TRPM7 in cells (FIG. 8) and have functional consequences (FIGS. 3A, 3B, 3C, and 3D). Thus, these sequences or related sequences could be used directly or with an appropriate delivery system to treat cells damaged by OGD or other cytodestructive disorders.

In one embodiment, the polypeptides of the invention are expressed in a cell by introducing a nucleic acid (e.g., a DNA expression vector or mRNA) encoding the desired protein or peptide into the cell. Expression can be either constitutive or inducible depending on the vector and choice of promoter. Methods for introduction and expression of nucleic acids into a cell are well known in the art and described herein.

In a specific embodiment, nucleic acids comprising a sequence encoding a peptide disclosed herein, are administered to a human subject. In this embodiment of the invention, the nucleic acid produces its encoded product that mediates a therapeutic effect. Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred embodiment of the invention, the therapeutic composition comprises a coding sequence that is part of an expression vector. In particular, such a nucleic acid has a promoter operably linked to the coding sequence, said promoter being inducible or constitutive, and, optionally, tissue-specific. In another specific embodiment, a nucleic acid molecule is used in which the coding sequence and any other desired sequences are flanked by regions that promote homologous recombination at a desired site in the genome, thus providing for intrachromosomal expression of the nucleic acid (Koller and Smithies, 1989, Proc. Natl. Acad. Sci. USA 86:8932-8935; Zijlstra et al., 1989, Nature 342: 435-438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, DuPont), by coating with lipids or cell-surface receptors or transfecting agents, by encapsulation in liposomes, microparticles, or microcapsules, by administering it in linkage to a peptide which is known to enter the nucleus, or by administering it in linkage to a ligand subject to receptor-mediated endocytosis (see e.g., Wu and Wu, 1987, J. Biol. Chem. 262: 4429-4432) which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/ 20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a preferred embodiment of the invention, adenoviruses as viral vectors can be used in gene therapy. Adenoviruses have the advantage of being capable of infecting non-dividing cells (Kozarsky and Wilson, 1993, Current Opinion in Genetics and Development 3:499-503). Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234. Furthermore, adenoviral vectors with modified tropism may be used for cell specific targeting (WO98/ 40508). Adeno-associated virus (AAV) has also been proposed for use in gene therapy (Walsh et al., 1993, Proc. Soc. Exp. Biol. Med. 204:289-300).

In addition, retroviral vectors (see Miller et al., 1993, Meth. Enzymol. 217:581-599) have been modified to delete retroviral sequences that are not necessary for packaging of the viral genome and integration into host cell DNA. The coding sequence to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Another approach to gene therapy involves transferring a gene to cells in tissue culture. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, lipofection, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. In a preferred embodiment, the cell used for gene therapy is autologous to the patient.

In a specific embodiment, the nucleic acid to be introduced for purposes of gene therapy comprises an inducible promoter operably linked to the coding sequence, such that expression of the nucleic acid is controllable by controlling the presence or absence of the appropriate inducer of transcription.

Oligonucleotides such as anti-sense RNA and DNA molecules, and ribozymes that function to inhibit the translation of a targeted mRNA, especially its C-terminus are also within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of a nucleotide sequence, are preferred.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of target RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

The anti-sense RNA and DNA molecules and ribozymes of the invention may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the RNA molecule. Such DNA sequences may be incorporated into a wide variety of vectors which contain suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include, but are not limited to, the addition of flanking sequences of ribo- or deoxynucleotides to the 5' and/or 3' ends of the molecule or the use of phosphorothioate or 2' O-methyl rather than phosphodiesterase linkages within the oligodeoxyribonucleotide backbone.

C. Other Pharmaceutical Compositions

The compounds of the invention, may be administered to a subject per se or in the form of a sterile composition or a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the active peptides or peptide analogues into preparations which can be used pharmaceutically. Proper formulation is dependent upon the route of administration chosen.

For topical administration the compounds of the invention can be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention can be formulated in aqueous solutions, preferably in physiologically compatible buffers such as Hanks's solution, Ringer's solution, or physiological saline buffer. The solution can contain formulatory agents such as suspending, stabilizing and/or dispersing agents.

Alternatively, the compounds can be in powder form for constitution with a suitable vehicle, e.g., sterile pyrogen-free water, before use.

For transmucosal administration, penetrants appropriate to the barrier to be permeated are used in the formulation. Such penetrants are generally known in the art. This route of administration may be used to deliver the compounds to the nasal cavity.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

D. Effective Dosages

The compounds of the invention will generally be used in an amount effective to achieve the intended purpose (e.g., treatment of a neuronal injury). The compounds of the invention or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein. An "inhibitory amount" or "inhibitory concentration" of a PL-PDZ binding inhibitor is an amount that reduces binding by at least about 40%, preferably at least about 50%, often at least about 70%, and even as much as at least about 90%. Binding can be measured in vitro (e.g., in an A assay or G assay) or in situ.

For systemic administration, a therapeutically effective dose can be estimated initially from in vitro assays. For example, a dose can be formulated in animal models to achieve a circulating concentration range that includes the IC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day. For usual peptide therapeutic treatment of stroke, acute administration of 0.03 nmol/g to 30 nmol/g within 6 hours of stroke or brain ischemia is typical. In other instances, 0.1 nmol/g to 20 nmol/g within 6 hours are administered. And in still other instances 1 nmol/g to 10 nmol/g is administered with in 6 hours.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

E. Toxicity

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1).

EXAMPLES

Example 1

Identification of TRPM7 Interactions with PDZ Domains

This example describes assays to identify binding between TRPM7 and PDZ domains. GST-PDZ fusions are produced that each contain an entire PDZ domain (or multiple PDZ domains), the collection encompassing approximately 90% of all PDZ domains identified in the human genome. (See Table 5 and Section V (PDZ Proteins and PL Protein Interactions Disclosure). Biotinylated peptide corresponding to 11 residues of Tat coupled to the C-terminal 9 amino acids of TRPM7 (YGRKKRRQRRRSTNSVRLML; SEQ ID NO:258) is synthesized and purified by HPLC.

Binding between these entities is detected through the G or the G3 Assays, calorimetric assays using avidin-HRP to bind the biotin and a peroxidase substrate.

Another type of assay is a fluorescence-based binding assay using the rhodamine derivative TAMRA (Molecular Probes) conjugated to the C-terminal 9 amino acids of TRPM7 (TAMRA-RRSTNSVRLML; SEQ ID NO:259).

A. G Assay for Identification of Interactions Between Peptides and Fusion Proteins Reagents And Materials:

Nunc Maxisorp 96 well Immuno-plate

PBS pH 7.4 (Gibco BRL Cat #16777-148) or (AVC phosphate buffered saline, 8 g NaCl, 0.29 g KCl, 1.44 g $Na_2HPO_4$, 0.24 g $KH_2PO_4$, add $H_2O$ to 1 liter and pH 7.4; 0.2 μm filter)

2% BSA/PBS (10 g of bovine serum albumin, fraction V (ICN Biomedicals Cat. # IC15142983) into 500 ml PBS Goat anti-GST mAb stock (5 mg/ml, store at 4° C., (Amersham Pharmacia Cat. #27-4577-01), dilute 1:1000 in PBS, final concentration 5 μg/ml HRP-Streptavidin, 2.5 mg/2 ml stock stored at 4° C. (Zymed Cat. #43-4323), dilute 1:2000 into 2% BSA, final concentration at 0.5 μg/ml Wash Buffer, PBS
TMB ready to use (Dako Cat #S1600)
1M H$_2$SO$_4$
12 w multichannel pipettor,
50 ml reagent reservoirs,
15 ml polypropylene conical tubes
Protocol
1) Coat plate with 100 µl of 5 µg/ml goat anti GST, overnight at 4° C.
2) Dump coating antibodies out and tap dry
3) Blocking—Add 200 µl per well 2% BSA, 2 hrs at room temperature
4) Prepare proteins at 5 µg/ml in 2% BSA (2 ml per row or per two columns)
5) 3 washes with cold PBS (must be cold through entire experiment) (at last wash leave PBS in wells until immediately adding next step)
6) Add proteins at 50 µl per well on ice (1 to 2 hrs at 4° C.)
7) Prepare Peptides at desired concentration in 2% BSA (2 ml/row or/columns)
8) 3× wash with cold PBS
9) Add peptides at 50 µl per well on ice (time on/time off)
  a. keep on ice after last peptide has been added for 10 minutes exactly
  b. place at room temp for 20 minutes exactly
10) Prepare 12 ml/plate of HRP-Streptavidin (1:2000 dilution in 2% BSA)
11) 3× wash with cold PBS, (must be cold, critical)
12) Add HRP-Streptavidin at 100 µl per well on ice, 20 minutes at 4° C.
13) Turn on plate reader
14) 5× washes with PBS at room temperature, avoid bubbles
15) Add TMB substrate at 100 µl per well
  a. incubate in dark at room temperature
  b. check plate periodically (5, 10, & 20 minutes)
  c. take early readings, if necessary, at 650 nm (blue)
  d. at 30 minutes, stop reaction with 100 µl of 1M H$_2$SO$_4$
  e. take last reading at 450 nm (yellow)

B. G3 Assay for Identification of Interactions Between Peptides and Fusion Proteins Reagents and Supplies
Nunc MaxiSorp 96 well Immuno-plate, Nunc
PBS pH 7.4 (phosphate buffered saline, 8 g NaCl, 0.29 g KCl, 1.44 g Na$_2$HPO$_4$, 0.24 g KH$_2$PO$_4$, add H$_2$O to 1 liter and pH 7.4; 0.2 µm filter)
Assay Buffer: 2% BSA in PBS (20 g of bovine serum albumin per liter PBS, fraction V, ICN Biomedicals, cat#IC15142983
Goat anti-GST polyclonal Ab, stock 5 mg/ml, stored at 4° C., Amersham Pharmacia cat#27-4577-01
Dilute 1:1000 in PBS, final concentration 5 µg/ml.
HRP-Streptavidin, 2.5 mg/2 ml stock stored at 4° C., Zymed cat#43-4323, dilute 1:2000 into Assay buffer, final concentration of 0.5 µg/ml
Wash Buffer, PBS
Biotinylated peptides (HPLC purified, stock solution stored in −20° C. freezer)
GST-PRISM proteins (stock stored at −80° C., after 1$^{st}$ thaw store in −10° C. freezer)
TMB (3,3',5,5', teramethylbensidine), tablets, Sigma cat.#T5525
  Per plate, dissolve 1 tablet in 1 ml DMSO, add 9 ml Citrate/Phosphate buffer pH 5.4 and 2 µL H$_2$O$_2$
0.18M H$_2$SO$_4$, Sigma cat.#S 1526
12-w multichannel pipettor & tips
50 ml reagent reservoirs, Costar#4870
50, 15 ml polypropylene conical tubes
Costar Transtar 96 Costar #7605
Transtar 96 Cartridge Costar #7610
Molecular Devices microplate reader (450 & 650 nm filters) with SoftMax Pro software
When using reagents stored at or 4° C. or −20° C., remove & keep on ice Protocol
1. Coat plate with 100 µl of 5 µg/ml anti-GST, overnight at 4° C.
2. Dump contents of plate & out tap dry on paper towels
3. Block with 200 µl Assay Buffer for 2 hrs at room temperature
4. Prepare proteins at 5 µg/ml in Assay Buffer
5. Wash 3× with cold PBS (4° C.), avoiding letting the plates dry out
6. Add proteins at 50 µl per well, incubate 1 to 2 hrs at 4° C.
7. Prepare peptides to desired concentration in Assay Buffer
8. Wash 3× with cold PBS (4° C.), avoiding letting the plates dry out
9. Add HRP-Streptavidin/peptide complex [prepared by incubating for 20 minutes at room temperature HRP-Streptavidin (1:2000) with the desired biotin-peptide concentration for 20 minutes at room temperature] at 50 µl per well on ice
10. Place at room temperature for exactly 30 minutes
11. Promptly wash 5× with PBS at room temperature
12. Add 100 µl/well TMB substrate (write time on plate)
13. Incubate in dark at room temperature for a maximum of 30 minutes
14. Read plate at 25 minutes (650 nm), optional
15. Stop reaction with 100 µl of 0.18 M H$_2$SO$_4$, 30 minutes after adding TMB Take last reading at 450 nm soon after stopping reaction C. Results of Binding Experiments The G3 assay was performed using 0.1 µM peptide representing 11 amino acids of Tat fused to the final 9 amino acids of TRPM7 (YGRKKRRQRRRSTNSVRLML; SEQ ID NO:258). Table 8 shows the PDZ domains which bound the peptide with an OD at least 2-fold over GST-only OD in the G3 assay as described above and/or had an ED$_{50}$ of less than 0.17 µM in the titration experiments described in Example (New2) below.

Example 2

Titration Experiments

The G3 assay was performed on a subset of the PDZ domains as in Example II except that the concentration of peptide was 0.002 µM, 002 µM, 0.1 µM, 0.2 µM, 1 µM, and 2 µM. Data was fitted to the equation:

$$y=100.0/(1+10^{((log(m1)-log(m0))*m2)}), \text{ where } m1=EC_{50},$$
m2=Hill coefficient, and m0=peptide concentration to calculate the EC$_{50}$ for the binding of the peptides to the PDZ domains.

Results:

EC$_{50}$ data are presented in Table 9. Graphs of titrations for the biotinylated peptide representing 11 amino acids of Tat fused to the final 9 amino acids of TRPM7 (YGRKKRRQR- RRSTNSVRLML; SEQ ID NO:258) peptide with RIM-2 d1, INADL d3, ZO-1 d2, and Par3 d3 are shown in FIGS. 9A, 9B, 9C, and 9D.

Example 3

Peptide Binding

Figure 10B:
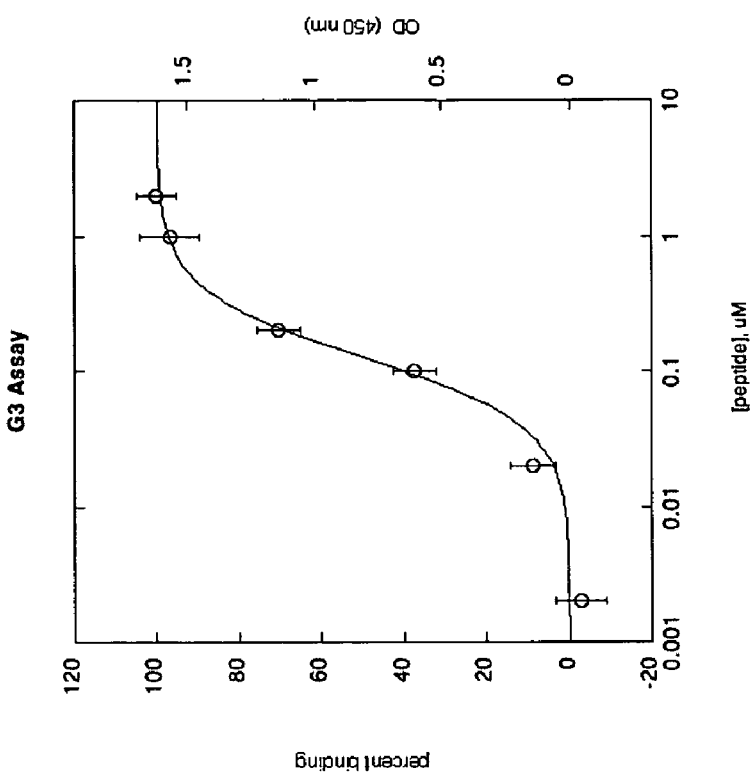
FIGS. 10A AND 10B show the results of titrations of Peptide #1829 with ZO-1 d2 and Peptide #1839 with INADL d3.
Figure 10A:
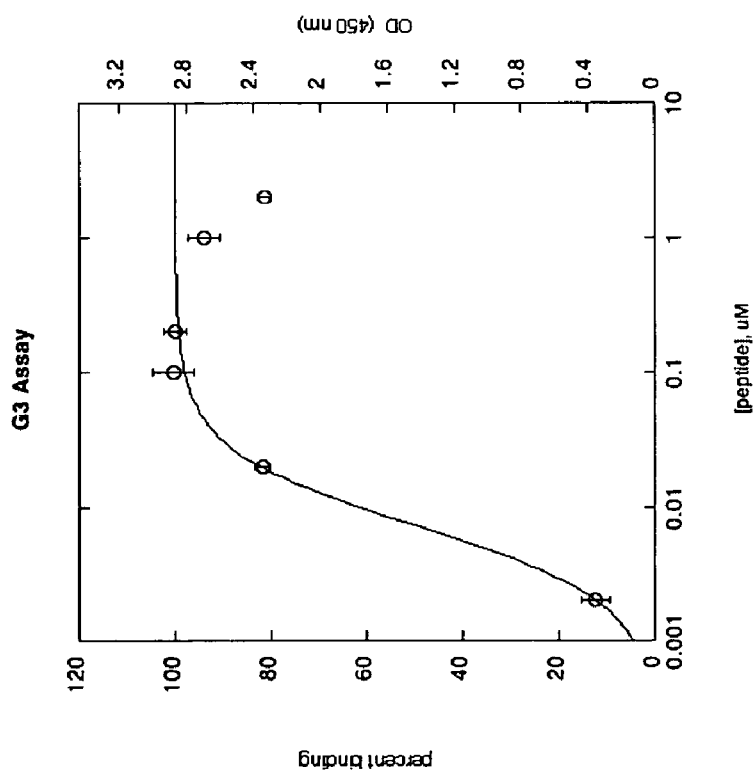

The G3 assay was performed to determine the binding of PDZ domains ZO-1 d2 and INADL d3 with the peptides listed in Table 10. EC50 results are shown in Table 10. FIGS. 10A and 10B show graphs of the titrations for the Peptide #1829 with ZO-1 d2 and for the Peptide #1839 with INADL d3.

The peptides shown in Table 11 have also been demonstrated to bind ZO-1 d2, INADL d3, PAR3 d3, syntrophin 1 alpha d1, and RIM2 d1 in G assays.

Example 4

Treatment of Ischemic Brain Damage by Modulating TRPM7 Expression Generation of a DNA Vector-Based siRNA System In brief, a small DNA insert (49 bp) encoding a short hairpin RNA targeting TRPM7 (the siRNA against TRPM7 corresponded to coding regions 5152-5172 (siRNATRPM7-1)) was cloned into a commercially available pAdTrack vector (see FIG. 11). The sequence was placed under the control of the H1 promoter and GFP was placed under a CMV promoter. The TRPM7 siRNA-pAdTrack insert-containing vector as well as adeno recombination sequences were co-transfected with pAdEasy (containing viral sequences) into HEK cells and the cells were selected with kanamycin. Recombined virus containing the TRPM7 siRNA and GFP sequences was produced from these cells. The hairpin RNA was rapidly processed by the cellular machinery into 45 nt double stranded RNA (siRNA). In this way, the siRNA was delivered using a viral vector. Two additional effective RNAi sequences for TRPM7 include siRNAs against TRPM7 corresponding to coding regions, 5023-5043 and 1318-1338 (siRNATRPM7-2 and siRNATRPM7-3, respectively) relative to the first nucleotide of the start codon of murine TRPM7 (GeneBank accession # AY032951).

Figure 12:
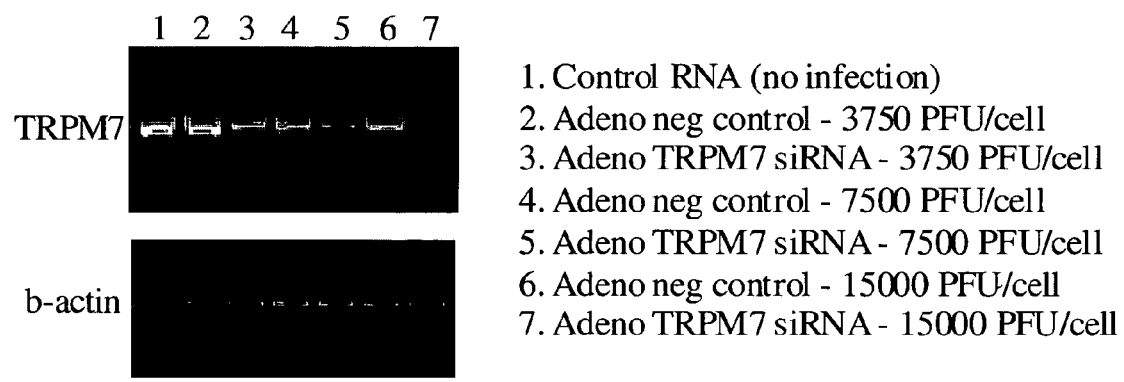
FIG. 12 shows the effects of infecting primary cultured neurons on TRPM7 mRNA by RT-PCR. Cultured cortical neurons plated in 12 well plates (106 cells/well) were infected at the time of plating with the corresponding adenoviral constructs and the RNA was harvested 5 days later. RT-PCR was performed on equivalent amounts of RNA using primers for TRPM7 or β-actin.

FIG. 12 shows the effects of infecting primary cultured neurons on TRPM7 mRNA by RT-PCR. Cultured cortical neurons plated in 12 well plates (106 cells/well) were infected at the time of plating with the corresponding adenoviral constructs and the RNA was harvested 5 days later. RT-PCR was performed on equivalent amounts of RNA using primers for TRPM7 or β-actin.

Figure 13:
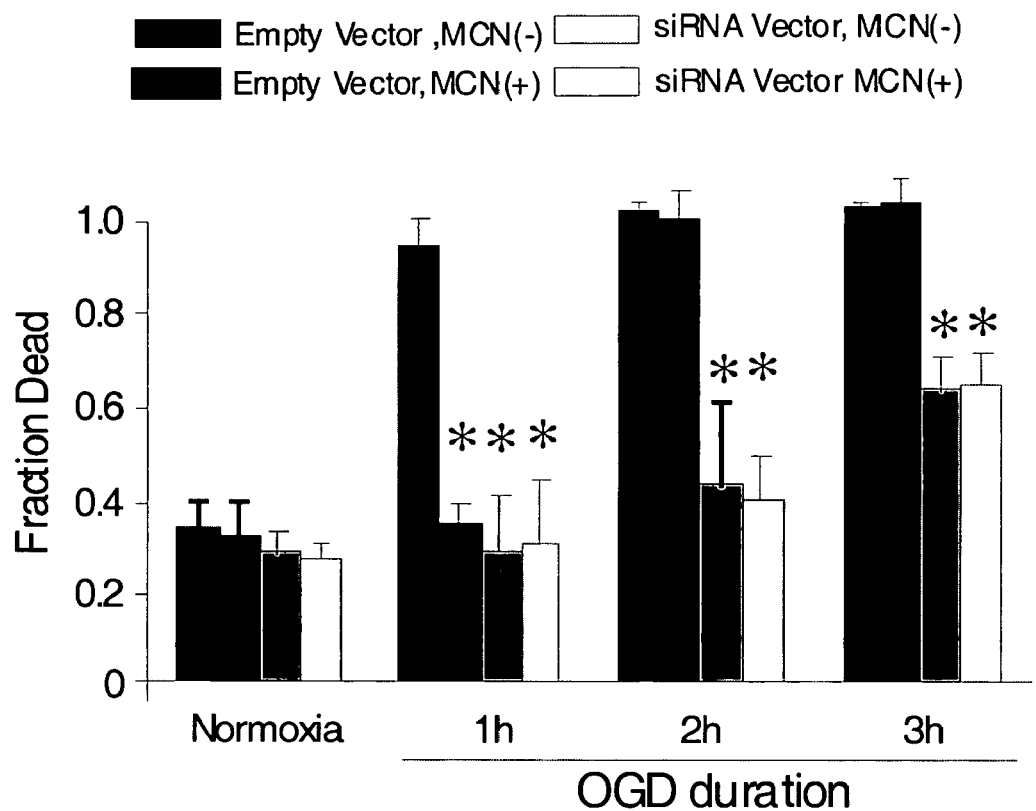
FIG. 13 shows the effect of oxygen glucose deprivation (OGD) for the indicated duration on neuronal cell death in the presence (MCN(+)) or absence (MCN(−)) of the combination of MK-801 (10 μM), CNQX (10 μM) and nimodipine (2 μM), denoted as MCN, antagonists of NMDA and AMPA/kainate glutamate receptors and L-type $Ca^{2+}$ channels, respectively. The fraction of dead cells was determining by dividing the number of neurons expressing GFP which became stained with propidium iodide 20 h after OGD by the number of neurons expressing GFP at the beginning of the experiment. Data for each culture was obtained from counting cells in 3 high power microscope fields per experiment.

FIG. 13 shows the effect of oxygen glucose deprivation (OGD) for the indicated duration on neuronal cell death in the presence (MCN(+)) or absence (MCN(−)) of the combination of MK-801 (10 μM), CNQX (10 μM) and nimodipine (2 μM), denoted as MCN, antagonists of NMDA and AMPA/kainate glutamate receptors and L-type Ca2+ channels, respectively. The fraction of dead cells was determining by dividing the number of neurons expressing GFP which became stained with propidium iodide 20 h after OGD by the number of neurons expressing GFP at the beginning of the experiment. Data for each culture was obtained from counting cells in 3 high power microscope fields per experiment.

The siRNA sequences for TRPM7 may also be placed under the control of the human U6 promoter in the shuttle vector pTrack CMV-EGFP, whereby the siRNA sequences and the EGFP sequence will be driven off separate promoters.

A control adenovirus expressing EGFP alone, using the same shuttle vector as above, will also be produced.

Regional infection of rat cortex and hippocampus with RNAi adenoviruses by microinjection.

3 μl of either TRPM7 vector or control vector are infused to the cortex (from bregma: AP=2 mm, ML=2.8 mm, DV=1.7 mm) or in the CA1 sector of the hippocampus. We infuse in the order of 104 particles. Animals are sacrificed 2, 5 and 10 days later and brain sections prepared and analyzed for GFP fluorescence in frozen brain sections and for GFP staining with anti-GFP antibodies in fixed sections. The technique can be titrated (amount of infectious particles, duration of treatment, number of treatments) to optimize TRPM7 suppression. All animals undergo bilateral injections, using the active vector on one side, and the control on the other, to control for effects of the adenovirus.

Effect of In-Vivo TrpM7 Suppression on Cerebral Ischemic Damage.

Experiments are performed using a permanent distal middle cerebral artery occlusion (MCAO) model as described by Brint et al. (1988). This results primarily in the death of cortical neurons. In brief, Wistar rats (250-300 g) are anesthetized with 1-2% halothane. Snares are placed around the CCAs and a 2 mm burr hole made at the junction of the zygomatic arch and squamous bone. The distal MCA is exposed and divided above the rhinal fissure. The CCA snares is tightened to occlude the CCAs, and released after 4 h.

Experiments are performed in animals in which TRPM7 was suppressed as in 5.2 bilaterally in the cortex. Animals are sacrificed 48 hr later and brain sections prepared and analyzed. Neuronal cell loss will be assessed in transfected areas as gauged by GFP expression, which is co-expressed with siRNA in the same vector and for infarct volumes. Experimental groups will include animals receiving injections of saline (10), Scrambled (inactive) RNAi vector (10), and TRPM7 RNAi vector (10). The hemisphere contralateral to the MCAO will serve as a control in each animal. If TRPM7 suppression is protective, then there will be improved survival of neurons in transfected (GFP positive) areas.

Example 5

Treatment of Ischemic Brain Damage by Modulating TRPM7-PDZ Protein Interactions Small peptides or fusion proteins containing C- and N-terminus TRPM7 subunit sequences, or encompassing intrinsic TRPM channel enzymatic domains will be synthesized or grown in bacteria. Some will be grown as Flag- or HA-tagged proteins fused to a peptide corresponding to the cell-membrane transduction domain of the HIV-1-Tat protein (YGRKKRRQRRR; Tat; SEQ ID NO:257). Tat-peptides and proteins permeate into cells in a rapid, dose-dependent manner independent of receptors and transporters.

FIG. 14 shows the effect of treating the cultures with Tat-9cTRPM7. The sequence of Tat-9cTRPM7 is: [YGRKKRRQRRR-STNSVRLML; SEQ ID NO:258], whereby the first 11 residues correspond to the cell-membrane transduction domain of the human immunodeficiency virus type 1 (HIV-1) Tat protein and the last 9 residues correspond to the last 9 amino acids of the C-terminus of human TRPM7 (accession Q96QT4). (A) Neuronal survival at 20 h in the indicated concentrations of Tat-9cTRPM7 in the absence of excitotoxic challenge. (B) Neuronal survival 20 h after challenging the cultures for 1 h with the indicated concentration of NMDA. Tat-9cTRPM7 was applied immediately after the NMDA challenge. Therefore, neurons treated with 9C-TRPM7 exhibited enhanced survival when challenged with NMDA.

We predict similar results with a Tat-conjugated peptide encoding the last 9 residues of the mouse TRPM7 C-terminus (YGRKKRRQRRR-ATNSVRLML; SEQ ID NO:380; accession Q923J1).

To examine whether treatment with these Tat-conjugated TRPM7 C-terminal peptides would reduce stroke damage, experiments are carried out in adult male Sprague-Dawley rats subjected to transient middle cerebral artery occlusion (MCAO) for 90 minutes by the intraluminal suture method. This produces an extensive infarction encompassing the cerebral cortex and basal ganglia. Animals are treated with either saline, the Tat-TRPM7 C-terminus, or with Tat-conjugated to a scrambled C-terminal peptide by a single intravenous bolus injection 1 hour after the onset of MCAO (3 nMoles/g). Physiological parameters (body temperature, blood pressure, blood gases) are monitored and maintained throughout the experiment. All experimental manipulations and analyses of data are performed by individuals blinded to the treatment groups. The extent of cerebral infarction is measured 24 h after MCAO onset (FIG. 3C inset). The postural reflex test, and the forelimb placing test is used to grade neurological function on a scale of 0 to 12 (normal=0; worst=12) during MCAO (at 50 minutes) and 24 h thereafter.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications cited herein are hereby incorporated by reference in their entirety for all purposes to the same extent as if each individual publication, patent or patent application were specifically and individually indicated to be so incorporated by reference.

What is claimed is:

1. A method for determining whether a test compound inhibits binding between a TRPM7 protein and a PDZ domain-containing polypeptide, comprising:
   (i) contacting a TRPM7 protein or a fragment thereof containing at least the four C-terminal amino acids of the protein with a PDZ domain-containing polypeptide in the presence and absence of the test compound; and
   (ii) measuring the amount of complex formed between the TRPM7 protein or fragment thereof and the PDZ domain-containing polypeptide in the presence and absence of the test compound,
   wherein less complex is formed in the presence relative to the absence of the test compound indicating the test compound is an inhibitor of binding between the TRPM7 protein and the PDZ domain-containing polypeptide.

2. The method of claim 1, wherein the PDZ domain is a PDZ domain selected from the group consisting of RIM-2, Mint1, INADL, Syntrophin 1 alpha, SITAC-18, LIM mystique, ZO-1, PAR3L, MAST2, PAR3, and novel serine protease (SEQ ID NO:158).

3. The method of claim 1, wherein the test compound is a peptide comprising at least two contiguous amino acids from the C-terminus of SEQ ID NO:260 or SEQ ID NO:384.

4. The method of claim 1, wherein the test compound comprises 4 residues from the C-terminus of SEQ ID NO:260 or SEQ ID NO:384.

5. The method of claim 1, wherein the test compound further comprises a transmembrane transporter peptide.

6. The method of claim 1, wherein the PDZ domain is a syntrophin-1 alpha PDZ domain.

* * * * *